US009011956B2

(12) United States Patent
Prakash et al.

(10) Patent No.: US 9,011,956 B2
(45) Date of Patent: *Apr. 21, 2015

(54) NATURAL HIGH-POTENCY SWEETENER COMPOSITIONS WITH IMPROVED TEMPORAL PROFILE AND/OR FLAVOR PROFILE, METHODS FOR THEIR FORMULATION, AND USES

(75) Inventors: Indra Prakash, Alpharetta, GA (US); Grant E. DuBois, Roswell, GA (US); Prashanthi Jella, Norcross, GA (US); George A. King, Atlanta, GA (US); Rafael I. San Miguel, Smyrna, GA (US); Kelly H. Specic, Mableton, GA (US); Deepthi K. Weerasinghe, Marietta, GA (US); Newton R. White, Decatur, GA (US)

(73) Assignee: The Coca-Cola Company, Atlanta, GA (US)

( * ) Notice: Subject to any disclaimer, the term of this patent is extended or adjusted under 35 U.S.C. 154(b) by 1023 days.

This patent is subject to a terminal disclaimer.

(21) Appl. No.: 11/561,148

(22) Filed: Nov. 17, 2006

(65) Prior Publication Data

US 2007/0128311 A1 Jun. 7, 2007

Related U.S. Application Data

(63) Continuation-in-part of application No. 11/556,113, filed on Nov. 2, 2006, now abandoned.

(60) Provisional application No. 61/739,302, filed on Nov. 23, 2005, provisional application No. 60/805,209, filed on Jun. 19, 2006, provisional application No. 60/805,216, filed on Jun. 19, 2006.

(51) Int. Cl.
| A23L 1/236 | (2006.01) |
| A23L 1/22 | (2006.01) |
| A23L 1/305 | (2006.01) |
| A23L 2/52 | (2006.01) |
| A23L 2/60 | (2006.01) |
| A61K 31/575 | (2006.01) |

(52) U.S. Cl.
CPC ............ *A23L 1/2364* (2013.01); *A23L 1/22091* (2013.01); *A23L 1/236* (2013.01); *A23L 1/2366* (2013.01); *A23L 1/3051* (2013.01); *A23L 2/52* (2013.01); *A23L 2/60* (2013.01); *A61K 31/575* (2013.01)

(58) Field of Classification Search
USPC .......... 426/548, 580, 590, 591, 594, 597, 599
See application file for complete search history.

(56) References Cited

U.S. PATENT DOCUMENTS

| 4,612,942 A | 9/1986 | Dobberstein et al. |
| 5,433,965 A | 7/1995 | Fischer et al. |
| 5,437,880 A * | 8/1995 | Takaichi et al. .................. 426/73 |
| 5,576,039 A | 11/1996 | Lewis |
| 5,731,025 A | 3/1998 | Mitchell |
| 5,962,678 A * | 10/1999 | Payzant et al. ................ 536/128 |
| 6,045,850 A | 4/2000 | Kondou |
| 6,652,901 B2 * | 11/2003 | Ishii .............................. 426/548 |
| 6,814,958 B1 * | 11/2004 | Sekimoto ........................ 424/58 |
| 6,838,107 B1 | 1/2005 | Bakal et al. |
| 7,067,150 B2 * | 6/2006 | Farber et al. .................. 424/488 |
| 7,186,431 B1 * | 3/2007 | Silver ............................ 426/548 |
| 7,267,835 B2 | 9/2007 | Kitazume et al. |
| 7,815,956 B2 | 10/2010 | Lee et al. |
| 7,851,005 B2 | 12/2010 | Bingley et al. |
| 2002/0132780 A1 | 9/2002 | Heisey et al. |
| 2002/0197372 A1 | 12/2002 | Janssen et al. |
| 2003/0035875 A1 * | 2/2003 | Dulebohn et al. ............. 426/548 |
| 2003/0152524 A1 | 8/2003 | Eshita |
| 2003/0152684 A1 * | 8/2003 | Saito et al. .................... 426/548 |
| 2003/0161879 A1 | 8/2003 | Ohmori |
| 2004/0022914 A1 | 2/2004 | Allen |
| 2004/0058050 A1 | 3/2004 | Guo |
| 2004/0120900 A1 | 6/2004 | Arsenault |
| 2006/0093720 A1 | 5/2006 | Tatz |
| 2007/0031561 A1 | 2/2007 | Lakkis et al. |
| 2009/0202697 A1 | 8/2009 | Erickson et al. |

FOREIGN PATENT DOCUMENTS

| EP | 0390299 B2 | 7/2000 |
| JP | 55050866 A2 | 4/1980 |
| JP | 60075252 A2 | 4/1985 |
| JP | 60188035 A | 9/1985 |

(Continued)

OTHER PUBLICATIONS

Geuns, Jan M.C., "Review: The safety of stevioside used as a sweetener", in Proceedings of the first symposium 'The Safety of Stevioside', p. 85-127 (2004).*
Sasaki, Kazuhito, "Application of Stevia Sweetener to Soft Drinks," *New Food Ind.*, 1983, pp. 38-43, vol. 25 No. 4, Sanyo Kokusaku Pulp Co. Ltd., Japan.
Kohda, Hiroshi, et al., "New Sweet Diterpene Glucosides from Stevia Rebaudiana," *Phytochemistry*, 1976, pp. 981-983, vol. 15 No. 6, School of Medicine, Hiroshima Univ., Hiroshima, Japan.

(Continued)

*Primary Examiner* — Leslie Wong
(74) *Attorney, Agent, or Firm* — King & Spalding

(57) ABSTRACT

The present invention relates generally to improving the taste of natural high-potency non-caloric or low-caloric sweeteners and compositions sweetened therewith. In particular, the present invention relates to compositions that can improve the tastes of natural high-potency non-caloric or low-caloric sweeteners by imparting a more sugar-like taste or characteristic. In particular, the compositions and methods provide a more sugar-like temporal profile, including sweetness onset and sweetness linger, and/or a more sugar-like flavor profile, including osmotic taste.

16 Claims, 5 Drawing Sheets

(56) References Cited

FOREIGN PATENT DOCUMENTS

| | | | |
|---|---|---|---|
| JP | 62079752 A | 4/1987 |
| JP | 62091161 A | 4/1987 |
| JP | 63258557 A | 10/1988 |
| JP | 63304964 A | 12/1988 |
| JP | 63304964 A2 | 12/1988 |
| JP | 04091753 A2 | 3/1992 |
| JP | 06192283 | 7/1994 |
| JP | 06192283 A | 7/1994 |
| JP | 07143860 | 6/1995 |
| JP | 07143860 A | 6/1995 |
| JP | 08000214 | 1/1996 |
| JP | 08089207 A | 4/1996 |
| JP | 09104625 A2 | 4/1997 |
| JP | 09173009 A2 | 7/1997 |
| JP | 09194370 A2 | 7/1997 |
| JP | 10150958 A | 6/1998 |
| JP | 10276712 A | 10/1998 |
| JP | 10304829 A | 11/1998 |
| JP | 11123069 A | 5/1999 |
| JP | 11243906 | 9/1999 |
| JP | 11346708 A | 12/1999 |
| JP | 2000236842 | 9/2000 |
| JP | 2001161308 A2 | 6/2001 |
| JP | 2003180288 | 7/2003 |
| JP | 2004073197 | 3/2004 |
| JP | 2004149481 | 5/2004 |
| JP | 2005237303 | 9/2005 |
| WO | WO 9418855 A1 | 9/1994 |
| WO | WO 9804156 A1 | 2/1998 |
| WO | WO 2004089113 A | 10/2004 |

OTHER PUBLICATIONS

Nabors, Lyn O'Brien, et. al., "Alternative Sweeteners," *Food Science and Technology*, 1985, pp. 295-307, vol. 17, Marcel Dekker, Inc., New York, NY, USA.

"SteviaClear™ Liquid Stevia," Jun. 2005, Advertisement.

Abudula, Reziwanggu, et al., "Rebaudioside A Potently Stimulates Insulin Secretion from Isolated Mice Islets: Studies on the Dose-Glucose-, and Calcium-Dependency," *Metabolism*, Oct. 2004, vol. 53 No. 10, Arhus University Hospital, Arhus, Denmark.

Mizutani, Kenji, et al., "Use of Stevia Rebaudiana Sweeteners in Japan," *Stevia: The Genus Stevia*, 2002, pp. 178-195, A. Douglas Kinghorn, ed., Taylor and Francis, Inc., New York, NY, USA.

Kim, Jinwoong, et al., "Use of Stevioside and Cultivation of Stevia Rebaudiana in Korea," *Stevia: The Genus Stevia*, 2002, pp. 196-202, A. Douglas Kinghorn, ed., Taylor and Francis, Inc., New York, NY, USA.

Chang, Shin S., et al., "Stability Studies of Stevioside and Rebaudioside A in Carbonated Beverages," *J. Agri. Food. Chem.*, 1983, pp. 409-412., vol. 31, American Chemical Society, USA.

Goettemoeller, Jeffrey, "Stevia Sweet Recipes: Sugar Free—Naturally!" 1998, pp. 1-17, Vital Health Publishing, Bloomingdale, Illinois, USA.

Depuydt, Rita, "Baking with Stevia 11," 1998, pp. 5-6, 9-10, 15, 104, Sun Coast Enterprises, Oak View, California, USA.

The Ministry of Health and Welfare, Food Chemical Department, "List of Food Additives excluding chemical synthetics," 1989, The Government of Japan, Tokyo, Japan.

Geuns, Jan M. C., "Review: The Safety of Stevioside used as a Sweetener," in Proceedings of the first symposium, 'The Safety of Stevioside,' 2004, pp. 85-127, Laboratory of Functional Biology, KULeuven, Leuven, Belgium.

Food Standards Australia New Zealand, "Draft Assessment Report, Application A540, Steviol Glycosides as Intense Sweeteners," 2007, Canberra, Australia.

Sunrider Product Catalog, Apr. 1994, pp. 3, 5, The Sunrider Corporation, Torrance, CA, USA.

Sunrider Product Catalog, Apr. 1999, pp. 1-2, The Sunrider Corporation, Torrance, CA, USA.

Sunrider Product Catalog, Apr. 2000, pp. 1-2, The Sunrider Corporation, Torrance, CA, USA.

Sunrider Product Catalog, Jan. 2001, pp. 1, 12-13, The Sunrider Corporation, Torrance, CA, USA.

Sunrider Product Catalog, Jan. 2002, pp. 6-7, 18-19, The Sunrider Corporation, Torrance, CA, USA.

Sunrider Product Catalog, May 2003, pp. 10-11, 18-19, The Sunrider Corporation, Torrance, CA, USA.

Sunrider Product Catalog, Feb. 2005, pp. 7-8, 21-22, The Sunrider Corporation, Torrance, CA, USA.

Sunrider Product Catalog, 2006, pp. 7-8, 21-22, The Sunrider Corporation, Torrance, CA, USA.

Sunrider Product Catalog, 2007, pp. 8-9, 14-15, The Sunrider Corporation, Torrance, CA, USA.

The Sunrider Corporation, "Delicious Nutritious Whole Food Sunrider Recipes," 2004, http://healthregeneration.com/recipes.html.

The Sunrider Corporation, VitaFruit product advertising flyer, 1994, Torrance, CA, USA.

Sunwriter Newsletter, "The Truth About Trusweet," Jul. 1983, p. 2, The Sunrider Corporation, Torrance, CA, USA.

Sunwriter Newsletter, "The Truth About Trusweet," Apr. 1984, p. 2, The Sunrider Corporation, Torrance, CA, USA.

The SunSpot Newsletter, "SunCare is Available," May 1985, p. 2, The Sunrider Corporation, Torrance, CA, USA.

The SunSpot Newsletter, Jan. 1988, pp. 1-2, The Sunrider Corporation, Torrance, CA, USA.

The SunSpot Newsletter, Nov. 1993, pp. 1-2, vol. 11, No. 11, The Sunrider Corporation, Torrance, CA, USA.

The SunSpot Newsletter, Dec. 1993, pp. 1-2, vol. 11, No. 12, The Sunrider Corporation, Torrance, CA, USA.

The SunSpot Newsletter, Mar. 1995, pp. 1, 3, vol. 13, No. 3, The Sunrider Corporation, Torrance, CA, USA.

Sunwriter Newsletter, "Sunectar," Holiday Issue 1995, vol. 12, No. 5, The Sunrider Corporation, Torrance, CA, USA.

Sunwriter Newsletter, "Sunnydew," May/Jun. 1996, vol. 13, No. 3, The Sunrider Corporation, Torrance, CA, USA.

Sunwriter Newsletter, Sep./Oct. 1996, vol. 13, No. 5, The Sunrider Corporation, Torrance, CA, USA.

The SunSpot Newsletter, "VitaSpray," Sep. 1996, vol. 14, No. 9, The Sunrider Corporation, Torrance, CA, USA.

The SunSpot Newsletter, pp. 1-2, Nov. 1996, vol. 14, No. 10, The Sunrider Corporation, Torrance, CA, USA.

The SunSpot Newsletter, pp. 1-2, Aug. 1997, vol. 15, No. 8, The Sunrider Corporation, Torrance, CA, USA.

The SunSpot Newsletter, pp. 1-2, May 1998, vol. 16, No. 5, The Sunrider Corporation, Torrance, CA, USA.

The SunSpot Newsletter, pp. 1-3, Jul. 1998, vol. 16, No. 7, The Sunrider Corporation, Torrance, CA, USA.

The SunSpot Newsletter, pp. 1-2, Oct. 1998, vol. 16, No. 10, The Sunrider Corporation, Torrance, CA, USA.

The SunSpot Newsletter, pp. 1, 4, Mar. 1999, vol. 18, No. 3, The Sunrider Corporation, Torrance, CA, USA.

The SunSpot Newsletter, pp. 1-2, Jan. 1999, vol. 18, No. 1, The Sunrider Corporation, Torrance, CA, USA.

Sunwriter Newsletter, pp. 12, 14, 1999, vol. 16, No. 1, The Sunrider Corporation, Torrance, CA, USA.

The SunSpot Newsletter, pp. 1-2, Mar. 2000, vol. 19, No. 3, The Sunrider Corporation, Torrance, CA, USA.

The SunSpot Newsletter, pp. 1, 4, Oct. 2000, vol. 19, No. 10, The Sunrider Corporation, Torrance, CA, USA.

The SunSpot Newsletter, pp. 1-2, Apr. 2001, vol. 20, No. 4, The Sunrider Corporation, Torrance, CA, USA.

The SunSpot Newsletter, pp. 1-2, Jun. 2002, vol. 21, No. 6, The Sunrider Corporation, Torrance, CA, USA.

The SunSpot Newsletter, pp. 1-2, Oct. 2002, vol. 21, No. 10, The Sunrider Corporation, Torrance, CA, USA.

Director Update Newsletter, "Sunrider VitaFruit Liquid Concentrate," Nov. 1993, The Sunrider Corporation, Torrance, CA, USA.

Director Update Newsletter, Dec. 1993, The Sunrider Corporation, Torrance, CA, USA.

Director Update Newsletter, Jun. 1994, The Sunrider Corporation, Torrance, CA, USA.

(56) References Cited

OTHER PUBLICATIONS

Director Update Newsletter, Dec. 1994, The Sunrider Corporation, Torrance, CA, USA.
Director Update Newsletter, Apr. 1995, The Sunrider Corporation, Torrance, CA, USA.
Director Update Newsletter, Jun. 1995, The Sunrider Corporation, Torrance, CA, USA.
Director Update Newsletter, Jul. 1995, The Sunrider Corporation, Torrance, CA, USA.
Director Update Newsletter, Nov. 1995, The Sunrider Corp., Torrance, CA, USA.
Director Update Newsletter, Dec. 1995, The Sunrider Corporation, Torrance, CA, USA.
Director Update Newsletter, Feb. 1996, The Sunrider Corporation, Torrance, CA, USA.
Director Update Newsletter, May 1996, The Sunrider Corporation, Torrance, CA, USA.
Director Update Newsletter, Jun. 1996, The Sunrider Corporation, Torrance, CA, USA.
Director Update Newsletter, Jul. 1996, The Sunrider Corporation, Torrance, CA, USA.
Director Update Newsletter, Aug. 1996, The Sunrider Corporation, Torrance, CA, USA.
Director Update Newsletter, Sep. 1996, The Sunrider Corporation, Torrance, CA, USA.
Director Update Newsletter, Nov. 1996, The Sunrider Corporation, Torrance, CA, USA.
Director Update Newsletter, Feb. 2000, The Sunrider Corporation, Torrance, CA, USA.
Director Update Newsletter, Nov. 2001, The Sunrider Corporation, Torrance, CA, USA.
Director Update Newsletter, Aug. 2003, The Sunrider Corporation, Torrance, CA, USA.
Director Update Newsletter, Nov. 2004, The Sunrider Corporation, Torrance, CA, USA.
Director Update Newsletter, Aug. 2005, The Sunrider Corporation, Torrance, CA, USA.
The Sunrider Corporation, Trusweet Extract product packaging, 1982, Torrance, CA, USA.
The Sunrider Corporation, Sunectar Dietary Supplement product label, 1995, 1996, 2002, 2003, Torrance, CA, USA.
Sunrider International, SunCare Natural Facial Masque product label, 1989, 1990, 1991, 1992, 1994, 1995, Torrance, CA, USA.
Sunrider International, SunCare Herbal Skincare product label, 1991, 1993, 1992, 1995, Torrance, CA, USA.
The Sunrider Corporation, VitaFruit Lemon Liquid Herb Fruit Concentrate product label, 1993, 1994, 1995, 1996, 1997, 2000, 2001, 2002, 2003, 2006, Torrance, CA, USA.
The Sunrider Corporation, VitaSpray Dietary Supplement product label, Dec. 2002, Torrance, CA, USA.
The Sunrider Corporation, Sunnydew Dietary Supplement product label, Jun. 1999, 2002, 2003, 2006, Torrance, CA, USA.
The Sunrider Corporation, SunSmile Tabs product label, 1998, Torrance, CA, USA.
The Sunrider Corporation, Herbal Cal Tab Dietary Supplement product label, 1999, 2000, 2001, 2002, 2003, Torrance, CA, USA.
The Sunrider Corporation, Calli product label, 1983, Torrance, CA, USA.
The Sunrider Corporation, Alpha 20C product label, 1999, 2000, Torrance, CA, USA.
The Sunrider Corporation, Sunrise product label, 1999.
The Sunrider Corporation, Evergreen product label, 2000.
The Sunrider Corporation, Quinary product label, year not indicated.
The Sunrider Corporation, Fortune Delight product label, Mar. 2003, Torrance, CA, USA.
The Sunrider Corporation, NuPlus product label, 2002, 2003, Torrance, CA, USA.
Adechy, Miriam, "International Search Report and Written Opinion of the International Searching Authority," Apr. 11, 2007, PCT/US2006/044574, European Patent Office, Rijswijk, The Netherlands.
Georgopoulos, N., "International Search Report and Written Opinion of the International Searching Authority," Mar. 14, 2007, PCT/US2006/044518, European Patent Office, Rijswijk, The Netherlands.
Couzy, Francois, "International Search Report and Written Opinion of the International Searching Authority," Mar. 22, 2007, PCT/US2006/044724, European Patent Office, Rijswijk, The Netherlands.
Couzy, Francois, "International Search Report and Written Opinion of the International Searching Authority," Jun. 22, 2007, PCT/US2006/044802, European Patent Office, Rijswijk, The Netherlands.
Popa, Marian, "International Search Report and Written Opinion of the International Searching Authority," May 11, 2007, PCT/US2006/044592, European Patent Office, Rijswijk, The Netherlands.
Ipinazar, Paula, "Partial International Search Report of the International Searching Authority," Apr. 2007, PCT/US2006/044600, European Patent Office, Rijswijk, The Netherlands.
Heirbaut, Marc, "International Search Report and Written Opinion of the International Searching Authority," Oct. 31, 2007, PCT/US2006/044513, European Patent Office, Rijswijk, The Netherlands.
Smeets, Dieter, "International Search Report and Written Opinion of the International Searching Authority," Apr. 10, 2007, PCT/US2006/044785, European Patent Office, Rijswijk, The Netherlands.
Couzy, Francois, "International Search Report and Written Opinion of the International Searching Authority," Mar. 23, 2007, PCT/US2006/044727, European Patent Office, Rijswijk, The Netherlands.
Couzy, Francois, "International Search Report and Written Opinion of the International Searching Authority," Mar. 21, 2007, PCT/US2006/044591, European Patent Office, Rijswijk, The Netherlands.
Georgopoulos, N., "International Search Report and Written Opinion of the International Searching Authority," Jun. 13, 2007, PCT/US2006/044599, European Patent Office, Rijswijk, The Netherlands.
Popa, Marian, "International Search Report and Written Opinion of the International Searching Authority," May 4, 2007, PCT/US2006/044577, European Patent Office, Rijswijk, The Netherlands.
Popa, Marian, "International Search Report and Written Opinion of the International Searching Authority," Mar. 15, 2007, PCT/US2006/044783, European Patent Office, Rijswijk, The Netherlands.
Donovan-Beerman, T., "International Search Report and Written Opinion of the International Searching Authority," Mar. 30, 2007, PCT/US2006/044573, European Patent Office, Rijswijk, The Netherlands.
Popa, Marian, "International Search Report and Written Opinion of the International Searching Authority," Mar. 16, 2007, PCT/US2006/044705, European Patent Office, Rijswijk, The Netherlands.
Groh, Bjorn, "International Search Report and Written Opinion of the International Searching Authority," Oct. 24, 2007, PCT/US2006/044803, European Patent Office, Rijswijk, The Netherlands.
Smeets, Dieter, "International Search Report and Written Opinion of the International Searching Authority," Apr. 3, 2007, PCT/US2006/044590, European Patent Office, Rijswijk, The Netherlands.
Groh, Bjorn, "International Search Report and Written Opinion of the International Searching Authority," Apr. 16, 2007, PCT/US2006/044706, European Patent Office, Rijswijk, The Netherlands.
Couzy, Francois, "International Search Report and Written Opinion of the International Searching Authority," Apr. 13, 2007, PCT/US2006/044703, European Patent Office, Rijswijk, The Netherlands.
Rinaldi, Francesco, "International Search Report and Written Opinion of the International Searching Authority," Mar. 20, 2007, PCT/US2006/044798, European Patent Office, Rijswijk, The Netherlands.
Hartlieb, Ariane, "International Search Report and Written Opinion of the International Searching Authority," Aug. 21, 2007, PCT/US2006/044801, European Patent Office, Rijswijk, The Netherlands.
Hicks, K., et. al., "Phytosterols and Phytostanols: Functional Food Cholesterol Busters," *Food Technology*, Jan. 1, 2001, pp. 63-67, vol. 55, No. 1, Inst. of Food Technologists, Chicago, IL, USA.
Sardesai, V. M., et. al., "Natural and Synthetic Intense Sweeteners," *Journal of Nutritional Biochemistry*, May 1991, pp. 236-244, vol. 2, No. 5, Butterworth Publishers, Stoneham, Great Britain.
Schiffman, S., et. al., "Investigation of Synergism in Binary Mixtures of Sweeteners," *Brain Research Bulletin*, 1995, pp. 105-120, vol. 38, No. 2, XP002428872.

(56) References Cited

OTHER PUBLICATIONS

Moriyama, et. al., "Soybean beta-conglycinin diet suppresses serum triglyceride levels in normal and genetically obese mice by induction of beta-oxidation, down regulation of fatty acid synthase, and inhibition of triglyceride absorption," *Bioscience, Biotechnology, and Biochemistry*, Dec. 2004, pp. 352-359, vol. 26, No. 6, XP018001511.

Nojiri, S., et. al., "Determination of sugar alcohols in confectionaries by high-performance liquid chromatography after nitrobenzoylation," Journal of Chromatography, Sep. 29, 2000, pp. 195-200, vol. 893, No. 1, Elsevier Science Publishers, B.V., Amsterdam, The Netherlands.

Abad, M. J., et. al., "Anti-Inflammatory Activity of two flavonoids from *Tanacetum microphyllum*," Journal of Natural Products, 1993, pp. 1164-1167, vol. 56, No. 7, Biosciences Information Service, Philadelphia, PA, USA.

Anon., "Sweet tasting amino acid, glycine, enhances flavor and provides functional properties," Food Processing USA, 1983, p. 90, vol. 44, No. 7, International Food Information Service, Frankfurt-Main, Germany.

Shamala, T. R., et. al., "Honey—it is more than just sweet," Indian Food Industry, 1999, pp. 349-357, vol. 18, No. 6, Dept. of Food Microbiology, Central Food Technology, Research Institute, Mysore, India.

Rajbhandari, A., "The Flavonoids of Stevia Rebaudiana," J. Nat. Prod., 1983, pp. 194-195, vol. 46, No. 2.

Geuns, Jan M. C., "Stevioside," Phytochemistry, Nov. 2003, pp. 913-921, vol. 64, No. 5, Pergamon Press, Great Britain.

Schiffman, S., et. al., "Synergism among ternary mixtures of fourteen sweeteners," Chemical Senses, 2000, pp. 131-140, vol. 25, IRL Press, Oxford, Great Britain.

Franke, S. I. R., et. al., "Influence of orange juice over the genotoxicity induced by alkylating agents: an in vivo analysis," Mutagenesis, Jun. 14, 2005, pp. 279-283, vol. 20, No. 4, IRL Press, Oxford, Great Britain.

Losada, M., et. al., "Toward a healthier diet for the colon: The influence of fructooligosaccharides and lactobacilli on intestinal health," Jan. 2002, Biosciences Information Service, Philadelphia, PA, USA.

Grenby, T. H., "Intense Sweeteners for the Food Industry: An Overview," *Trends in Food Science and Technology*, Jan. 1991, pp. 2-6, vol. 2, No. 1, Elsevier Science Publishers, Great Britain.

N. N., "Rebaudioside A and Stevia Extract," retrieved from the Internet on Mar. 16, 2007, pp. 1-5, http://emperorsherbologist.com/rabaudioside_a.php.

Anon., "Sugar-free Cake Mix Preparation by combining maltoligosyl-sucrose, sorbitol, and Stevia extract with glycine and/or DL-alanine," WPI/Thomson, Nov. 10, 1981, XP002425501.

Schiffman, Susan S., et al., "Selective Inhibition of Sweetness by Na-PMP," Apr. 26, 1999, pp. 439-437, Oxford University Press.

Schiffman, S. S. et al., "Investigation of synergism in binary mixtures", Brain Research Bulletin, vol. 38, No. 2, pp. 105-120, 1995.

Schiffman, S. S. et al., "Effect of repeated presentation on sweetness intensity of binary and ternary mixtures of sweeteners", Chemical Senses, vol. 28, pp. 219-229, 2003.

Parpinello, G. P. et al., "Stevioside as a replacement of sucrose in peach juice: sensory evaluation", Journal of Sensory Studies, vol. 16, pp. 471-484, 2001.

Schiffman, S. S. et al., "Synergism among ternary mixtures of fourteen sweeteners", Chemical Senses, vol. 25, pp. 131-140, 2000.

Kinghorn, A. D. "Discovery of Terpenoid and Phenolic Sweeteners From Plants" 2002, vol. 74, No. 7, pp. 1169-1179.

Hirata, K. et al. "Analysis of Stevia Glycosides in Stevia Products of Natural Sweetening and Evaluation of their Chemical Quality", Ann. Rep. Tokyo Metr. Res. Lab. P.H., vol. 53, pp. 108-112, 2002.

Morita Kagaku Kogyo Co., Ltd., The rebaudio A9 series, http://www.morita-kagaku-kogyo.co.jp/a9.htm.

Morita Kagaku Kogyo Co., Ltd., The rebaudio J series, http://www.morita-kagaku-kogyo.co.jp/j.htm.

Sardesai, M. and Waldshan, T.H., "Natural and synthetic intense sweeteners," *J. Nutr. Biochem.*, 1991, vol. 2, pp. 236-244.

\* cited by examiner

NATURAL HIGH-POTENCY SWEETENER COMPOSITIONS WITH IMPROVED TEMPORAL PROFILE AND/OR FLAVOR PROFILE, METHODS FOR THEIR FORMULATION, AND USES

RELATED APPLICATION DATA

The present application is a continuation-in-part of U.S. patent application Ser. No. 11/556,113, now abandoned, entitled "Natural High-Potency Sweetener Compositions With Improved Temporal Profile And/Or Flavor Profile, Methods For Their Formulations, and Uses," filed in the U.S. Patent and Trademark Office on Nov. 2, 2006, which claims priority under 35 U.S.C. §119 to U.S. Provisional Application No. 60/739,302, entitled "Natural High-Potency Sweetener Compositions With Improved Temporal Profile And/Or Flavor Profile, Methods For Their Formulations, and Uses," filed on Nov. 23, 2005; U.S. Provisional Application No. 60/805,209, entitled "Natural High-Potency Tabletop Sweetener Compositions with Improved Temporal and/or Flavor Profiles, Methods for Their Formulation, and Uses," filed on Jun. 19, 2006; and U.S. Provisional Application No. 60/805,216, entitled "Rebaudioside A Composition and Method for Purifying Rebaudioside A," filed on Jun. 19, 2006. These applications are hereby incorporated by reference in their entirety.

FIELD OF THE INVENTION

The present invention relates generally to improving the taste of natural high-potency non-caloric or low-caloric sweeteners and compositions sweetened therewith. In particular, the present invention relates to compositions that can improve the tastes of natural high-potency non-caloric or low-caloric sweeteners by imparting a more sugar-like taste or characteristic. In particular, the compositions and methods provide a more sugar-like temporal profile, including sweetness onset and sweetness linger, and/or a more sugar-like flavor profile, including osmotic taste.

BACKGROUND OF THE INVENTION

Natural caloric sugars, such as sucrose, fructose, and glucose are utilized heavily in beverage, food, pharmaceutical, and oral hygienic/cosmetic industries due to their pleasant taste. In particular, sucrose imparts a desirable taste for consumers. Although sucrose provides superior sweetness characteristics, it is caloric. While calories are necessary for proper bodily functions, there is a need in the market to provide alternative non-caloric or low-caloric sweeteners with sugar-like taste for consumers with sedentary lifestyles or those who are calorie conscious. However, in general, non-caloric or low caloric sweeteners have associated undesirable tastes to consumers such as delayed sweetness onset; lingering sweet aftertaste; bitter taste; metallic taste; astringent taste; cooling taste; licorice-like taste; and/or the like.

Natural high-potency sweeteners, such as rebaudioside A, rebaudioside B, rebaudioside C, rebaudioside D, rebaudioside E, rebaudioside F, dulcoside A, dulcoside B, rubusoside, stevia, stevioside, mogroside IV, mogroside V, Luo Han Guo sweetener, siamenoside, monatin and its salts (monatin SS, RR, RS, SR), curculin, glycyrrhizic acid and its salts, thaumatin, monellin, mabinlin, brazzein, hernandulcin, phyllodulcin, glycyphyllin, phloridzin, trilobatin, baiyunoside, osladin, polypodoside A, pterocaryoside A, pterocaryoside B, mukuroziosude, phlomisoside I, periandrin I, abrusoside A, and cyclocarioside I generally exhibit a sweet taste that has a different temporal profile, maximal response, flavor profile, mouthfeel, and/or adaptation behavior than that of sugar. For example, the sweet tastes of natural high-potency sweeteners are slower in onset and longer in duration than the sweet taste produced by sugar and thus change the taste balance of a food composition. Because of these differences, use of a natural high-potency sweetener to replace a bulk sweetener, such as sugar, in a food or beverage, causes an unbalanced temporal profile and/or flavor profile. In addition to the difference in temporal profile, high-potency sweeteners generally exhibit (i) lower maximal response than sugar, (ii) off tastes including bitter, metallic, cooling, astringent, licorice-like taste, etc., and/or (iii) sweetness which diminishes on iterative tasting. It is well known to those skilled in the art of food/beverage formulation that changing the sweetener in a composition requires re-balancing of the flavor and other taste components, (e.g., acidulants). If the taste profile of natural high-potency sweeteners could be modified to impart specific desired taste characteristics to be more sugar-like, the type and variety of compositions that may be prepared with that sweetener would be significantly expanded. Accordingly, it would be desirable to selectively modify the taste characteristics of natural high-potency sweeteners. As a result, several processes and/or compositions have been described for modifying the taste profile of beverage, food, pharmaceutical, nutraceutical, tobacco, and oral hygienic/cosmetic products sweetened with non-caloric or low-caloric sugar alternative sweeteners.

However, improvement in sweetness and sugar-like characters of non-caloric or low-caloric natural sweeteners to provide consumer satisfaction more like that of sucrose, fructose, or glucose still is desired.

SUMMARY OF THE INVENTION

Generally, this invention addresses the above described need by providing a natural high-potency sweetener (NHPS) composition with improved temporal profile or flavor profile or both, a method for improving the temporal profile and/or flavor profile of a NHPS, NHPS sweetened compositions with improved temporal profile and/or flavor profile, and a method for improving the temporal profile and/or flavor profile of NHPS sweetened compositions. In particular, this invention improves the temporal profile and/or flavor profile by imparting a more sugar-like temporal profile and/or flavor profile.

More particularly, this invention encompasses a NHPS composition with a more sugar-like temporal profile and/or flavor profile comprising at least one NHPS and/or at least one modified NHPS and at least one sweet taste improving composition selected from the group consisting of carbohydrates, polyols, amino acids, other sweet taste improving additives, and combinations thereof.

According to another aspect, this invention encompasses a method for imparting a more sugar-like temporal profile and/or flavor profile to a NHPS by combining with at least one NHPS and/or at least one modified NHPS, at least one sweet taste improving composition selected from the group consisting of carbohydrates, polyols, amino acids, other sweet taste improving additives, and combinations thereof.

According to still another aspect, this invention encompasses a NHPS sweetened composition with a more sugar-like temporal profile and/or flavor profile comprising a sweetenable composition, at least one NHPS and/or at least one modified NHPS, and at least one sweet taste improving composition selected from the group consisting of carbohydrates, polyols, amino acids, other sweet taste improving additives, and combinations thereof. According to particular embodiments of this invention, the NHPS sweetened composition is selected from the group consisting of beverage, food, pharmaceutical, nutraceutical, tobacco, oral hygienic/cosmetic products, and the like.

According to still another aspect, this invention encompasses a method for imparting a more sugar-like temporal profile and/or flavor profile to a NHPS sweetened composition by combining with a sweetenable composition, at least one NHPS and/or at least one modified NHPS, and at least one sweet taste improving composition selected from the group consisting of carbohydrates, polyols, amino acids, other sweet taste improving additives, and combinations thereof. Again, according to particular embodiments of this invention, the NHPS sweetened composition is selected from the group consisting of beverage, food, pharmaceutical, tobacco, oral hygienic/cosmetic product, nutraceutical, and the like.

Objects and advantages of the invention will be set forth in part in the following description, or may be obvious from the description, or may be learned through practice of the invention. Unless otherwise defined, all technical and scientific terms and abbreviations used herein have the same meaning as commonly understood by one of ordinary skill in the art to which this invention pertains. Although methods and compositions similar or equivalent to those described herein can be used in the practice of the present invention, suitable methods and compositions are described without intending that any such methods and compositions limit the invention herein.

DETAILED DESCRIPTION OF THE INVENTION

I. Introduction

Figure 1:
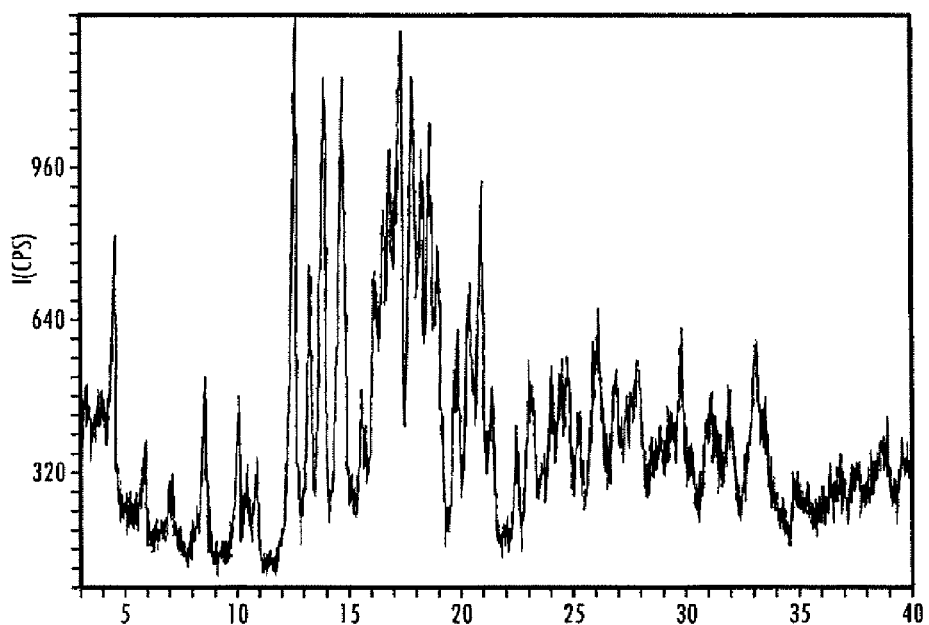
FIG. 1 is a powder x-ray diffraction scan of rebaudioside A polymorph Form 1 on a plot of the scattering intensity versus the scattering angle 2θ in accordance with an embodiment of this invention.

Reference now will be made in detail to the presently proffered embodiments of the invention. Each example is provided by way of explanation of embodiments of the invention, not limitation of the invention. In fact, it will be apparent to those skilled in the art that various modifications and variations can be made in the present invention without departing from the spirit or scope of the invention. For instance, features illustrated or described as part of one embodiment, can be used on another embodiment to yield a still further embodiment. Thus, it is intended that the present invention cover such modifications and variations within the scope of the appended claims and their equivalents.

As summarized above, this invention encompasses a natural high-potency sweetener (NHPS) composition with improved temporal profile and/or flavor profile, a method for improving the temporal profile and/or flavor profile of a NHPS, NHPS sweetened compositions with improved temporal profile and/or flavor profile, and a method for improving the temporal profile and/or flavor profile of NHPS sweetened compositions. In particular, this invention improves the temporal profile and/or flavor profile of a NHPS by imparting a more sugar-like temporal profile and/or flavor profile to compositions comprising a NHPS.

II. Sweet Taste

A. Sugar-Like Taste

As used herein, the phrases "sugar-like characteristic," "sugar-like taste," "sugar-like sweet," "sugary," and "sugar-like" are synonymous. Sugar-like characteristics include any characteristic similar to that of sucrose and include, but are not limited to, maximal response, flavor profile, temporal profile, adaptation behavior, mouthfeel, concentration/response function, tastant/and flavor/sweet taste interactions, spatial pattern selectivity, and temperature effects. These characterisitics are dimensions in which the taste of sucrose is different from the tastes of NHPSs. Of these, however, the flavor profile and temporal profile are particularly important. In a single tasting of a sweet food or beverage, differences (1) in the attributes that constitute a sweetener's flavor profile and (2) in the rates of sweetness onset and dissipation, which constitute a sweetener's temporal profile, between those observed for sucrose and for a NHPS can be noted. Desirable embodiments of this invention exhibit a more sugar-like temporal profile, sugar-like flavor profile, or both, than compositions comprising a NHPS, but without a sweet taste improving composition. Whether or not a characteristic is more sugar-like is determined by an expert sensory panel who taste compositions comprising sugar and compositions comprising a NHPS, both with and without a sweet taste improving composition, and provide their impression as to the similarities of the characteristics of compositions comprising a NHPS, both with and without a sweet taste improving composition, with those comprising sugar. A suitable procedure for determining whether a composition has a more sugar-like taste is described in embodiments described hereinbelow.

In a particular embodiment, a panel of assessors is used to measure the reduction of sweetness linger. Briefly described, a panel of assessors (generally 8 to 12 individuals) is trained to evaluate sweetness perception and measure sweetness at several time points from when the sample is initially taken into the mouth until 3 minutes after it has been expectorated. Using statistical analysis, the results are compared between samples containing additives and samples that do not contain additives. A decrease in score for a time point measured after the sample has cleared the mouth indicates there has been a reduction in sweetness perception.

The panel of assessors may be trained using procedures well known to those of ordinary skill in the art. In a particular embodiment, the panel of assessors may be trained using the Spectrum™ Descriptive Analysis Method (Meilgaard et al, Sensory Evaluation Techniques, 3$^{rd}$ edition, Chapter 11). Desirably, the focus of training should be the recognition of and the measure of the basic tastes; specifically, sweet. In order to ensure accuracy and reproducibility of results, each assessor should repeat the measure of the reduction of sweetness linger about three to about five times per sample, taking at least a five minute break between each repetition and/or sample and rinsing well with water to clear the mouth.

Generally, the method of measuring sweetness comprises taking a 10 mL sample into the mouth, holding the sample in the mouth for 5 seconds and gently swirling the sample in the mouth, rating the sweetness intensity perceived at 5 seconds, expectorating the sample (without swallowing following expectorating the sample), rinsing with one mouthful of water (e.g., vigorously moving water in mouth as if with mouth wash) and expectorating the rinse water, rating the sweetness intensity perceived immediately upon expectorating the rinse water, waiting 45 seconds and, while waiting those 45 seconds, identifying the time of maximum perceived sweetness intensity and rating the sweetness intensity at that time (moving the mouth normally and swallowing as needed), rating the sweetness intensity after another 10 seconds, rating the sweetness intensity after another 60 seconds (cumulative 120 seconds after rinse), and rating the sweetness intensity after still another 60 seconds (cumulative 180 seconds after rinse). Between samples take a 5 minute break, rinsing well with water to clear the mouth.

In order to clarify the nature of preferred embodiments of this invention, some further explanation of the differences in flavor and temporal profiles between that of sugar and NHPSs may be helpful. While not wishing to be bound by theory, this further explanation is as follows.

B. Flavor Profile

The flavor profile of a sweetener is a quantitative profile of the relative intensities of all of the taste attributes exhibited. Such profiles often are plotted as histograms or radar plots. Sucrose, heretofore, has been accepted as exhibiting only sweetness and generally is employed as a standard for pure sweet taste quality. Most high-potency sweeteners exhibit other qualities of taste in addition to sweetness. Thus, as an example, saccharin, which is a synthetic sweetener, has been found to exhibit both bitter and metallic off tastes. As another example, cyclamate exhibits bitter and salty off tastes. For another example, stevioside and hernandulcin, both NHPSs also have a bitter off taste. Other taste attributes commonly observed for high-potency sweeteners include cooling and licorice-like, and an occasional astringent taste.

It has been discovered, however, that sucrose exhibits a taste attribute, or perhaps even attributes, beyond sweetness. The attributes bitter, sour, salty and umami do not describe it. Nonetheless, its taste is easily discerned from that of high-potency sweeteners exhibiting only sweetness (e.g., aspartame) within the first few seconds of tasting. Thus the taste of sucrose is unique among sweeteners, even among those which do not exhibit any of the "off" tastes noted above.

In the literature, this unique taste character of sucrose has been referred to in various ways. Terms such as "mouthfeel" and "body" often are used, both terms suggestive of viscosity or other tactile sensations. "Mouthfeel" also can refer to the texture, body, physical, and overall feel a human consumer detects in his or her mouth when tasting the composition. Thus, for example, a sugar-like mouthfeel refers to texture, body, physical, and overall feel similar to that of sugar. However, it is believed now that the unique taste of sucrose relative to that of high-potency sweeteners is not a tactile sensation. A plausible explanation for the unique taste of sucrose as well as other carbohydrate sweeteners is that hyperosmotic solutions induce rapid and sustained decreases in taste bud cell volumes. Specific effects accompany the taste bud cell shrinkage, including enhanced signaling from salt-sensitive taste bud cells in response to NaCl and signaling from sour-sensitive taste bud cells even in the absence of acid. Although effects on sweet-sensitive taste bud cells were not evaluated, this suggests that sucrose, and carbohydrate sweeteners in general, must elicit taste responses by a pathway in addition to that mediated by the sweetener receptor $T_1R_2/T_1R_3$. This additional pathway likely is mediated by the taste bud cell shrinkage induced by the hyperosmotic character of sugar solutions. Thus, the unique taste of sucrose likely derives from a superimposition of these two pathways of signaling. Sucrose is not perceived as sour or salty nor, for that matter, bitter or umami either. However, it seems that the unique taste of sucrose is derived from signaling to the brain by taste bud cells which normally signal distinct modalities (e.g., strong signaling from sweet-sensitive cells, weak signaling from sour-sensitive cells, weak signaling from salt-sensitive cells, etc.). It is believed that this pattern of activity is in significant part responsible for the unique taste of sucrose. In summary, it appears that sucrose is not only a pure sweet stimulus, but also exhibits a second taste attribute, and the superimposition of these two attributes constitutes "sucrose taste." Given that this second taste attribute of sucrose is due to its osmotic character, it is referred to herein as "osmotic taste."

Consistent with the line of reasoning developed above, the osmotic taste of sucrose can be observed in the absence of sucrose sweetness. Lactisole is a well known sweetness inhibitor, and if sucrose is tasted at 10% (w/v) in the presence of lactisole at 0.2% (w/v), the osmotic taste character of sucrose can be observed uncomplicated by the presence of intense sweetness. The taste of this sucrose/lactisole formulation exhibits faint sweetness, faint sourness, as well as "thickness" or "body." NHPSs do not exhibit osmotic taste and accordingly will not reproduce the flavor profile of sucrose unless additives which reproduce the osmolarity of the sucrose solution targeted without off taste are included.

In principle, any level of osmolarity higher than that of normal saliva exhibits at least some osmotic taste in the mouth. Average concentrations of inorganic ions present in saliva, which are responsible for nearly all of the osmolarity of saliva, are as illustrated in Table 1 below. From the data shown, it is clear that saliva typically has an osmolarity of 70 mOsM. Sucrose at 10%, however, is 292 mOsM, more than 4-fold higher, and therefore will cause significant shrinkage of taste bud cell volume and signaling to the central nervous system (CNS).

TABLE 1

| Inorganic Ions | Saliva Concentration (mM) |
| --- | --- |
| $Na^+$ | 10 |
| $K^+$ | 10-25 |
| $Ca^{2+}$ | 1.7-3 |
| $Mg^{2+}$ | 0.5-1 |
| $Cl^-$ | 15-29 |
| $H_2PO_4^-$ | 4-5 |
| $HCO_3^-$ | 5-7 |

In the foregoing, it is suggested that the unique taste of sucrose is an outcome of two pathways of taste bud cell signaling, the first pathway proceeding only by activation of sweet-sensitive taste bud cells by direct action at the sweetener receptor $T_1R_2/T_1R_3$, and the second pathway proceeding by activation of several taste bud cell subtypes (e.g., sweet-, sour- and salt-sensitive taste bud cells) by a mechanism mediated by cell shrinkage due to the increased osmolarity of the sucrose stimulus. While this is believed to be the case, it could be that the complete explanation for the unique taste of sucrose is still somewhat more complicated. It is known that the sweetener receptor $T_1R_2/T_1R_3$ is a heterodimeric receptor constituted of two proteins associated with each other where each of them contains an extracellular domain generally referred to as the Venus Flytrap Domain (VFD). Evidence has been provided that sucrose binds in both VFDs to activate the receptor. At the same time, it is known that high-potency sweeteners bind differently. Thus, aspartame and neotame bind only to the VFD of $T_1R_2$ while, at the same time, cyclamate does not bind in either VFD domain, but rather binds in the transmembrane domain of $T_1R_3$. The activated $T_1R_2/T_1R_3$ receptor which follows from sucrose stimulation through binding in both VFDs will be somewhat different in shape from that of activated receptors which derive from the quite different binding of high-potency sweeteners. Thus, complete reproduction of sucrose taste with non-caloric sweeteners also may require simultaneous binding of sweeteners in both VFDs of $T_1R_2/T_1R_3$.

C. Temporal Profile

1. Sweetness Onset and Linger

Sucrose exhibits a sweet taste in which the maximal response is perceived quickly and where perceived sweetness disappears relatively quickly on swallowing a food or beverage. In contrast, the sweet tastes of essentially all high-potency sweeteners reach their maximal responses somewhat more slowly and they then decline in intensity more slowly than is the case for sucrose. This decline in sweetness is often referred to as "Sweetness Linger" and is a major limitation for high-potency sweeteners including NHPSs. Slow onset of sweetness also can be a problem. In general, however, sweetness linger is a more significant problem. And so, preferred embodiments of this invention exhibit significant reductions in sweetness linger. As used herein, "temporal profile" of a composition means the intensity of sweetness perceived over time in tasting of the composition by a human. As explained above, the sweet taste of sugar, as well as other carbohydrate and polyol sweeteners, has a quick onset followed by a rapid decrease in sweetness, whereas a NHPS typically has a slower sweet taste onset than sugar followed by a sweetness linger that is longer than sugar.

It is believed that most, if not all, NHPSs bind nonspecifically throughout the oral cavity. Thus, they may stick to the periphery of cells, diffuse into the membranes of cells and even diffuse into cells, the majority of which are not even taste bud cells. This can explain a delay in sweetness onset since attainment of maximal receptor occupancy will occur only subsequent to diffusion of the non-caloric sweetener past an enormous concentration of non-specific binding sites and the delay in onset of maximal sweetness will be proportional to the propensity for the sweetener to engage in non-specific binding. At the same time, sweetener molecules that are released from the receptor have a very high likelihood of non-specific binding nearby the receptor only to diffuse back to the receptor and stimulate it again and again. Such a process also would delay the time required for clearance of sweetener from the sweetener receptor (i.e., the time for disappearance of sweetness perception). Thus, two approaches for modulating the atypical temporal profiles of a NHPS comprise (i) inhibition of the nonspecific binding of a NHPS by taste bud and epithelial cells and (ii) inhibition of the rate of egress of a NHPS from taste bud and epithelial cells and their membranes.

Thus, in particularly desirable embodiments of this invention, the combination of a NHPS with certain sweet taste improving additives reduces the non-specific binding of non-caloric sweeteners to membranes of cells in the oral cavity. Particularly, certain of the sweet taste improving additives are hyperosmotic stimuli and cause shrinkage of epithelial and taste bud cell membranes, thus retarding the ability of the membranes to engage in non-specific absorption of NHPSs. Particularly desirable sweet taste improving additives increase osmolarity without introducing excessive off taste.

In addition, particularly desirable sweet taste improving additives reduce sweetness linger by retarding the rate of egress of non-specifically absorbed high-potency sweeteners from cell membranes. For example, polymers that bind to the surfaces of cells so as to reduce the fluidities of cell membranes are effective in this manner.

According to still other embodiments of this invention, sweetness linger of a NHPS is masked by the presence of other ingredients which exhibit lingering taste characteristics. For example, NHPSs can be combined with food acids (e.g., acidulants such as citric acid, malic acid, tartaric acid, fumaric acid, and adipic acid) which exhibit sourness that lingers relative to that of mineral acids (e.g., $H_3PO_4$), astringent compounds, and other compounds which introduce lingering sensory notes. These embodiments overlay the objectionable sweetness linger with sourness linger and other lingering characteristics such that the overall taste remains in balance over time.

2. Inhibiting the Nonspecific Binding of NHPS by Taste Bud and Epithelial Cells

Again, without being bound by theory, high osmolarity solutions improve the temporal profile of NHPSs to be more sugar-like. NHPSs normally exhibit slow sweetness onset and lingering sweetness. The high osmolarity nature of sucrose and other carbohydrate or polyol sweetener solutions contributes to the sweet taste sensation. It generally is known that (i) high osmolarity solutions cause marked shrinkage of taste bud cells and (ii) taste bud cells absorb and/or adsorb high-potency sweeteners of a variety of chemical structures. Thus, it is hypothesized that high osmolarity solutions cause tightened packing of membrane lipid molecules in taste bud cells as well as in other epithelial cells in the oral cavity and thereby diminish the abilities of such cells to absorb NHPSs. Therefore, any compounds which impart osmolarities sufficient to affect the taste bud and epithelial cell membranes should diminish non-specific binding and thereby would cause NHPSs to exhibit sweetness with more sugar-like temporal profiles. In one embodiment, any sweet taste improving composition that imparts increased osmolarity will be effective by this mechanism.

3, Inhibit the Rate of Egress of NHPS from Taste Bud and Epithelial Cells and their Membranes Another pathway whereby temporal profiles of NHPSs may be improved is to slow the rates of egress of absorbed sweeteners from the taste bud and epithelial cells and their membranes. Thus, in one embodiment, sweet taste improving compositions which reduce the fluidity of the cell membranes improve the temporal profile of NHPS to be more sugar-like. Non-limiting examples of compositions which slow the rates of egress of absorbed sweeteners from the taste bud and epithelial cells and their membranes include sweet taste improving surfactant additives, sweet taste improving cationic polymer additives, sweet taste improving hydrocolloid additives, and other sweet taste improving polymer additives. In yet another embodiment, suitable compositions which slow the rates of egress of absorbed sweeteners from the taste bud and epithelial cells and their membranes include, but are not limited to, cationic polymeric agents such as poly-L-lysines (e.g., poly-L-α-lysine and poly-L-ε-lysine), poly-L-orthinine (e.g., poly-L-α-omithine and poly-L-ε-ornithine), polyethylenimine, and chitosan, as well as surface active compositions including sucrose esters, sorbic acid esters, sorbitan, sorbitan esters, anionic detergents, polysorbates, polyethylene sorbitan esters, propylene glycol esters, glycerol esters, polyglycerol esters, polyethylene esters, complex esters, (e.g., lactate, tartrate, and the like), cationic detergents, gum *acacia* senegal, gum *acacia* seyal, anionic polymers (e.g., polyaspartic acid), polyethylene glycol, lecithins, and saponins. The polymeric agents are hypothesized to bind to cell surfaces and engage in multiple points of binding contact and reduce the fluidity of the cell membranes.

II. NHPS Sweetener And Sweetened Compositions

It has been discovered that at least one NHPS and/or modified NHPS in combination with at least one sweet taste improving composition imparts a more sugar-like taste. In a desired embodiment, a composition and method with an improved temporal profile and/or flavor profile are provided. In another embodiment, NHPS-sweetened compositions with a more sugar-like temporal profile and/or flavor profile comprising a sweetenable composition, at least one NHPS and/or at least one modified NHPS, and at least one sweet taste improving composition are provided.

A. Orally Ingestible Sweetenable Compositions

A suitable sweetenable composition can be any material suitable for sweetening with a sweetener and desirably is an orally ingestible composition. By the term "orally ingestible composition", as used herein, is meant substances which are contacted with the mouth of man or animal, including substances which are taken into and subsequently ejected from the mouth and substances which are drunk, eaten, swallowed or otherwise ingested, and are safe for human or animal consumption when used in a generally acceptable range.

There are no restrictions on the type of orally ingestible compositions encompassed by embodiments of this invention as long as they are safe for human consumption when used in a generally acceptable range. These compositions include food, beverage, pharmaceutical, tobacco, nutraceutical, oral hygienic/cosmetic products, and the like. Non-limiting examples of these products include non-carbonated and carbonated beverages such as colas, ginger ales, root beers, ciders, fruit-flavored soft drinks (e.g., citrus-flavored soft drinks such as lemon-lime or orange), powdered soft drinks (e.g., cola, juice, tea, water, coffee), and the like; fruit juices originating in fruits or vegetables, fruit juices including squeezed juices or the like, fruit juices containing fruit particles, fruit beverages, fruit juice beverages, beverages containing fruit juices, beverages with fruit flavorings, vegetable juices, juices containing vegetables, and mixed juices containing fruits and vegetables; sport drinks, energy drinks, near water and the like drinks (e.g., water with natural or artificial flavorants); tea type or favorite type beverages such as coffee, cocoa, black tea, green tea, oolong tea and the like; beverages containing milk components such as milk beverages, coffee containing milk components, café au lait, milk tea, fruit milk beverages, drinkable yogurt, lactic acid bacteria beverages or the like; dairy products; bakery products; desserts such as yogurt, jellies, drinkable jellies, puddings, Bavarian cream, blancmange, cakes, brownies, mousse and the like, sweetened food products eaten at tea time or following meals; frozen foods; cold confections, e.g. types of ice cream such as ice cream, ice milk, lacto-ice and the like (food products in which sweeteners and various other types of raw materials are added to milk products, and the resulting mixture is agitated and frozen), and ice confections such as sherbets, dessert ices and the like (food products in which various other types of raw materials are added to a sugary liquid, and the resulting mixture is agitated and frozen); ice cream; general confections, e. g., baked confections or steamed confections such as cakes, crackers, biscuits, buns with bean-jam filling and the like; rice cakes and snacks; table top products; general sugar confections such as chewing gum (e.g. including compositions which comprise a substantially water-insoluble, chewable gum base, such as chicle or substitutes thereof, including jetulong, guttakay rubber or certain comestible natural synthetic resins or waxes), hard candy, soft candy, mints, nougat candy, jelly beans and the like; sauces including fruit flavored sauces, chocolate sauces and the like; edible gels; crémes including butter cremes, flour pastes, whipped cream and the like; jams including strawberry jam, marmalade and the like; breads including sweet breads and the like or other starch products; spice; general condiments including seasoned soy sauce used on roasted meats, roast fowl, barbecued meat and the like, as well as tomato catsup, sauces, noodle broth and the like; processed agricultural products, livestock products or seafood; processed meat products such as sausage and the like; retort food products, pickles, preserves boiled in soy sauce, delicacies, side dishes; snacks such as potato chips, cookies, or the like; cereal products; drugs or quasi-drugs that are administered orally or used in the oral cavity (e.g., vitamins, cough syrups, cough drops, chewable medicine tablets, amino acids, bitter-tasting agents, acidulants or the like), wherein the drug may be in solid, liquid, gel, or gas form such as a pill, tablet, spray, capsule, syrup, drop, troche agent, powder, and the like; personal care products such as other oral compositions used in the oral cavity such as mouth freshening agents, gargling agents, mouth rinsing agents, toothpaste, tooth polish, dentrifices, mouth sprays, teeth-whitening agent and the like; dietary supplements; tobacco products including smoke and smokeless tobacco products such as snuff, cigarette, pipe and cigar tobacco, and all forms of tobacco such as shredded filler, leaf, stem, stalk, homogenized leaf cured, reconstituted binders and reconstituted tobacco from tobacco dust, fines or ether sources in sheet, pellet or other forms, tobacco substitutes formulated from non-tobacco materials, dip or chewing tobacco; animal feed; nutraceutical products, which includes any food or part of a food that may provide medicinal or health benefits, including the prevention and treatment of disease (e.g., cardiovascular disease and high cholesterol, diabetes, osteoporosis, inflammation, or autoimmune disorders), non-limiting examples of nutraceuticals include naturally nutrient-rich or medicinally active food, such as garlic, soybeans, antioxidants, phytosterols and phytostanols and their esters, fibers, glucosamine, chondroitin sulfate, *ginseng*, ginko, *Echinacea*, or the like; other nutrients that provide health benefits, such as amino acids, vitamins, minerals, carotenoids, dietary fiber, fatty acids such as omega-3 or omega-6 fatty acids, DHA, EPA, or ALA which can be derived from plant or animal sources (e.g., salmon and other cold-water fish or *algae*), flavonoids, phenols, polyphenols (e.g., catechins, proanthocyanidins, procyanidins, anthocyanins, quercetin, resveratrol, isoflavones, curcumin, punicalagin, ellagitannin, citrus flavonoids such as hesperidin and naringin, and chlorogenic acid), polyols, prebiotics/probiotics, phytoestrogens, sulfides/thiols, policosanol, saponin, rubisco peptide, appetite suppressants, hydration agents, autoimmune agents, C-reactive protein reducing agents, or anti-inflammatory agents; or any other functional ingredient that is beneficial to the treatment of specific diseases or conditions, such as diabetes, osteoporosis, inflammation, or high cholesterol levels in the blood. In accordance with desirable embodiments of this invention, NIPS sweetened compositions such as those described hereinabove comprise a sweetenable orally ingestible composition, at least one NHPS and/ or at least one modified NHPS, and at least one sweet taste improving composition selected from the group consisting of carbohydrates, polyols, amino acids, other sweet taste improving additives, and combinations thereof. For example, according to a particular embodiment of this invention, a NHPS sweetened beverage comprises an orally ingestible beverage composition, such as an aqueous beverage composition or the like, and a NHPS composition with a more sugar-like temporal profile and/or flavor profile, as disclosed herein. In addition, according to a particular embodiment of this invention, a NHPS sweetened food comprises an orally ingestible food composition and a NHPS composition with a more sugar-like temporal profile and/or flavor profile, as disclosed herein. In addition, according to a particular embodiment of this invention, a NHPS sweetened pharmaceutical comprises a pharmaceutically active composition and/or pharmaceutically acceptable salts thereof, and a NHPS composition with a more sugar-like temporal profile and/or flavor profile, as disclosed herein. Alternatively, in addition, according to a particular embodiment of this invention, a NHPS sweetened pharmaceutical comprises a pharmaceutically active composition and/or pharmaceutically acceptable salts thereof and a coating comprising an orally ingestible composition and a NHPS composition with a more sugar-like temporal profile and/or flavor profile, as disclosed herein. In addition, according to a particular embodiment of this invention, a NHPS sweetened tobacco product comprises a tobacco and a NHPS composition with a more sugar-like temporal profile and/or flavor profile, as disclosed herein. In addition, according to a particular embodiment of this invention, a NHPS sweetened nutraceutical product comprises an orally ingestible nutraceutical composition and a NHPS composition with a more sugar-like temporal profile and/or flavor profile, as disclosed herein. In addition, according to a particular embodiment of this invention, a NHPS sweetened oral hygenic product comprises an orally ingestible oral hygenic composition and a NHPS composition with a more sugar-like temporal profile and/or flavor profile, as disclosed herein. In addition, according to a particular embodiment of this invention, a NHPS sweetened cosmetic product comprises an orally ingestible cosmetic composition and a NHPS composition with a more sugar-like temporal profile and/or flavor profile, as disclosed herein.

B. Natural High-Potency Sweeteners

As used herein, the phrase "natural high-potency sweetener" or "NHPS" means any sweetener found in nature which may be in raw, extracted, purified, or any other form, singularly or in combination thereof and characteristically have a sweetness potency greater than sucrose, fructose, or glucose, yet have less calories. Non-limiting examples of NHPSs suitable for embodiments of this invention includes natural high-potency sweeteners, such as rebaudioside A, rebaudioside B, rebaudioside C, rebaudioside D, rebaudioside E, rebaudioside F, dulcoside A, dulcoside B, rubusoside, stevia, stevioside, mogroside IV, mogroside V, Luo Han Guo sweetener, siamenoside, monatin and its salts (monatin SS, RR, RS, SR), curculin, glycyrrhizic acid and its salts, thaumatin, monellin, mabinlin, brazzein, hernandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, and cyclocarioside I. Alternatively, the raw, extracted, or purified NHPS may be modified. Modified NHPSs includes NHPSs which have been altered naturally or synthetically. For example, a modified NHPS includes, but is not limited to, NHPSs which have been fermented, contacted with enzyme, or derivatized, or the product of any process wherein at least one atom has been added to, removed from, or substituted on the NHPS. In one embodiment, at least one modified NHPS may be used in combination with at least one NHPS. In another embodiment, at least one modified NHPS may be used without a NHPS. Thus, a modified NHPS may be substituted for a NHPS or be used in combination with a NHPS for any of the embodiments described herein. For the sake of brevity, however, in the description of embodiments of this invention, a modified NHPS is not described expressly as an alternative to an unmodified NHPS, but it should be understood that a modified NHPS can be substituted for a NHPS in any embodiment disclosed herein.

In one embodiment, extracts of NHPSs may be used in any purity percentage. In another embodiment, when a NHPS is used as a non-extract, the purity of the NHPS may range, for example, from about 25% to about 100%. In another example, the purity of the NHPS may range from about 50% to about 100%; from about 70% to about 100%; from about 80% to about 100%; from about 90% to about 100%; from about 95% to about 100%; from about 95% to about 99.5%; from about 97% to about 100%; from about 98% to about 100%; and from about 99% to about 100%.

Purity, as used here, represents the weight percentage of a respective NHPS compound present in a NHPS extract, in raw or purified form. In one embodiment, a steviolglycoside extract comprises a particular steviolglycoside in a particular purity, with the remainder of the stevioglycoside extract comprising a mixture of other steviolglycosides.

To obtain a particularly pure extract of a NHPS, such as rebaudioside A, it may be necessary to purify the crude extract to a substantially pure form. Such methods generally are known to those of ordinary skill in the art.

An exemplary method for purifying a NHPS, such as rebaudioside A, is described in the co-pending patent application No. 60/805,216, entitled "Rebaudioside A Composition and Method for Purifying Rebaudioside A," filed on Jun. 19, 2006, by inventors DuBois, et al., the disclosure of which is incorporated herein by reference in its entirety.

Briefly described, substantially pure rebaudioside A is crystallized in a single step from an aqueous organic solution comprising at least one organic solvent and water in an amount from about 10% to about 25% by weight, more particularly from about 15% to about 20% by weight. Organic solvents desirably comprise alcohols, acetone, and acetonitrile. Non-limiting examples of alcohols include ethanol, methanol, isopranol, 1-propanol, 1-butanol, 2-butanol, tert-butanol, and isobutanol. Desirably, the at least one organic solvent comprises a mixture of ethanol and methanol present in the aqueous organic solution in a weight ratio ranging from about 20 parts to about 1 part ethanol to 1 part methanol, more desirably from about 3 parts to about 1 part ethanol to 1 part methanol.

Desirably, the weight ratio of the aqueous organic solvent and crude rebaudioside A ranges from about 10 to about 4 parts aqueous organic solvent to 1 part crude rebaudioside A, more particularly from about 5 to about 3 parts aqueous organic solvent to 1 part crude rebaudioside A.

In an exemplary embodiment, the method of purifying rebaudioside A is carried out at approximately room temperature. In another embodiment, the method of purifying rebaudioside A further comprises the step of heating the rebaudioside A solution to a temperature in a range from about 20° C. to about 40° C., or in another embodiment to a reflux temperature, for about 0.25 hours to about 8 hours. In another exemplary embodiment, wherein the method for purifying rebaudioside A comprises the step of heating the rebaudioside A solution, the method further comprises the step of cooling the rebaudioside A solution to a temperature in the range from about 4° C. to about 25° C. for about 0.5 hours to about 24 hours.

According to particular embodiments, the purity of rebaudioside A may range from about 50% to about 100%; from about 70% to about 100%; from about 80% to about 100%; from about 90% to about 100%; from about 95% to about 100%; from about 95% to about 99.5%; from about 96% to about 100%; from about 97% to about 100%; from about 98% to about 100%; and from about 99% to about 100%. According to particularly desirable embodiments, upon crystallization of crude rebaudioside A, the substantially pure rebaudioside A composition comprises rebaudioside A in a purity greater than about 95% by weight up to about 100% by weight on a dry basis. In other exemplary embodiments, substantially pure rebaudioside A comprises purity levels of rebaudioside A greater than about 97% up to about 100% rebaudioside A by weight on a dry basis, greater than about 98% up to about 100% by weight on a dry basis, or greater than about 99% up to about 100% by weight on a dry basis. The rebaudioside A solution during the single crystallization step may be stirred or unstirred.

In an exemplary embodiment, the method of purifying rebaudioside A further comprises the step of seeding (optional step) the rebaudioside A solution at an appropriate temperature with high-purity crystals of rebaudioside A sufficient to promote crystallization of the rebaudioside A to form pure rebaudioside A. An amount of rebaudioside A sufficient to promote crystallization of substantially pure rebaudioside A comprises an amount of rebaudioside A from about 0.0001% to about 1% by weight of the rebaudioside A present in the solution, more particularly from about 0.01% to about 1% by weight. An appropriate temperature for the step of seeding comprises a temperature in a range from about 18° C. to about 35° C.

In another exemplary embodiment, the method of purifying rebaudioside A further comprises the steps of separating and washing the substantially pure rebaudioside A composition. The substantially pure rebaudioside A composition may be separated from the aqueous organic solution by a variety of solid-liquid separation techniques that utilize centrifugal force, that include, without limitation, vertical and horizontal perforated basket centrifuge, solid bowl centrifuge, decanter centrifuge, peeler type centrifuge, pusher type centrifuge, Heinkel type centrifuge, disc stack centrifuge and cyclone separation. Additionally, separation may be enhanced by any of pressure, vacuum, and gravity filtration methods, that include, without limitation, the use of belt, drum, nutsche type, leaf, plate, Rosenmund type, sparkler type, and bag filters and filter press. Operation of the rebaudioside A solid-liquid separation device may be continuous, semi-continuous or in batch mode. The substantially pure rebaudioside A composition also may be washed on the separation device using various aqueous organic solvents and mixtures thereof. The substantially pure rebaudioside A composition can be dried partially or totally on the separation device using any number of gases, including, without limitation, nitrogen and argon, to evaporate residual liquid solvent. The substantially pure rebaudioside A composition may be removed automatically or manually from the separation device using liquids, gases or mechanical means by either dissolving the solid or maintaining the solid form.

In still another exemplary embodiment, the method of purifying rebaudioside A further comprises the step of drying the substantially pure rebaudioside A composition using techniques well known to those skilled in the art, non-limiting examples of which include the use of a rotary vacuum dryer, fluid bed dryer, rotary tunnel dryer, plate dryer, tray dryer, Nauta type dryer, spray dryer, flash dryer, micron dryer, pan dryer, high and low speed paddle dryer and microwave dryer. In an exemplary embodiment, the step of drying comprises drying the substantially pure rebaudioside A composition using a nitrogen or argon purge to remove the residual solvent at a temperature in a range from about 40° C. to about 60° C. for about 5 hours to about 100 hours.

In yet another exemplary embodiment, wherein the crude rebaudioside A mixture comprises substantially no rebaudioside D impurity, the method of purifying rebaudioside A further comprises the step of slurrying the composition of substantially pure rebaudioside A with an aqueous organic solvent prior to the step of drying the substantially pure rebaudioside A composition. The slurry is a mixture comprising a solid and an aqueous organic or organic solvent, wherein the solid comprises the substantially pure rebaudioside A composition and is soluble only sparingly in the aqueous organic or organic solvent. In an embodiment, the substantially pure rebaudioside A composition and aqueous organic solvent are present in the slurry in a weight ratio ranging from about 15 parts to 1 part aqueous organic solvent to 1 part substantially pure rebaudioside A composition. In one embodiment, the slurry is maintained at room temperature. In another embodiment, the step of slurrying comprises heating the slurry to a temperature in a range from about 20 to about 40° C. The substantially pure rebaudioside A composition is slurried for about 0.5 hours to about 24 hours.

In still yet another exemplary embodiment, the method of purifying rebaudioside A further comprises the steps of separating the substantially pure rebaudioside A composition from the aqueous organic or organic solvent of the slurry and washing the substantially pure rebaudioside A composition followed by the step of drying the substantially pure rebaudioside A composition.

If further purification is desired, the method of purifying rebaudioside A described herein may be repeated or the substantially pure rebaudioside A composition may be purified further using an alternative purification method, such as the column chromatography.

It also is contemplated that other NHPSs may be purified using the purification method described herein, requiring only minor experimentation that would be obvious to those of ordinary skill in the art.

Figure 2:
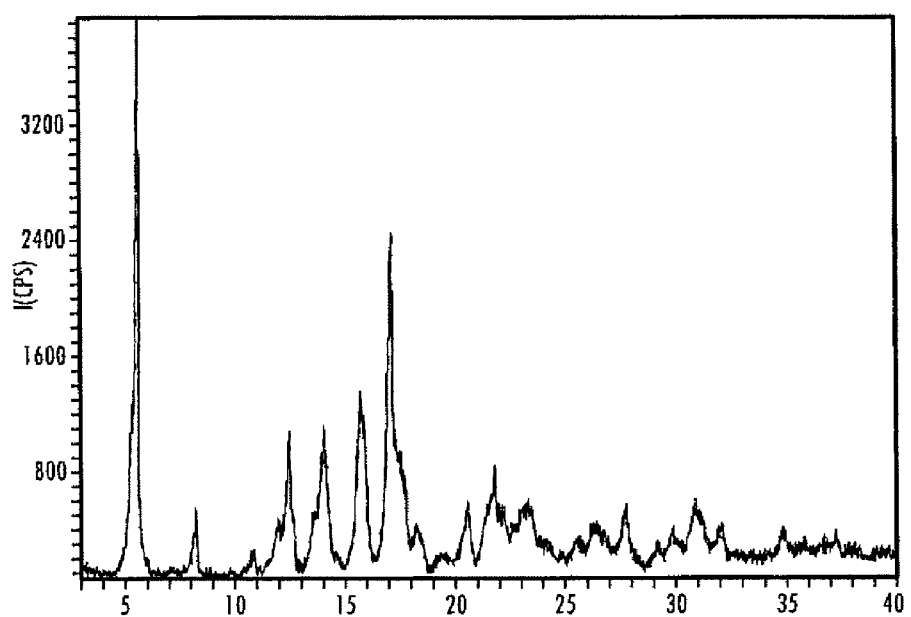
FIG. 2 is a powder x-ray diffraction scan of rebaudioside A polymorph Form 2 on a plot of the scattering intensity versus the scattering angle 2θ in accordance with an embodiment of this invention.
Figure 3:
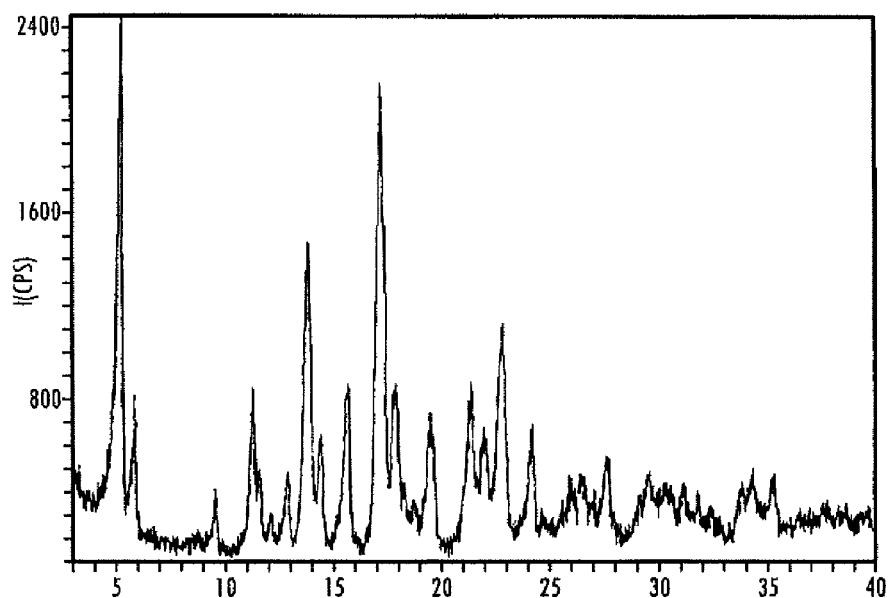
FIG. 3 is a powder x-ray diffraction scan of rebaudioside A polymorph Form 3A on a plot of the scattering intensity versus the scattering angle 2θ in accordance with an embodiment of this invention.
Figure 4:
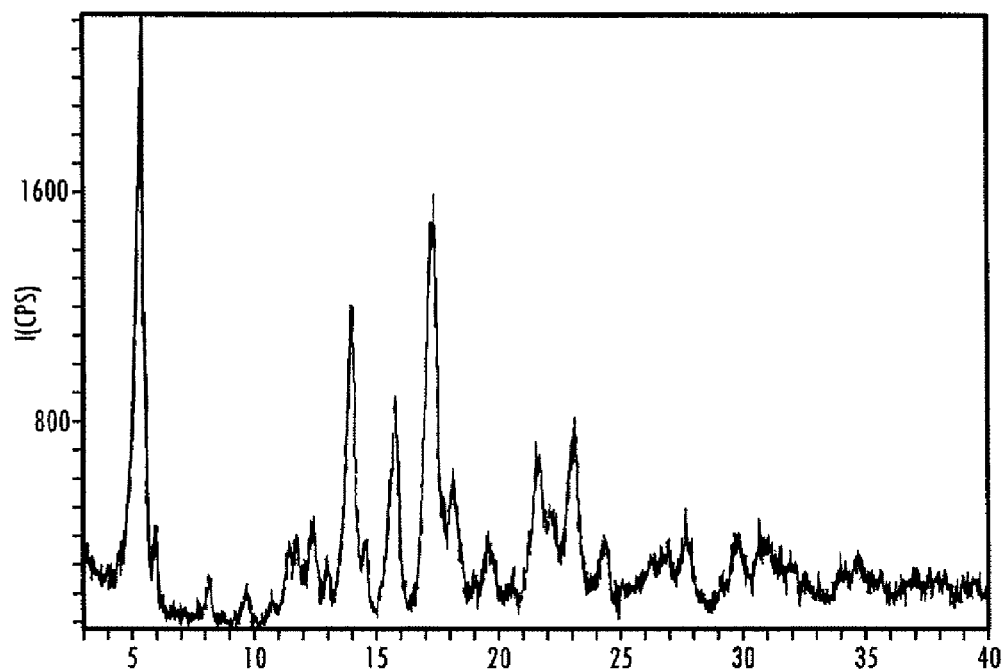
FIG. 4 is a powder x-ray diffraction scan of rebaudioside A polymorph Form 3B on a plot of the scattering intensity versus the scattering angle 2θ in accordance with an embodiment of this invention.
Figure 5:
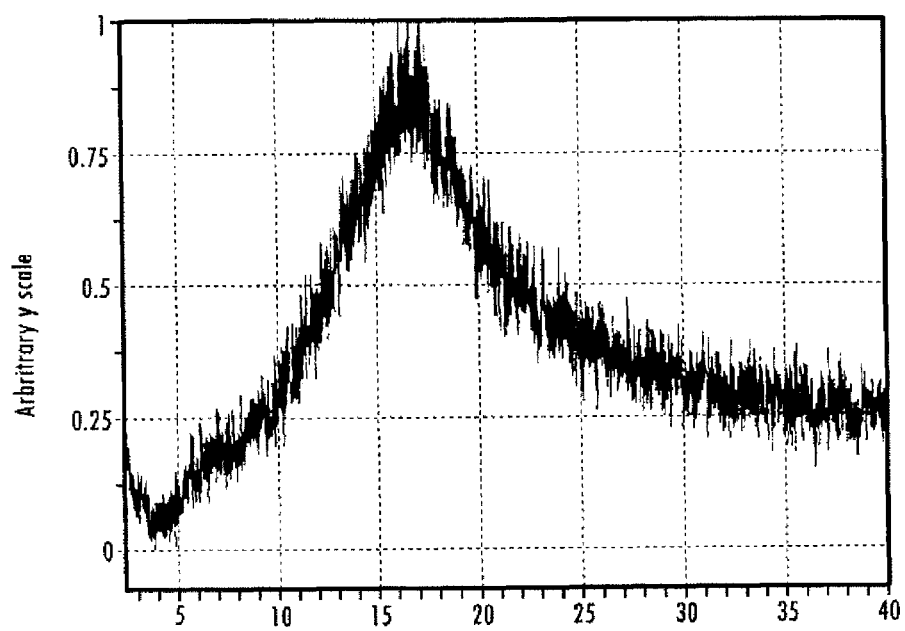
FIG. 5 is a powder x-ray diffraction scan of rebaudioside A polymorph Form 4 on a plot of the scattering intensity versus the scattering angle 2θ in accordance with an embodiment of this invention.

The purification of rebaudioside A by crystallization as described above results in the formation of at least three different polymorphs: Form 1: a rebaudioside A hydrate; Form 2: an anhydrous rebaudioside A; and Form 3: a rebaudioside A solvate. In addition to the at least three polymorph forms of rebaudioside A, the purification of rebaudioside A may result in the formation of an amorphous form of rebaudioside A, Form 4. The aqueous organic solution and temperature of the purification process influence the resulting polymorph and amorphous forms in the substantially pure rebaudioside A composition. FIGS. 1-5 are exemplary powder x-ray diffraction (XRPD) scans of the polymorph and amorphous forms of rebaudioside A: Form 1 (hydrate), Form 2 (anhydrate), Form 3A (methanol solvate), Form 3B (ethanol solvate), and Form 4 (amorphous), respectively.

The material properties of the three rebaudioside A polymorph and amorphous forms are summarized in the following table:

TABLE 2

Rebaudioside A Polymorphs

|  | Form 1 Polymorph | Form 2 Polymorph | Form 3 Polymorph | Form 4 Amorphous |
| --- | --- | --- | --- | --- |
| Rate of dissolution in H2O at 25° C. | Very low (<0.2%/ 60 minutes) | Intermediate (<30%/ 5 minutes) | High (>30%/5 minutes) | High (>35%/ 5 minutes) |
| Alcohol content | <0.5% | <1% | 1-3% | <0.05% |
| Moisture content | >5% | <1% | <3% | 6.74% |

The type of polymorph formed is dependent on the composition of the aqueous organic solution, the temperature of the crystallization step, and the temperature during the drying step. Form 1 and Form 3 are formed during the single crystallization step while Form 2 is formed during the drying step after conversion from Form 1 or Form 3.

Low temperatures during the crystallization step, in the range of about 20° C. to about 50° C., and a low ratio of water to the organic solvent in the aqueous organic solvent results in the formation of Form 3. High temperatures during the crystallization step, in the range of about 50° C. to about 80° C., and a high ratio of water to the organic solvent in the aqueous organic solvent results in the formation of the Form 1. Form 1 can be converted to Form 3 by slurrying in an anhydrous solvent at room temperature (2-16 hours) or at reflux for approximately (0.5-3 hours). Form 3 can be converted to Form 1 by slurrying the polymorph in water at room temperature for approximately 16 hours or at reflux for approximately 2-3 hours. Form 3 can be converted to the Form 2 during the drying process; however, increasing either the drying temperature above 70° C. or the drying time of a substantially pure rebaudioside A composition can result in decomposition of the rebaudioside A and increase the remaining rebaudioside B impurity in the substantially pure rebaudioside A composition. Form 2 can be converted to Form 1 with the addition of water.

Form 4 may be formed from Form 1, 2, 3, or combinations thereof, using methods well known to those of ordinary skill in the art. Non-limiting examples of such methods include melt-processing, ball milling, crystallization, lyophilization, cryogrinding, and spray drying. In a particular embodiment, Form 4 can be prepared from a substantially pure rebaudioside A composition obtained by the purification methods described hereinabove by spray-drying a solution of the substantially pure rebaudioside A composition.

The NHPSs may be used individually or in combination with other NHPSs, as long as the combined effect does not adversely affect the taste of the sweetener composition or orally sweetened composition. For example, particular embodiments comprise combinations of NHPS, such as steviolglycosides. Non-limiting examples of suitable stevioglycosides which may be combined include rebaudioside A, rebaudioside B, rebaudioside C, rebaudioside D, rebaudioside E, rebaudioside F, dulcoside A, dulcoside B, rubusoside, stevioside, and steviolbioside. According to particularly desirable embodiments of the present invention, the combination of high-potency sweeteners comprises rebaudioside A in combination with rebaudioside B, rebaudioside C, rebaudioside E, rebaudioside F, stevioside, steviolbioside, dulcoside A, or combinations thereof.

Generally, according to a particular embodiment, rebaudioside A is present in the combination of steviolglycosides in an amount in the range of about 50 to about 99.5 weight percent of the combination of high-potency sweeteners, more desirably in the range of about 70 to about 90 weight percent, and still more desirably in the range of about 75 to about 85 weight percent.

In another particular embodiment, rebaudioside B is present in the combination of high-potency sweeteners in an amount in the range of about 1 to about 8 weight percent of the combination of high-potency sweeteners, more desirably in the range of about 2 to about 5 weight percent, and still more desirably in the range of about 2 to about 3 weight percent.

In another particular embodiment, rebaudioside C is present in the combination of high-potency sweeteners in an amount in the range of about 1 to about 10 weight percent of the combination of high-potency sweeteners, more desirably in the range of about 3 to about 8 weight percent, and still more desirably in the range of about 4 to about 6 weight percent.

In still another particular embodiment, rebaudioside E is present in the combination of high-potency sweeteners in an amount in the range of about 0.1 to about 4 weight percent of the combination of high-potency sweeteners, more desirably in the range of about 0.1 to about 2 weight percent, and still more desirably in the range of about 0.5 to about 1 weight percent.

In still another particular embodiment, rebaudioside F is present in the combination of high-potency sweeteners in an amount in the range of about 0.1 to about 4 weight percent of the combination of high-potency sweeteners, more desirably in the range of about 0.1 to about 2 weight percent, and still more desirably in the range of about 0.5 to about 1 weight percent.

In still yet another particular embodiment, dulcoside A is present in the combination of high-potency sweeteners in an amount in the range of about 0.1 to about 4 weight percent of the combination of high-potency sweeteners, more desirably in the range of about 0.1 to about 2 weight percent, and still more desirably in the range of about 0.5 to about 1 weight percent.

In yet another particular embodiment, dulcoside B is present in the combination of high-potency sweeteners in an amount in the range of about 0.1 to about 4 weight percent of the combination of high-potency sweeteners, more desirably in the range of about 0.1 to about 2 weight percent, and still more desirably in the range of about 0.5 to about 1 weight percent.

In another particular embodiment, stevioside is present in the combination of high-potency sweeteners in an amount in the range of about 0.5 to about 10 weight percent of the combination of high-potency sweeteners, more desirably in the range of about 1 to about 6 weight percent, and still more desirably in the range of about 1 to about 4 weight percent.

In still another particular embodiment, steviolbioside is present in the combination of high-potency sweeteners in an amount in the range of about 0.1 to about 4 weight percent of the combination of high-potency sweeteners, more desirably in the range of about 0.1 to about 2 weight percent, and still more desirably in the range of about 0.5 to about 1 weight percent.

According to a particularly desirable embodiment, the high-potency sweetener composition comprises a combination of rebaudioside A, stevioside, rebaudioside B, rebaudioside C, and rebaudioside F; wherein rebaudioside A is present in the combination of high-potency sweeteners in an amount in the range of about 75 to about 85 weight percent based on the total weight of the combination of high-potency sweeteners, stevioside is present in an amount in the range of about 1 to about 6 weight percent, rebaudioside B is present in an amount in the range of about 2 to about 5 weight percent, rebaudioside C is present in an amount in the range of about 3 to about 8 weight percent, and rebaudioside F is present in an amount in the range of about 0.1 to about 2 weight percent.

In addition, those of ordinary skill in the art should appreciate that the sweetener composition can be customized to obtain a desired calorie content. For example, a low-caloric or non-caloric NHPS and/or other caloric additives may be combined with a caloric natural sweetener to produce a sweetener composition with a preferred calorie content.

C. Sweet Taste Improving Compositions

As used herein, the phrase "sweet taste improving composition" includes any composition which imparts a more sugar-like temporal profile or sugar-like flavor profile or both to a NHPS. Examples of sweet taste improving compositions include, but are not limited to, carbohydrates, polyols, amino acids, and other sweet taste improving taste additives imparting such sugar-like characteristics.

The term "carbohydrate" generally refers to aldehyde or ketone compounds substituted with multiple hydroxyl groups, of the general formula $(CH_2O)_n$, wherein n is 3-30, as well as their oligomers and polymers. The carbohydrates of the present invention can, in addition, be substituted or deoxygenated at one or more positions. Carbohydrates as used herein encompasses unmodified carbohydrates, carbohydrate derivatives, substituted carbohydrates, and modified carbohydrates. Modified carbohydrate means any carbohydrate wherein at least one atom has been added, removed, substituted, or combinations thereof. Thus, carbohydrate derivatives or substituted carbohydrates include substituted and unsubstituted monosaccharides, disaccharides, oligosaccharides, and polysaccharides. The carbohydrate derivatives or substituted carbohydrates optionally can be deoxygenated at any corresponding C-position, and/or substituted with one or more moieties such as hydrogen, halogen, haloalkyl, carboxyl, acyl, acyloxy, amino, amido, carboxyl derivatives, alkylamino, dialkylamino, arylamino, alkoxy, aryloxy, nitro, cyano, sulfa, mercapto, imino, sulfonyl, sulfenyl, sulfinyl, sulfamoyl, carboalkoxy, carboxamido, phosphonyl, phosphinyl, phosphoryl, phosphino, thioester, thioether, oximino, hydrazino, carbamyl, phospho, phosphonato, or any other viable functional group provided the carbohydrate derivative or substituted carbohydrate functions to improve the sweet taste of a NHPS.

Non-limiting examples of carbohydrates in embodiments of this invention include tagatose, trehalose, galactose, rhamnose, cyclodextrin (e.g., α-cyclodextrin, β-cyclodextrin, and γ-cyclodextrin), maltodextrin (including resistant maltodextrins such as Fibersol-2™), dextran, sucrose, glucose, ribulose, fructose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, gluconolactone, abequose, galactosamine, beet oligosaccharides, isomalto-oligosaccharides (isomaltose, isomaltotriose, panose and the like), xylo-oligosaccharides (xylobiose, xylobiose and the like), gentio-oligoscaccharides (gentiobiose, gentiotriose, gentiotetraose and the like), sorbose, nigero-oligosaccharides, palatinose oligosaccharides, fucose, fructooligosaccharides (kestose, nystose and the like), maltotetraol, maltotriol, malto-oligosaccharides (maltotriose, maltotetraose, maltopentaose, maltohexaose, maltoheptaose and the like), lactulose, melibiose, raffinose, rhamnose, ribose, isomerized liquid sugars such as high fructose cornstarch syrup (e.g., HFCS55, HFCS42, or HFCS90), coupling sugars, soybean oligosaccharides, and glucose syrup. Additionally, the carbohydrates may be in either the D- or L-configuration.

The term "alkyl", as used herein, unless otherwise specified, refers to a saturated straight, branched, or cyclic, primary, secondary, or tertiary hydrocarbon, typically of $C_1$ to $C_{18}$, and specifically includes methyl, ethyl, propyl, isopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, 2,3-dimethylbutyl, and 3,3-dimethylbutyl. The alkyl group optionally can be substituted with one or more moieties selected from the group consisting of hydroxyl, carboxy, carboxamido, carboalkoxy, acyl, amino, alkylamino, arylamino, alkoxy, aryloxy, nitro, cyano, sulfa, sulfato, phospho, phosphato, or phosphonato.

The term "alkenyl", as referred to herein, and unless otherwise specified, refers to a straight, branched, or cyclic hydrocarbon of $C_2$ to $C_{10}$ with at least one double bond. The alkenyl groups optionally can be substituted in the same manner as described above for the alkyl groups and also optionally can be substituted with a substituted or unsubstituted alkyl group.

The term "alkynyl", as referred to herein, and unless otherwise specified, refers to a $C_2$ to $C_{10}$ straight or branched hydrocarbon with at least one triple bond. The alkynyl groups optionally can be substituted in the same manner as described above for the alkyl groups and also optionally can be substituted with a substituted or unsubstituted alkyl group.

The term "aryl", as used herein, and unless otherwise specified, refers to phenyl, biphenyl, or naphthyl, and preferably phenyl. The aryl group optionally can be substituted with one or more moieties selected from the group consisting of hydroxyl, acyl, amino, halo, carboxy, carboxamido, carboalkoxy, alkylamino, alkoxy, aryloxy, nitro, cyano, sulfo, sulfato, phospho, phosphato, or phosphonato.

The team "heteroaryl" or "heteroaromatic", as used herein, refers to an aromatic or unsaturated cyclic moiety that includes at least one sulfur, oxygen, nitrogen, or phosphorus in the aromatic ring. Non-limiting examples are furyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, pyridazinyl, pyrazinyl, cinnolinyl, phthalazinyl, quinoxalinyl, xanthinyl, hypoxanthinyl, and pteridinyl. The heteroaryl or heteroaromatic group optionally can be substituted with one or more moieties selected from the group consisting of hydroxyl, acyl, amino, halo, alkylamino, alkoxy, aryloxy, nitro, cyano, sulfa, sulfato, phospho, phosphato, or phosphonato.

The term "heterocyclic" refers to a saturated nonaromatic cyclic group which may be substituted, and wherein there is at least one heteroatom, such as oxygen, sulfur, nitrogen, or phosphorus in the ring. The heterocyclic group optionally can be substituted in the same manner as described above for the heteroaryl group.

The term "aralkyl", as used herein, and unless otherwise specified, refers to an aryl group as defined above linked to the molecule through an alkyl group as defined above. The term alkaryl, as used herein, and unless otherwise specified, refers to an alkyl group as defined above linked to the molecule through an aryl group as defined above. The aralkyl or alkaryl group optionally can be substituted with one or more moieties selected from the group consisting of hydroxyl, carboxy, carboxamido, carboalkoxy, acyl, amino, halo, alkylamino, alkoxy, aryloxy, nitro, cyano, sulfo, sulfato, phospho, phosphato, or phosphonato.

The term "halo", as used herein, specifically includes chloro, bromo, iodo, and fluoro.

The term "alkoxy", as used herein, and unless otherwise specified, refers to a moiety of the structure —O-alkyl, wherein alkyl is as defined above.

The term "acyl", as used herein, refers to a group of the formula C(O)R', wherein R' is an alkyl, aryl, alkaryl or aralkyl group, or substituted alkyl, aryl, aralkyl or alkaryl, wherein these groups are as defined above.

The term "polyol", as used herein, refers to a molecule that contains more than one hydroxyl group. A polyol may be a diol, triol, or a tetraol which contains 2, 3, and 4 hydroxyl groups, respectively. A polyol also may contain more than four hydroxyl groups, such as a pentaol, hexaol, heptaol, or the like, which contain, 5, 6, or 7 hydroxyl groups, respectively. Additionally, a polyol also may be a sugar alcohol, polyhydric alcohol, or polyalcohol which is a reduced form of carbohydrate, wherein the carbonyl group (aldehyde or ketone, reducing sugar) has been reduced to a primary or secondary hydroxyl group.

Non-limiting examples of polyols in embodiments of this invention include erythritol, maltitol, mannitol, sorbitol, lactitol, xylitol, isomalt, propylene glycol, glycerol (glycerine), threitol, galactitol, palatinose, reduced isomalto-oligosaccharides, reduced xylo-oligosaccharides, reduced gentio-oligosaccharides, reduced maltose syrup, reduced glucose syrup, and sugar alcohols or any other carbohydrates capable of being reduced which do not adversely affect the taste of the NHPS or the orally ingestible composition.

As used herein, the phrase "sweet taste improving additive" means any material that imparts a more sugar-like temporal profile or sugar-like flavor profile or both to a NHPS. Suitable sweet taste improving additives useful in embodiments of this invention include amino acids and their salts, polyamino acids and their salts, peptides, sugar acids and their salts, nucleotides and their salts, organic acids, inorganic acids, organic salts including organic acid salts and organic base salts, inorganic acid salts (e.g., sodium chloride, potassium chloride, magnesium chloride), bitter compounds, flavorants and flavoring ingredients, astringent compounds, polymers, proteins or protein hydrolysates, surfactants, emulsifiers, flavonoids, alcohols, and synthetic sweeteners.

Suitable sweet taste improving amino acid additives for use in embodiments of this invention include but are not limited to aspartic acid, arginine, glycine, glutamic acid, proline, threonine, theanine, cysteine, cystine, alanine, valine, tyrosine, leucine, isoleucine, asparagine, serine, lysine, histidine, ornithine, methionine, carnitine, aminobutyric acid (alpha-, beta-, or gamma-isomers), glutamine, hydroxyproline, taurine, norvaline, sarcosine, and their salt forms such as sodium or potassium salts or acid salts. The sweet taste improving amino acid additives also may be in the D- or L-configuration and in the mono-, di-, or tri-form of the same or different amino acids. Additionally, the amino acids may be $\alpha$-, $\beta$-, $\gamma$-, $\delta$-, and $\epsilon$-isomers if appropriate. Combinations of the foregoing amino acids and their corresponding salts (e.g., sodium, potassium, calcium, magnesium salts or other alkali or alkaline earth metal salts thereof, or acid salts) also are suitable sweet taste improving additives in embodiments of this invention. The amino acids may be natural or synthetic. The amino acids also may be modified. Modified amino acids refers to any amino acid wherein at least one atom has been added, removed, substituted, or combinations thereof (e.g., N-alkyl amino acid, N-acyl amino acid, or N-methyl amino acid). Non-limiting examples of modified amino acids include amino acid derivatives such as trimethyl glycine, N-methyl-glycine, and N-methyl-alanine. As used herein, modified amino acids encompass both modified and unmodified amino acids. As used herein, amino acids also encompass both peptides and polypeptides (e.g., dipeptides, tripeptides, tetrapeptides, and pentapeptides) such as glutathione and L-alanyl-L-glutamine.

Suitable sweet taste improving polyamino acid additives include poly-L-aspartic acid, poly-L-lysine (e.g., poly-L-$\alpha$-lysine or poly-L-$\epsilon$-lysine), poly-L-ornithine (e.g., poly-L-$\alpha$-ornithine or poly-L-$\epsilon$-ornithine), poly-L-arginine, other polymeric forms of amino acids, and salt forms thereof (e.g., magnesium, calcium, potassium, or sodium salts such as L-glutamic acid mono sodium salt). The sweet taste improving polyamino acid additives also may be in the D- or L-configuration. Additionally, the polyamino acids may be $\alpha$-, $\beta$-, $\gamma$-, $\delta$-, and $\epsilon$-isomers if appropriate. Combinations of the foregoing polyamino acids and their corresponding salts (e.g., sodium, potassium, calcium, magnesium salts or other alkali or alkaline earth metal salts thereof or acid salts) also are suitable sweet taste improving additives in embodiments of this invention. The polyamino acids described herein also may comprise co-polymers of different amino acids. The polyamino acids may be natural or synthetic. The polyamino acids also may be modified such that at least one atom has been added, removed, substituted, or combinations thereof (e.g., N-alkyl polyamino acid or N-acyl polyamino acid). As used herein, polyamino acids encompass both modified and unmodified polyamino acids. In accordance with particular embodiments of this invention, modified polyamino acids include, but are not limited to polyamino acids of various molecular weights (MW), such as poly-L-$\alpha$-lysine with a MW of 1,500, MW of 6,000, MW of 25,200, MW of 63,000, MW of 83,000, or MW of 300,000.

Suitable sweet taste improving sugar acid additives for use in embodiments of this invention include, but are not limited to, aldonic, uronic, aldaric, alginic, gluconic, glucuronic, glucaric, galactaric, galacturonic, and their salts (e.g., sodium, potassium, calcium, magnesium salts or other physiologically acceptable salts), and combinations thereof.

Suitable sweet taste improving nucleotide additives for use in embodiments of this invention include, but are not limited to, inosine monophosphate ("IMP"), guanosine monophosphate ("GMP"), adenosine monophosphate ("AMP"), cytosine monophosphate (CMP), uracil monophosphate (UMP), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, and their alkali or alkaline earth metal salts, and combinations thereof. The nucleotides described herein also may comprise nucleotide-related additives, such as nucleosides or nucleic acid bases (e.g., guanine, cytosine, adenine, thymine, uracil).

Suitable sweet taste improving organic acid additives include any compound which comprises a —COOH moiety. Suitable sweet taste improving organic acid additives for use in embodiments of this invention include, but are not limited to, C2-C30 carboxylic acids, substituted hydroxyl C1-C30 carboxylic acids, benzoic acid, substituted benzoic acids (e.g., 2,4-dihydroxybenzoic acid), substituted cinnamic acids, hydroxyacids, substituted hydroxybenzoic acids, substituted cyclohexyl carboxylic acids, tannic acid, lactic acid, tartaric acid, citric acid, gluconic acid, glucoheptonic acids, adipic acid, hydroxycitric acid, malic acid, fruitaric acid (a blend of malic, fumaric, and tartaric acids), fumaric acid, maleic acid, succinic acid, chlorogenic acid, salicylic acid, creatine, glucono delta lactone, caffeic acid, bile acids, acetic acid, ascorbic acid, alginic acid, erythorbic acid, polyglutamic acid, and their alkali or alkaline earth metal salt derivatives thereof. In addition, the organic acid additives also may be in either the D- or L-configuration.

Suitable sweet taste improving organic acid additive salts include, but are not limited to, sodium, calcium, potassium, and magnesium salts of all organic acids, such as salts of citric acid, malic acid, tartaric acid, fumaric acid, lactic acid (e.g., sodium lactate), alginic acid (e.g., sodium alginate), ascorbic acid (e.g., sodium ascorbate), benzoic acid (e.g., sodium benzoate or potassium benzoate), and adipic acid. The examples of the sweet taste improving organic acid additives described optionally may be substituted with one or more of the following moiety selected from the group consisting of hydrogen, alkyl, alkenyl, alkynyl, halo, haloalkyl, carboxyl, acyl, acyloxy, amino, amido, carboxyl derivatives, alkylamino, dialkylamino, arylamino, alkoxy, aryloxy, nitro, cyano, sulfo, thiol, imine, sulfonyl, sulfenyl, sulfonyl, sulfamyl, carboxalkoxy, carboxamido, phosphonyl, phosphinyl, phosphoryl, phosphino, thioester, thioether, anhydride, oximino, hydrazino, carbamyl, phospho, phosphonato, or any other viable functional group provided the substituted organic acid additives function to improve the sweet taste of a NHPS.

Suitable sweet taste improving inorganic acid additives for use in embodiments of this invention include, but are not limited to, phosphoric acid, phosphorous acid, polyphosphoric acid, hydrochloric acid, sulfuric acid, carbonic acid, sodium dihydrogen phosphate, and their corresponding alkali or alkaline earth metal salts thereof (e.g., inositol hexaphosphate Mg/Ca).

Suitable sweet taste improving bitter compound additives for use in embodiments of this invention include, but are not limited to, caffeine, quinine, urea, bitter orange oil, naringin, quassia, and salts thereof.

Suitable sweet taste improving flavorant and flavoring ingredient additives for use in embodiments of this invention include, but are not limited to, vanillin, vanilla extract, mango extract, cinnamon, citrus, coconut, ginger, viridiflorol, almond, menthol (including menthol without mint), grape skin extract, and grape seed extract, "Flavorant" and "flavoring ingredient" are synonymous and can include natural or synthetic substances or combinations thereof. Flavorants also include any other substance which imparts flavor and may include natural or non-natural (synthetic) substances which are safe for human or animals when used in a generally accepted range. Non-limiting examples of proprietary flavorants include Döhler™ Natural Flavoring Sweetness Enhancer K14323 (Döhler™, Darmstadt, Germany), Symrise™ Natural Flavor Mask for Sweeteners 161453 and 164126 (Symrise™, Holzminden, Germany), Natural Advantage™ Bitterness Blockers 1, 2, 9 and 10 (Natural Advantage™, Freehold, N.J., U.S.A.), and Sucramask™ (Creative Research Management, Stockton, Calif., U.S.A.).

Suitable sweet taste improving polymer additives for use in embodiments of this invention include, but are not limited to, chitosan, pectin, pectic, pectinic, polyuronic, polygalacturonic acid, starch, food hydrocolloid or crude extracts thereof (e.g., gum *acacia* senegal (Fibergum™), gum *acacia* seyal, carageenan), poly-L-lysine (e.g., poly-L-α-lysine or poly-L-ε-lysine), poly-L-ornithine (e.g., poly-L-α-ornithine or poly-L-ε-ornithine), polypropylene glycol, polyethylene glycol, poly(ethylene glycol methyl ether), polyarginine, polyaspartic acid, polyglutamic acid, polyethylene imine, alginic acid, sodium alginate, propylene glycol alginate, and sodium polyethyleneglycolalginate, sodium hexametaphosphate and its salts, and other cationic polymers and anionic polymers.

Suitable sweet taste improving protein or protein hydrolysate additives for use in embodiments of this invention include, but are not limited to, bovine serum albumin (BSA), whey protein (including fractions or concentrates thereof such as 90% instant whey protein isolate, 34% whey protein, 50% hydrolyzed whey protein, and 80% whey protein concentrate), soluble rice protein, soy protein, protein isolates, protein hydrolysates, reaction products of protein hydrolysates, glycoproteins, and/or proteoglycans containing amino acids (e.g., glycine, alanine, serine, threonine, asparagine, glutamine, arginine, valine, isoleucine, leucine, norvaline, methionine, proline, tyrosine, hydroxyproline, and the like), collagen (e.g., gelatin), partially hydrolyzed collagen (e.g., hydrolyzed fish collagen), and collagen hydrolysates (e.g., porcine collagen hydrolysate).

Suitable sweet taste improving surfactant additives for use in embodiments of this invention include, but are not limited to, polysorbates (e.g., polyoxyethylene sorbitan monooleate (polysorbate 80), polysorbate 20, polysorbate 60), sodium dodecylbenzenesulfonate, dioctyl sulfosuccinate or dioctyl sulfosuccinate sodium, sodium dodecyl sulfate, cetylpyridinium chloride (hexadecylpyridinium chloride), hexadecyltrimethylammonium bromide, sodium cholate, carbamoyl, choline chloride, sodium glycocholate, sodium taurodeoxycholate, lauric arginate, sodium stearoyl lactylate, sodium taurocholate, lecithins, sucrose oleate esters, sucrose stearate esters, sucrose palmitate esters, sucrose laurate esters, and other emulsifiers, and the like.

Suitable sweet taste improving flavonoid additives for use in embodiments of this invention generally are classified as flavonols, flavones, flavanones, flavan-3-ols, isoflavones, or anthocyanidins. Non-limiting examples of flavonoid additives include catechins (e.g., green tea extracts such as Polyphenon™ 60, Polyphenon™ 30, and Polyphenon™ 25 (Mitsui Norin Co., Ltd., Japan), polyphenols, rutins (e.g., enzyme modified rutin Sanmelin™ AO (San-fi Gen F.F.I., Inc., Osaka, Japan)), neohesperidin, naringin, neohesperidin dihydrochalcone, and the like.

Suitable sweet taste improving alcohol additives for use in embodiments of this invention include, but are not limited to, ethanol.

Suitable sweet taste improving astringent compound additives include, but are not limited to, tannic acid, europium chloride ($EuCl_3$), gadolinium chloride ($GdCl_3$), terbium chloride ($TbCl_3$), alum, tannic acid, and polyphenols (e.g., tea polyphenols).

Suitable sweet taste improving vitamins include nicotinamide (Vitamin B3) and pyridoxal hydrochloride (Vitamin B6).

Suitable sweet taste improving synthetic sweetener additives for use in embodiments of this invention include, but are not limited to, sucralose, acesulfame potassium or other salts, aspartame, alitame, saccharin, neohesperidin dihydrochalcone, cyclamate, neotame, N—[N-[3-(3-hydroxy-4-methoxyphenyl)propyl]-L-α-aspartyl]-L-phenylalanine 1-methyl ester, N-[N-[3-(3-hydroxy-4-methoxyphenyl)-3-methylbutyl]-L-α-aspartyl]-L-phenylalanine 1-methyl ester, N—[N-[3-(3-methoxy-4-hydroxyphenyl)propyl]-L-α-aspartyl]-L-phenylalanine 1-methyl ester, salts thereof, and the like. Specific embodiments of synthetic sweetener compositions comprising sweet taste improving compositions are disclosed in U.S. Provisional Application No. 60/739,124, entitled "Synthetic Sweetener Compositions with Improved Temporal Profile and/or Flavor Profile, Methods for Their Formulation, and Uses," filed on Nov. 23, 2005, by DuBois, et al., the disclosure of which is incorporated herein by reference in its entirety.

The sweet taste improving compositions also may be in salt form which may be obtained using standard procedures well known in the art. The term "salt" also refers to complexes that retain the desired chemical activity of the sweet taste improving compositions of the present invention and are safe for human or animal consumption in a generally acceptable range. Alkali metal (for example, sodium or potassium) or alkaline earth metal (for example calcium or magnesium) salts also can be made. Salts also may include combinations of alkali and alkaline earth metals. Non-limiting examples of such salts are (a) acid addition salts formed with inorganic acids and salts formed with organic acids; (b) base addition salts formed with metal cations such as calcium, bismuth, barium, magnesium, aluminum, copper, cobalt, nickel, cadmium, sodium, potassium, and the like, or with a cation formed from ammonia, N,N-dibenzylethylenediamine, D-glucosamine, tetraethylammonium, or ethylenediamine; or (c) combinations of (a) and (b). Thus, any salt forms which may be derived from the sweet taste improving compositions may be used with the embodiments of the present invention as long as the salts of the sweet taste improving additives do not adversely affect the taste of NHPSs or the orally ingestible compositions which comprises NHPSs. The salt forms of the additives can be added to the NHPS sweetener composition in the same amounts as their acid or base forms.

In particular embodiments, suitable sweet taste improving inorganic salt additives useful as sweet taste improving additives include but are not limited to sodium chloride, potassium chloride, sodium sulfate, potassium citrate, europium chloride ($EuCl_3$), gadolinium chloride ($GdCl_3$), terbium chloride ($TbCl_3$), magnesium sulfate, alum, magnesium chloride, magnesium phosphate, mono-, di-, tri-basic sodium or potassium salts of phosphoric acid (e.g., inorganic phosphates), salts of hydrochloric acid (e.g., inorganic chlorides), sodium carbonate, sodium bisulfate, and sodium bicarbonate. Furthermore, in particular embodiments, suitable organic salts useful as sweet taste improving additives include but are not limited to choline chloride, alginic acid sodium salt (sodium alginate), glucoheptonic acid sodium salt, gluconic acid sodium salt (sodium gluconate), gluconic acid potassium salt (potassium gluconate), guanidine HCl, glucosamine HCl, monosodium glutamate (MSG), adenosine monophosphate salt, amiloride HCl, magnesium gluconate, potassium tartrate (monohydrate), and sodium tartrate (dihydrate).

Embodiments of the sweet taste improving compositions of this invention can impart a more sharp and clean sensation to the taste of NHPSs. Furthermore, embodiments of the sweet taste improving compositions of the present invention have a superior effect in improving the temporal profile and/or flavor profile of NHPSs while at the same time providing a sweetener composition with a low-caloric or non-caloric content, imparting more sugar-like characteristics.

D. Temporal Profile Modulation

According to an embodiment of this invention, a NHPS composition comprises at least one sweet taste improving composition present in the NHPS composition in an amount effective for the NHPS composition to impart an osmolarity of at least 10 mOsmoles/L to an aqueous solution of the NHPS composition wherein the NHPS is present in the aqueous solution in an amount sufficient to impart a maximum sweetness intensity equivalent to that of a 10% aqueous solution of sucrose by weight. As used herein, "mOsmoles/L" refers to milliosmoles per liter. According to another embodiment, a NHPS composition comprises at least one sweet taste improving composition in an amount effective for the NHPS composition to impart an osmolarity of 10 to 500 mOsmoles/L, preferably 25 to 500 mOsmoles/L preferably, more preferably 100 to 500 mOsmoles/L, more preferably 200 to 500 mOsmoles/L, and still more preferably 300 to 500 mOsmoles/L to an aqueous solution of the NHPS composition wherein the NHPS is present in the aqueous solution in an amount sufficient to impart a maximum sweetness intensity equivalent to that of a 10% aqueous solution of sucrose by weight. In particular embodiments, a plurality of sweet taste improving compositions may be combined with a NHPS, and in that case, the osmolarity imparted is that of the total combination of the plurality of sweet taste improving compositions.

Osmolarity refers to the measure of osmoles of solute per liter of solution, wherein osmole is equal to the number of moles of osmotically active particles in an ideal solution (e.g., a mole of glucose is one osmole), whereas a mole of sodium chloride is two osmoles (one mole of sodium and one mole of chloride). Thus, in order to improve in the quality of taste of NHPSs, the osmotically active compounds or the compounds which impart osmolarity must not introduce significant off taste to the formulation.

In one embodiment, suitable sweet taste improving compositions which improve the temporal profile of the natural high-potency sweetener or sweetenable composition to be more sugar-like include carbohydrates, polyols, amino acids, other sweet taste improving additives (e.g., sugar acids and their salts, nucleotides, organic acids, inorganic acids, organic salts including organic acid salts and organic base salts, inorganic salts, bitter compounds, astringent compounds, proteins or protein hydrolysates, surfactants, emulsifiers, flavonoids, alcohols, and synthetic sweeteners).

In more preferred embodiments, non-limiting examples of suitable compounds which impart osmolarity include sweet taste improving carbohydrate additives, sweet taste improving polyol additives, sweet taste improving alcohol additives, sweet taste improving inorganic acid additives, sweet taste improving organic acid additives, sweet taste improving inorganic salt additives, sweet taste improving organic salt additives, sweet taste improving organic base salt additives, sweet taste improving amino acid additives, sweet taste improving amino acid salt additives, sweet taste improving bitter additives, and sweet taste improving astringent additives. In one embodiment, suitable compounds which impart osmolarity include, but are not limited to, sucrose, fructose, glucose, maltose, lactose, mannose, galactose, tagatose, erythritol, glycerol, propylene glycol, ethanol, phosphoric acid (including corresponding sodium, potassium, and magnesium salts thereof), citric acid, malic acid, tartaric acid, fumaric acid, gluconic acid, adipic acid, glucosamine and glucosamine salt, choline salt, guanidine salt, protein or protein hydrolysate, glycine, alanine, serine, threonine, theanine, caffeine, quinine, urea, naringin, tannic acid, $AlNa(SO_4)_2$, $AlK(SO_4)_2$ and other forms of alum, and combinations thereof.

In one embodiment, suitable sweet taste improving carbohydrate additives for the present invention have a molecular weight less than or equal to 500 and desirably have a molecular weight from 50 to 500. In particular embodiments, suitable carbohydrates with a molecular weight less than or equal to 500 include but are not limited to sucrose, fructose, glucose, maltose, lactose, mannose, galactose, and tagatose. Generally, in accordance with desirable embodiments of this invention, a carbohydrate is present in the NHPS compositions in an amount from about 1,000 to about 100,000 ppm. (Throughout this specification, the term ppm means parts per million by weight or volume. For example, 500 ppm means 500 mg in a liter.) In accordance with other desirable embodiments of this invention, a carbohydrate is present in the NHPS sweetened compositions in an amount from about 2,500 to about 10,000 ppm. In another embodiment, suitable sweet taste improving carbohydrate additives for imparting osmolarities ranging from about 10 mOsmoles/L to about 500 mOsmoles/L to a sweetenable composition include, but are not limited to sweet taste improving carbohydrate additives with a molecular weight ranging from about 50 to about 500.

In one embodiment, suitable polyol have a molecular weight less than or equal to 500 and desirably have a molecular weight from 76 to 500. In particular embodiments, suitable polyols with a molecular weight less than or equal to 500 include but are not limited to erythritol, glycerol, and propylene glycol. Generally, in accordance with desirable embodiments of this invention, a polyol is present in the NHPS compositions in an amount from about 100 ppm to about 80,000 ppm. In accordance with other desirable embodiments of this invention, a polyol is present in the NHPS sweetened compositions in an amount from about 400 to about 80,000 ppm. In other embodiments of this invention, a polyol is present in NHPS sweetened compositions in an amount from about 5,000 to about 40,000 ppm of the composition, more particularly from about 10,000 to about 35,000 ppm of the composition. Desirably, the at least one NHPS and at least one sweet taste improving polyol are present in the sweetener composition in a ratio from about 1:4 to about 1:800, respectively; more particularly from about 1:20 to about 1:600; even more particularly from about 1:50 to about 1:300; and still more particularly from about 1:75 to about 1:150. In a sub-embodiment, suitable sweet taste improving polyol additives for imparting osmolarities ranging from about 10 mOsmoles/L to about 500 mOsmoles/L to a sweetenable composition include, but are not limited to sweet taste improving polyol additives with a molecular weight ranging from about 76 to about 500.

Generally, in accordance with another embodiment of this invention, a suitable sweet taste improving alcohol is present in the NHPS compositions in an amount from about 625 to about 10,000 ppm. In another embodiment, suitable sweet taste improving alcohol additives for imparting osmolarities ranging from about 10 mOsmoles/L to about 500 mOsmoles/L to a sweetenable composition include, but are not limited to sweet taste improving alcohol additives with a molecular weight ranging from about 46 to about 500. A non-limiting example of sweet taste improving alcohol additive with a molecular weight ranging from about 46 to about 500 includes ethanol.

In one embodiment, suitable sweet taste improving amino acid additives have a molecular weight of less than or equal to 250 and desirably have a molecular weight from 75 to 250. In particular embodiments, suitable sweet taste improving amino acid additives with a molecular weight less than or equal to 250 include but are not limited to glycine, alanine, serine, valine, leucine, isoleucine, proline, theanine, and threonine. Preferred amino acids include those which are sweet tasting at high concentrations, but are desirably present in embodiments of this invention at amounts below or above their sweetness taste detection threshold. Even more preferred are mixtures of amino acids at amounts below or above their sweetness taste detection threshold. Generally, in accordance with desirable embodiments of this invention, a sweet taste improving amino acid additive is present in the NHPS compositions in an amount from about 100 ppm to about 25,000 ppm, more particularly from about 1,000 to about 10,000 ppm, and still more particularly from about 2,500 to about 5,000 ppm. In accordance with other desirable embodiments of this invention, a sweet taste improving amino acid additive is present in the NHPS sweetened compositions in an amount from about 250 ppm to about 7,500 ppm. In a sub-embodiment, suitable sweet taste improving amino acid additives for imparting osmolarities ranging from about 10 mOsmoles/L to about 500 mOsmoles/L to a sweetenable composition include, but are not limited to sweet taste improving amino acid additives with a molecular weight ranging from about 75 to about 250.

Generally, in accordance with yet another embodiment of this invention, a suitable sweet taste improving amino acid salt additive is present in the NHPS compositions in an amount from about 25 to about 10,000 ppm more particularly from about 1,000 to about 7,500 ppm, and still more particularly from about 2,500 to about 5,000 ppm. In another embodiment, suitable sweet taste improving amino acid salt additives for imparting osmolarities ranging from about 10 mOsmoles/L to about 500 mOsmoles/L to a sweetenable composition include, but are not limited to, sweet taste improving amino acid additives with a molecular weight ranging from about 75 to about 300. Non-limiting examples of sweet taste improving amino acid salt additives with a molecular weight ranging from about 75 to about 300 include salts of glycine, alanine, serine, theanine, and threonine.

Generally, in accordance with still another embodiment of this invention, a suitable sweet taste improving protein or protein hydroyslate additive is present in the NHPS compositions in an amount from about 200 to about 50,000 ppm. In another embodiment, suitable sweet taste improving protein or protein hydrolysate additives for imparting osmolarities ranging from about 10 mOsmoles/L to about 500 mOsmoles/L to a sweetenable composition include, but are not limited to, sweet taste improving protein or protein hydrolysate additives with a molecular weight ranging from about 75 to about 300. Non-limiting examples of sweet taste improving protein or protein hydrolysate additives with a molecular weight ranging from about 75 to about 300 include proteins or protein hydrolysates containing glycine, alanine, serine, and threonine.

Generally, in accordance with another embodiment of this invention, a suitable sweet taste improving inorganic acid additive is present in the NHPS compositions in an amount from about 25 to about 5,000 ppm. In another embodiment, suitable sweet taste improving inorganic acid additives for imparting osmolarities ranging from about 10 mOsmoles/L to about 500 mOsmoles/L to a sweetenable composition include, but are not limited to phosphoric acid, HCl, and $H_2SO_4$ and any other inorganic acid additives which are safe for human or animal consumption when used in a generally acceptable range. In a sub-embodiment, suitable sweet taste improving inorganic acid additives for imparting osmolarities ranging from about 10 mOsmoles/L to about 500 mOsmoles/L to a sweetenable composition include but are not limited to sweet taste improving inorganic acid additives with a molecular weight range from about 36 to about 98.

Generally, in accordance with still another embodiment of this invention, a suitable sweet taste improving inorganic acid salt additive is present in the NHPS compositions in an amount from about 25 to about 5,000 ppm. In another embodiment, suitable sweet taste improving inorganic acid salt additives for imparting osmolarities ranging from about 10 mOsmoles/L to about 500 mOsmoles/L to a sweetenable composition include, but are not limited to salts of inorganic acids, for example sodium, potassium, calcium, and magnesium salts of phosphoric acid, and any other alkali or alkaline earth metal salts of other inorganic acid additives (e.g., sodium bisulfate) which are safe for human or animal consumption when used in a generally acceptable range. In a particular embodiment, suitable sweet taste improving inorganic acid salt additives include magnesium chloride, magnesium sulfate, sodium chloride, or combinations thereof. In a sub-embodiment, suitable sweet taste improving inorganic acid salt additives for imparting osmolarities ranging from about 10 mOsmoles/L to about 500 mOsmoles/L to a sweetenable composition include, but are not limited to, sweet taste improving inorganic acid salt additives with a molecular weight range from about 58 to about 120.

Generally, in accordance with still another embodiment of this invention, a suitable sweet taste improving organic acid additive is present in the NHPS compositions in an amount from about 10 to about 5,000 ppm. In another embodiment, suitable sweet taste improving organic acid additives for imparting osmolarities ranging from about 10 mOsmoles/L to about 500 mOsmoles/L to a sweetenable composition include, but are not limited to, creatine, citric acid, malic acid, succinic acid, hydroxycitric acid, tartaric acid, fumaric acid, gluconic acid, glutaric acid, adipic acid, and any other sweet taste improving organic acid additives which are safe for human or animal consumption when used in a generally acceptable range. In one embodiment, the sweet taste improving organic acid additive comprises a molecular weight range from about 60 to about 208.

Generally, in accordance with still another embodiment of this invention, a suitable sweet taste improving organic acid salt additive is present in the NHPS compositions in an amount from about 20 to about 10,000 ppm. In another embodiment, suitable sweet taste improving organic acid salt additives for imparting osmolarities ranging from about 10 mOsmoles/L to about 500 mOsmoles/L to a sweetenable composition include, but are not limited to, salts of the sweet taste improving organic acid additive, such as sodium, potassium, calcium, magnesium, and other alkali or alkaline metal salts of citric acid, malic acid, tartaric acid, fumaric acid, gluconic acid, adipic acid, hydroxycitric acid, succinic acid, glutaric acid, and salts of any other sweet taste improving organic acid additives which are safe for human or animal consumption when used in a generally acceptable range. In one embodiment, the sweet taste improving organic acid salt additive comprises a molecular weight range from about 140 to about 208.

Generally, in accordance with yet another embodiment of this invention, a suitable sweet taste improving organic base salt additive is present in the NHPS compositions in an amount from about 10 to about 5,000 ppm. In another embodiment, suitable sweet taste improving organic base salt additives for imparting osmolarities ranging from about 10 mOsmoles/L to about 500 mOsmoles/L to a sweetenable composition include, but are not limited to, inorganic and organic acid salts of organic bases such as glucosamine salts, choline salts, and guanidine salts.

Generally, in accordance with yet another embodiment of this invention, a suitable sweet taste improving astringent additive is present in the NHPS compositions in an amount from about 25 to about 1,000 ppm. In another embodiment, suitable sweet taste improving astringent additives for imparting osmolarities ranging from about 10 mOsmoles/L to about 500 mOsmoles/L to a sweetenable composition include, but are not limited to, tannic acid, tea polyphenols, catechins, aluminum sulfate, $AlNa(SO_4)_2$, $AlK(SO_4)_2$ and other forms of alum.

Generally, in accordance with yet another embodiment of this invention, a suitable sweet taste improving nucleotide additive is present in the NHPS compositions in an amount from about 5 to about 1,000 ppm. In another embodiment, suitable sweet taste improving nucleotide additives for imparting osmolarities ranging from about 10 mOsmoles/L to about 500 mOsmoles/L to a sweetenable composition include, but are not limited to, adenosine monophosphate.

Generally, in accordance with yet another embodiment of this invention, a suitable sweet taste improving polyamino acid additive is present in the NHPS compositions in an amount from about 30 to about 2,000 ppm. In another embodiment, suitable sweet taste improving polyamino acid additives for imparting osmolarities ranging from about 10 mOsmoles/L to about 500 mOsmoles/L to a sweetenable composition include, but are not limited to, poly-L-lysine (e.g., poly-L-α-lysine or poly-L-ε-lysine), poly-L-omithine (e.g., poly-L-α-ornithine or poly-L-ε-ornithine), and poly-L-arginine.

Generally, in accordance with yet another embodiment of this invention, a suitable sweet taste improving polymer additive is present in the NHPS compositions in an amount from about 30 to about 2,000 ppm. In another embodiment, suitable sweet taste improving polymer additives for imparting osmolarities ranging from about 10 mOsmoles/L to about 500 mOsmoles/L to a sweetenable composition include, but are not limited to, chitosan, pectin, hydrocolloids such as gum *acacia* senegal, propylene glycol, polyethylene glycol, and poly(ethylene glycol methyl ether).

Generally, in accordance with yet another embodiment of this invention, a suitable sweet taste improving surfactant additive is present in the NHPS compositions in an amount from about 1 to about 5,000 ppm. In another embodiment, suitable sweet taste improving surfactant additives for imparting osmolarities ranging from about 10 mOsmoles/L to about 500 mOsmoles/L to a sweetenable composition include, but are not limited to, polysorbates, choline chloride, sodium taurocholate, lecithins, sucrose oleate esters, sucrose stearate esters, sucrose palmitate esters, and sucrlose laurate esters.

Generally, in accordance with yet another embodiment of this invention, a suitable sweet taste improving flavonoid additive is present in the NHPS compositions in an amount from about 0.1 to about 1,000 ppm. In another embodiment, suitable sweet taste improving flavonoid additives for imparting osmolarities ranging from about 10 mOsmoles/L to about 500 mOsmoles/L to a sweetenable composition include, but are not limited to, naringin, catechins, rutins, neohesperidin, and neohesperidin dihydrochalcone.

E. Flavor Profile Modulation

As hypothesized above, flavor profile imparts a sugar-like characteristic to NHPS. In one embodiment, any sweet taste improving composition that imparts a sugar-like flavor profile to a NHPS will be effective by this mechanism. In particular, any sweet taste improving composition that imparts a more sugar-like osmotic taste will be effective by this mechanism. In one embodiment, suitable sweet taste improving compositions which improve the flavor profile, including the osmotic taste, of the natural high-potency sweetener or sweetenable composition to be more sugar-like include carbohydrates, polyols, amino acid, and other sweet taste improving additives (e.g., polyamino acids, peptides, sugar acids and their salts, nucleotides, organic acids, inorganic acids, organic salts including organic acid salts and organic base salts, inorganic salts, bitter compounds, flavorants and flavoring ingredients, astringent compounds, proteins or protein hydrolysates, surfactants, emulsifiers, flavonoids, alcohols, and synthetic sweeteners).

In a preferred embodiment, non-limiting examples of sweet taste improving compositions enhancing a NHPS's osmotic taste to be more sugar-like include sweet taste improving carbohydrate additives, sweet taste improving alcohol additives, sweet taste improving polyol additives, sweet taste improving amino acid additives, sweet taste improving amino acid salt additives, sweet taste improving inorganic acid salt additives, sweet taste improving polymer additives, and sweet taste improving protein or protein hydrolysate additives.

In another embodiment, suitable sweet improving amino acid additives include amino acids comprising a molecular weight less than or equal to 250. In one example, suitable sweet taste improving amino acids include, but are not limited to, low molecular weight amino acids such as glycine, leucine, valine, isoleucine, proline, hydroxyproline, alanine, serine, theanine, and threonine.

In another embodiment, suitable sweet taste improving carbohydrate additives for improving the osmotic taste of the NHPS to be more sugar-like include, but are not limited to, sweet taste improving carbohydrate additives with a molecular weight ranging from about 50 to about 500. Non-limiting examples of sweet taste improving carbohydrate additives with a molecular weight ranging from about 50 to about 500 include sucrose, fructose, glucose, maltose, lactose, mannose, galactose, ribose, rhamnose, trehalose, and tagatose.

In another embodiment, suitable sweet taste improving polyol additives for improving the osmotic taste of the NHPS to be more sugar-like include, but are not limited to, sweet taste improving polyol additives with a molecular weight ranging from about 76 to about 500. Non-limiting examples of sweet taste improving polyol additives with a molecular weight ranging from about 76 to about 500 include erythritol, glycerol, and propylene glycol. In a sub-embodiment, other suitable sweet taste improving polyol additives include sugar alcohols.

In another embodiment, suitable sweet taste improving alcohol additives for improving the osmotic taste of the NHPS to be more sugar-like include, but are not limited to, sweet taste improving alcohol additives with a molecular weight ranging from about 46 to about 500. A non-limiting example of sweet taste improving alcohol additive with a molecular weight ranging from about 46 to about 500 includes ethanol.

In another embodiment, suitable sweet taste improving amino acid additives for improving the osmotic taste of the NHPS to be more sugar-like include, but are not limited to, sweet taste improving amino acid additives with a molecular weight ranging from about 75 to about 250, Non-limiting examples of sweet taste improving amino acid additives with a molecular weight ranging from about 75 to about 250 include glycine, alanine, serine, leucine, valine, isoleucine, proline, hydroxyproline, glutamine, theanine, and threonine, In another embodiment, suitable sweet taste improving amino acid salt additives for improving the osmotic taste of the NHPS to be more sugar-like include, but are not limited to, sweet taste improving amino acid salt additives with a molecular weight ranging from about 75 to about 300. Non-limiting examples of sweet taste improving amino acid salt additives with a molecular weight ranging from about 75 to about 300 include salts of glycine, alanine, serine, leucine, valine, isoleucine, proline, hydroxyproline, glutamine, theanine, and threonine.

In another embodiment, suitable sweet taste improving protein or protein hydrolysate additives for improving the osmotic taste of the NHPS to be more sugar-like include, but are not limited to, sweet taste improving protein or protein hydrolysate additives with a molecular weight ranging from about 75 to about 300. Non-limiting examples of sweet taste improving protein or protein hydrolysate additives with a molecular weight ranging from about 75 to about 300 include protein or protein hydrolysates containing glycine, alanine, serine, leucine, valine, isoleucine, proline, hydroxyproline, glutamine, and threonine.

In another embodiment, suitable sweet taste improving inorganic acid salt additives for improving the osmotic taste of the NHPS to be more sugar-like include, but are not limited to, sodium chloride, potassium chloride, magnesium chloride, $KH_2PO_4$ and $NaH_2PO_4$. Suitable sweet taste improving inorganic acid salt additives for improving the osmotic taste may comprise a molecular weight from about 58 to about 120.

In another embodiment, suitable sweet taste improving bitter additives for improving the osmotic taste of the NHPS to be more sugar-like include, but are not limited to, caffeine, quinine, urea, quassia, tannic acid, and naringin.

In a further embodiment, the sweet taste improving compositions improve the NHPS taste to be similar to that of sucrose by at least one mechanism selected from temporal profile (e.g., sweetness onset or sweetness linger), maximal response, flavor profile (e.g., osmotic taste), adaptation behavior, and flavor profile. In a sub-embodiment, the sweet taste improving compositions improve the NHPS taste to be similar to that of sucrose by at least one mechanism selected from temporal profile, maximal response, flavor profile, adaptation behavior, and flavor profile, and optionally impart a masking effect to suppress, reduce, or eliminate the undesirable taste of the NHPS and/or impart sugar-like characteristics to the NHPS.

F. Combinations of NHPSs and Sweet Taste Improving Compositions

It has been discovered that combinations of at least one NHPS and at least one sweet taste improving composition improve the temporal profile and/or flavor profile, including the osmotic taste, to be more sugar-like. One of ordinary skill in the art, with the teachings of the present invention, may arrive at all the possible combinations of the NHPS and sweet taste improving compositions. For example, non-limiting combinations of the NHPS and sweet taste improving compositions include:

1. at least one NHPS and at least one carbohydrate;
2. at least one NHPS and at least one polyol;
3. at least one NHPS and at least one amino acid;
4. at least one NHPS and at least one other sweet taste improving additive;
5. at least one NHPS, at least one carbohydrate, at least one polyol, at least one amino acid, and at least one other sweet taste improving additive;
6. at least one NHPS, at least one carbohydrate, and at least one polyol;
7. at least one NHPS, at least one carbohydrate, and at least one amino acid;
8. at least one NHPS, at least one carbohydrate, and at least one other sweet taste improving additive;
9. at least one NHPS, at least one polyol, and at least one amino acid;
10. at least one NHPS, at least one polyol, and at least one other sweet taste improving additive;
11. at least one NHPS, at least one amino acid, and at least one other sweet taste improving additive
12. at least one NHPS, at least one carbohydrate, at least one polyol, and at least one amino acid;
13. at least one NHPS, at least one carbohydrate, at least one polyol, and at least one other sweet taste improving additive;
14. at least one NHPS, at least one polyol, at least one amino acid, and at least one other sweet taste improving additive; and
15. at least one NHPS, at least one carbohydrate, at least one amino acid, and at least one other sweet taste improving additive.

These fifteen major combinations further may be broken down into further combinations in order to improve the overall taste of the NHPS or the orally ingestible compositions comprising a NHPS.

1. Combinations of NHPSs

A single NHPS may be combined with at least one sweet taste improving composition or a plurality of NHPSs may be combined with at least one sweet taste improving composition. Likewise, the sweet taste improving composition can include combinations of the foregoing identified polyols, carbohydrates, amino acids, other sweet taste improving additives, and combinations thereof. Multiple NHPSs can be combined as long as the combined effect does not adversely affect the taste of the NHPS in combination with the sweet taste improving compositions or the taste of the orally ingestible compositions comprising NHPSs. Furthermore, multiple NHPSs can be combined to offset undesirable tastes of the individual NHPSs in the combination.

2. Combinations of Sweet Taste Improving Compositions

As explained above, the sweet taste improving composition is selected from the group consisting of polyols, carbohydrates, amino acids, other sweet taste improving additives, and combinations thereof. The other sweet taste improving additives useful in embodiments of this invention are described herein above. In one embodiment, a single sweet taste improving composition may be used with a single NHPS. In another embodiment of the present invention, a single sweet taste improving composition may be used with one or more NHPSs. In yet another embodiment, one or more sweet taste improving compositions may be used with a single NHPS. In a further embodiment, there may be a plurality of sweet taste improving compositions used in combination with one or more NHPSs. Thus, non-limiting examples of sweet taste improving composition combinations for embodiments of this invention include:

i. at least one polyol, at least one carbohydrate, at least one amino acid, and at least one other sweet taste improving additive;
ii. at least one polyol, at least one carbohydrate, and at least one other sweet taste improving additive;
iii. at least one polyol and at least one other sweet taste improving additive;
iv. at least one polyol and at least one carbohydrate;
v. at least one carbohydrate and at least one other sweet taste improving additive;
vi. at least one polyol and at least one amino acid;
vii. at least one carbohydrate and at least one amino acid;
viii. at least one amino acid and at least one other sweet taste improving additive.

Other sweet taste improving composition combinations in accordance with embodiments of this invention include:

1. at least one polyol, at least one carbohydrate, and at least one amino acid;
2. at least one polyol, at least one carbohydrate, and at least one polyamino acid;
3. at least one polyol, at least one carbohydrate, and at least one sugar acid;
4. at least one polyol, at least one carbohydrate, and at least one nucleotide;
5. at least one polyol, at least one carbohydrate, and at least one organic acid;
6. at least one polyol, at least one carbohydrate, and at least one inorganic acid;
7. at least one polyol, at least one carbohydrate, and at least one bitter compound;
8. at least one polyol, at least one carbohydrate, and at least one flavorant or flavoring ingredient;
9. at least one polyol, at least one carbohydrate, and at least one polymer;
10. at least one polyol, at least one carbohydrate, and at least one protein or protein hydrolysate or protein hydrolysate with low molecular weight amino acid;
11. at least one polyol, at least one carbohydrate, and at least one surfactant;
12. at least one polyol, at least one carbohydrate, and at least one flavonoid;
13. at least one polyol, at least one carbohydrate, and at least one alcohol;
14. at least one polyol, at least one carbohydrate, and at least one emulsifier;
15. at least one polyol, at least one carbohydrate, and at least one inorganic salt,
16. at least one polyol, at least one carbohydrate, and at least one organic salt,
17. at least one polyol, at least one carbohydrate, at least one amino acid, and at least one other sweet taste improving additive;
18. at least one polyol, at least one carbohydrate, at least one polyamino acid, and at least one other sweet taste improving additive;
19. at least one polyol, at least one carbohydrate, at least one sugar acid, and at least one other sweet taste improving additive;
20. at least one polyol, at least one carbohydrate, at least one nucleotide, and at least one other sweet taste improving additive;
21. at least one polyol, at least one carbohydrate, at least one organic acid, and at least one other sweet taste improving additive;
22. at least one polyol, at least one carbohydrate, at least one inorganic acid, and at least one other sweet taste improving additive;
23. at least one polyol, at least one carbohydrate, at least one bitter compound, and at least one other sweet taste improving additive;
24. at least one polyol, at least one carbohydrate, at least one flavorant or flavoring ingredient, and at least one other sweet taste improving additive;
25. at least one polyol, at least one carbohydrate, at least one polymer, and at least one other sweet taste improving additive;
26. at least one polyol, at least one carbohydrate, at least one protein or protein hydrolysate, and at least one other sweet taste improving additive;
27. at least one polyol, at least one carbohydrate, at least one surfactant, and at least one other sweet taste improving additive;
28. at least one polyol, at least one carbohydrate, at least one flavonoid, and at least one other sweet taste improving additive;
29. at least one polyol, at least one carbohydrate, at least one alcohol, and at least one other sweet taste improving additive;
30. at least one polyol, at least one carbohydrate, at least one amino acid, and at least one polyamino acid;
31. at least one polyol, at least one carbohydrate, at least one amino acid, at least one polyamino acid, and at least one sugar acid;
32. at least one polyol, at least one carbohydrate, at least one amino acid, at least one polyamino acid, at least one sugar acid, and at least one nucleotide;
33. at least one polyol, at least one carbohydrate, at least one amino acid, at least one polyamino acid, at least one sugar acid, at least one nucleotide, and at least one organic acid;
34. at least one polyol, at least one carbohydrate, at least one amino acid, at least one polyamino acid, at least one sugar acid, at least one nucleotide, at least one organic acid, and at least one inorganic acid;
35. at least one polyol, at least one carbohydrate, at least one amino acid, at least one polyamino acid, at least one sugar acid, at least one nucleotide, at least one organic acid, at least one inorganic acid, and at least one bitter compound;
36. at least one polyol, at least one carbohydrate, at least one amino acid, at least one polyamino acid, at least one sugar acid, at least one nucleotide, at least one organic acid, at least one inorganic acid, at least one bitter compound, and at least one polymer;

37. at least one polyol, at least one carbohydrate, at least one amino acid, at least one polyamino acid, at least one sugar acid, at least one nucleotide, at least one organic acid, at least one inorganic acid, at least one bitter compound, at least one polymer, and at least one protein or protein hydrolysate;
38. at least one polyol, at least one carbohydrate, at least one amino acid, at least one polyamino acid, at least one sugar acid, at least one nucleotide, at least one organic acid, at least one inorganic acid, at least one bitter compound, at least one polymer, at least one protein or protein hydrolysate, and at least one surfactant;
39. at least one polyol, at least one carbohydrate, at least one amino acid, at least one polyamino acid, at least one sugar acid, at least one nucleotide, at least one organic acid, at least one inorganic acid, at least one bitter compound, at least one polymer, at least one protein or protein hydrolysate, at least one surfactant, and at least one flavonoid;
40. at least one polyol, at least one carbohydrate, at least one amino acid, at least one polyamino acid, at least one sugar acid, at least one nucleotide, at least one organic acid, at least one inorganic acid, at least one bitter compound, at least one polymer, at least one protein or protein hydrolysate, at least one surfactant, at least one flavonoid, and at least one alcohol;
41. at least one polyol, at least one carbohydrate, at least one amino acid, and at least one sugar acid;
42. at least one polyol, at least one carbohydrate, at least one amino acid, and at least one nucleotide;
43. at least one polyol, at least one carbohydrate, at least one amino acid, and at least one organic acid;
44. at least one polyol, at least one carbohydrate, at least one amino acid, and at least one inorganic acid;
45. at least one polyol, at least one carbohydrate, at least one amino acid, and at least one bitter compound;
46. at least one polyol, at least one carbohydrate, at least one amino acid, and at least one polymer;
47. at least one polyol, at least one carbohydrate, at least one amino acid, and at least one protein or protein hydrolysate;
48. at least one polyol, at least one carbohydrate, at least one amino acid, and at least one surfactant;
49. at least one polyol, at least one carbohydrate, at least one amino acid, and at least one flavonoid;
50. at least one polyol, at least one carbohydrate, at least one amino acid, and at least one alcohol;
51. at least one polyol, at least one carbohydrate, at least one polyamino acid, and at least one sugar acid;
52. at least one polyol, at least one carbohydrate, at least one polyamino acid, and at least one nucleotide;
53. at least one polyol, at least one carbohydrate, at least one polyamino acid, and at least one organic acid;
54. at least one polyol, at least one carbohydrate, at least one polyamino acid, and at least one inorganic acid;
55. at least one polyol, at least one carbohydrate, at least one polyamino acid, and at least one bitter compound;
56. at least one polyol, at least one carbohydrate, at least one polyamino acid, and at least one polymer;
57. at least one polyol, at least one carbohydrate, at least one polyamino acid, and at least one protein or protein hydrolysate;
58. at least one polyol, at least one carbohydrate, at least one polyamino acid, and at least one surfactant;
59. at least one polyol, at least one carbohydrate, at least one polyamino acid, and at least one flavonoid;
60. at least one polyol, at least one carbohydrate, at least one polyamino acid, and at least one alcohol;
61. at least one polyol, at least one carbohydrate, at least one sugar acid, and at least one nucleotide;
62. at least one polyol, at least one carbohydrate, at least one sugar acid, and at least one organic acid;
63. at least one polyol, at least one carbohydrate, at least one sugar acid, and at least one inorganic acid;
64. at least one polyol, at least one carbohydrate, at least one sugar acid, and at least one bitter compound;
65. at least one polyol, at least one carbohydrate, at least one sugar acid, and at least one polymer;
66. at least one polyol, at least one carbohydrate, at least one sugar acid, and at least one protein or protein hydrolysate;
67. at least one polyol, at least one carbohydrate, at least one sugar acid, and at least one surfactant;
68. at least one polyol, at least one carbohydrate, at least one sugar acid, and at least one flavonoid;
69. at least one polyol, at least one carbohydrate, at least one sugar acid, and at least one alcohol;
70. at least one polyol, at least one carbohydrate, at least one nucleotide, and at least one organic acid;
71. at least one polyol, at least one carbohydrate, at least one nucleotide, and at least one inorganic acid;
72. at least one polyol, at least one carbohydrate, at least one nucleotide, and at least one bitter compound;
73. at least one polyol, at least one carbohydrate, at least one nucleotide, and at least one polymer;
74. at least one polyol, at least one carbohydrate, at least one nucleotide, and at least one protein or protein hydrolysate;
75. at least one polyol, at least one carbohydrate, at least one nucleotide, and at least one surfactant;
76. at least one polyol, at least one carbohydrate, at least one nucleotide, and at least one flavonoid;
77. at least one polyol, at least one carbohydrate, at least one nucleotide, and at least one alcohol;
78. at least one polyol, at least one carbohydrate, at least one organic acid, and at least one inorganic acid;
79. at least one polyol, at least one carbohydrate, at least one organic acid, and at least one bitter compound;
80. at least one polyol, at least one carbohydrate, at least one organic acid, and at least one polymer;
81. at least one polyol, at least one carbohydrate, at least one organic acid, and at least one protein or protein hydrolysate;
82. at least one polyol, at least one carbohydrate, at least one organic acid, and at least one surfactant;
83. at least one polyol, at least one carbohydrate, at least one organic acid, and at least one flavonoid;
84. at least one polyol, at least one carbohydrate, at least one organic acid, and at least one alcohol;
85. at least one polyol, at least one carbohydrate, at least one inorganic acid, and at least one bitter compound;
86. at least one polyol, at least one carbohydrate, at least one inorganic acid, and at least one polymer;
87. at least one polyol, at least one carbohydrate, at least one inorganic acid, and at least one protein or protein hydrolysate;
88. at least one polyol, at least one carbohydrate, at least one inorganic acid, and at least one surfactant;
89. at least one polyol, at least one carbohydrate, at least one inorganic acid, and at least one flavonoid;
90. at least one polyol, at least one carbohydrate, at least one inorganic acid, and at least one alcohol;

91. at least one polyol, at least one carbohydrate, at least one bitter compound, and at least one polymer;
92. at least one polyol, at least one carbohydrate, at least one bitter compound, and at least one protein or protein hydrolysate;
93. at least one polyol, at least one carbohydrate, at least one bitter compound, and at least one surfactant;
94. at least one polyol, at least one carbohydrate, at least one bitter compound, and at least one flavonoid;
95. at least one polyol, at least one carbohydrate, at least one bitter compound, and at least one alcohol;
96. at least one polyol, at least one carbohydrate, at least one polymer, and at least one protein or protein hydrolysate;
97. at least one polyol, at least one carbohydrate, at least one polymer, and at least one surfactant;
98. at least one polyol, at least one carbohydrate, at least one polymer, and at least one flavonoid;
99. at least one polyol, at least one carbohydrate, at least one polymer, and at least one alcohol;
100. at least one polyol, at least one carbohydrate, at least one protein or protein hydrolysate, and at least one surfactant;
101. at least one polyol, at least one carbohydrate, at least one protein or protein hydrolysate, and at least one flavonoid;
102. at least one polyol, at least one carbohydrate, at least one surfactant, and at least one flavonoid;
103. at least one polyol, at least one carbohydrate, at least one surfactant, and at least one alcohol; and
104. at least one polyol, at least one carbohydrate, at least one flavonoid, and at least one alcohol.

Other sweet taste improving composition combinations in accordance with embodiments of this invention include:

1. at least one polyol and at least one amino acid;
2. at least one polyol and at least one polyamino acid;
3. at least one polyol and at least one sugar acid;
4. at least one polyol and at least one nucleotide;
5. at least one polyol and at least one organic acid;
6. at least one polyol and at least one inorganic acid;
7. at least one polyol and at least one bitter compound;
8. at least one polyol and at least one flavorant or flavoring ingredient;
9. at least one polyol and at least one polymer;
10. at least one polyol and at least one protein or protein hydrolysate;
11. at least one polyol and at least one surfactant;
12. at least one polyol and at least one flavonoid;
13. at least one polyol and at least one alcohol;
14. at least one polyol and at least one emulsifier;
15. at least one polyol and at least one inorganic salt;
16. at least one polyol and at least one organic salt;
17. at least one polyol and at least one protein or protein hydrolysate or mixture of low molecular weight amino acids;
18. at least one polyol, at least one amino acid, and at least one other sweet taste improving additive;
19. at least one polyol, at least one polyamino acid, and at least one other sweet taste improving additive;
20. at least one polyol, at least one sugar acid, and at least one other sweet taste improving additive;
21. at least one polyol, at least one nucleotide, and at least one other sweet taste improving additive;
22. at least one polyol, at least one organic acid, and at least one other sweet taste improving additive;
23. at least one polyol, at least one inorganic acid, and at least one other sweet taste improving additive;
24. at least one polyol, at least one bitter compound, and at least one other sweet taste improving additive;
25. at least one polyol, at least one flavorant or flavoring ingredient, and at least one other sweet taste improving additive;
26. at least one polyol, at least one polymer, and at least one other sweet taste improving additive;
27. at least one polyol, at least one protein or protein hydrolysate, and at least one other sweet taste improving additive;
28. at least one polyol, at least one surfactant, and at least one other sweet taste improving additive;
29. at least one polyol, at least one flavonoid, and at least one other sweet taste improving additive;
30. at least one polyol, at least one alcohol, and at least one other sweet taste improving additive;
31. at least one polyol, at least one amino acid, and at least one polyamino acid;
32. at least one polyol, at least one amino acid, at least one polyamino acid, and at least one sugar acid;
33. at least one polyol, at least one amino acid, at least one polyamino acid, at least one sugar acid, and at least one nucleotide;
34. at least one polyol, at least one amino acid, at least one polyamino acid, at least one sugar acid, at least one nucleotide, and at least one organic acid;
35. at least one polyol, at least one amino acid, at least one polyamino acid, at least one sugar acid, at least one nucleotide, at least one organic acid, and at least one inorganic acid;
36. at least one polyol, at least one amino acid, at least one polyamino acid, at least one sugar acid, at least one nucleotide, at least one organic acid, at least one inorganic acid, and at least one bitter compound;
37. at least one polyol, at least one amino acid, at least one polyamino acid, at least one sugar acid, at least one nucleotide, at least one organic acid, at least one inorganic acid, at least one bitter compound, and at least one polymer;
38. at least one polyol, at least one amino acid, at least one polyamino acid, at least one sugar acid, at least one nucleotide, at least one organic acid, at least one inorganic acid, at least one bitter compound, at least one polymer, and at least one protein or protein hydrolysate;
39. at least one polyol, at least one amino acid, at least one polyamino acid, at least one sugar acid, at least one nucleotide, at least one organic acid, at least one inorganic acid, at least one bitter compound, at least one polymer, at least one protein or protein hydrolysate, and at least one surfactant;
40. at least one polyol, at least one amino acid, at least one polyamino acid, at least one sugar acid, at least one nucleotide, at least one organic acid, at least one inorganic acid, at least one bitter compound, at least one polymer, at least one protein or protein hydrolysate, at least one surfactant, and at least one flavonoid;
41. at least one polyol, at least one amino acid, at least one polyamino acid, at least one sugar acid, at least one nucleotide, at least one organic acid, at least one inorganic acid, at least one bitter compound, at least one polymer, at least one protein or protein hydrolysate, at least one surfactant, at least one flavonoid, and at least one alcohol;
42. at least one polyol, at least one amino acid, and at least one sugar acid;
43. at least one polyol, at least one amino acid, and at least one nucleotide;

44. at least one polyol, at least one amino acid, and at least one organic acid;
45. at least one polyol, at least one amino acid, and at least one inorganic acid;
46. at least one polyol, at least one amino acid, and at least one bitter compound;
47. at least one polyol, at least one amino acid, and at least one polymer;
48. at least one polyol, at least one amino acid, and at least one protein or protein hydrolysate;
49. at least one polyol, at least one amino acid, and at least one surfactant;
50. at least one polyol, at least one amino acid, and at least one flavonoid;
51. at least one polyol, at least one amino acid, and at least one alcohol;
52. at least one polyol, at least one polyamino acid, and at least one sugar acid;
53. at least one polyol, at least one polyamino acid, and at least one nucleotide;
54. at least one polyol, at least one polyamino acid, and at least one organic acid;
55. at least one polyol, at least one polyamino acid, and at least one organic salt;
56. at least one polyol, at least one polyamino acid, and at least one inorganic acid;
57. at least one polyol, at least one polyamino acid, and at least one inorganic salt;
58. at least one polyol, at least one polyamino acid, and at least one bitter compound;
59. at least one polyol, at least one polyamino acid, and at least one polymer;
60. at least one polyol, at least one polyamino acid, and at least one protein or protein hydrolysate;
61. at least one polyol, at least one polyamino acid, and at least one surfactant;
62. at least one polyol, at least one polyamino acid, and at least one flavonoid;
63. at least one polyol, at least one polyamino acid, and at least one alcohol;
64. at least one polyol, at least one sugar acid, and at least one nucleotide;
65. at least one polyol, at least one sugar acid, and at least one organic acid;
66. at least one polyol, at least one sugar acid, and at least one inorganic acid;
67. at least one polyol, at least one sugar acid, and at least one bitter compound;
68. at least one polyol, at least one sugar acid, and at least one polymer;
69. at least one polyol, at least one sugar acid, and at least one protein or protein hydrolysate;
70. at least one polyol, at least one sugar acid, and at least one surfactant;
71. at least one polyol, at least one sugar acid, and at least one flavonoid;
72. at least one polyol, at least one sugar acid, and at least one alcohol;
73. at least one polyol, at least one nucleotide, and at least one organic acid;
74. at least one polyol, at least one nucleotide, and at least one inorganic acid;
75. at least one polyol, at least one nucleotide, and at least one bitter compound;
76. at least one polyol, at least one nucleotide, and at least one polymer;
77. at least one polyol, at least one nucleotide, and at least one or protein hydrolysate;
78. at least one polyol, at least one nucleotide, and at least one surfactant;
79. at least one polyol, at least one nucleotide, and at least one flavonoid;
80. at least one polyol, at least one nucleotide, and at least one alcohol;
81. at least one polyol, at least one organic acid, and at least one inorganic acid;
82. at least one polyol, at least one organic acid, and at least one bitter compound;
83. at least one polyol, at least one organic acid, and at least one polymer;
84. at least one polyol, at least one organic acid, and at least one protein or protein hydrolysate;
85. at least one polyol, at least one organic acid, and at least one surfactant;
86. at least one polyol, at least one organic acid, and at least one flavonoid;
87. at least one polyol, at least one organic acid, and at least one alcohol;
88. at least one polyol, at least one inorganic acid, and at least one bitter compound;
89. at least one polyol, at least one inorganic acid, and at least one polymer;
90. at least one polyol, at least one inorganic acid, and at least one protein or protein hydrolysate;
91. at least one polyol, at least one inorganic acid, and at least one surfactant;
92. at least one polyol, at least one inorganic acid, and at least one flavonoid;
93. at least one polyol, at least one inorganic acid, and at least one alcohol;
94. at least one polyol, at least one bitter compound, and at least one polymer;
95. at least one polyol, at least one bitter compound, and at least one protein or protein hydrolysate;
96. at least one polyol, at least one bitter compound, and at least one surfactant;
97. at least one polyol, at least one bitter compound, and at least one flavonoid;
98. at least one polyol, at least one bitter compound, and at least one alcohol;
99. at least one polyol, at least one polymer, and at least one protein or protein hydrolysate;
100. at least one polyol, at least one polymer, and at least one surfactant;
101. at least one polyol, at least one polymer, and at least one flavonoid;
102. at least one polyol, at least one polymer, and at least one alcohol;
103. at least one polyol, at least one protein or protein hydrolysate, and at least one surfactant;
104. at least one polyol, at least one protein or protein hydrolysate, and at least one flavonoid;
105. at least one polyol, at least one surfactant, and at least one flavonoid;
106. at least one polyol, at least one surfactant, and at least one alcohol;
107. at least one polyol, at least one flavonoid, and at least one alcohol;
108. at least one sweet taste improving additive and erythritol;
109. at least one sweet taste improving additive and maltitol;

110. at least one sweet taste improving additive and mannitol;
111. at least one sweet taste improving additive and sorbitol;
112. at least one sweet taste improving additive and lactitol;
113. at least one sweet taste improving additive and xylitol;
114. at least one sweet taste improving additive and isomalt;
115. at least one sweet taste improving additive and propylene glycol;
116. at least one sweet taste improving additive and glycerol;
117. at least one sweet taste improving additive and palatinose;
118. at least one sweet taste improving additive and reduced isomalto-oligosaccharides;
119. at least one sweet taste improving additive and reduced xylo-oligosaccharides;
120. at least one sweet taste improving additive and reduced gentio-oligosaccharides;
121. at least one sweet taste improving additive and reduced maltose syrup;
122. at least one sweet taste improving additive and reduced glucose syrup;
123. at least one sweet taste improving additive, erythritol, and at least one other polyol;
124. at least one sweet taste improving additive, maltitol, and at least one other polyol;
125. at least one sweet taste improving additive, mannitol, and at least one other polyol;
126. at least one sweet taste improving additive, sorbitol, and at least one other polyol;
127. at least one sweet taste improving additive, lactitol, and at least one other polyol;
128. at least one sweet taste improving additive, xylitol, and at least one other polyol;
129. at least one sweet taste improving additive, isomalt, and at least one other polyol;
130. at least one sweet taste improving additive, propylene glycol, and at least one other polyol;
131. at least one sweet taste improving additive, glycerol, and at least one other polyol;
132. at least one sweet taste improving additive, palatinose, and at least one other polyol;
133. at least one sweet taste improving additive, reduced isomalto-oligosaccharides, and at least one other polyol;
134. at least one sweet taste improving additive, reduced xylo-oligosaccharides, and at least one other polyol;
135. at least one sweet taste improving additive, reduced gentio-oligosaccharides, and at least one other polyol;
136. at least one sweet taste improving additive, reduced maltose syrup, and at least one other polyol; and
137. at least one sweet taste improving additive, reduced glucose syrup, and at least one other polyol.

Other sweet taste improving composition combinations in accordance with embodiments of this invention include:
1. at least one polyol and tagatose;
2. at least one polyol and trehalose;
3. at least one polyol and galactose;
4. at least one polyol and rhamnose;
5. at least one polyol and dextrin;
6. at least one polyol and cyclodextrin;
7. at least one polyol and α-cyclodextrin, β-cyclodextrin, or γ-cyclodextrin;
8. at least one polyol and maltodextrin;
9. at least one polyol and dextran;
10. at least one polyol and sucrose;
11. at least one polyol and glucose;
12. at least one polyol and fructose;
13. at least one polyol and threose;
14. at least one polyol and arabinose;
15. at least one polyol and xylose;
16. at least one polyol and lyxose;
17. at least one polyol and allose;
18. at least one polyol and altrose;
19. at least one polyol and mannose;
20. at least one polyol and idose;
21. at least one polyol and talose;
22. at least one polyol and lactose;
23. at least one polyol and maltose;
24. at least one polyol and invert sugar;
25. at least one polyol and trehalose;
26. at least one polyol and isotrehalose;
27. at least one polyol and neotrehalose;
28. at least one polyol and palatinose;
29. at least one polyol and galactose;
30. at least one polyol and beet oligosaccharides;
31. at least one polyol and isomalto-oligosaccharides;
32. at least one polyol and isomaltose;
33. at least one polyol and isomaltotriose;
34. at least one polyol and panose;
35. at least one polyol and xylo-oligosaccharides;
36. at least one polyol and xylotriose;
37. at least one polyol and xylobiose;
38. at least one polyol and gentio-oligoscaccharides;
39. at least one polyol and gentiobiose;
40. at least one polyol and gentiotriose;
41. at least one polyol and gentiotetraose;
42. at least one polyol and sorbose;
43. at least one polyol and nigero-oligosaccharides;
44. at least one polyol and palatinose oligosaccharides;
45. at least one polyol and fucose;
46. at least one polyol and fructooligosaccharides;
47. at least one polyol and kestose;
48. at least one polyol and nystose;
49. at least one polyol and maltotetraol;
50. at least one polyol and maltotriol;
51. at least one polyol and malto-oligosaccharides;
52. at least one polyol and maltotriose;
53. at least one polyol and maltotetraose;
54. at least one polyol and maltopentaose;
55. at least one polyol and maltohexaose;
56. at least one polyol and maltoheptaose;
57. at least one polyol and lactulose;
58. at least one polyol and melibiose;
59. at least one polyol and raffinose;
60. at least one polyol and rhamnose;
61. at least one polyol and ribose;
62. at least one polyol and isomerized liquid sugars;
63. at least one polyol and high fructose corn syrup (e.g. HFCS55, HFCS42, or HFCS90) or starch syrup;
64. at least one polyol and coupling sugars;
65. at least one polyol and soybean oligosaccharides;
66. at least one polyol and glucose syrup;
67. at least one polyol, tagatose, and at least one other carbohydrate;
68. at least one polyol, trehalose, and at least one other carbohydrate;
69. at least one polyol, galactose, and at least one other carbohydrate;
70. at least one polyol, rhamnose, and at least one other carbohydrate;

71. at least one polyol, dextrin, and at least one other carbohydrate;
72. at least one polyol, cyclodextrin, and at least one other carbohydrate;
73. at least one polyol, β-cyclodextrin, and at least one other carbohydrate;
74. at least one polyol, maltodextrin, and at least one other carbohydrate;
75. at least one polyol, dextran, and at least one other carbohydrate;
76. at least one polyol, sucrose, and at least one other carbohydrate;
77. at least one polyol, glucose, and at least one other carbohydrate;
78. at least one polyol, fructose, and at least one other carbohydrate;
79. at least one polyol, threose, and at least one other carbohydrate;
80. at least one polyol, arabinose, and at least one other carbohydrate;
81. at least one polyol, xylose, and at least one other carbohydrate;
82. at least one polyol, lyxose, and at least one other carbohydrate;
83. at least one polyol, allose, and at least one other carbohydrate;
84. at least one polyol, altrose, and at least one other carbohydrate;
85. at least one polyol, mannose, and at least one other carbohydrate;
86. at least one polyol, idose, and at least one other carbohydrate;
87. at least one polyol, talose, and at least one other carbohydrate;
88. at least one polyol, lactose, and at least one other carbohydrate;
89. at least one polyol, maltose, and at least one other carbohydrate;
90. at least one polyol, invert sugar, and at least one other carbohydrate;
91. at least one polyol, trehalose, and at least one other carbohydrate;
92. at least one polyol, isotrehalose, and at least one other carbohydrate;
93. at least one polyol, neotrehalose, and at least one other carbohydrate;
94. at least one polyol, palatinose, and at least one other carbohydrate;
95. at least one polyol, galactose, and at least one other carbohydrate;
96. at least one polyol, beet oligosaccharides, and at least one other carbohydrate;
97. at least one polyol, isomalto-oligosaccharides, and at least one other carbohydrate;
98. at least one polyol, isomaltose, and at least one other carbohydrate;
99. at least one polyol, isomaltotriose, and at least one other carbohydrate;
100. at least one polyol, panose, and at least one other carbohydrate;
101. at least one polyol, xylo-oligosaccharides, and at least one other carbohydrate;
102. at least one polyol, xylotriose, and at least one other carbohydrate;
103. at least one polyol, xylobiose, and at least one other carbohydrate;
104. at least one polyol, gentio-oligoscaccharides, and at least one other carbohydrate;
105. at least one polyol, gentiobiose, and at least one other carbohydrate;
106. at least one polyol, gentiobiose, and at least one other carbohydrate;
107. at least one polyol, gentiotetraose, and at least one other carbohydrate;
108. at least one polyol, sorbose, and at least one other carbohydrate;
109. at least one polyol, nigero-oligosaccharides, and at least one other carbohydrate;
110. at least one polyol, palatinose oligosaccharides, and at least one other carbohydrate;
111. at least one polyol, fucose, and at least one other carbohydrate;
112. at least one polyol, fructooligosaccharides, and at least one other carbohydrate;
113. at least one polyol, kestose, and at least one other carbohydrate;
114. at least one polyol, nystose, and at least one other carbohydrate;
115. at least one polyol, maltotetraol, and at least one other carbohydrate;
116. at least one polyol, maltotriol, and at least one other carbohydrate;
117. at least one polyol, malto-oligosaccharides, and at least one other carbohydrate;
118. at least one polyol, maltotriose, and at least one other carbohydrate;
119. at least one polyol, maltotetraose, and at least one other carbohydrate;
120. at least one polyol, maltopentaose, and at least one other carbohydrate;
121. at least one polyol, maltohexaose, and at least one other carbohydrate;
122. at least one polyol, maltoheptaose, and at least one other carbohydrate;
123. at least one polyol, lactulose, and at least one other carbohydrate;
124. at least one polyol, melibiose, and at least one other carbohydrate;
125. at least one polyol, raffinose, and at least one other carbohydrate;
126. at least one polyol, rhamnose, and at least one other carbohydrate;
127. at least one polyol, ribose, and at least one other carbohydrate;
128. at least one polyol, isomerized liquid sugars, and at least one other carbohydrate;
129. at least one polyol, high fructose corn syrup (e.g. HFCS55, HFCS42, or HFCS90) or starch syrup, and at least one other carbohydrate;
130. at least one polyol, coupling sugars, and at least one other carbohydrate;
131. at least one polyol, soybean oligosaccharides, and at least one other carbohydrate;
132. at least one polyol, glucose syrup, and at least one other carbohydrate;
133. at least one carbohydrate and erythritol;
134. at least one carbohydrate and maltitol;
135. at least one carbohydrate and mannitol;
136. at least one carbohydrate and sorbitol;
137. at least one carbohydrate and lactitol;
138. at least one carbohydrate and xylitol;
139. at least one carbohydrate and isomalt;
140. at least one carbohydrate and propylene glycol;

141. at least one carbohydrate and glycerol;
142. at least one carbohydrate and palatinose;
143. at least one carbohydrate and reduced isomalto-oligosaccharides;
144. at least one carbohydrate and reduced xylo-oligosaccharides;
145. at least one carbohydrate and reduced gentio-oligosaccharides;
146. at least one carbohydrate and reduced maltose syrup;
147. at least one carbohydrate and reduced glucose syrup;
148. at least one carbohydrate, erythritol, and at least one other polyol;
149. at least one carbohydrate, maltitol, and at least one other polyol;
150. at least one carbohydrate, mannitol, and at least one other polyol;
151. at least one carbohydrate, sorbitol, and at least one other polyol;
152. at least one carbohydrate, lactitol, and at least one other polyol;
153. at least one carbohydrate, xylitol, and at least one other polyol;
154. at least one carbohydrate, isomalt, and at least one other polyol;
155. at least one carbohydrate, propylene glycol, and at least one other polyol;
156. at least one carbohydrate, glycerol, and at least one other polyol;
157. at least one carbohydrate, palatinose, and at least one other polyol;
158. at least one carbohydrate, reduced isomalto-oligosaccharides, and at least one other polyol;
159. at least one carbohydrate, reduced xylo-oligosaccharides, and at least one other polyol;
160. at least one carbohydrate, reduced gentio-oligosaccharides, and at least one other polyol;
161. at least one carbohydrate, reduced maltose syrup, and at least one other polyol; and
162. at least one carbohydrate, reduced glucose syrup, and at least one other polyol.

Other sweet taste improving composition combinations in accordance with embodiments of this invention include:
1. at least one carbohydrate and at least one amino acid;
2. at least one carbohydrate and at least one polyamino acid;
3. at least one carbohydrate and at least one sugar acid;
4. at least one carbohydrate and at least one nucleotide;
5. at least one carbohydrate and at least one organic acid;
6. at least one carbohydrate and at least one inorganic acid;
7. at least one carbohydrate and at least one bitter compound;
8. at least one carbohydrate and at least one flavorant or flavoring ingredient;
9. at least one carbohydrate and at least one polymer;
10. at least one carbohydrate and at least one protein or protein hydrolysate;
11. at least one carbohydrate and at least one surfactant;
12. at least one carbohydrate and at least one flavonoid;
13. at least one carbohydrate and at least one alcohol;
14. at least one carbohydrate and at least one protein or protein hydrolysate or mixture of low molecular weight amino acids;
15. at least one carbohydrate and at least one emulsifier;
16. at least one carbohydrate and at least one inorganic salt;
17. at least one carbohydrate, at least one amino acid, and at least one other sweet taste improving additive;
18. at least one carbohydrate, at least one polyamino acid, and at least one other sweet taste improving additive;
19. at least one carbohydrate, at least one sugar acid, and at least one other sweet taste improving additive;
20. at least one carbohydrate, at least one nucleotide, and at least one other sweet taste improving additive;
21. at least one carbohydrate, at least one organic acid, and at least one other sweet taste improving additive;
22. at least one carbohydrate, at least one inorganic acid, and at least one other sweet taste improving additive;
23. at least one carbohydrate, at least one bitter compound, and at least one other sweet taste improving additive;
24. at least one carbohydrate, at least one flavorant or flavoring ingredient, and at least one other sweet taste improving additive;
25. at least one carbohydrate, at least one polymer, and at least one other sweet taste improving additive;
26. at least one carbohydrate, at least one protein or protein hydrolysate, and at least one other sweet taste improving additive;
27. at least one carbohydrate, at least one surfactant, and at least one other sweet taste improving additive;
28. at least one carbohydrate, at least one flavonoid, and at least one other sweet taste improving additive;
29. at least one carbohydrate, at least one alcohol, and at least one other sweet taste improving additive;
30. at least one carbohydrate, at least one amino acid, and at least one polyamino acid;
31. at least one carbohydrate, at least one amino acid, at least one polyamino acid, and at least one sugar acid;
32. at least one carbohydrate, at least one amino acid, at least one polyamino acid, at least one sugar acid, and at least one nucleotide;
33. at least one carbohydrate, at least one amino acid, at least one polyamino acid, at least one sugar acid, at least one nucleotide, and at least one organic acid;
34. at least one carbohydrate, at least one amino acid, at least one polyamino acid, at least one sugar acid, at least one nucleotide, at least one organic acid, and at least one inorganic acid;
35. at least one carbohydrate, at least one amino acid, at least one polyamino acid, at least one sugar acid, at least one nucleotide, at least one organic acid, at least one inorganic acid, and at least one bitter compound;
36. at least one carbohydrate, at least one amino acid, at least one polyamino acid, at least one sugar acid, at least one nucleotide, at least one organic acid, at least one inorganic acid, at least one bitter compound, and at least one polymer;
37. at least one carbohydrate, at least one amino acid, at least one polyamino acid, at least one sugar acid, at least one nucleotide, at least one organic acid, at least one inorganic acid, at least one bitter compound, at least one polymer, and at least one protein or protein hydrolysate;
38. at least one carbohydrate, at least one amino acid, at least one polyamino acid, at least one sugar acid, at least one nucleotide, at least one organic acid, at least one inorganic acid, at least one bitter compound, at least one polymer, at least one protein or protein hydrolysate, and at least one surfactant;
39. at least one carbohydrate, at least one amino acid, at least one polyamino acid, at least one sugar acid, at least one nucleotide, at least one organic acid, at least one inorganic acid, at least one bitter compound, at least one polymer, at least one protein or protein hydrolysate, at least one surfactant, and at least one flavonoid;

40. at least one carbohydrate, at least one amino acid, at least one polyamino acid, at least one sugar acid, at least one nucleotide, at least one organic acid, at least one inorganic acid, at least one bitter compound, at least one polymer, at least one protein hydrolysate, at least one surfactant, at least one flavonoid, and at least one alcohol;
41. at least one carbohydrate, at least one amino acid, and at least one sugar acid;
42. at least one carbohydrate, at least one amino acid, and at least one nucleotide;
43. at least one carbohydrate, at least one amino acid, and at least one organic acid;
44. at least one carbohydrate, at least one amino acid, and at least one inorganic acid;
45. at least one carbohydrate, at least one amino acid, and at least one bitter compound;
46. at least one carbohydrate, at least one amino acid, and at least one polymer;
47. at least one carbohydrate, at least one amino acid, and at least one protein or protein hydrolysate;
48. at least one carbohydrate, at least one amino acid, and at least one surfactant;
49. at least one carbohydrate, at least one amino acid, and at least one flavonoid;
50. at least one carbohydrate, at least one amino acid, and at least one alcohol;
51. at least one carbohydrate, at least one polyamino acid, and at least one sugar acid;
52. at least one carbohydrate, at least one polyamino acid, and at least one nucleotide;
53. at least one carbohydrate, at least one polyamino acid, and at least one organic acid;
54. at least one carbohydrate, at least one polyamino acid, and at least one inorganic acid;
55. at least one carbohydrate, at least one polyamino acid, and at least one bitter compound;
56. at least one carbohydrate, at least one polyamino acid, and at least one polymer;
57. at least one carbohydrate, at least one polyamino acid, and at least one protein or protein hydrolysate;
58. at least one carbohydrate, at least one polyamino acid, and at least one surfactant;
59. at least one carbohydrate, at least one polyamino acid, and at least one flavonoid;
60. at least one carbohydrate, at least one polyamino acid, and at least one alcohol;
61. at least one carbohydrate, at least one sugar acid, and at least one nucleotide;
62. at least one carbohydrate, at least one sugar acid, and at least one organic acid;
63. at least one carbohydrate, at least one sugar acid, and at least one inorganic acid;
64. at least one carbohydrate, at least one sugar acid, and at least one bitter compound;
65. at least one carbohydrate, at least one sugar acid, and at least one polymer;
66. at least one carbohydrate, at least one sugar acid, and at least one protein or protein hydrolysate;
67. at least one carbohydrate, at least one sugar acid, and at least one surfactant;
68. at least one carbohydrate, at least one sugar acid, and at least one flavonoid;
69. at least one carbohydrate, at least one sugar acid, and at least one alcohol;
70. at least one carbohydrate, at least one nucleotide, and at least one organic acid;
71. at least one carbohydrate, at least one nucleotide, and at least one inorganic acid;
72. at least one carbohydrate, at least one nucleotide, and at least one bitter compound;
73. at least one carbohydrate, at least one nucleotide, and at least one polymer;
74. at least one carbohydrate, at least one nucleotide, and at least one protein or protein hydrolysate;
75. at least one carbohydrate, at least one nucleotide, and at least one surfactant;
76. at least one carbohydrate, at least one nucleotide, and at least one flavonoid;
77. at least one carbohydrate, at least one nucleotide, and at least one alcohol;
78. at least one carbohydrate, at least one organic acid, and at least one inorganic acid;
79. at least one carbohydrate, at least one organic acid, and at least one bitter compound;
80. at least one carbohydrate, at least one organic acid, and at least one polymer;
81. at least one carbohydrate, at least one organic acid, and at least one protein or protein hydrolysate;
82. at least one carbohydrate, at least one organic acid, and at least one surfactant;
83. at least one carbohydrate, at least one organic acid, and at least one flavonoid;
84. at least one carbohydrate, at least one organic acid, and at least one alcohol;
85. at least one carbohydrate, at least one inorganic acid, and at least one bitter compound;
86. at least one carbohydrate, at least one inorganic acid, and at least one polymer;
87. at least one carbohydrate, at least one inorganic acid, and at least one protein or protein hydrolysate;
88. at least one carbohydrate, at least one inorganic acid, and at least one surfactant;
89. at least one carbohydrate, at least one inorganic acid, and at least one flavonoid;
90. at least one carbohydrate, at least one inorganic acid, and at least one alcohol;
91. at least one carbohydrate, at least one bitter compound, and at least one polymer;
92. at least one carbohydrate, at least one bitter compound, and at least one protein or protein hydrolysate;
93. at least one carbohydrate, at least one bitter compound, and at least one surfactant;
94. at least one carbohydrate, at least one bitter compound, and at least one flavonoid;
95. at least one carbohydrate, at least one bitter compound, and at least one alcohol;
96. at least one carbohydrate, at least one polymer, and at least one protein or protein hydrolysate;
97. at least one carbohydrate, at least one polymer, and at least one surfactant;
98. at least one carbohydrate, at least one polymer, and at least one flavonoid;
99. at least one carbohydrate, at least one polymer, and at least one alcohol;
100. at least one carbohydrate, at least one protein or protein hydrolysate, and at least one surfactant;
101. at least one carbohydrate, at least one protein or protein hydrolysate, and at least one flavonoid;
102. at least one carbohydrate, at least one surfactant, and at least one flavonoid;
103. at least one carbohydrate, at least one surfactant, and at least one alcohol;

104. at least one carbohydrate, at least one flavonoid, and at least one alcohol;
105. at least one sweet taste improving additive and D-tagatose;
106. at least one sweet taste improving additive and trehalose;
107. at least one sweet taste improving additive and D-galactose;
108. at least one sweet taste improving additive and rhamnose;
109. at least one sweet taste improving additive and dextrin;
110. at least one sweet taste improving additive and cyclodextrin;
111. at least one sweet taste improving additive and β-cyclodextrin;
112. at least one sweet taste improving additive and maltodextrin;
113. at least one sweet taste improving additive and dextran;
114. at least one sweet taste improving additive and sucrose;
115. at least one sweet taste improving additive and glucose;
116. at least one sweet taste improving additive and fructose;
117. at least one sweet taste improving additive and threose;
118. at least one sweet taste improving additive and arabinose;
119. at least one sweet taste improving additive and xylose;
120. at least one sweet taste improving additive and lyxose;
121. at least one sweet taste improving additive and allose;
122. at least one sweet taste improving additive and altrose;
123. at least one sweet taste improving additive and mannose;
124. at least one sweet taste improving additive and idose;
125. at least one sweet taste improving additive and talose;
126. at least one sweet taste improving additive and lactose;
127. at least one sweet taste improving additive and maltose;
128. at least one sweet taste improving additive and invert sugar;
129. at least one sweet taste improving additive and trehalose;
130. at least one sweet taste improving additive and isotrehalose;
131. at least one sweet taste improving additive and neotrehalose;
132. at least one sweet taste improving additive and palatinose;
133. at least one sweet taste improving additive and galactose;
134. at least one sweet taste improving additive and beet oligosaccharides;
135. at least one sweet taste improving additive and isomalto-oligosaccharides;
136. at least one sweet taste improving additive and isomaltose;
137. at least one sweet taste improving additive and isomaltotriose;
138. at least one sweet taste improving additive and panose;
139. at least one sweet taste improving additive and xylo-oligosaccharides;
140. at least one sweet taste improving additive and xylotriose;
141. at least one sweet taste improving additive and xylobiose;
142. at least one sweet taste improving additive and gentio-oligoscaccharides;
143. at least one sweet taste improving additive and gentiobiose;
144. at least one sweet taste improving additive and gentiotriose;
145. at least one sweet taste improving additive and gentiotetraose;
146. at least one sweet taste improving additive and sorbose;
147. at least one sweet taste improving additive and nigero-oligosaccharides;
148. at least one sweet taste improving additive and palatinose oligosaccharides;
149. at least one sweet taste improving additive and fucose;
150. at least one sweet taste improving additive and fructooligosaccharides;
151. at least one sweet taste improving additive and kestose;
152. at least one sweet taste improving additive and nystose;
153. at least one sweet taste improving additive and maltotetraol;
154. at least one sweet taste improving additive and maltotriol;
155. at least one sweet taste improving additive and malto-oligosaccharides;
156. at least one sweet taste improving additive and maltotriose;
157. at least one sweet taste improving additive and maltotetraose;
158. at least one sweet taste improving additive and maltopentaose;
159. at least one sweet taste improving additive and maltohexaose;
160. at least one sweet taste improving additive and maltoheptaose;
161. at least one sweet taste improving additive and lactulose;
162. at least one sweet taste improving additive and melibiose;
163. at least one sweet taste improving additive and raffinose;
164. at least one sweet taste improving additive and rhamnose;
165. at least one sweet taste improving additive and ribose;
166. at least one sweet taste improving additive and isomerized liquid sugars;
167. at least one sweet taste improving additive and high fructose corn syrup (e.g., HFCS55, HFCS42, or HFCS90) or starch syrup;
168. at least one sweet taste improving additive and coupling sugars;
169. at least one sweet taste improving additive and soybean oligosaccharides;
170. at least one sweet taste improving additive and glucose syrup;
171. at least one sweet taste improving additive, D-tagatose, and at least one other carbohydrate;
172. at least one sweet taste improving additive, trehalose, and at least one other carbohydrate;
173. at least one sweet taste improving additive, D-galactose, and at least one other carbohydrate;

174. at least one sweet taste improving additive, rhamnose, and at least one other carbohydrate;
175. at least one sweet taste improving additive, dextrin, and at least one other carbohydrate;
176. at least one sweet taste improving additive, cyclodextrin, and at least one other carbohydrate;
177. at least one sweet taste improving additive, β-cyclodextrin, and at least one other carbohydrate;
178. at least one sweet taste improving additive, maltodextrin, and at least one other carbohydrate;
179. at least one sweet taste improving additive, dextran, and at least one other carbohydrate;
180. at least one sweet taste improving additive, sucrose, and at least one other carbohydrate;
181. at least one sweet taste improving additive, glucose, and at least one other carbohydrate;
182. at least one sweet taste improving additive, fructose, and at least one other carbohydrate;
183. at least one sweet taste improving additive, threose, and at least one other carbohydrate;
184. at least one sweet taste improving additive, arabinose, and at least one other carbohydrate;
185. at least one sweet taste improving additive, xylose, and at least one other carbohydrate;
186. at least one sweet taste improving additive, lyxose, and at least one other carbohydrate;
187. at least one sweet taste improving additive, allose, and at least one other carbohydrate;
188. at least one sweet taste improving additive, altrose, and at least one other carbohydrate;
189. at least one sweet taste improving additive, mannose, and at least one other carbohydrate;
190. at least one sweet taste improving additive, idose, and at least one other carbohydrate;
191. at least one sweet taste improving additive, talose, and at least one other carbohydrate;
192. at least one sweet taste improving additive, lactose, and at least one other carbohydrate;
193. at least one sweet taste improving additive, maltose, and at least one other carbohydrate;
194. at least one sweet taste improving additive, invert sugar, and at least one other carbohydrate;
195. at least one sweet taste improving additive, trehalose, and at least one other carbohydrate;
196. at least one sweet taste improving additive, isotrehalose, and at least one other carbohydrate;
197. at least one sweet taste improving additive, neotrehalose, and at least one other carbohydrate;
198. at least one sweet taste improving additive, palatinose, and at least one other carbohydrate;
199. at least one sweet taste improving additive, galactose, and at least one other carbohydrate;
200. at least one sweet taste improving additive, beet oligosaccharides, and at least one other carbohydrate;
201. at least one sweet taste improving additive, isomaltooligosaccharides, and at least one other carbohydrate;
202. at least one sweet taste improving additive, isomaltose, and at least one other carbohydrate;
203. at least one sweet taste improving additive, isomaltotriose, and at least one other carbohydrate;
204. at least one sweet taste improving additive, panose, and at least one other carbohydrate;
205. at least one sweet taste improving additive, xylo-oligosaccharides, and at least one other carbohydrate;
206. at least one sweet taste improving additive, xylotriose, and at least one other carbohydrate;
207. at least one sweet taste improving additive, xylobiose, and at least one other carbohydrate;
208. at least one sweet taste improving additive, gentio-oligoscaccharides, and at least one other carbohydrate;
209. at least one sweet taste improving additive, gentiobiose, and at least one other carbohydrate;
210. at least one sweet taste improving additive, gentiotriose, and at least one other carbohydrate;
211. at least one sweet taste improving additive, gentiotetraose, and at least one other carbohydrate;
212. at least one sweet taste improving additive, sorbose, and at least one other carbohydrate;
213. at least one sweet taste improving additive, nigero-oligosaccharides, and at least one other carbohydrate;
214. at least one sweet taste improving additive, palatinose oligosaccharides, and at least one other carbohydrate;
215. at least one sweet taste improving additive, fucose, and at least one other carbohydrate;
216. at least one sweet taste improving additive, fructooligosaccharides, and at least one other carbohydrate;
217. at least one sweet taste improving additive, kestose, and at least one other carbohydrate;
218. at least one sweet taste improving additive, nystose, and at least one other carbohydrate;
219. at least one sweet taste improving additive, maltotetraol, and at least one other carbohydrate;
220. at least one sweet taste improving additive, maltotriol, and at least one other carbohydrate;
221. at least one sweet taste improving additive, malto-oligosaccharides, and at least one other carbohydrate;
222. at least one sweet taste improving additive, maltotriose, and at least one other carbohydrate;
223. at least one sweet taste improving additive, maltotetraose, and at least one other carbohydrate;
224. at least one sweet taste improving additive, maltopentaose, and at least one other carbohydrate;
225. at least one sweet taste improving additive, maltohexaose, and at least one other carbohydrate;
226. at least one sweet taste improving additive, maltoheptaose, and at least one other carbohydrate;
227. at least one sweet taste improving additive, lactulose, and at least one other carbohydrate;
228. at least one sweet taste improving additive, melibiose, and at least one other carbohydrate;
229. at least one sweet taste improving additive, raffinose, and at least one other carbohydrate;
230. at least one sweet taste improving additive, rhamnose, and at least one other carbohydrate;
231. at least one sweet taste improving additive, ribose, and at least one other carbohydrate;
232. at least one sweet taste improving additive, isomerized liquid sugars, and at least one other carbohydrate;
233. at least one sweet taste improving additive, high fructose corn syrup (e.g. HFCS55, HFCS42, or HFCS90) or starch syrup, and at least one other carbohydrate;
234. at least one sweet taste improving additive, coupling sugars, and at least one other carbohydrate;
235. at least one sweet taste improving additive, soybean oligosaccharides, and at least one other carbohydrate; and
236. at least one sweet taste improving additive, glucose syrup, and at least one other carbohydrate.

In one embodiment, combinations of the at least one NHPS and at least one sweet taste improving composition suppress, reduce, or eliminate undesirable taste and impart sugar-like characteristics to the NHPS composition. As used herein, the phrase "undesirable taste" includes any taste property which is not imparted by sugars such as glucose, sucrose, fructose, or similar saccharides. Non-limiting examples of undesirable tastes include delayed sweetness onset, lingering sweet aftertaste, metallic taste, bitter taste, cooling sensation taste or menthol-like taste, licorice-like taste, and/or the like.

In another embodiment, at least one NHPS is combined with a plurality of sweet taste improving additives, desirably 3 or more sweet taste improving additives, and even more desirably 4 or more sweet taste improving additives, wherein each sweet taste improving additive is present in an amount such that no one sweet taste improving additive imparts a substantial off taste to the NHPS composition. In other words, the amounts of the sweet taste improving additives in the NHPS composition are balanced so that no one sweet taste improving additive imparts a substantial off taste to the NHPS composition. Desirably, each of the plurality of sweet taste improving additives is present in the NHPS composition in an amount which imparts an osmlarity ranging from 10 to 100 mOsmoles/L to a sweetenable composition, but the combination of sweet improving additives imparts an osmolarity ranging from about 10 mOsmoles/L to about 500 mOsmoles/L to a sweetenable composition.

In one embodiment, a sweetener composition is provided comprising at least one NHPS chosen from rebaudioside-A, *stevia*, stevioside, mogroside IV, mogroside V, Luo Han Guo sweetener, monatin, or curculin in combination with at least one sweet taste improving nucleotide additive chosen from inosine monophosphate ("IMP"), guanosine monophosphate ("GMP"), adenosine monophosphate ("AMP"), cytosine monophosphate (CMP), uracil monophosphate (UMP), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, nucleosides thereof, nucleic acid bases thereof, or salts thereof.

In one embodiment, a sweetener composition is provided comprising at least one NHPS chosen from rebaudioside-A, *stevia*, stevioside, mogroside IV, mogroside V, Luo Han Guo sweetener, monatin, or curculin in combination with at least one sweet taste improving carbohydrate additive chosen from tagatose, trehalose, galactose, rhamnose, cyclodextrin (e.g., α-cyclodextrin, β-cyclodextrin, and γ-cyclodextrin), maltodextrin (including resistant maltodextrins such as Fibersol-2™), dextran, sucrose, glucose, ribulose, fructose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, glucono-lactone, abequose, galactosamine, beet oligosaccharides, isomalto-oligosaccharides (isomaltose, isomaltotriose, panose and the like), xylo-oligosaccharides (xylotriose, xylobiose and the like), gentio-oligoscaccharides (gentiobiose, gentiotriose, gentiotetraose and the like), sorbose, nigero-oligosaccharides, palatinose oligosaccharides, fucose, fructooligosaccharides (kestose, nystose and the like), maltotetraol, maltotriol, malto-oligosaccharides (maltotriose, maltotetraose, maltopentaose, maltohexaose, maltoheptaose and the like), lactulose, melibiose, raffinose, rhamnose, ribose, isomerized liquid sugars such as high fructose cornstarch syrup (e.g., HFCS55, HFCS42, or HFCS90), coupling sugars, soybean oligosaccharides, or glucose syrup.

In another embodiment, a sweetener composition is provided comprising at least one NHPS chosen from rebaudioside-A, *stevia*, stevioside, mogroside TV, mogroside V, Luo Han Guo sweetener, monatin, or curculin in combination with at least one sweet taste improving polyol additive chosen from erythritol, maltitol, mannitol, sorbitol, lactitol, xylitol, isomalt, propylene glycol, glycerol (glycerine), threitol, galactitol, palatinose, reduced isomalto-oligosaccharides, reduced xylo-oligosaccharides, reduced gentio-oligosaccharides, reduced maltose syrup, or reduced glucose syrup.

In another embodiment, a sweetener composition is provided comprising at least one NHPS chosen from rebaudioside-A, *stevia*, stevioside, mogroside IV, mogroside V, Luo Han Guo sweetener, monatin, or curculin in combination with at least one sweet taste improving amino acid additive chosen from aspartic acid, arginine, glycine, glutamic acid, praline, threonine, theanine, cysteine, cystine, alanine, valine, tyrosine, leucine, isoleucine, asparagine, serine, lysine, histidine, ornithine, methionine, carnitine, aminobutyric acid (alpha-, beta-, and gamma-isomers), glutamine, hydroxyproline, taurine, norvaline, sarcosine, or salts thereof.

In another embodiment, a sweetener composition is provided comprising at least one NHPS chosen from rebaudioside-A, *stevia*, stevioside, mogroside IV, mogroside V, Luo Han Guo sweetener, monatin, or curculin in combination with at least one sweet taste improving polyamino acid additive chosen from poly-L-aspartic acid, poly-L-lysine (e.g., poly-L-α-lysine or poly-L-ε-lysine), poly-L-ornithine (e.g., poly-L-α-omithine or poly-L-ε-ornithine), poly-L-arginine, other polymeric forms of amino acids, or salts thereof In another embodiment, a sweetener composition is provided comprising at least one NHPS chosen from rebaudioside-A, *stevia*, stevioside, mogroside IV, mogroside V, Luo Han Guo sweetener, monatin, or curculin in combination with at least one sweet taste improving sugar acid additive chosen from aldonic, uronic, aldaric, alginic, gluconic, glucuronic, glucaric, galactaric, galacturonic, or salts thereof.

In another embodiment, a sweetener composition is provided comprising at least one NHPS chosen from rebaudioside-A, *stevia*, stevioside, mogroside IV, mogroside V, Luo Han Guo sweetener, monatin, or curculin in combination with at least one sweet taste improving organic acid additive chosen from the group C2-C30 carboxylic acids, substituted hydroxyl C1-C30 carboxylic acids, benzoic acid, substituted benzoic acids (e.g., 2,4-dihydroxybenzoic acid), substituted cinnamic acids, hydroxyacids, substituted hydroxybenzoic acids, substituted cyclohexyl carboxylic acids, tannic acid, lactic acid, tartaric acid, citric acid, gluconic acid, glucaric acid, creatine, glucoheptonic acids, adipic acid, hydroxycitric acid, malic acid, fruitaric acid, fumaric acid, maleic acid, succinic acid, chlorogenic acid, salicylic acid, caffeic acid, bile acids, acetic acid, ascorbic acid, alginic acid, erythorbic acid, polyglutamic acid, or salts thereof.

In another embodiment, a sweetener composition is provided comprising at least one NHPS chosen from rebaudioside-A, *stevia*, stevioside, mogroside IV, mogroside V, Luo Han Guo sweetener, monatin, or curculin in combination with at least one sweet taste improving inorganic acid additive chosen from phosphoric acid, phosphorous acid, polyphosphoric acid, hydrochloric acid, sulfuric acid, carbonic acid, sodium dihydrogen phosphate, or salts thereof.

In another embodiment, a sweetener composition is provided comprising at least one NHPS chosen from rebaudioside-A, *stevia*, stevioside, mogroside IV, mogroside V, Luo Han Guo sweetener, monatin, or curculin in combination with at least one sweet taste improving bitter compound additive chosen from caffeine, quinine, urea, bitter orange oil, naringin, quassia, or salts thereof.

In another embodiment, a sweetener composition is provided comprising at least one NHPS chosen from rebaudioside-A, *stevia*, stevioside, mogroside IV, mogroside V, Luo Han Guo sweetener, monatin, or curculin in combination with at least one sweet taste improving flavorant additive chosen from vanillin, vanilla extract, mango extract, cinnamon, citrus, coconut, ginger, viridiflorol, almond, menthol, grape skin extract, or grape seed extract. In another particular embodiment, the at least one sweet taste improving flavorant additive comprises a proprietary sweetener chosen from Dobler™ Natural Flavoring Sweetness Enhancer K14323 (Döhler™, Darmstadt, Germany), Symrise™ Natural Flavor Mask for Sweeteners 161453 or 164126 (Symrise™, Holzminden, Germany), Natural Advantage™ Bitterness Blockers 1, 2, 9 or 10 (Natural Advantage™, Freehold, N.J., U.S.A.), or Sucramask™ (Creative Research Management, Stockton, Calif., U.S.A.)

In another embodiment, a sweetener composition is provided comprising at least one NHPS chosen from rebaudioside-A, *stevia*, stevioside, mogroside IV, mogroside V, Luo Han Guo sweetener, monatin, or curculin in combination with at least one sweet taste improving polymer additive chosen from chitosan, pectin, pectic, pectinic, polyuronic, polygalacturonic acid, starch, food hydrocolloid or crude extracts thereof (e.g., gum *acacia* senegal, gum *acacia* seyal, carageenan), poly-L-lysine (e.g., poly-L-α-lysine or poly-L-ϵ-lysine), poly-L-ornithine (e.g., poly-L-α-ornithine or poly-L-ϵ-ornithine), polypropylene glycol, polyethylene glycol, poly(ethylene glycol methyl ether), polyarginine, polyaspartic acid, polyglutamic acid, polyethylene imine, alginic acid, sodium alginate, propylene glycol alginate, sodium polyethyleneglycolalginate, sodium hexametaphosphate or its salts, or other cationic and anionic polymers.

In another embodiment, a sweetener composition is provided comprising at least one NHPS chosen from rebaudioside-A, *stevia*, stevioside, mogroside IV, mogroside V, Luo Han Guo sweetener, monatin, or curculin in combination with at least one sweet taste improving protein or protein hydrolysate additive chosen from bovine serum albumin (BSA), whey protein (including fractions or concentrates thereof such as 90% instant whey protein isolate, 34% whey protein, 50% hydrolyzed whey protein, and 80% whey protein concentrate), soluble rice protein, soy protein, protein isolates, protein hydrolysates, reaction products of protein hydrolysates, glycoproteins, and/or proteoglycans containing amino acids (e.g., glycine, alanine, serine, threonine, theanine, asparagine, glutamine, arginine, valine, isoleucine, leucine, norvaline, methionine, praline, tyrosine, hydroxyproline, or the like), collagen (e.g., gelatin), partially hydrolyzed collagen (e.g., hydrolyzed fish collagen), and collagen hydrolysates (e.g., porcine collagen hydrolysate).

In another embodiment, a sweetener composition is provided comprising at least one NHPS chosen from rebaudioside-A, *stevia*, stevioside, mogroside IV, mogroside V, Luo Han Guo sweetener, monatin, or curculin in combination with at least one sweet taste improving surfactant additive chosen from polysorbates (e.g., polyoxyethylene sorbitan monooleate (polysorbate 80), polysorbate 20, polysorbate 60), sodium dodecylbenzenesulfonate, dioctyl sulfosuccinate or dioctyl sulfosuccinate sodium, sodium dodecyl sulfate, cetylpyridinium chloride, hexadecyltrimethylammonium bromide, sodium cholate, carbamoyl, choline chloride, sodium glycocholate, sodium taurodeoxycholate, lauric arginate, sodium stearoyl lactylate, lecithins, sucrose oleate esters, sucrose stearate esters, and other emulsifiers, or the like.

In another embodiment, a sweetener composition is provided comprising at least one NHPS chosen from rebaudioside-A, *stevia*, stevioside, mogroside IV, mogroside V, Luo Han Guo sweetener, monatin, or curculin in combination with at least one sweet taste improving flavonoid additive chosen from catechins, polyphenols, neohesperidin, naringin, neohesperidin dihydrochalcone, or the like.

In another embodiment, a sweetener composition is provided comprising at least one NHPS chosen from rebaudioside-A, *stevia*, stevioside, mogroside IV, mogroside V, Luo Han Guo sweetener, monatin, or curculin in combination with ethanol.

In another embodiment, a sweetener composition is provided comprising at least one NHPS chosen from rebaudioside-A, *stevia*, stevioside, mogroside IV, mogroside V, Luo Han Guo sweetener, monatin, or curculin in combination with at least one sweet taste improving astringent compound additive chosen from tannic acid, europium chloride ($EuCl_3$), gadolinium chloride ($GdCl_3$), terbium chloride ($TbCl_3$), alum, tannic acid, and polyphenols (e.g., tea polyphenol).

In another embodiment, a sweetener composition is provided comprising at least one NHPS chosen from rebaudioside-A, *stevia*, stevioside, mogroside IV, mogroside V, Luo Han Guo sweetener, monatin, or curculin in combination with at least one sweet taste improving inorganic salt additive chosen from sodium chloride, potassium chloride, sodium sulfate, potassium citrate, europium chloride ($EuCl_3$), gadolinium chloride ($GdCl_3$), terbium chloride ($TbCl_3$), magnesium sulfate, magnesium phosphate, alum, magnesium chloride, mono-, di-, tri-basic, sodium or potassium salts of phosphoric acid (e.g., inorganic phosphates), salts of hydrochloric acid (e.g., inorganic chlorides), sodium carbonate, sodium bisulfate, or sodium bicarbonate.

In another embodiment, a sweetener composition is provided comprising at least one NHPS chosen from rebaudioside-A, *stevia*, stevioside, mogroside IV, mogroside V, Luo Han Guo sweetener, monatin, or curculin in combination with at least one sweet taste improving nucleotide additive, at least one sweet taste improving carbohydrate additive, and at least one sweet taste improving amino acid additive; wherein the at least one nucleotide additive is chosen from inosine monophosphate ("IMP"), guanosine monophosphate ("GMP"), adenosine monophosphate ("AMP"), cytosine monophosphate (CMP), uracil monophosphate (UMP), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, nucleosides thereof, nucleic acid bases thereof, or salts thereof; wherein the at least one carbohydrate additive is chosen from tagatose, trehalose, galactose, rhamnose, cyclodextrin (e.g., α-cyclodextrin, β-cyclodextrin, and γ-cyclodextrin), maltodextrin (including resistant maltodextrins such as Fibersol-2™), dextran, sucrose, glucose, ribulose, fructose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, glucono-lactone, abequose, galactosamine, beet oligosaccharides, isomalto-oligosaccharides (isomaltose, isomaltotriose, panose and the like), xylo-oligosaccharides (xylotriose, xylobiose and the like), gentiooligoscaccharides (gentiobiose, gentiotriose, gentiotetraose and the like), sorbose, nigero-oligosaccharides, palatinose oligosaccharides, fucose, fructooligosaccharides (kestose, nystose and the like), maltotetraol, maltotriol, malto-oligosaccharides (maltotriose, maltotetraose, maltopentaose, maltohexaose, maltoheptaose and the like), lactulose, melibiose, raffinose, rhamnose, ribose, isomerized liquid sugars such as high fructose corn/starch syrup (e.g., HFCS55, HFCS42, or HFCS90), coupling sugars, soybean oligosaccharides, or glucose syrup; and wherein the at least one amino acid additive is chosen from aspartic acid, arginine, glycine, glutamic acid, proline, threonine, theanine, cysteine, cystine, alanine, valine, tyrosine, leucine, isoleucine, asparagine, serine, lysine, histidine, ornithine, methionine, carnitine, aminobutyric acid (alpha-, beta-, and gamma-isomers), glutamine, hydroxyproline, taurine, norvaline, sarcosine, or salts thereof.

In another embodiment, a sweetener composition is provided comprising at least one NHPS chosen from rebaudioside-A, *stevia*, stevioside, mogroside IV, mogroside V, Luo Han Guo sweetener, monatin, or curculin in combination with at least one sweet taste improving nucleotide additive and at least one sweet taste improving carbohydrate additive; wherein the at least one nucleotide additive is chosen from inosine monophosphate ("IMP"), guanosine monophosphate ("GMP"), adenosine monophosphate ("AMP"), cytosine monophosphate (CMP), uracil monophosphate (UMP), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, nucleosides thereof, nucleic acid bases thereof, or salts thereof; and wherein the at least one carbohydrate additive is chosen from tagatose, trehalose, galactose, rhamnose, cyclodextrin (e.g., α-cyclodextrin, β-cyclodextrin, and γ-cyclodextrin), maltodextrin (including resistant maltodextrins such as Fibersol-2™), dextran, sucrose, glucose, ribulose, fructose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, glucono-lactone, abequose, galactosamine, beet oligosaccharides, isomalto-oligosaccharides (isomaltose, isomaltotriose, panose and the like), xylo-oligosaccharides (xylotriose, xylobiose and the like), gentio-oligoscaccharides (gentiobiose, gentiotriose, gentiotetraose and the like), sorbose, nigero-oligosaccharides, palatinose oligosaccharides, fucose, fructooligosaccharides (kestose, nystose and the like), maltotetraol, maltotriol, malto-oligosaccharides (maltotriose, maltotetraose, maltopentaose, maltohexaose, maltoheptaose and the like), lactulose, melibiose, raffinose, rhamnose, ribose, isomerized liquid sugars such as high fructose corn/starch syrup (e.g., HFCS55, HFCS42, or HFCS90), coupling sugars, soybean oligosaccharides, or glucose syrup.

In another embodiment, a sweetener composition is provided comprising at least one NHPS chosen from rebaudioside-A, *stevia*, stevioside, mogroside IV, mogroside V, Luo Han Guo sweetener, monatin, or curculin in combination with at least one sweet taste improving nucleotide additive and at least one sweet taste improving polyol additive; wherein the at least one nucleotide additive is chosen from inosine monophosphate ("IMP"), guanosine monophosphate ("GMP"), adenosine monophosphate ("AMP"), cytosine monophosphate (CMP), uracil monophosphate (UMP), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, nucleosides thereof, nucleic acid bases thereof, or salts thereof; and wherein the at least one polyol additive is chosen from erythritol, maltitol, mannitol, sorbitol, lactitol, xylitol, inositol, isomalt, propylene glycol, glycerol (glycerine), threitol, galactitol, palatinose, reduced isomalto-oligosaccharides, reduced xylo-oligosaccharides, reduced gentio-oligosaccharides, reduced maltose syrup, or reduced glucose syrup.

In another embodiment, a sweetener composition is provided comprising at least one NHPS chosen from rebaudioside-A, *stevia*, stevioside, mogroside IV, mogroside V, Luo Han Guo sweetener, monatin, or curculin in combination with at least one sweet taste improving nucleotide additive and at least one sweet taste improving amino acid additive; wherein the at least one nucleotide additive is chosen from inosine monophosphate ("IMP"), guanosine monophosphate ("GMP"), adenosine monophosphate ("AMP"), cytosine monophosphate (CMP), uracil monophosphate (UMP), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, nucleosides thereof, nucleic acid bases thereof, or salts thereof; and wherein the at least one amino acid additive is chosen from aspartic acid, arginine, glycine, glutamic acid, proline, threonine, theanine, cysteine, cystine, alanine, valine, tyrosine, leucine, isoleucine, asparagine, serine, lysine, histidine, ornithine, methionine, carnitine, aminobutyric acid (alpha-, beta-, and gamma-isomers), glutamine, hydroxyproline, taurine, norvaline, sarcosine, or salts thereof.

In another embodiment, a sweetener composition is provided comprising at least one NHPS chosen from rebaudioside-A, *stevia*, stevioside, mogroside IV, mogroside V, Luo Han Guo sweetener, monatin, or curculin in combination with at least one sweet taste improving carbohydrate additive, at least one sweet taste improving polyol additive, and at least one sweet taste improving amino acid additive; wherein the at least one carbohydrate additive is chosen from tagatose, trehalose, galactose, rhamnose, cyclodextrin (e.g., α-cyclodextrin, β-cyclodextrin, and γ-cyclodextrin), maltodextrin (including resistant maltodextrins such as Fibersol-2™), dextran, sucrose, glucose, ribulose, fructose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, glucono-lactone, abequose, galactosamine, beet oligosaccharides, isomalto-oligosaccharides (isomaltose, isomaltotriose, panose and the like), xylo-oligosaccharides (xylobiose, xylobiose and the like), gentio-oligoscaccharides (gentiobiose, gentiobiose, gentiotetraose and the like), sorbose, nigero-oligosaccharides, palatinose oligosaccharides, fucose, fructooligosaccharides (kestose, nystose and the like), maltotetraol, maltotriol, malto-oligosaccharides (maltotriose, maltotetraose, maltopentaose, maltohexaose, maltoheptaose and the like), lactulose, melibiose, raffinose, rhamnose, ribose, isomerized liquid sugars such as high fructose corn/starch syrup (e.g., HFCS55, HFCS42, or HFCS90), coupling sugars, soybean oligosaccharides, or glucose syrup; wherein the at least one polyol additive is chosen from erythritol, maltitol, mannitol, sorbitol, lactitol, xylitol, inositol, isomalt, propylene glycol, glycerol (glycerine), threitol, galactitol, palatinose, reduced isomalto-oligosaccharides, reduced xylo-oligosaccharides, reduced gentio-oligosaccharides, reduced maltose syrup, or reduced glucose syrup; and wherein the at least one amino acid additive is chosen from aspartic acid, arginine, glycine, glutamic acid, proline, threonine, theanine, cysteine, cystine, alanine, valine, tyrosine, leucine, isoleucine, asparagine, serine, lysine, histidine, ornithine, methionine, carnitine, aminobutyric acid (alpha-, beta-, and gamma-isomers), glutamine, hydroxyproline, taurine, norvaline, sarcosine, or salts thereof.

In another embodiment, a sweetener composition is provided comprising at least one NHPS chosen from rebaudioside-A, *stevia*, stevioside, mogroside IV, mogroside V, Luo Han Guo sweetener, monatin, or curculin in combination with at least one sweet taste improving carbohydrate additive and at least one sweet taste improving polyol additive; wherein the at least one carbohydrate additive is chosen from tagatose, trehalose, galactose, rhamnose, cyclodextrin (e.g., α-cyclodextrin, β-cyclodextrin, and γ-cyclodextrin), maltodextrin (including resistant maltodextrins such as Fibersol-2™), dextran, sucrose, glucose, ribulose, fructose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, glucono-lactone, abequose, galactosamine, beet oligosaccharides, isomalto-oligosaccharides (isomaltose, isomaltotriose, panose and the like), xylo-oligosaccharides (xylotriose, xylobiose and the like), gentio-oligoscaccharides (gentiobiose, gentiotriose, gentiotetraose and the like), sorbose, nigero-oligosaccharides, palatinose oligosaccharides, fucose, fructooligosaccharides (kestose, nystose and the like), maltotetraol, maltotriol, malto-oligosaccharides (maltotriose, maltotetraose, maltopentaose, maltohexaose, maltoheptaose and the like), lactulose, melibiose, raffinose, rhamnose, ribose, isomerized liquid sugars such as high fructose corn/starch syrup (e.g., HFCS55, HFCS42, or HFCS90), coupling sugars, soybean oligosaccharides, or glucose syrup; and wherein the at least one polyol additive is chosen from erythritol, maltitol, mannitol, sorbitol, lactitol, xylitol, inositol, isomalt, propylene glycol, glycerol (glycerine), threitol, galactitol, palatinose, reduced isomalto-oligosaccharides, reduced xylo-oligosaccharides, reduced gentio-oligosaccharides, reduced maltose syrup, or reduced glucose syrup.

In another embodiment, a sweetener composition is provided comprising at least one NHPS chosen from rebaudioside-A, *stevia*, stevioside, mogroside IV, mogroside V, Luo Han Guo sweetener, monatin, or curculin in combination with at least one sweet taste improving carbohydrate additive and at least one sweet taste improving amino acid additive; wherein the at least one carbohydrate additive is chosen from tagatose, trehalose, galactose, rhamnose, cyclodextrin (e.g., α-cyclodextrin, β-cyclodextrin, and γ-cyclodextrin), maltodextrin (including resistant maltodextrins such as Fibersol-2™), dextran, sucrose, glucose, ribulose, fructose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, glucono-lactone, abequose, galactosamine, beet oligosaccharides, isomalto-oligosaccharides (isomaltose, isomaltotriose, panose and the like), xylo-oligosaccharides (xylotriose, xylobiose and the like), gentio-oligoscaccharides (gentiobiose, gentiotriose, gentiotetraose and the like), sorbose, nigero-oligosaccharides, palatinose oligosaccharides, fucose, fructooligosaccharides (kestose, nystose and the like), maltotetraol, maltotriol, malto-oligosaccharides (maltotriose, maltotetraose, maltopentaose, maltohexaose, maltoheptaose and the like), lactulose, melibiose, raffinose, rhamnose, ribose, isomerized liquid sugars such as high fructose corn/starch syrup (e.g., HFCS55, HFCS42, or HFCS90), coupling sugars, soybean oligosaccharides, or glucose syrup; and wherein the at least one amino acid additive is chosen from aspartic acid, arginine, glycine, glutamic acid, proline, threonine, theanine, cysteine, cystine, alanine, valine, tyrosine, leucine, isoleucine, asparagine, serine, lysine, histidine, ornithine, methionine, carnitine, aminobutyric acid (alpha-, beta-, and gamma-isomers), glutamine, hydroxyproline, taurine, norvaline, sarcosine, or salts thereof.

In another embodiment, a sweetener composition is provided comprising at least one NHPS chosen from rebaudioside-A, *stevia*, stevioside, mogroside IV, mogroside V, Luo Han Guo sweetener, monatin, or curculin in combination with at least one sweet taste improving polyol additive and at least one sweet taste improving amino acid additive; wherein the at least one polyol additive is chosen from erythritol, maltitol, mannitol, sorbitol, lactitol, xylitol, inositol, isomalt, propylene glycol, glycerol (glycerin), threitol, galactitol, palatinose, reduced isomalto-oligosaccharides, reduced xylo-oligosaccharides, reduced gentio-oligosaccharides, reduced maltose syrup, or reduced glucose syrup; and wherein the at least one amino acid additive is chosen from aspartic acid, arginine, glycine, glutamic acid, proline, threonine, theanine, cysteine, cystine, alanine, valine, tyrosine, leucine, isoleucine, asparagine, serine, lysine, histidine, ornithine, methionine, carnitine, aminobutyric acid (alpha-, beta-, and gamma-isomers), glutamine, hydroxyproline, taurine, norvaline, sarcosine, or salts thereof.

In another embodiment, a sweetener composition is provided comprising at least one NHPS chosen from rebaudioside-A, *stevia*, stevioside, mogroside IV, mogroside V, Luo Han Guo sweetener, monatin, or curculin in combination with at least one sweet taste improving polyol additive and at least one sweet taste improving inorganic salt additive; wherein the at least one polyol additive is chosen from erythritol, maltitol, mannitol, sorbitol, lactitol, xylitol, inositol, isomalt, propylene glycol, glycerol (glycerin), threitol, galactitol, palatinose, reduced isomalto-oligosaccharides, reduced xylo-oligosaccharides, reduced gentio-oligosaccharides, reduced maltose syrup, or reduced glucose syrup; and wherein the at least one inorganic salt additive is chosen from sodium chloride, potassium chloride, sodium sulfate, potassium citrate, europium chloride ($EuCl_3$), gadolinium chloride ($GdCl_3$), terbium chloride ($TbCl_3$), magnesium sulfate, alum, magnesium chloride, mono-, di-, tri-basic sodium or potassium salts of phosphoric acid (e.g., inorganic phosphates), salts of hydrochloric acid (e.g., inorganic chlorides), sodium carbonate, sodium bisulfate, or sodium bicarbonate.

In another embodiment, a sweetener composition is provided comprising at least one NHPS chosen from rebaudioside-A, *stevia*, stevioside, mogroside IV, mogroside V, Luo Han Guo sweetener, monatin, or curculin in combination with at least one sweet taste improving carbohydrate additive and at least one sweet taste improving inorganic salt additive; wherein the at least one carbohydrate additive is chosen from tagatose, trehalose, galactose, rhamnose, cyclodextrin (e.g., α-cyclodextrin, β-cyclodextrin, and γ-cyclodextrin), maltodextrin (including resistant maltodextrins such as Fibersol-2™), dextran, sucrose, glucose, ribulose, fructose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, glucono-lactone, abequose, galactosamine, beet oligosaccharides, isomalto-oligosaccharides (isomaltose, isomaltotriose, panose and the like), xylo-oligosaccharides (xylotriose, xylobiose and the like), gentio-oligoscacchairdes (gentiobiose, gentiotriose, gentiotetraose and the like), sorbose, nigero-oligosaccharides, palatinose oligosaccharides, fucose, fructooligosaccharides (kestose, nystose and the like), maltotetraol, maltotriol, malto-oligosaccharides (maltotriose, maltotetraose, maltopentaose, maltohexaose, maltoheptaose and the like), lactulose, melibiose, raffinose, rhamnose, ribose, isomerized liquid sugars such as high fructose corn/starch syrup (e.g., HFCS55, HFCS42, or HFCS90), coupling sugars, soybean oligosaccharides, or glucose syrup; and wherein the at least one inorganic salt additive is chosen from sodium chloride, potassium chloride, sodium sulfate, potassium citrate, europium chloride ($EuCl_3$), gadolinium chloride ($GdCl_3$), terbium chloride ($TbCl_3$), magnesium phosphate, magnesium sulfate, alum, magnesium chloride, mono-, di-, tri-basic sodium or potassium salts of phosphoric acid (e.g., inorganic phosphates), salts of hydrochloric acid (e.g., inorganic chlorides), sodium carbonate, sodium bisulfate, or sodium bicarbonate.

In another embodiment, a sweetener composition is provided comprising at least one NHPS chosen from rebaudioside-A, *stevia*, stevioside, mogroside IV, mogroside V, Luo Han Guo sweetener, monatin, or curculin in combination with at least one sweet taste improving carbohydrate additive, at least one sweet taste improving amino acid additive, and at least one sweet taste improving inorganic salt additive; wherein the at least one carbohydrate additive is chosen from tagatose, trehalose, galactose, rhamnose, cyclodextrin (e.g., α-cyclodextrin, β-cyclodextrin, and γ-cyclodextrin), maltodextrin (including resistant maltodextrins such as Fibersol-2™), dextran, sucrose, glucose, ribulose, fructose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, glucono-lactone, abequose, galactosamine, beet oligosaccharides, isomalto-oligosaccharides (isomaltose, isomaltotriose, panose and the like), xylo-oligosaccharides (xylotriose, xylobiose and the like), gentio-oligoscacchairdes (gentiobiose, gentiotriose, gentiotetraose and the like), sorbose, nigero-oligosaccharides, palatinose oligosaccharides, fucose, fructooligosaccharides (kestose, nystose and the like), maltotetraol, maltotriol, malto-oligosaccharides (maltotriose, maltotetraose, maltopentaose, maltohexaose, maltoheptaose and the like), lactulose, melibiose, raffinose, rhamnose, ribose, isomerized liquid sugars such as high fructose corn/starch syrup (e.g., HFCS55, HFCS42, or HFCS90), coupling sugars, soybean oligosaccharides, or glucose syrup; wherein the at least one amino acid additive is chosen from aspartic acid, arginine, glycine, glutamic acid, proline, threonine, theanine, cysteine, cystine, alanine, valine, tyrosine, leucine, isoleucine, asparagine, serine, lysine, histidine, ornithine, methionine, carnitine, aminobutyric acid (alpha-, beta-, and gamma-isomers), glutamine, hydroxyproline, taurine, norvaline, sarcosine, or salts thereof; and wherein the at least one inorganic salt additive is chosen from sodium chloride, potassium chloride, sodium sulfate, potassium citrate, europium chloride ($EuCl_3$), gadolinium chloride ($GdCl_3$), terbium chloride ($TbCl_3$), magnesium phosphate, magnesium sulfate, alum, magnesium chloride, mono-, di-, tri-basic sodium or potassium salts of phosphoric acid (e.g., inorganic phosphates), salts of hydrochloric acid (e.g., inorganic chlorides), sodium carbonate, sodium bisulfate, or sodium bicarbonate.

In another embodiment, a sweetener composition is provided comprising at least one NHPS chosen from rebaudioside-A, *stevia*, stevioside, mogroside IV, mogroside V, Luo Han Guo sweetener, monatin, or curculin in combination with at least one sweet taste improving polyol additive and at least one sweet taste improving polyamino acid additive; wherein the at least one polyol additive is chosen from erythritol, maltitol, mannitol, sorbitol, lactitol, xylitol, inositol, isomalt, propylene glycol, glycerol (glycerin), threitol, galactitol, palatinose, reduced isomalto-oligosaccharides, reduced xylo-oligosaccharides, reduced gentio-oligosaccharides, reduced maltose syrup, or reduced glucose syrup; and wherein the at least one polyamino acid additive is chosen from poly-L-aspartic acid, poly-L-lysine (e.g., poly-L-α-lysine or poly-L-ϵ-lysine), poly-L-omithine (e.g., poly-L-α-ornithine or poly-L-ϵ-ornithine), poly-L-arginine, and other polymeric forms of amino acids, or salts thereof.

In another embodiment, a sweetener composition is provided comprising at least one functional ingredient and at least one NHPS chosen from rebaudioside-A, *stevia*, stevioside, mogroside IV, mogroside V, Luo Han Guo sweetener, monatin, or curculin in combination with at least one sweet taste improving protein or protein hydrolysate additive and at least one sweet taste improving inorganic salt additive; wherein the at least one sweet taste improving protein hydrolysate additive is chosen from bovine serum albumin (BSA), whey protein (including fractions or concentrates thereof such as 90% instant whey protein isolate, 34% whey protein, 50% hydrolyzed whey protein, and 80% whey protein concentrate), soluble rice protein, soy protein, protein isolates, protein hydrolysates, reaction products of protein hydrolysates, glycoproteins, and/or proteoglycans containing amino acids (e.g., glycine, alanine, serine, threonine, asparagine, glutamine, arginine, valine, isoleucine, leucine, norvaline, methionine, praline, tyrosine, hydroxyproline, or the like), collagen (e.g., gelatin), partially hydrolyzed collagen (e.g., hydrolyzed fish collagen), and collagen hydrolysates (e.g., porcine collagen hydrolysate); and wherein the at least one sweet taste improving inorganic salt additive is chosen from sodium chloride, potassium chloride, sodium sulfate, potassium citrate, europium chloride ($EuCl_3$), gadolinium chloride ($GdCl_3$), terbium chloride ($TbCl_3$), magnesium phosphate, magnesium sulfate, alum, magnesium chloride, mono-, di-, tri-basic sodium or potassium salts of phosphoric acid (e.g., inorganic phosphates), salts of hydrochloric acid (e.g., inorganic chlorides), sodium carbonate, sodium bisulfate, or sodium bicarbonate.

In another embodiment, a sweetener composition is provided comprising rebaudioside A in combination with at least one NHPS other than rebaudioside-A and at least one sweet taste improving composition.

In another embodiment, a sweetener composition is provided comprising at least one NHPS chosen from rebaudioside-A, *stevia*, stevioside, mogroside IV, mogroside V, Luo Han Guo sweetener, monatin, or curculin in combination with at least one synthetic sweetener chosen from sucralose, acesulfame potassium and other salts, aspartame, alitame, saccharin, neohesperidin dihydrochalcone, cyclamate, neotame, N-[N-[3-(3-hydroxy-4-methoxyphenyl)propyl]-L-α-aspartyl]-L-phenylalanine 1-methyl ester, N—[N-[3-(3-hydroxy-4-methoxyphenyl)-3-methylbutyl]-L-α-aspartyl]-L-phenylalanine 1-methyl ester, N—[N-[3-(3-methoxy-4-hydroxyphenyl)propyl]-L-α-aspartyl]-L-phenylalanine 1-methyl ester, salts thereof, and the like.

In one embodiment, a composition comprising rebaudioside-A (REBA) in combination with at least one sweet taste improving amino acid additive and at least one sweet taste improving polyol additive is provided. In a particular embodiment, the at least one sweet taste improving amino acid additive is present in an amount from about 100 ppm to about 25,000 ppm of the composition, and the at least one sweet taste improving polyol additive is present in an amount from about 400 to about 80,000 ppm of the composition. In a still more particular embodiment, the at least one sweet taste improving amino acid additive is glycine or alanine, and the at least one sweet taste improving polyol additive is erythritol.

In one embodiment, a NHPS composition comprising rebaudioside-A (REBA) (with at least 50% REBA in a steviol glycoside mixture) in combination with at least one sweet taste improving polyol additive is provided. Desirably, the at least one sweet taste improving polyol additive comprises erythritol. In a particular embodiment of the NHPS composition, rebaudioside A is present in an amount from about 100 to about 3,000 ppm and the erythritol is present in an amount from about 400 to about 80,000 ppm of the total sweetener composition. In another embodiment of the functional sweetener composition, rebaudioside A is present in an amount from about 100 to about 3,000 ppm and the erythritol is present in an amount from about 5,000 to about 40,000 ppm of the total sweetener composition. In still another embodiment of the NHPS composition, rebaudioside A is present in an amount from about 100 to about 3,000 ppm and the erythritol is present in an amount from about 10,000 to about 35,000 ppm of the total sweetener composition. In another particular embodiment of the NHPS composition, rebaudioside A and erythritol are present in the sweetener composition in a ratio from about 1:4 to about 1:800, respectively. In yet another particular embodiment of the NHPS composition, rebaudioside A and erythritol are present in the sweetener composition in a ratio from about 1:20 to about 1:600, respectively; more particularly from about 1:50 to about 1:300; and still more particularly from about 1:75 to about 1:150.

In another embodiment, a functional sweetener composition comprising at least one functional ingredient and a sweetener composition comprising rebaudioside-A (REBA), stevia, stevioside, mogroside IV, mogroside V, Luo Han Guo sweetener, monatin, or curculin, in combination with at least one sweet taste improving synthetic sweetener additive is provided. In a particular embodiment, the functional sweetener composition comprises at least one functional ingredient and a sweetener comprising rebaudioside-A (REBA) in combination with saccharin or acesulfame potassium or other salts in an amount from about 10 ppm to about 100 ppm of the composition.

In one embodiment, a composition comprising REBA in combination with at least one sweet taste improving amino acid additive and at least one sweet taste improving protein or protein hydrolysate additive is provided. In a particular embodiment, the at least one sweet taste improving amino acid additive is present in an amount from about 100 to about 25,000 ppm of the composition, and the at least one sweet taste improving protein or protein hydrolysate additive is present in an amount from about 200 ppm to about 50,000 ppm of the composition. In a still more particular embodiment, the at least one sweet taste improving amino acid additive is glycine or lysine, and the at least one sweet taste improving protein or protein hydrolysate additive is protein, a hydrolysate, or a reaction product of a hydrolysate of a protein containing glycine, alanine, serine, leucine, valine, isoleucine, praline, or threonine.

In one embodiment, a composition comprising REBA in combination with at least one sweet taste improving protein hydrolysate additive and at least one sweet taste improving polyol additive is provided. In a particular embodiment, the at least one sweet taste improving protein or protein hydrolysate additive is present in an amount from about 200 to about 50,000 ppm of the composition, and at least one sweet taste improving polyol additive is present in an amount from about 400 to about 80,000 ppm of the composition. In a still more particular embodiment, the at least one sweet taste improving protein or protein hydrolysate additive is a protein, a hydrolysate, or a reaction product of a hydrolysate of proteins containing glycine, alanine, serine, leucine, valine, isoleucine, proline, or threonine, and the at least one sweet taste improving polyol additive is erythritol.

In one embodiment, a composition comprising REBA in combination with at least one sweet taste improving carbohydrate additive is provided. In a particular embodiment, the at least one sweet taste improving carbohydrate additive is present in an amount from about 1,000 to about 100,000 ppm of the composition. In a still more particular embodiment, the composition comprises REBA and glucose, sucrose, HFCS, or D-fructose in an amount from about 10,000 ppm to about 80,000 ppm of the composition.

In one embodiment, a composition comprising REBA in combination with at least one sweet taste improving polyol additive is provided. In a particular embodiment, the at least one sweet taste improving polyol additive is present in an amount from about 400 to about 80,000 ppm of the composition. In another particular embodiment, the at least one sweet taste improving polyol additive is present in an amount from about 5,000 to about 60,000 ppm of the composition. Non-limiting examples include REBA in combination with propylene glycol, erythritol, or combinations thereof.

In one embodiment, a composition comprising REBA in combination with at least one sweet taste improving polyol additive is provided. Desirably, the at least one sweet taste improving polyol comprises erythritol. In a particular embodiment of the composition, REBA is present in an amount from about 100 to about 3,000 ppm and the erythritol is present in an amount from about 400 to about 80,000 ppm of the total composition. In another particular embodiment of the composition, REBA and erythritol are present in the composition in a ratio from about 1:4 to about 1:800, respectively. In yet another particular embodiment of the composition, REBA and erythritol are present in the composition in a ratio from about 1:20 to about 1:600, respectively; more particularly from about 1:50 to about 1:300; and still more particularly from about 1:75 to about 1:150. Desirably, the REBA has a purity of at least 50% REBA by weight in a steviolglycoside mixture.

In one embodiment, a composition comprising REBA in combination with at least one sweet taste improving carbohydrate additive and at least one sweet taste improving polyol additive is provided. In a particular embodiment, the at least one sweet taste improving carbohydrate additive is present in an amount from about 1,000 to about 100,000 ppm of the composition and at least one sweet taste improving polyol additive is present in an amount from about 400 to about 80,000 ppm of the composition. Non-limiting examples include REBA in combination with tagatose, fructose or sucrose and erythritol.

In one embodiment, a composition comprising REBA in combination with at least one sweet taste improving inorganic salt additive is provided. Non-limiting examples include REBA in combination with NaCl, KCl, $NaHSO_4.H_2O$, $NaH_2PO_4$, $MgSO_4$, $KAl(SO_4)_2$ (alum), magnesium phosphate, magnesium chloride, KCl and $KH_2PO_4$, or other combinations thereof. A particularly desirable embodiment comprises REBA in combination with a mixture of inorganic salt additives, such as chlorides, phosphates, and sulfates of sodium, magnesium, potassium, and calcium (e.g., sodium chloride and potassium chloride; potassium phosphate and potassium chloride; sodium chloride and sodium phosphate; calcium phosphate and calcium sulfate; magnesium chloride and magnesium phosphate; and calcium phosphate, calcium sulfate, and potassium sulfate).

In one embodiment, a composition comprising REBA in combination with at least one sweet taste improving organic acid salt additive is provided. Non-limiting examples include REBA in combination with choline chloride in citrate buffer, D-gluconic acid sodium salt, guanidine HCl, D-glucosamine HCl, amiloride HCl, or combinations thereof.

In one embodiment, a composition comprising REBA in combination with at least one sweet taste improving organic acid additive is provided. Non-limiting examples include REBA in combination with fumaric acid, malic acid, tartaric acid, citric acid, adipic acid, ascorbic acid, tannic acid, lauric arginate, or combinations thereof.

In one embodiment, a composition comprising REBA in combination with at least one sweet taste improving amino acid additive is provided. In a particular embodiment, the at least one sweet taste improving amino acid additive is present in an amount from about 100 to about 15,000 ppm of the composition. Non-limiting examples include REBA in combination with glycine, L-alanine, L-serine, L-threonine, β-alanine, aminobutyric acid (alpha-, beta-, and gamma-isomers), L-aspartic acid, L-glutamic acid, L-lysine, glycine and L-alanine mixture, salt derivatives or combinations thereof.

In one embodiment, a composition comprising REBA in combination with at least one sweet taste improving surfactant additive is provided. Non-limiting examples include REBA in combination with dioctyl sulfosuccinate sodium, cetylpyridinium chloride, hexadecyltrimethylammonium bromide, sucrose oleate, polysorbate 20, polysorbate 80, lecithin, or combinations thereof.

In one embodiment, a composition comprising REBA in combination with at least one sweet taste improving polymer additive is provided. Non-limiting examples include REBA in combination with cationic polymers such as polyethyleneimine, poly-L-lysine (e.g., poly-L-α-lysine or poly-L-ϵ-lysine), poly-L-ornithine (e.g., poly-L-α-ornithine or poly-L-ϵ-ornithine), chitosan, or combinations thereof.

In one embodiment, a composition comprising REBA in combination with at least one sweet taste improving polymer additive and at least one sweet taste improving polyol additive is provided. In a particular embodiment, the at least one sweet taste improving polymer additive is present in an amount from about 30 to about 2,000 ppm of the composition, and the at least one sweet taste improving polyol additive is present in an amount from about 400 to about 80,000 ppm of the composition. Non-limiting examples include REBA in combination with a hydrocolloid, such as a gum *acacia* seyal, and erythritol.

In one embodiment, a composition comprising REBA in combination with at least one sweet taste improving protein or protein hydrolysate additive is provided. Non-limiting examples include REBA in combination with bovine serum albumin (BSA), whey protein or combinations thereof.

In another embodiment, a composition comprising REBA in combination with at least one sweet taste improving amino acid additive and at least one sweet taste improving inorganic acid salt additive is provided. In a particular embodiment, the at least one sweet taste improving amino acid additive is present in an amount from about 100 to about 25,000 ppm of the composition and the at least one sweet taste improving inorganic acid salt additive is present in an amount from about 25 to about 5,000 ppm of the composition. Non-limiting examples include REBA in combination with glycine and alum; REBA in combination with glycine and potassium chloride; REBA in combination with glycine and sodium chloride; REBA in combination with glycine, potassium phosphate, and potassium chloride; and REBA in combination with glycine, sodium chloride, and potassium chloride.

In another embodiment, a composition comprising REBA in combination with at least one sweet taste improving carbohydrate additive and at least one sweet taste improving inorganic acid salt additive is provided. In a particular embodiment, the at least one sweet taste improving carbohydrate additive is present in an amount from about 1,000 to about 100,000 ppm of the composition and the at least one sweet taste improving inorganic acid salt additive is present additive is present in an amount from about 25 to about 5,000 ppm of the composition. Non-limiting examples include REBA in combination with fructose, sucrose, or glucose and alum; REBA in combination with fructose, sucrose, or glucose and potassium chloride; REBA in combination with fructose, sucrose, or glucose and sodium chloride; REBA in combination with fructose, sucrose, or glucose, potassium phosphate, and potassium chloride; and REBA in combination with fructose, sucrose, or glucose, sodium chloride, and potassium chloride.

In another embodiment, a composition comprising REBA in combination with at least one sweet taste improving bitter additive and at least one sweet taste improving inorganic salt additive is provided. A non-limiting example includes REBA in combination with urea and sodium chloride.

In another embodiment, a composition comprising REBA in combination with at least one sweet taste improving amino acid additive and at least one sweet taste improving polyamino acid additive is provided. In a particular embodiment, the at least one sweet taste improving amino acid additive is present in an amount from about 100 to about 25,000 ppm of the composition and the at least one sweet taste improving polyamino acid additive is present in an amount from about 30 to about 2,000 ppm of the composition. Non-limiting examples include REBA in combination with glycine and poly-L-α-lysine; and REBA in combination with glycine and poly-L-ϵ-lysine.

In another embodiment, a composition comprising REBA in combination with at least one sweet taste improving amino acid additive and at least one sweet taste improving organic acid additive is provided. In a particular embodiment, the at least one sweet taste improving amino acid additive is present in an amount from about 100 to about 25,000 ppm of the composition and the at least one sweet taste improving organic acid additive is present in an amount from about 10 to about 5,000 ppm of the composition. A non-limiting example includes REBA in combination with glycine and sodium gluconate.

In another embodiment, a composition comprising REBA in combination with at least one sweet taste improving amino acid additive and at least one sweet taste improving carbohydrate additive is provided. In a particular embodiment, the at least one sweet taste improving amino acid additive is present in an amount from about 100 to about 25,000 ppm of the composition and the at least one sweet taste improving carbohydrate additive is present in an amount from about 1,000 to about 100,000 ppm of the composition. A non-limiting example includes REBA in combination with L-alanine and fructose.

In another embodiment, a composition comprising REBA in combination with at least one sweet taste improving amino acid additive, at least one sweet taste improving polyol additive, at least one sweet taste improving inorganic salt additive, and at least one sweet taste improving organic acid salt additive is provided. In a particular embodiment, the at least one sweet taste improving amino acid additive is present in an amount from about 100 to about 25,000 ppm of the composition, the at least one sweet taste improving polyol additive is present in an amount from about 400 to about 80,000 ppm of the composition, the at least one sweet taste improving inorganic salt additive is present in an amount from about 25 to about 5,000 ppm of the composition, and the at least one sweet taste improving organic acid salt additive is present in an amount from about 20 to about 10,000 ppm of the composition. A non-limiting example includes REBA in combination with erythritol, glycine, KCl, $KH_2PO_4$, and choline chloride.

In another embodiment, a composition comprising REBA in combination with at least one sweet taste improving amino acid additive, at least one sweet taste improving carbohydrate additive, and at least one sweet taste improving polyol additive is provided. In a particular embodiment, the at least one sweet taste improving amino acid additive is present in an amount from about 100 to about 25,000 ppm of the composition, the at least one sweet taste improving carbohydrate additive is present in an amount from about 1,000 to about 100,000 ppm of the composition, and the at least one sweet taste improving polyol additive is present in an amount from about 400 to about 80,000 ppm of the composition. A non-limiting example includes REBA in combination with L-alanine, fructose, and erythritol.

In another embodiment, a composition comprising REBA in combination with at least one sweet taste improving amino acid additive, at least one sweet taste improving polyol, additive, and at least one sweet taste improving inorganic acid salt additive is provided. In a particular embodiment, the at least one sweet taste improving amino acid additive is present in an amount from about 100 to about 25,000 ppm of the composition, the at least one sweet taste improving polyol additive is present in an amount from about 400 to about 80,000 ppm of the composition, and the at least one sweet taste improving inorganic acid salt additive is present in an amount from about 25 to about 5,000 ppm of the composition. A non-limiting example includes REBA in combination with erythritol, glycine, KCl, and $KH_2PO_4$.

In another embodiment, a composition comprising REBA in combination with a sweet taste improving inorganic acid salt additive is provided. A non-limiting example includes REBA in combination with sodium chloride.

In one embodiment, a composition is provided comprising at least one NHPS chosen from rebaudioside-A, *stevia*, stevioside, mogroside IV, mogroside V, Luo Han Guo sweetener, monatin, or curculin in combination with at least one sweet taste improving polyol additive and at least one sweet taste improving organic acid additive. Desirably, the at least one sweet taste improving polyol additive is present in an amount from about 20,000 to about 50,000 ppm of the composition and the at least one sweet taste improving organic acid additive is present in an amount from about 10 to about 5,000 ppm of the composition. Wherein more than one sweet taste improving organic acid additive is present in the composition, the plurality of sweet taste improving organic acid additives are present in an amount from about 500 to about 2,500 ppm of the composition, more particularly in an amount from about 500 to about 1,500 ppm of the composition. In a particular embodiment, the composition described hereinabove further comprises at least one sweet taste improving inorganic acid additive, at least one sweet taste improving inorganic acid salt additive, at least one sweet taste improving organic acid salt additive, or combinations thereof.

In another embodiment, a composition comprising REBA in combination with at least one sweet taste improving polyol additive and at least one sweet taste improving organic acid additive is provided. Desirably, the REBA has a purity from about 50 to about 100% by weight of REBA, more desirably from about 80 to about 99.5% by weight REBA, most desirably from about 97 to about 99.5% by weight REBA in a steviolglycoside mixture. In a particular embodiment, the REBA is present in the composition in an amount from about 100 to about 3,000 ppm, more desirably in an amount from about 200 to about 2,000 ppm, and even more desirably in an amount from about 250 to about 750 ppm of the composition. Desirably, the at least one sweet taste improving polyol additive is present in an amount from about 20,000 to about 50,000 ppm of the composition and the at least one sweet taste improving organic acid additive is present in an amount from about 10 to about 5,000 ppm of the composition. In a particularly desirable embodiment, the at least one sweet taste improving polyol additive is present in an amount from about 30,000 to about 40,000 ppm and the at least one sweet taste improving organic acid additive is present in an amount from about 500 to about 2,500 ppm of the composition. In a particular embodiment, a plurality of sweet taste improving organic acid additives are present in the sweetener composition in an amount from about 500 to about 2,500 ppm of the composition, the plurality of organic acid additives comprising a mixture of lactic acid in an amount from about 40 to about 250 ppm, citric acid in an amount from about 150 to about 460 ppm, malic acid in an amount from about 150 to about 460 ppm, and tartaric acid in an amount from about 150 to about 460 ppm. A non-limiting example includes REBA in combination with erythritol, lactic acid, citric acid, mane acid, tartaric acid, or combinations thereof. In a particular embodiment, the composition comprises 34,000 ppm of erythritol, 80 ppm of lactic acid, 310 ppm of citric acid, 310 ppm of malic acid, 310 ppm or tartaric acid, and 550 ppm of REBA. Desirably, the REBA has a purity from about 80 to about 99.5% by weight of REBA, more desirably from about 97 to about 99.5% by weight REBA in a steviolglycoside mixture. The composition optionally also may include flavorants such as caramel, vanilla, or other such flavorants as described herein, or combinations thereof. In a particular embodiment, such a composition is a carbonated soft drink, such as a cola, although other types of beverages are contemplated as well. Those of ordinary skill in the art should appreciate that the amounts of the sweet taste improving organic acids in a carbonated beverage may be modified to obtain a pH from about 2.3 to about 3.5. In addition, those of ordinary skill in the art also should appreciate that sweet taste improving inorganic acid additives, such as phorphoric acid, benzoic acid, and sorbic acid, may be used individually or in combination in a carbonated beverage in order to obtain a pH from about 2.3 to about 3.5.

In another embodiment, the composition comprising REBA in combination with at least one sweet taste improving polyol additive and at least one sweet taste improving organic acid additive described hereinabove further comprises at least one sweet taste improving inorganic acid additive. Desirably, at least one sweet taste improving inorganic acid additive is present in an amount from about 25 to about 5,000 ppm of the composition. Non-limiting examples of sweet taste improving inorganic acid additives include phosphoric acid, benzoic acid, sorbic acid, and combinations thereof.

In yet another embodiment, the composition comprising REBA in combination with at least one sweet taste improving polyol additive and at least one sweet taste improving organic acid additive described hereinabove further comprises at least one sweet taste improving inorganic acid salt additive and/or at least one sweet taste improving organic acid salt additive.

Desirably, the at least one sweet taste improving inorganic acid salt additive is present in an amount from about 25 to about 5,000 ppm of the composition, more desirably in an amount from about 50 to about 250 ppm, most desirably in an amount of about 150 ppm. Desirably, the at least one sweet taste improving organic acid salt additive is present in an amount from about 20 to about 10,000 ppm of the composition, more desirably in an amount from about 50 to about 350 ppm, most desirably in an amount of about 148 ppm. Non-limiting examples include REBA in combination with erythritol, sodium chloride or magnesium chloride, and lactic acid, citric acid, malic acid, tartaric acid, or combinations thereof; REBA in combination with erythritol, potassium citrate or sodium citrate, and lactic acid, citric acid, malic acid, tartaric acid, or combinations thereof; or REBA in combination with erythritol, sodium chloride and sodium citrate, lactic acid, citric acid, malic acid, and tartaric acid, or combinations thereof.

In another embodiment, the composition comprising REBA in combination with at least one sweet taste improving polyol additive, at least one sweet taste improving inorganic acid additive, and at least one sweet taste improving organic acid additive described hereinabove further comprises at least one sweet taste improving inorganic acid salt additive and/or at least one sweet taste improving organic acid salt additive. Desirably, the at least one sweet taste improving inorganic acid salt additive is present in an amount from about 25 to about 5,000 ppm of the composition, more desirably in an amount from about 50 to about 250 ppm, most desirably in an amount of about 150 ppm. Desirably, the at least one sweet taste improving organic acid salt additive is present in an amount from about 20 to about 10,000 ppm of the composition, more desirably in an amount from about 50 to about 350 ppm, most desirably in an amount of about 148 ppm. Non-limiting examples include REBA in combination with erythritol, phosphoric acid, sodium chloride or magnesium chloride, and lactic acid, citric acid, malic acid, tartaric acid, or combinations thereof; REBA in combination with erythritol, phosphoric acid, potassium citrate or sodium citrate, and lactic acid, citric acid, malic acid, tartaric acid, or combinations thereof; or REBA in combination with erythritol, phosphoric acid, sodium chloride and sodium citrate, lactic acid, citric acid, malic acid, and tartaric acid, or combinations thereof.

In another embodiment, a composition comprising glycyrrihizin such as mono-ammonium glycyrrhizic acid salt hydrate in combination with a sweet taste improving inorganic acid salt additive is provided. A non-limiting example includes monoammonium glycyrrhizic acid salt hydrate in combination with sodium chloride.

The desired weight ratio of the NHPS to sweet taste improving composition(s) in the NHPS composition will depend on the particular NHPS, and the sweetness and other characteristics desired in the final product or orally ingestible composition. NHPSs vary greatly in their potency, ranging from about 30 times more potent than sucrose to about 8,000 times more potent than sucrose on a weight basis. In general, the weight ratio of the NHPS to sweet taste improving composition may for example range from between 10,000:1 to about 1:10,000; a further non-limiting example may range from about 9,000:1 to about 1:9,000; yet another example may range from about 8,000:1 to about 1:8,000; a further example may range from about 7,000:1 to about 1:7,000; another example may range from about 6,000:1 to about 1:6000; in yet another example may range from about 5,000:1 to about 1:5,000; in yet another example may range from about 4,000:1 to about 1:4,000; in yet another example may range from about 3,000:1 to about 1:3,000; in yet another example may range from about 2,000:1 to about 1:2,000; in yet another example may range from about 1,500:1 to about 1:1,500; in yet another example may range from about 1,000:1 to about 1:1,000; in yet another example may range from about 900:1 to about 1:900; in yet another example may range from about 800:1 to about 1:800; in yet another example may range from about 700:1 to about 1:700; in yet another example may range from about 600:1 to about 1:600; in yet another example may range from about 500:1 to about 1:500; in yet another example may range from about 400:1 to about 1:400; in yet another example may range from about 300:1 to about 1:300; in yet another example may range from about 200:1 to about 1:200; in yet another example may range from about 150:1 to about 1:150; in yet another example may range from about 100:1 to about 1:100; in yet another example may range from about 90:1 to about 1:90; in yet another example may range from about 80:1 to about 1:80; in yet another example may range from about 70:1 to about 1:70; in yet another example may range from about 60:1 to about 1:60; in yet another example may range from about 50:1 to about 1:50; in yet another example may range from about 40:1 to about 1:40; in yet another example may range from about 30:1 to about 1:30; in yet another example may range from about 20:1 to about 1:20; in yet another example may range from about 15:1 to about 1:15; in yet another example may range from about 10:1 to about 1:10; in yet another example may range from about 9:1 to about 1:9; in yet another example may range from about 8:1 to about 1:8; in yet another example may range from about 7:1 to about 1:7; in yet another example may range from about 6:1 to about 1:6; in yet another example may range from about 5:1 to about 1:5; in yet another example may range from about 4:1 to about 1:4; in yet another example may range from about 3:1 to about 1:3; in yet another example may range from about 2:1 to about 1:2; and in yet another example may be about 1:1; depending on the particular NHPS selected.

It is contemplated that the combination of at least one NHPS to at least one sweet taste improving composition may be carried out in any pH range that does not materially or adversely affect the taste of a NHPS or the orally ingestible composition which comprises a NITS. A non-limiting example of the pH range may be from about 2 to about 8. A further example includes a pH range from about 2 to about 5.

One of ordinary skill in the art may combine at least one NHPS with at least one sweet taste improving composition in any manner which does not materially or adversely affect the taste of the orally ingestible composition. For example, a NHPS may be added to the orally ingestible composition before the sweet taste improving composition. In another example, a NHPS may be added to the orally ingestible composition after the sweet taste improving composition. In yet another example, a NHPS may be added to the orally ingestible composition simultaneously with the sweet taste improving composition.

In another embodiment, a NHPS may be combined with the sweet taste improving composition prior to being added to the orally ingestible composition. For example, a NHPS may be in a pure, diluted, or concentrated form as a liquid (e.g., solution), solid (e.g., powder, chunk, pellet, grain, block, crystalline, or the like), suspension, gas state, or combinations thereof may be contacted with the sweet taste improving composition which may be in a pure, diluted, or concentrated form as a liquid (e.g., solution), solid (e.g., powder, chunk, pellet, grain, block, crystalline, or the like), suspension, gas state, or combinations thereof before both are contacted with an orally ingestible composition. In yet another embodiment, when there are more than one NHPSs or more than one sweet taste improving composition, each component of the NHPS and sweet taste improving composition may be added simultaneously, in an alternating pattern, in a random pattern, or any other pattern which will not adversely affect the taste of the orally ingestible composition.

3. Tabletop Compositions

In a particular embodiment of the present invention, the NHPS compositions comprise a tabletop sweetener composition comprising at least one NHPS in combination with at least one bulking agent and optionally at least one sweet taste improving composition and/or anti-caking agent with improved temporal and/or flavor profile.

In accordance with particular embodiments, suitable "bulking agents" include maltodextrin (10 DE, 18 DE, or 5 DE), corn syrup solids (20 or 36 DE), sucrose, fructose, glucose, invert sugar, sorbitol, xylose, ribulose, mannose, xylitol, mannitol, galactitol, erythritol, maltitol, lactitol, isomalt, maltose, tagatose, lactose, inulin, glycerol, propylene glycol, polyols, polydextrose, fructooligosaccharides, cellulose and cellulose derivatives, and the like, and mixtures thereof. Additionally, in accordance with still other embodiments of the invention, granulated sugar (sucrose) or other caloric sweeteners such as crystalline fructose, other carbohydrates, or sugar alcohol can be used as a bulking agent due to their provision of good content uniformity without the addition of significant calories. In one embodiment, a bulking agent may be used as a sweet taste improving composition.

As used herein the phrase "anti-caking agent" and "flow agent" refer to any composition which prevents, reduces, inhibits, or suppresses at least one natural and/or synthetic high-potency sweetener molecule from attaching, binding, or contacting to another natural and/or synthetic high-potency sweetener molecule. Alternatively, anti-caking agent may refer to any composition which assists in content uniformity and uniform dissolution. In accordance with particular embodiments, non-limiting examples of anti-caking agents include cream of tartar, calcium silicate, silicon dioxide, microcrystalline cellulose (Avicel, FMC BioPolymer, Philadelphia, Pa.), and tricalcium phosphate. In one embodiment, the anti-caking agents are present in the tabletop functional sweetener composition in an amount from about 0.001 to about 3% by weight of the tabletop functional sweetener composition.

Tabletop NHPS compositions are embodied and packaged in numerous different forms and it is intended that the tabletop NHPS compositions of the present invention may be of any form known in the art. In accordance with particular embodiments, non-limiting examples include powder form, granular form, packets, tablets, sachets, pellets, cubes, solids, and liquids.

In an embodiment, a tabletop NHPS composition comprises a single-serving (portion control) packet comprising a dry-blend of a functional sweetener formulation. Dry-blend formulations generally may comprise powder or granules. Although the tabletop NHPS composition may be in a packet of any size, an illustrative non-limiting example of conventional portion control tabletop sweetener packets are approximately 2.5 by 1.5 inches and hold approximately 1 gram of a sweetener composition having a sweetness equivalent to 2 teaspoons of granulated sugar (~8 g). The amount of NHPS in a dry-blend tabletop NHPS formulation will vary due to the varying potency of different NHPSs. In a particular embodiment, a dry-blend tabletop NHPS formulation may comprise a NHPS in an amount from about 1% (w/w) to about 10% (w/w) of the tabletop NHPS composition.

Solid tabletop NHPS embodiments include cubes and tablets. A non-limiting example of conventional cubes are equivalent in size to a standard cube of granulated sugar, which is approximately 2.2×2.2×2.2 $cm^3$ and weigh approximately 8 g. In one embodiment, a solid tabletop sweetener is in the form of a tablet or any other form known to those skilled in the art.

A tabletop NHPS composition also may be embodied in the form of a liquid, wherein the NHPS is combined with a liquid carrier. Suitable non-limiting examples of carrier agents for liquid tabletop functional sweeteners include water, alcohol, polyol, glycerin base or citric acid base dissolved in water, and mixtures thereof. Due to the varying potencies of the different high-potency sweeteners, the amount of high-potency sweetener in a liquid tabletop NHPS formulation will also vary. The sweetness equivalent of a tabletop NHPS composition for any of the forms described herein or known in the art may be varied to obtain a desired sweetness profile. For example, a tabletop NHPS composition may comprise a sweetness comparable to that of an equivalent amount of standard sugar. In another embodiment, the tabletop NHPS composition may comprise a sweetness of up to 100 times that of an equivalent amount of sugar. In another embodiment, the tabletop NHPS composition may comprise a sweetness of up to 90 times, 80 times, 70 times, 60 times, 50 times, 40 times, 30 times, 20 times, 10 times, 9 times, 8 times, 7 times, 6 times, 5 times, 4 times, 3 times, and 2 times that of an equivalent amount of sugar.

In one embodiment, the tabletop NHPS composition also may be formulated for targeted uses, for example, in beverage, food, pharmaceutical, cosmetics, herbal/vitamins, tobacco, and in any other products which may be sweetened. For example, a tabletop NHPS composition for baking may be formulated having additional protecting agents such as encapsulants. Other forms will be readily apparent to those skilled in the tabletop sweetener art.

Commonly used methods for making powder or granulated NHPS formulations for packets include fluid bed agglomeration processes. Other methods for making tabletop sweetener compositions are well known to those of ordinary skill in the art.

Those skilled in the art appreciate that the amount of NHPS and amount and types of sweet taste improving composition, bulking agent, and/or anti-caking agent can be modified in order to tailor the taste of the tabletop sweetener composition to a desired profile and end use.

Specific embodiments of tabletop sweetener compositions and methods of making tabletop functional sweetener compositions are disclosed in U.S. Provisional Application No. 60/805,209, entitled "Natural High-Potency Tabletop Sweetener Compositions with Improved Temporal and/or Flavor Profile, Methods for Their Formulation, and Uses," filed on Jun. 19, 2006, by DuBois, et al., the disclosure of which is incorporated herein by reference in its entirety.

4. Orally Ingestible Sweetened Compositions

As explained hereinabove, sweetened compositions in accordance with embodiments of this invention comprise a sweetenable composition, at least one NHPS and/or at least one modified NHPS, and at least one sweet taste improving composition. A multitude of suitable sweetenable compositions are described hereinabove.

Generally, the amount of NHPS present in a sweetened composition varies widely depending on the particular type of sweetened composition and its desired sweetness. Those of ordinary skill in the art can readily discern the appropriate amount of sweetener to put in the sweetened composition. In a particular embodiment, the at least one NHPS is present in the sweetened composition in an amount in the range of about 1 to about 5,000 ppm of the sweetened composition, and the at least one sweet taste improving composition is present in the sweetened composition in an amount in the range of about 0.1 to about 100,000 ppm of the sweetened composition.

In accordance with particular embodiments, suitable amounts of NHPSs for sweetenable compositions comprise amounts in the range from about 100 ppm to about 3,000 ppm for rebaudioside A; from about 50 ppm to about 3,000 ppm for *stevia*; from about 50 ppm to about 3,000 ppm for stevioside; from about 50 ppm to about 3,000 ppm for morgroside IV; from about 50 ppm to about 3,000 ppm for morgroside V; from about 50 ppm to about 3,000 ppm for Luo Han Guo sweetener; from about 5 ppm to about 300 ppm for monatin, from about 5 ppm to about 200 ppm for curculin; and from about 50 ppm to about 3,000 ppm for mono-ammonium glycyrrhizic acid salt hydrate.

In one particular embodiment, an orally ingestible composition comprises a carbonated beverage comprising at least one NHPS and at least one sweet taste improving composition; wherein the at least one NHPS is chosen from rebaudioside A, rebaudioside B, rebaudioside C, rebaudioside D, rebaudioside E, rebaudioside F, dulcoside A, dulcoside B, rubusoside, *stevia*, stevioside, mogroside IV, mogroside V, Luo Han Guo sweetener, siamenoside, monatin and its salts (monatin SS, RR, RS, SR), curculin, glycyrrhizic acid and its salts, thaumatin, monellin, mabinlin, brazzein, hernandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, cyclocarioside I, or combinations thereof; and wherein the at least one sweet taste improving composition is selected from the group consisting of carbohydrates, polyols, amino acids and their corresponding salts, polyamino acids and their corresponding salts, sugar acids and their corresponding salts, organic acids, inorganic acids, organic salts, inorganic salts, bitter compounds, flavorants, astringent compounds, polymers, proteins or protein hydrolysates, surfactants, emulsifiers, flavonoids, alcohols, and combinations thereof.

IV. Examples

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description therein, may suggest themselves to those skilled in the art without departing from the spirit of the present invention and/or the scope of the appended claims. Unless otherwise specified, %'s are by weight.

A. Example A

An exemplary method of sensory evaluation is provided in the following protocol, similar to that described hereinabove. In this test protocol, none of the samples were swallowed. All samples were expectorated and the mouth was rinsed with water after the tasting. In step 1, the 10% sucrose control sample was tasted by distributing ca. 10 mL of sample quickly throughout the oral cavity, wherein the maximal "Sweetness Intensity" was measured. This intensity is defined as a 10 on a 0-15 scale where 0 is defined as no perceptible sweetness and 15, the sweetness of 15% sucrose. Immediately upon sensing maximal sweetness, the sample was expectorated, the mouth was rinsed with water and the rate of sweetness decay ("Sweetness Linger") was measured, where attention was focused on the sweetness 3-4 min after the water rinse. The sweetness linger was rated by a panel of experts in the sensory evaluation of foods and beverages using the following scale: 0=no sweetness linger, 1=very slight sweetness linger, 2=slight sweetness linger, 3=moderate sweetness linger, 4=moderately high sweetness linger, 5=high sweetness linger. After sample tasting was complete, a salty oyster cracker was chewed followed by a water rinse, and at least 5 minutes followed before tasting the next sample.

The "Sweetness Linger" rating for sucrose observed by this protocol was defined as 0. Experimental samples were tasted by the same protocol, always allowing sufficient time between samples to ensure re-equilibration of the sensory system. Re-tasting of control samples during the course of the experiment was allowed and encouraged.

The comparison taste test was performed between two controls and addition of sweet taste improving additive on the onset and/or sweetness linger.

B. Example Set B

Where there are ranges provided in the examples, a number of beverages comprising the NHPS, such as rebaudioside-A (REBA), were made 5-7 levels from the top to the bottom range, using a 1:1 dilution of the corresponding sweet taste improving compositions. The sweetness linger rating reported was the most sugar-like in sweetness linger (the lowest numerical value) attained of all the samples (i.e., the shortest sweetness linger). The tasting protocol and sensory scores described in the exemplary protocol of Example A were used in the Examples of Set B.

Control Samples

REBA is a natural non-caloric sweetener with a very clean flavor profile (i.e., only sweet) and an acceptable sweetness onset rate but with a sweetness which lingers quite noticeably more than that of carbohydrate sweeteners.

The effects of formulation change on the sweetness linger of 400 ppm REBA (equivalent to 8 g sucrose) in a citric acid/potassium citrate composition equivalent to that in a diet lemon-lime beverage were evaluated. The sweetness linger rating of this solution was determined to be 5.

8 g of sugar was dissolved in 100 ml of citrate buffer. The sweetness linger rating of this control sample was determined to be 0.

Example B1

400 mg of REBA was dissolved in a citrate buffer. 35 g of erythritol was then mixed with the base solution. The sweetness linger rating of this solution was determined to be 1.

Example B2

400 mg of REBA was dissolved in a citrate buffer. 10 g of D-Tagatose was then mixed with the base solution. The sweetness linger of this solution was determined to be 2.

Example B3

180 ppm of REBA was dissolved in a citrate buffer. 70 g of HFCS 55 was then mixed with the base solution. The sweetness linger of this solution was determined to be 1.

Example B4

400 ppm of REBA was dissolved in a citric acid/potassium citrate matrix equivalent to that in a diet lemon-lime beverage.

1,175 ppm of choline chloride was then mixed with the base solution. The sweetness linger of this solution was determined to be 3.

Example B5

400 ppm of REBA was dissolved in a citric acid/potassium citrate composition equivalent to that in a diet lemon-lime beverage. 7,500 ppm of D-tagatose was then mixed with the base solution. The sweetness linger of this solution was determined to be 2.

Example B6

400 ppm of REBA was dissolved in a citric acid/potassium citrate composition equivalent to that in a diet lemon-lime beverage. 10,000 ppm of D-tagatose was then mixed with the base solution. The sweetness linger of this solution was determined to be 2.

Example B7

400 ppm of REBA was dissolved in a citric acid/potassium citrate composition equivalent to that in a diet lemon-lime beverage. 64 ppm of mono sodium glutamate was then mixed with the base solution. The sweetness linger of this solution was determined to be 4.

Example B8

400 ppm of REBA was dissolved in a citric acid/potassium citrate composition equivalent to that in a diet lemon-lime beverage. 1.2 ppm of viridiflorol was then mixed with the base solution. The sweetness linger of this solution was determined to be 3.

Example B9

400 ppm of REBA was dissolved in a citric acid/potassium citrate composition equivalent to that in a diet lemon-lime beverage. 25 ppm of naringin was then mixed with the base solution. The sweetness linger of this solution was determined to be 3.

Example B10

400 ppm of REBA was dissolved in a citric acid/potassium citrate composition equivalent to that in a diet lemon-lime beverage. 25 ppm of AMP was then mixed with the base solution. The sweetness linger of this solution was determined to be 3.

Example B11

400 ppm of REBA was dissolved in a citric acid/potassium citrate composition equivalent to that in a diet lemon-lime beverage. 800 ppm of malic acid was then mixed with the base solution. The sweetness linger of this solution was determined to be 4.

Example B12

400 ppm of REBA was dissolved in a citric acid/potassium citrate composition equivalent to that in a diet lemon-lime beverage. 1 ppm of quinine was then mixed with the base solution. The sweetness linger of this solution was determined to be 3.

Example B13

400 ppm REBA was dissolved in a citric acid/potassium citrate composition equivalent to that in a diet lemon-lime beverage. 150 ppm of sodium chloride was then mixed with the base solution. The sweetness linger of this solution was determined to be 4.

Example B14

400 ppm of REBA was dissolved in a citric acid/potassium citrate composition equivalent to that in a diet lemon-lime beverage. 500 ppm of sodium gluconate was then mixed with the base solution. The sweetness linger of this solution was determined to be 4.

Example B15

400 ppm of REBA was dissolved in a citric acid/potassium citrate composition equivalent to that in a diet lemon-lime beverage. 100 ppm of D/L alanine was then mixed with the base solution. The sweetness linger of this solution was determined to be 3.

Example B16

400 ppm of REBA was dissolved in a citric acid/potassium citrate composition equivalent to that in a diet lemon-lime beverage. 1,250 ppm of trehalose was then mixed with the base solution. The sweetness linger of this solution was determined to be 2.

Example B17

400 ppm of REBA was dissolved in a citric acid/potassium citrate composition equivalent to that in a diet lemon-lime beverage. 250 ppm of 2,4-dihydroxybenzoic acid was then mixed with the base solution. The sweetness linger of this solution was determined to be 2.

Example B18

400 ppm of REBA was dissolved in a citric acid/potassium citrate composition equivalent to that in a diet lemon-lime beverage. 100 ppm of theanine was then mixed with the base solution. The sweetness linger of this solution was determined to be 3.

Example B19

400 ppm of REBA was dissolved in a citric acid/potassium citrate composition equivalent to that in a diet lemon-lime beverage. 112 ppm of caffeic acid was then mixed with the base solution. The sweetness linger of this solution was 3.

Example B20

400 ppm of REBA was dissolved in a citric acid/potassium citrate composition equivalent to that in a diet lemon-lime beverage. 10,000 ppm of fructooligosaccharides was then mixed with the base solution. The sweetness linger of this solution was determined to be 2.

Example B21

400 ppm of REBA was dissolved in a citric acid/potassium citrate composition equivalent to that in a diet lemon-lime beverage. 10,000 ppm fructooligosaccharide (55%) was then mixed with the base solution. The sweetness linger of this solution was determined to be 3.

Example B22

400 ppm of REBA was dissolved in a citric acid/potassium citrate composition equivalent to that in a diet lemon-lime beverage. 150 ppm of potassium chloride was then mixed with the base solution. The sweetness linger of this solution was determined to be 2.

Example B23

400 ppm of REBA was dissolved in a citric acid/potassium citrate composition equivalent to that in a diet lemon-lime beverage. 300 ppm of potassium dihydrogenphosphate was then mixed with the base solution. The sweetness linger of this solution was determined to be 3.

Example B24

400 ppm of REBA was dissolved in a citric acid/potassium citrate composition equivalent to that in a diet lemon-lime beverage. 125 ppm of potassium tartrate was then mixed with the base solution. The sweetness linger of this solution was determined to be 3.

Example B25

400 ppm of REBA was dissolved in a citric acid/potassium citrate composition equivalent to that in a diet lemon-lime beverage. 200 ppm of sodium tartrate was then mixed with the base solution. The sweetness linger of this solution was determined to be 3.

Example B26

400 ppm of REBA was dissolved in a citric acid/potassium citrate composition equivalent to that in a diet lemon-lime beverage. 400 ppm of *acacia* senegal was then mixed with the base solution. The sweetness linger of this solution was determined to be 2.

Example B27

400 ppm of REBA was dissolved in a citric acid/potassium citrate composition equivalent to that in a diet lemon-lime beverage. 200 ppm *acacia* senegal was then mixed with the base solution. The sweetness linger of this solution was determined to be 3.

Example B28

400 ppm of REBA was dissolved in a citric acid/potassium citrate composition equivalent to that in a diet lemon-lime beverage. 400 ppm of Fibergum was then mixed with the base solution. The sweetness linger of this solution was determined to be 2.

Example B29

400 ppm of REBA was dissolved in a citric acid/potassium citrate composition equivalent to that in a diet lemon-lime beverage. 100 ppm of chlorogenic acid was then mixed with the base solution. The sweetness linger of this solution was determined to be 4.

Example B30

400 ppm of REBA was dissolved in a citric acid/potassium citrate composition equivalent to that in a diet lemon-lime beverage. 2,500 ppm of ethanol was then mixed with the base solution. The sweetness linger of this solution was determined to be 2.

Example B31

400 ppm of REBA was dissolved in a citric acid/potassium citrate composition equivalent to that in a diet lemon-lime beverage. 2,500 ppm of taurine was then mixed with the base solution. The sweetness linger of this solution was determined to be 3.

Example B32

400 ppm of REBA was dissolved in a citric acid/potassium citrate composition equivalent to that in a diet lemon-lime beverage. 625 ppm of propylene glycol was then mixed with the base solution. The sweetness linger of this solution was 4.

Example B33

400 ppm of REBA was dissolved in a citric acid/potassium citrate composition equivalent to that in a diet lemon-lime beverage. 5,000 ppm of glycine was then mixed with the base solution. The sweetness linger of this solution was determined to be 2.

Example B34

400 ppm of REBA was dissolved in a citric acid/potassium citrate composition equivalent to that in a diet lemon-lime beverage. β-Cyclodextrin was then mixed with the base solution. The sweetness linger of this solution was determined to be 2.

Example B35

400 ppm of REBA was dissolved in a citric acid/potassium citrate composition equivalent to that in a diet lemon-lime beverage. 2,500 ppm β-Cyclodextrin was then mixed with the base solution. The sweetness linger of this solution was determined to be 3.

Examples B36-B40 were 50% calorie-reduced products that were prepared by diluting commercially available products 1:1 with a 360 ppm REBA/citrate composition. The resulting products contained 180 ppm REBA (equivalent to 5% sucrose), and were compared to the products diluted 1:1 with a 10% sucrose/citrate composition (to compare the products at similar flavor levels).

Example B36

Commercially available Nestea Cool lemon Iced Tea product was diluted 1:1 with a 360 ppm REBA/citrate composition. This gave a product that contained 180 ppm REBA (equivalent to 5% sucrose). This product was compared to the commercially available Nestea Cool Lemon Iced Tea. The REBA product was very similar to the corresponding sucrose products in flavor and taste. The sweetness linger of this solution was determined to be 1.

Example B37

Commercially available Welch's 100% Grape Juice product was diluted 1:1 with a 360 ppm REBA/citrate composition. This gave a product that contained 180 ppm REBA (equivalent to 5% sucrose). This product was compared to the commercially available Welch's 100% Grape Juice. The REBA product was very similar to the corresponding sucrose products in flavor and taste. The sweetness linger of this solution was determined to be 1.

Example B38

Commercially available Minute Maid Apple Juice 100% juice product was diluted 1:1 with a 360 ppm REBA/citrate composition. This gave a product that contained 180 ppm REBA (equivalent to 5% sucrose). This product was compared to the commercially available Minute Maid Apple Juice 100% juice. The REBA product was very similar to the corresponding sucrose products in flavor and taste. The sweetness linger of this solution was determined to be 1.

Example B39

Commercially available Minute Maid Cranberry/Apple/Raspberry 25% juice product was diluted 1:1 with a 360 ppm REBA/citrate composition. This gave a product that contained 180 ppm REBA (equivalent to 5% sucrose). This product was compared to the commercially available Minute Maid Cranberry/Apple/Raspberry 25% juice. The REBA product was very similar to the corresponding sucrose products in flavor and taste. The sweetness linger of this solution was determined to be 1.

Example B40

Commercially available Minute Maid Cranberry/Grape 25% juice product was diluted 1:1 with a 360 ppm REBA/citrate composition. This gave a product that contained 180 ppm REBA (equivalent to 5% sucrose). This product was compared to the commercially available Minute Maid Cranberry/Grape 25% juice. The REBA product was very similar to the corresponding sucrose products in flavor and taste. The sweetness linger of this solution was determined to be 1.

Example B41

A 500 ppm REBA sweetened diet lemon-lime beverage (sweetness level 10% sucrose equivalent) was prepared. The sweetness linger of this product was determined to be 5.

Example B42

A 400 ppm REBA sweetened diet lemon-lime beverage (sweetness level 10% sucrose equivalent) was prepared with 3.5% erythritol. The sweetness linger of this product was determined to be 2.

Example B43

A 180 ppm REBA sweetened diet lemon-lime beverage (sweetness level 10% sucrose equivalent) was prepared with 8% erythritol. The sweetness linger of this product was determined to be 1.

Example B44

A 180 ppm REBA sweetened diet lemon-lime beverage (sweetness level 10% sucrose equivalent) was prepared with 3.3% sucrose and 3.5% erythritol. The sweetness linger of this product was determined to be 1.

Example B45

400 ppm of REBA was dissolved in a citric acid/potassium citrate composition equivalent to that in a diet lemon-lime beverage. 400 ppm of Fibergum-P (e.g., gum *acacia* senegal) was then mixed with the base solution. The sweetness linger of this solution was determined to be 3.

Example B46

500 ppm of REBA was dissolved in one liter citric acid/potassium citrate composition equivalent to that in a diet lemon-lime beverage. 100 ppm to 300 ppm of poly-L-α-lysine, MW 83,000, was then mixed with the base solution. The sweetness linger of this solution was determined to be 2.

Example B47

5% sucrose (weight by volume of the final product) and 80 ppm REBA were dissolved in a citric acid/potassium citrate composition equivalent to that in a lemon-lime beverage. 3.5% erythritol was then mixed with the base solution. The sweetness linger of this solution was determined to be 0.

Example B48

5% sucrose (weight by volume of the final product) and 180 ppm of REBA were dissolved in a citric acid/potassium citrate composition equivalent to that in a lemon-lime beverage. The sweetness linger of this solution was determined to be 2.

Example B49

5% sucrose (weight by volume of the final product) and 80 ppm of REBA were dissolved in a citric acid/potassium citrate composition equivalent to that in a lemon-lime beverage. 0.75% D-tagatose was then mixed with the base solution. The sweetness linger of this solution was determined to be 2.

Example B50

5% sucrose (weight by volume of the final product) and 80 ppm of REBA were dissolved in a citric acid/potassium citrate composition equivalent to that in a lemon-lime beverage. 3.5% erythritol and 0.75% D-tagatose were then mixed with the base solution. The sweetness linger of this solution was determined to be 0.

Example B51

3.3% sucrose (weight by volume of the final product) and 160 ppm of REBA were dissolved in a citric acid/potassium citrate composition equivalent to that in a lemon-lime beverage. 3.5% erythritol was then mixed with the base solution. The sweetness linger of this solution was determined to be 1.

Example B52

3.3% sucrose (weight by volume of the final product) and 160 ppm of REBA were dissolved in a citric acid/potassium citrate composition equivalent to that in a lemon-lime beverage. 3.5% erythritol and 0.75% D-tagatose were then mixed with the base solution. The sweetness linger of this solution was determined to be 1.

Example B53

3.3% sucrose and 280 ppm of REBA were dissolved in a citric acid/potassium citrate composition equivalent to that in a lemon-lime beverage. The sweetness linger of this solution was determined to be 0.

Example B54

360 ppm of REBA was dissolved in a citric acid/potassium citrate composition equivalent to that in a diet lemon-lime beverage. 3.5% erythritol, 0.75% glycine, 250 ppm of potassium chloride and 650 ppm of potassium dihydrogen phosphate were then mixed with the base solution. The sweetness linger of this solution was determined to be 2.

Example B55

480 ppm of REBA was dissolved in a citric acid/potassium citrate composition equivalent to that in a diet lemon-lime beverage. 0.75% glycine, 250 ppm of potassium chloride and 650 ppm of potassium dihydrogen phosphate were then mixed with the base solution. The sweetness linger of this solution was determined to be 2.

Example B56

320 ppm of REBA was dissolved in a citric acid/potassium citrate composition equivalent to that in a diet lemon-lime beverage. 3.5% erythritol, 0.75% fructose, 250 ppm of potassium chloride and 650 ppm of potassium dihydrogen phosphate were then mixed with the base solution. The sweetness linger of this solution was determined to be 2.

Example B57

450 ppm of REBA was dissolved in a citric acid/potassium citrate composition equivalent to that in a diet lemon-lime beverage. 0.75% fructose, 250 ppm of potassium chloride and 650 ppm potassium dihydrogen phosphate were then mixed with the base solution. The sweetness linger of this solution was determined to be 3.

Example B58

360 ppm of REBA was dissolved in a citric acid/potassium citrate composition equivalent to that in a diet lemon-lime beverage. 3.5% erythritol and 400 ppm of Fibergum-P (e.g., gum *acacia* senegal) were then mixed with the base solution. The sweetness linger of this solution was determined to be 2.

Example B59

480 ppm of REBA was dissolved in a citric acid/potassium citrate composition equivalent to that in a diet lemon-lime beverage. 400 ppm of Fibergum-P (e.g., gum *acacia* senegal) was then mixed with the base solution. The sweetness linger of this solution was determined to be 3.

Example B60

360 ppm of REBA was dissolved in a citric acid/potassium citrate composition equivalent to that in a diet lemon-lime beverage. 3.5% erythritol, 0.5% glycine, 0.25% alanine, 250 ppm of potassium chloride and 650 ppm of potassium dihydrogen phosphate were then mixed with the base solution. The sweetness linger of this solution was determined to be 1.

Example B61

480 ppm of REBA was dissolved in a citric acid/potassium citrate composition equivalent to that in a diet lemon-lime beverage. 0.5% glycine, 0.25% alanine, 250 ppm of potassium chloride and 650 ppm of potassium dihydrogen phosphate were then mixed with the base solution. The sweetness linger of this solution was determined to be 3.

Example B62

400 ppm of REBA was dissolved in a citric acid/potassium citrate composition equivalent to that in a diet lemon-lime beverage. 2,500 ppm of creatine was then mixed with the base solution. The sweetness linger of this solution was determined to be 2. This formulation was found to have sugar-like taste characteristics.

Example B63

400 ppm of REBA was dissolved in a citric acid/potassium citrate composition equivalent to that in a diet lemon-lime beverage. 250-500 ppm of L-sodium lactate was then mixed with the base solution. The sweetness linger of this solution was determined to be 3. This formulation was found to have sugar-like taste characteristics.

Example B64

Two solutions were prepared. In each, 400 ppm of REBA was dissolved in a citric acid/potassium citrate composition equivalent to that in a diet lemon-lime beverage. 78 ppm to 156 ppm and 1,250 ppm of soluble rice protein were then mixed with their respective base solutions. The sweetness linger of these solutions was determined to be 3. These formulations were found to have sugar-like taste characteristics.

Example B65

400 ppm of REBA was dissolved in a citric acid/potassium citrate composition equivalent to that in a diet lemon-lime beverage. 312 ppm to 625 ppm of soluble rice protein was then mixed with the base solution. The sweetness linger of this solution was determined to be 2. This formulation was found to have sugar-like taste characteristics.

Example B66

400 ppm of REBA was dissolved in a citric acid/potassium citrate composition equivalent to that in a diet lemon-lime beverage. 1,000 ppm to 2,000 ppm of polypropylene glycol alginate (PGA) was then mixed with the base solution. The sweetness linger of this solution was determined to be 5. This formulation was found to have sugar-like taste characteristics.

Example B67

400 ppm of REBA was dissolved in a citric acid/potassium citrate composition equivalent to that in a diet lemon-lime beverage. 5,000 ppm Glycerin was then mixed with the base solution. The sweetness linger of this solution was determined to be 3.

Example B68

400 ppm of REBA was dissolved in a citric acid/potassium citrate composition equivalent to that in a diet lemon-lime beverage. 2,500 ppm of Fibersol-2 was then mixed with the base solution. The sweetness linger of this solution was determined to be 1.

Example B69

400 ppm of REBA was dissolved in a citric acid/potassium citrate composition equivalent to that in a diet lemon-lime beverage. 125 ppm collagen (unflavored gelatin) was then mixed with the base solution. The sweetness linger of this solution was determined to be 2. This formulation was found to have sugar-like taste characteristics.

Example B70

400 ppm of REBA was dissolved in a citric acid/potassium citrate composition equivalent to that in a diet lemon-lime beverage. 2,000 ppm collagen (unflavored gelatin) was then mixed with the base solution. The sweetness linger of this solution was determined to be 3. This formulation was found to have sugar-like taste characteristics.

Example B71

400 ppm of REBA was dissolved in a citric acid/potassium citrate composition equivalent to that in a diet lemon-lime beverage. 125 ppm of enzyme modified rutin Sanmelin™ AO (San-Ei Gen F.F.I., Inc., Osaka, Japan) was then mixed with the base solution. The sweetness linger of this solution was determined to be 4. This formulation was found to have sugar-like taste characteristics.

Example B72

400 ppm of REBA was dissolved in a citric acid/potassium citrate composition equivalent to that in a diet lemon-lime beverage. 250 ppm of enzyme modified rutin Sanmelin™ AO (San-Ei Gen F.F.I., Inc., Osaka, Japan) was then mixed with the base solution. The sweetness linger of this solution was determined to be 3. This formulation was found to have sugar-like taste characteristics.

Example B73

400 ppm of REBA was dissolved in a citric acid/potassium citrate composition equivalent to that in a diet lemon-lime beverage. 625 ppm of grape skin extract was then mixed with the base solution. The sweetness linger of this solution was determined to be 4. This formulation was found to have sugar-like taste characteristics.

Example B74

400 ppm of REBA was dissolved in a citric acid/potassium citrate composition equivalent to that in a diet lemon-lime beverage. 625 ppm of Symrise™ Natural Flavor Mask for Sweeteners, 164126 (Symrise™, Holzminden, Germany) was then mixed with the base solution. The sweetness linger of this solution was determined to be 4. This formulation was found to have sugar-like taste characteristics.

Example B75

400 ppm of REBA was dissolved in a citric acid/potassium citrate composition equivalent to that in a diet lemon-lime beverage. 1,250 ppm to 2,500 ppm of Symrise™ Natural Flavor Mask for Sweeteners 164126 (Symrise™, Holzminden, Germany) was then mixed with the base solution. The sweetness linger of this solution was determined to be 3. This formulation was found to have sugar-like taste characteristics.

Example B76

400 ppm of REBA was dissolved in a citric acid/potassium citrate composition equivalent to that in a diet lemon-lime beverage. 2 ppm of Natural Advantage™ Bitterness Blocker 9 (Natural Advantage, Freehold, N.J., U.S.A.) was then mixed with the base solution. The sweetness linger of this solution was determined to be 2. This formulation was found to have sugar-like taste characteristics.

Example B77

400 ppm of REBA was dissolved in a citric acid/potassium citrate composition equivalent to that in a diet lemon-lime beverage. 1 ppm to 2 ppm of Natural Advantage™ Bitterness Blocker 2 (Natural Advantage, Freehold, N.J., U.S.A.) was then mixed with the base solution. The sweetness linger of this solution was determined to be 2.

Example B78

400 ppm of REBA was dissolved in a citric acid/potassium citrate composition equivalent to that in a diet lemon-lime beverage. 2 ppm of Natural Advantage™ Bitterness Blocker 1 (Natural Advantage, Freehold, N.J., U.S.A.) was then mixed with the base solution. The sweetness linger of this solution was determined to be 3.

Example B79

400 ppm of REBA was dissolved in a citric acid/potassium citrate composition equivalent to that in a diet lemon-lime beverage. 4 ppm to 8 ppm of Natural Advantage™ Bitterness Blocker 10 (Natural Advantage, Freehold, N.J., U.S.A.) was then mixed with the base solution. The sweetness linger of this solution was determined to be 2.

C. Example Set C

Control Samples 375 mg of mono-ammonium glycyrrhizic acid salt hydrate (sweetness level 4% sucrose equivalent) was dissolved in one liter of carbon-treated water. The sweetness linger of this solution was determined to be 5.

10 g of sucrose was dissolved in 100 ml of carbon treated water. The sweetness linger rating of this control sample was determined to be 0.

Example C1

375 mg of monoammonium glycyrrhizic acid salt hydrate, was dissolved in one liter of carbon-treated water. 50,000 ppm of NaCl was then mixed with the base solution. The sweetness linger of this solution was determined to be 1.

Example C2

375 mg of monoammonium glycyrrhizic acid salt hydrate, was dissolved in one liter of carbon-treated water. 25,000 ppm of NaCl was then mixed with the base solution. The sweetness linger of this solution was determined to be 2.

Example C3

375 mg of mono-ammonium glycyrrhizic acid salt hydrate, was dissolved in one liter of carbon-treated water. 10,000 ppm of NaCl was then mixed with the base solution. The sweetness linger of this solution was determined to be 3.

Example C4

375 mg of mono-ammonium glycyrrhizic acid salt hydrate, was dissolved in one liter of carbon-treated water. 5,000 ppm of NaCl was then mixed with the base solution. The sweetness linger of this solution was determined to be 4.5.

D. Example Set D

Example D1

400-500 ppm of *stevia* are dissolved in a citric acid/potassium citrate composition equivalent to that in a diet lemon-lime beverage. Fibergum (e.g., gum *acacia* seyal) is then mixed with the base solution.

Example D2

5% sucrose and 400-500 ppm *stevia* are dissolved in a citric acid/potassium citrate composition equivalent to that in a lemon-lime beverage. Erythritol is then mixed with the base solution.

Example D3

5% sucrose and 400-500 ppm of *stevia* are dissolved in a citric acid/potassium citrate composition equivalent to that in a lemon-lime beverage. D-Tagatose is then mixed with the base solution.

Example D4

5% sucrose and 400-500 ppm of *stevia* are dissolved in a citric acid/potassium citrate composition equivalent to that in a lemon-lime beverage. Erythritol and D-tagatose are then mixed with the base solution.

Example D5

3.3% sucrose and 400-500 ppm of *stevia* are dissolved in a citric acid/potassium citrate composition equivalent to that in a lemon-lime beverage. Erythritol is then mixed with the base solution.

Example D6

3.3% sucrose and 400-500 ppm of *stevia* are dissolved in a citric acid/potassium citrate composition equivalent to that in a lemon-lime beverage. Erythritol and D-tagatose are then mixed with the base solution.

Example D7

3.3% sucrose and 400-500 ppm of *stevia* are dissolved in a citric acid/potassium citrate composition equivalent to that in a lemon-lime beverage.

Example D8

400-500 ppm of *stevia* is dissolved in a citric acid/potassium citrate composition equivalent to that in a diet lemon-lime beverage. Erythritol, glycine, potassium chloride and potassium dihydrogen phosphate are then mixed with the base solution.

Example D9

400-500 ppm of *stevia* is dissolved in a citric acid/potassium citrate composition equivalent to that in a diet lemon-lime beverage. Glycine, potassium chloride and potassium dihydrogen phosphate are then mixed with the base solution.

Example D10

400-500 ppm of *stevia* is dissolved in a citric acid/potassium citrate composition equivalent to that in a diet lemon-lime beverage. Erythritol, fructose, potassium chloride and potassium dihydrogen phosphate are then mixed with the base solution.

Example D11

400-500 ppm of *stevia* is dissolved in a citric acid/potassium citrate composition equivalent to that in a diet lemon-lime beverage. Fructose, potassium chloride and potassium dihydrogen phosphate are then mixed with the base solution.

Example D12

400-500 ppm of *stevia* is dissolved in a citric acid/potassium citrate composition equivalent to that in a diet lemon-lime beverage. Erythritol and fibergum (e.g., gum *acacia* seyal) are then mixed with the base solution.

Example D13

400-500 ppm of *stevia* is dissolved in a citric acid/potassium citrate composition equivalent to that in a diet lemon-lime beverage. Fibergum (e.g., gum *acacia* seyal) is then mixed with the base solution.

Example D14

400-500 ppm of *stevia* is dissolved in a citric acid/potassium citrate composition equivalent to that in a diet lemon-lime beverage. Erythritol, glycine, alanine, potassium chloride and potassium dihydrogen phosphate are then mixed with the base solution.

Example D15

400-500 ppm of *stevia* is dissolved in a citric acid/potassium citrate composition equivalent to that in a diet lemon-lime beverage. Glycine, alanine, potassium chloride and potassium dihydrogen phosphate are then mixed with the base solution.

Example D16

400-500 mg of *stevia* is dissolved in one liter carbon-treated water and phosphoric acid (75%) is added until a pH between pH 2.4 and 2.5 is reached. D-Gluconic acid is then mixed with the base solution.

Example D17

400-500 mg of *stevia* is dissolved in one liter carbon-treated water and phosphoric acid (75%) is added until a pH between pH 2.4 and 2.5 is reached. D-Gluconic acid, potassium salt is then mixed with the base solution.

Example D18

400-500 mg of *stevia* is dissolved in one liter carbon-treated water and phosphoric acid (75%) is added until a pH between pH 2.4 and 2.5 is reached. L-threonine is then mixed with the base solution.

Example D19

400-500 mg of *stevia* is dissolved in one liter carbon-treated water and phosphoric acid (75%) is added until a pH between pH 2.4 and 2.5 is reached. L-serine is then mixed with the base solution.

Example D20

400-500 mg of *stevia* is dissolved in one liter carbon-treated water and phosphoric acid (75%) is added until a pH between pH 2.4 and 2.5 is reached. L-alanine is then mixed with the base solution.

Example D21

400-500 mg of *stevia* is dissolved in one liter carbon-treated water and phosphoric acid (75%) is added until a pH between pH 2.4 and 2.5 is reached. Glycine is then mixed with the base solution.

Example D22

400-500 mg of *stevia* is dissolved in one liter carbon-treated water and phosphoric acid (75%) is added until a pH between pH 2.4 and 2.5 is reached. β-alanine is then mixed with the base solution.

Example D23

400-500 mg of *stevia* is dissolved in one liter carbon-treated water and phosphoric acid (75%) is added until a pH between pH 2.4 and 2.5 is reached. Glycine and poly-L-α-lysine are then mixed with the base solution.

Example D24

400-500 mg of *stevia* is dissolved in one liter carbon-treated water and phosphoric acid (75%) is added until a pH between pH 2.4 and 2.5 is reached. Glycine and poly-L-ε-lysine are then mixed with the base solution.

Example D25

400-500 mg of *stevia* is dissolved in one liter carbon-treated water and phosphoric acid (75%) is added until a pH between pH 2.4 and 2.5 is reached. Adipic acid is then mixed with the base solution.

Example D26

400-500 mg of *stevia* is dissolved in one liter carbon-treated water and phosphoric acid (75%) is added until a pH between pH 2.4 and 2.5 is reached. Poly-L-α-lysine (molecular weight ~63,000) is then mixed with the base solution.

Example D27

400-500 mg of *stevia* is dissolved in one liter carbon-treated water and phosphoric acid (75%) is added until a pH between pH 2.4 and 2.5 is reached. Poly-L-α-lysine (molecular weight ~6,000) is then mixed with the base solution,

Example D28

400-500 mg of *stevia* is dissolved in one liter carbon-treated water and phosphoric acid (75%) is added until a pH between pH 2.4 and 2.5 is reached. Poly-L-α-lysine (molecular weight ~83,000) is then mixed with the base solution.

Example D29

400-500 mg of *stevia* is dissolved in one liter carbon-treated water and phosphoric acid (75%) is added until a pH between pH 2.4 and 2.5 is reached. Poly-L-α-lysine (molecular weight ~1,300,000) is then mixed with the base solution.

Example D30

400-500 mg of *stevia* is dissolved in one liter carbon-treated water and phosphoric acid (75%) is added until a pH between pH 2.4 and 2.5 is reached. Fruitaric acid is then mixed with the base solution.

Example D31

400-500 mg of *stevia* is dissolved in one liter carbon-treated water and phosphoric acid (75%) is added until a pH between pH 2.4 and 2.5 is reached. Tartaric acid is then mixed with the base solution.

Example D32

400-500 mg of *stevia* is dissolved in one liter carbon-treated water and phosphoric acid (75%) is added until a pH between pH 2.4 and 2.5 is reached. Sodium bisulfate is then mixed with the base solution.

Example D33

400-500 mg of *stevia* is dissolved in one liter carbon-treated water and phosphoric acid (75%) is added until a pH between pH 2.4 and 2.5 is reached. Lauric arginate is then mixed with the base solution.

Example D34

400-500 mg of *stevia* is dissolved in one liter carbon-treated water and phosphoric acid (75%) is added until a pH between pH 2.4 and 2.5 is reached. L-lysine is then mixed with the base solution.

Example D35

400-500 mg of *stevia* is dissolved in one liter carbon-treated water and phosphoric acid (75%) is added until a pH between pH 2.4 and 2.5 is reached. Guanidine hydrochloride is then mixed with the base solution.

Example D36

400-500 mg of *stevia* is dissolved in one liter carbon-treated water and phosphoric acid (75%) is added until a pH between pH 2.4 and 2.5 is reached. Urea and sodium chloride are then mixed with the base solution.

Example D37

400-500 mg of *stevia* is dissolved in one liter carbon-treated water and phosphoric acid (75%) is added until a pH between pH 2.4 and 2.5 is reached. Urea is then mixed with the base solution.

Example D38

400-500 mg of *stevia* is dissolved in one liter carbon-treated water and phosphoric acid (75%) is added until a pH between pH 2.4 and 2.5 is reached. Choline chloride is then mixed with the base solution.

Example D39

400-500 mg of *stevia* is dissolved in one liter carbon-treated water and phosphoric acid (75%) is added until a pH between pH 2.4 and 2.5 is reached. D-glucosamine hydrochloride is then mixed with the base solution.

Example D40

400-500 mg of *stevia* is dissolved in one liter carbon-treated water and phosphoric acid (75%) is added until a pH between pH 2.4 and 2.5 is reached. Poly-L-$\epsilon$-lysine is then mixed with the base solution.

Example D41

400-500 mg of *stevia* is dissolved in one liter carbon-treated water and phosphoric acid (75%) is added until a pH between pH 2.4 and 2.5 is reached. Glycine, sodium chloride and potassium chloride are then mixed with the base solution.

Example D42

400-500 mg of *stevia* is dissolved in one liter carbon-treated water and phosphoric acid (75%) is added until a pH between pH 2.4 and 2.5 is reached. Glycine and aluminum sulfate (alum) are then mixed with the base solution.

Example D43

400-500 mg of *stevia* is dissolved in one liter carbon-treated water and phosphoric acid (75%) is added until a pH between pH 2.4 and 2.5 is reached. Glycine and potassium chloride are then mixed with the base solution.

Example D44

400-500 mg of *stevia* is dissolved in one liter carbon-treated water and phosphoric acid (75%) is added until a pH between pH 2.4 and 2.5 is reached. Glycine and sodium gluconate are then mixed with the base solution.

Example D45

400-500 mg of *stevia* is dissolved in one liter carbon-treated water and phosphoric acid (75%) is added until a pH between pH 2.4 and 2.5 is reached. Polyethylenimine is then mixed with the base solution.

Example D46

400-500 mg of *stevia* is dissolved in one liter carbon-treated water and phosphoric acid (75%) is added until a pH between pH 2.4 and 2.5 is reached. Chitosan is then mixed with the base solution.

Example D47

400-500 mg of *stevia* is dissolved in one liter carbon-treated water and phosphoric acid (75%) is added until a pH between pH 2.4 and 2.5 is reached. Poly L-ornithine is then mixed with the base solution.

Example D48

400-500 mg of *stevia* is dissolved in one liter carbon-treated water and phosphoric acid (75%) is added until a pH between pH 2.4 and 2.5 is reached. Magnesium chloride is then mixed with the base solution.

Example D49

400-500 mg of *stevia* is dissolved in one liter carbon-treated water and phosphoric acid (75%) is added until a pH between pH 2.4 and 2.5 is reached. Whey protein (concentrate 34%) is then mixed with the base solution.

400-500 mg of *stevia* is dissolved in one liter carbon-treated water and phosphoric acid (75%) is added until a pH between pH 2.4 and 2.5 is reached. Fumaric acid, malic acid and tartaric acid are then mixed with the base solution.

Example D50

400-500 ppm of stevioside is dissolved in a citric acid/potassium citrate composition equivalent to that in a diet lemon-lime beverage. Fibergum (e.g., gum *acacia* seyal) is then mixed with the base solution.

Example D51

5% sucrose and 400-500 ppm stevioside are dissolved in a citric acid/potassium citrate composition equivalent to that in a lemon-lime beverage. Erythritol is then mixed with the base solution.

Example D52

5% sucrose and 400-500 ppm of stevioside are dissolved in a citric acid/potassium citrate composition equivalent to that in a lemon-lime beverage. D-Tagatose is then mixed with the base solution.

Example D53

5% sucrose and 400-500 ppm of stevioside are dissolved in a citric acid/potassium citrate composition equivalent to that in a lemon-lime beverage. Erythritol and D-tagatose are then mixed with the base solution.

Example D54

3.3% sucrose and 400-500 ppm of stevioside are dissolved in a citric acid/potassium citrate composition equivalent to that in a lemon-lime beverage. Erythritol is then mixed with the base solution.

Example D55

3.3% sucrose and 400-500 ppm of stevioside are dissolved in a citric acid/potassium citrate composition equivalent to that in a lemon-lime beverage. Erythritol and D-tagatose are then mixed with the base solution.

Example D56

400-500 ppm of stevioside are dissolved in a citric acid/potassium citrate composition equivalent to that in a diet lemon-lime beverage. Erythritol, glycine, potassium chloride and potassium dihydrogen phosphate are then mixed with the base solution.

Example D57

400-500 ppm of stevioside is dissolved in a citric acid/potassium citrate composition equivalent to that in a diet lemon-lime beverage. Glycine, potassium chloride and potassium dihydrogen phosphate are then mixed with the base solution.

Example D58

400-500 ppm of stevioside is dissolved in a citric acid/potassium citrate composition equivalent to that in a diet lemon-lime beverage. Erythritol, fructose, potassium chloride and potassium dihydrogen phosphate are then mixed with the base solution.

Example D59

400-500 ppm of stevioside is dissolved in a citric acid/potassium citrate composition equivalent to that in a diet lemon-lime beverage. Fructose, potassium chloride and potassium dihydrogen phosphate are then mixed with the base solution.

Example D60

400-500 ppm of stevioside is dissolved in a citric acid/potassium citrate composition equivalent to that in a diet lemon-lime beverage. Erythritol and fibergum (e.g., gum *acacia* seyal) are then mixed with the base solution.

Example D61

400-500 ppm of stevioside is dissolved in a citric acid/potassium citrate composition equivalent to that in a diet lemon-lime beverage. Fibergum (e.g., gum *acacia* seyal) is then mixed with the base solution.

Example D62

400-500 ppm of stevioside is dissolved in a citric acid/potassium citrate composition equivalent to that in a diet lemon-lime beverage. Erythritol, glycine, alanine, potassium chloride and potassium dihydrogen phosphate are then mixed with the base solution.

Example D63

400-500 ppm of stevioside is dissolved in a citric acid/potassium citrate composition equivalent to that in a diet lemon-lime beverage. Glycine, alanine, potassium chloride and potassium dihydrogen phosphate are then mixed with the base solution.

Example D64

400-500 mg of stevioside is dissolved in one liter carbon-treated water and phosphoric acid (75%) is added until a pH between pH 2.4 and 2.5 is reached. D-Gluconic acid is then mixed with the base solution.

Example D65

400-500 mg of stevioside is dissolved in one liter carbon-treated water and phosphoric acid (75%) is added until a pH between pH 2.4 and 2.5 is reached. D-Gluconic acid, potassium salt is then mixed with the base solution.

Example D66

400-500 mg of stevioside is dissolved in one liter carbon-treated water and phosphoric acid (75%) is added until a pH between pH 2.4 and 2.5 is reached. L-Threonine is then mixed with the base solution.

Example D67

400-500 mg of stevioside is dissolved in one liter carbon-treated water and phosphoric acid (75%) is added until a pH between pH 2.4 and 2.5 is reached L-serine is then mixed with the base solution.

Example D68

400-500 mg of stevioside is dissolved in one liter carbon-treated water and phosphoric acid (75%) is added until a pH between pH 2.4 and 2.5 is reached. L-alanine is then mixed with the base solution.

Example D69

400-500 mg of stevioside is dissolved in one liter carbon-treated water and phosphoric acid (75%) is added until a pH between pH 2.4 and 2.5 is reached. Glycine is then mixed with the base solution.

Example D70

400-500 mg of stevioside is dissolved in one liter carbon-treated water and phosphoric acid (75%) is added until a pH between pH 2.4 and 2.5 is reached. β-alanine is then mixed with the base solution.

Example D71

400-500 mg of stevioside is dissolved in one liter carbon-treated water and phosphoric acid (75%) is added until a pH between pH 2.4 and 2.5 is reached. Glycine and poly-L-α-lysine are then mixed with the base solution.

Example D72

400-500 mg of stevioside is dissolved in one liter carbon-treated water and phosphoric acid (75%) is added until a pH between pH 2.4 and 2.5 is reached. Glycine and poly-L-ϵ-lysine are then mixed with the base solution.

Example D73

400-500 mg of stevioside is dissolved in one liter carbon-treated water and phosphoric acid (75%) is added until a pH between pH 2.4 and 2.5 is reached. Adipic acid is then mixed with the base solution.

Example D74

400-500 mg of stevioside is dissolved in one liter carbon-treated water and phosphoric acid (75%) is added until a pH between pH 2.4 and 2.5 is reached. Poly-L-α-lysine (molecular weight ~63,000) is then mixed with the base solution.

Example D75

400-500 mg of stevioside is dissolved in one liter carbon-treated water and phosphoric acid (75%) is added until a pH between pH 2.4 and 2.5 is reached. Poly-L-α-lysine (molecular weight ~6,000) is then mixed with the base solution.

Example D76

400-500 mg of stevioside is dissolved in one liter carbon-treated water and phosphoric acid (75%) is added until a pH between pH 2.4 and 2.5 is reached. Poly-L-α-lysine (molecular weight ~93,000) is then mixed with the base solution.

Example D77

400-500 mg of stevioside is dissolved in one liter carbon-treated water and phosphoric acid (75%) is added until a pH between pH 2.4 and 2.5 is reached. Poly-L-α-lysine (molecular weight ~1,300,000) is then mixed with the base solution.

Example D78

400-500 mg of stevioside is dissolved in one liter carbon-treated water and phosphoric acid (75%) is added until a pH between pH 2.4 and 2.5 is reached. Fruitaric acid is then mixed with the base solution.

Example D79

400-500 mg of stevioside is dissolved in one liter carbon-treated water and phosphoric acid (75%) is added until a pH between pH 2.4 and 2.5 is reached Tartaric acid is then mixed with the base solution.

Example D80

400-500 mg of stevioside is dissolved in one liter carbon-treated water and phosphoric acid (75%) is added until a pH between pH 2.4 and 2.5 is reached. Sodium bisulfate is then mixed with the base solution.

Example D81

400-500 mg of stevioside is dissolved in one liter carbon-treated water and phosphoric acid (75%) is added until a pH between pH 2.4 and 2.5 is reached. Lauric arginate is then mixed with the base solution.

Example D82

400-500 mg of stevioside is dissolved in one liter carbon-treated water and phosphoric acid (75%) is added until a pH between pH 2.4 and 2.5 is reached. L-lysine is then mixed with the base solution.

Example D83

400-500 mg of stevioside is dissolved in one liter carbon-treated water and phosphoric acid (75%) is added until a pH between pH 2.4 and 2.5 is reached. Guanidine hydrochloride is then mixed with the base solution.

Example D84

400-500 mg of stevioside is dissolved in one liter carbon-treated water and phosphoric acid (75%) is added until a pH between pH 2.4 and 2.5 is reached. Urea and sodium chloride are then mixed with the base solution.

Example D85

400-500 mg of stevioside is dissolved in one liter carbon-treated water and phosphoric acid (75%) is added until a pH between pH 2.4 and 2.5 is reached. Urea is then mixed with the base solution.

Example D86

400-500 mg of stevioside is dissolved in one liter carbon-treated water and phosphoric acid (75%) is added until a pH between pH 2.4 and 2.5 is reached. Choline chloride is then mixed with the base solution.

Example D87

400-500 mg of stevioside is dissolved in one liter carbon-treated water and phosphoric acid (75%) is added until a pH between pH 2.4 and 2.5 is reached. D-glucosamine hydrochloride is then mixed with the base solution.

Example D88

400-500 mg of stevioside is dissolved in one liter carbon-treated water and phosphoric acid (75%) is added until a pH between pH 2.4 and 2.5 is reached. Poly-L-ϵ-lysine is then mixed with the base solution.

Example D89

400-500 mg of stevioside is dissolved in one liter carbon-treated water and phosphoric acid (75%) is added until a pH between pH 2.4 and 2.5 is reached. Glycine, sodium chloride and potassium chloride are then mixed with the base solution.

Example D90

400-500 mg of stevioside is dissolved in one liter carbon-treated water and phosphoric acid (75%) is added until a pH between pH 2.4 and 2.5 is reached. Glycine and aluminum sulfate (alum) are then mixed with the base solution.

Example D91

400-500 mg of stevioside is dissolved in one liter carbon-treated water and phosphoric acid (75%) is added until a pH between pH 2.4 and 2.5 is reached. Glycine and potassium chloride are then mixed with the base solution.

Example D92

400-500 mg of stevioside is dissolved in one liter carbon-treated water and phosphoric acid (75%) is added until a pH between pH 2.4 and 2.5 is reached. Glycine and sodium gluconate are then mixed with the base solution.

Example D93

400-500 mg of stevioside is dissolved in one liter carbon-treated water and phosphoric acid (75%) is added until a pH between pH 2.4 and 2.5 is reached. Polyethylenimine is then mixed with the base solution.

Example D94

400-500 mg of stevioside is dissolved in one liter carbon-treated water and phosphoric acid (75%) is added until a pH between pH 2.4 and 2.5 is reached. Chitosan is then mixed with the base solution.

Example D95

400-500 mg of stevioside is dissolved in one liter carbon-treated water and phosphoric acid (75%) is added until a pH between pH 2.4 and 2.5 is reached. Poly L-ornithine is then mixed with the base solution.

Example D96

400-500 mg of stevioside is dissolved in one liter carbon-treated water and phosphoric acid (75%) is added until a pH between pH 2.4 and 2.5 is reached. Magnesium chloride is then mixed with the base solution.

Example D97

400-500 mg of stevioside is dissolved in one liter carbon-treated water and phosphoric acid (75%) is added until a pH between pH 2.4 and 2.5 is reached. Whey protein (concentrate 34%) is then mixed with the base solution.

400-500 mg of stevioside is dissolved in one liter carbon-treated water and phosphoric acid (75%) is added until a pH between pH 2.4 and 2.5 is reached. Fumaric acid, malic acid and tartaric acid are then mixed with the base solution.

Example D98

400-500 ppm of Mogroside IV is dissolved in a citric acid/potassium citrate composition equivalent to that in a diet lemon-lime beverage. Fibergum (e.g., gum *acacia* seyal) is then mixed with the base solution.

Example D99

5% sucrose and 400-500 ppm Mogroside IV are dissolved in a citric acid/potassium citrate composition equivalent to that in a lemon-lime beverage. Erythritol is then mixed with the base solution.

Example D100

5% sucrose and 400-500 ppm of Mogroside IV are dissolved in a citric acid/potassium citrate composition equivalent to that in a lemon-lime beverage.

Example D101

5% sucrose and 400-500 ppm of Mogroside IV are dissolved in a citric acid/potassium citrate composition equivalent to that in a lemon-lime beverage. D-Tagatose is then mixed with the base solution.

Example D102

5% sucrose and 400-500 ppm of Mogroside IV are dissolved in a citric acid/potassium citrate composition equivalent to that in a lemon-lime beverage. Erythritol and D-tagatose are then mixed with the base solution.

Example D103

3.3% sucrose and 400-500 ppm of Mogroside IV are dissolved in a citric acid/potassium citrate composition equivalent to that in a lemon-lime beverage. Erythritol is then mixed with the base solution.

Example D104

3.3% sucrose and 400-500 ppm of Mogroside IV are dissolved in a citric acid/potassium citrate composition equivalent to that in a lemon-lime beverage. Erythritol and D-tagatose are then mixed with the base solution.

Example D105

3.3% sucrose and 400-500 ppm of Mogroside IV are dissolved in a citric acid/potassium citrate composition equivalent to that in a lemon-lime beverage.

Example D106

400-500 ppm of Mogroside IV is dissolved in a citric acid/potassium citrate composition equivalent to that in a diet lemon-lime beverage. Erythritol, glycine, potassium chloride and potassium dihydrogen phosphate are then mixed with the base solution.

Example D107

400-500 ppm of Mogroside IV is dissolved in a citric acid/potassium citrate composition equivalent to that in a diet lemon-lime beverage. Glycine, potassium chloride and potassium dihydrogen phosphate are then mixed with the base solution.

Example D108

400-500 ppm of Mogroside IV is dissolved in a citric acid/potassium citrate composition equivalent to that in a diet lemon-lime beverage. Erythritol, fructose, potassium chloride and potassium dihydrogen phosphate are then mixed with the base solution.

Example D109

400-500 ppm of Mogroside IV is dissolved in a citric acid/potassium citrate composition equivalent to that in a diet lemon-lime beverage. Fructose, potassium chloride and potassium dihydrogen phosphate are then mixed with the base solution.

Example D110

400-500 ppm of Mogroside IV is dissolved in a citric acid/potassium citrate composition equivalent to that in a diet lemon-lime beverage. Erythritol and fibergum (e.g., gum *acacia seyal*) are then mixed with the base solution.

Example D111

400-500 ppm of Mogroside IV is dissolved in a citric acid/potassium citrate composition equivalent to that in a diet lemon-lime beverage. Fibergum (e.g., gum *acacia* seyal) is then mixed with the base solution.

Example D112

400-500 ppm of Mogroside IV is dissolved in a citric acid/potassium citrate composition equivalent to that in a diet lemon-lime beverage. Erythritol, glycine, alanine, potassium chloride and potassium dihydrogen phosphate are then mixed with the base solution.

Example D113

400-500 ppm of Mogroside IV is dissolved in a citric acid/potassium citrate composition equivalent to that in a diet lemon-lime beverage. Glycine, alanine, potassium chloride and potassium dihydrogen phosphate are then mixed with the base solution.

Example D114

400-500 mg of Mogroside IV is dissolved in one liter carbon-treated water and phosphoric acid (75%) is added until a pH between pH 2.4 and 2.5 is reached. D-Gluconic acid is then mixed with the base solution.

Example D115

400-500 mg of Mogroside IV is dissolved in one liter carbon-treated water and phosphoric acid (75%) is added until a pH between pH 2.4 and 2.5 is reached. D-Gluconic acid, potassium salt is then mixed with the base solution.

Example D116

400-500 mg of Mogroside IV is dissolved in one liter carbon-treated water and phosphoric acid (75%) is added until a pH between pH 2.4 and 2.5 is reached. L-Threonine is then mixed with the base solution.

Example D117

400-500 mg of Mogroside IV is dissolved in one liter carbon-treated water and phosphoric acid (75%) is added until a pH between pH 2.4 and 2.5 is reached. L-Serine is then mixed with the base solution.

Example D118

400-500 mg of Mogroside IV is dissolved in one liter carbon-treated water and phosphoric acid (75%) is added until a pH between pH 2.4 and 2.5 is reached. L-alanine is then mixed with the base solution.

Example D119

400-500 mg of Mogroside IV is dissolved in one liter carbon-treated water and phosphoric acid (75%) is added until a pH between pH 2.4 and 2.5 is reached. Glycine is then mixed with the base solution.

Example D120

400-500 mg of Mogroside IV is dissolved in one liter carbon-treated water and phosphoric acid (75%) is added until a pH between pH 2.4 and 2.5 is reached. $\beta$-alanine is then mixed with the base solution.

Example D121

400-500 mg of Mogroside IV is dissolved in one liter carbon-treated water and phosphoric acid (75%) is added until a pH between pH 2.4 and 2.5 is reached. Glycine and poly-L-$\alpha$-lysine are then mixed with the base solution.

Example D122

400-500 mg of Mogroside IV is dissolved in one liter carbon-treated water and phosphoric acid (75%) is added until a pH between pH 2.4 and 2.5 is reached. Glycine and poly-L-$\epsilon$-lysine are then mixed with the base solution.

Example D123

400-500 mg of Mogroside IV is dissolved in one liter carbon-treated water and phosphoric acid (75%) is added until a pH between pH 2.4 and 2.5 is reached. Adipic acid is then mixed with the base solution.

Example D124

400-500 mg of Mogroside IV is dissolved in one liter carbon-treated water and phosphoric acid (75%) is added until a pH between pH 2.4 and 2.5 is reached. Poly-L-$\alpha$-lysine (molecular weight ~63,000) is then mixed with the base solution.

Example D125

400-500 mg of Mogroside IV is dissolved in one liter carbon-treated water and phosphoric acid (75%) is added

Example D126

400-500 mg of Mogroside IV is dissolved in one liter carbon-treated water and phosphoric acid (75%) is added until a pH between pH 2.4 and 2.5 is reached. Poly-L-α-lysine (molecular weight ~93,000) is then mixed with the base solution.

Example D127

400-500 mg of Mogroside IV is dissolved in one liter carbon-treated water and phosphoric acid (75%) is added until a pH between pH 2.4 and 2.5 is reached. Poly-L-α-lysine (molecular weight ~1,300,000) is then mixed with the base solution.

Example D128

400-500 mg of Mogroside IV is dissolved in one liter carbon-treated water and phosphoric acid (75%) is added until a pH between pH 2.4 and 2.5 is reached. Fruitaric acid is then mixed with the base solution.

Example D129

400-500 mg of Mogroside IV is dissolved in one liter carbon-treated water and phosphoric acid (75%) is added until a pH between pH 2.4 and 2.5 is reached. Tartaric acid is then mixed with the base solution.

Example D130

400-500 mg of Mogroside IV is dissolved in one liter carbon-treated water and phosphoric acid (75%) is added until a pH between pH 2.4 and 2.5 is reached. Sodium bisulfate is then mixed with the base solution.

Example D131

400-500 mg of Mogroside IV is dissolved in one liter carbon-treated water and phosphoric acid (75%) is added until a pH between pH 2.4 and 2.5 is reached. Lauric arginate is then mixed with the base solution.

Example D132

400-500 mg of Mogroside IV is dissolved in one liter carbon-treated water and phosphoric acid (75%) is added until a pH between pH 2.4 and 2.5 is reached. L-lysine is then mixed with the base solution.

Example D133

400-500 mg of Mogroside IV is dissolved in one liter carbon-treated water and phosphoric acid (75%) is added until a pH between pH 2.4 and 2.5 is reached. Guanidine hydrochloride is then mixed with the base solution.

Example D134

400-500 mg of Mogroside IV is dissolved in one liter carbon-treated water and phosphoric acid (75%) is added until a pH between pH 2.4 and 2.5 is reached. Urea and sodium chloride are then mixed with the base solution.

Example D135

400-500 mg of Mogroside IV is dissolved in one liter carbon-treated water and phosphoric acid (75%) is added until a pH between pH 2.4 and 2.5 is reached. Urea is then mixed with the base solution.

Example D136

400-500 mg of Mogroside IV is dissolved in one liter carbon-treated water and phosphoric acid (75%) is added until a pH between pH 2.4 and 2.5 is reached. Choline chloride is then mixed with the base solution.

Example D137

400-500 mg of Mogroside IV is dissolved in one liter carbon-treated water and phosphoric acid (75%) is added until a pH between pH 2.4 and 2.5 is reached. D-glucosamine hydrochloride is then mixed with the base solution.

Example D138

400-500 mg of Mogroside IV is dissolved in one liter carbon-treated water and phosphoric acid (75%) is added until a pH between pH 2.4 and 2.5 is reached. Poly-L-ϵ-lysine is then mixed with the base solution.

Example D139

400-500 mg of Mogroside IV is dissolved in one liter carbon-treated water and phosphoric acid (75%) is added until a pH between pH 2.4 and 2.5 is reached. Glycine, sodium chloride and potassium chloride are then mixed with the base solution.

Example D140

400-500 mg of Mogroside IV is dissolved in one liter carbon-treated water and phosphoric acid (75%) is added until a pH between pH 2.4 and 2.5 is reached. Glycine and aluminum sulfate (alum) are then mixed with the base solution.

Example D141

400-500 mg of Mogroside IV is dissolved in one liter carbon-treated water and phosphoric acid (75%) is added until a pH between pH 2.4 and 2.5 is reached. Glycine and potassium chloride are then mixed with the base solution.

Example D142

400-500 mg of Mogroside IV is dissolved in one liter carbon-treated water and phosphoric acid (75%) is added until a pH between pH 2.4 and 2.5 is reached. Glycine and sodium gluconate are then mixed with the base solution.

Example D143

400-500 mg of Mogroside IV is dissolved in one liter carbon-treated water and phosphoric acid (75%) is added until a pH between pH 2.4 and 2.5 is reached. Polyethylenimine is then mixed with the base solution.

Example D144

400-500 mg of Mogroside IV is dissolved in one liter carbon-treated water and phosphoric acid (75%) is added until a pH between pH 2.4 and 2.5 is reached. Chitosan is then mixed with the base solution.

Example D145

400-500 mg of Mogroside IV is dissolved in one liter carbon-treated water and phosphoric acid (75%) is added until a pH between pH 2.4 and 2.5 is reached. Poly L-ornithine is then mixed with the base solution.

Example D146

400-500 mg of Mogroside IV is dissolved in one liter carbon-treated water and phosphoric acid (75%) is added until a pH between pH 2.4 and 2.5 is reached. Magnesium chloride is then mixed with the base solution.

Example D147

400-500 mg of Mogroside IV is dissolved in one liter carbon-treated water and phosphoric acid (75%) is added until a pH between pH 2.4 and 2.5 is reached. Whey protein (concentrate 34%) is then mixed with the base solution.

Example D148

400-500 mg of Mogroside IV is dissolved in one liter carbon-treated water and phosphoric acid (75%) is added until a pH between pH 2.4 and 2.5 is reached. Fumaric acid, malic acid and tartaric acid are then mixed with the base solution.

Example D149

400-500 ppm of Mogroside V is dissolved in a citric acid/potassium citrate composition equivalent to that in a diet lemon-lime beverage. Fibergum (e.g., gum *acacia* seyal) is then mixed with the base solution.

Example D150

5% sucrose and 400-500 ppm Mogroside V are dissolved in a citric acid/potassium citrate composition equivalent to that in a lemon-lime beverage. Erythritol is then mixed with the base solution.

Example D151

5% sucrose and 400-500 ppm of Mogroside V are dissolved in a citric acid/potassium citrate composition equivalent to that in a lemon-lime beverage. D-Tagatose is then mixed with the base solution.

Example D152

5% sucrose and 400-500 ppm of Mogroside V are dissolved in a citric acid/potassium citrate composition equivalent to that in a lemon-lime beverage. Erythritol and D-tagatose are then mixed with the base solution.

Example D153

3.3% sucrose and 400-500 ppm of Mogroside V are dissolved in a citric acid/potassium citrate composition equivalent to that in a lemon-lime beverage. Erythritol is then mixed with the base solution.

Example D154

3.3% sucrose and 400-500 ppm of Mogroside V are dissolved in a citric acid/potassium citrate composition equivalent to that in a lemon-lime beverage. Erythritol and D-tagatose are then mixed with the base solution.

Example D155

3.3% sucrose and 400-500 ppm of Mogroside V are dissolved in a citric acid/potassium citrate composition equivalent to that in a lemon-lime beverage.

Example D156

400-500 ppm of Mogroside V is dissolved in a citric acid/potassium citrate composition equivalent to that in a diet lemon-lime beverage. Erythritol, glycine, potassium chloride and potassium dihydrogen phosphate are then mixed with the base solution.

Example D157

400-500 ppm of Mogroside V is dissolved in a citric acid/potassium citrate composition equivalent to that in a diet lemon-lime beverage. Glycine, potassium chloride and potassium dihydrogen phosphate are then mixed with the base solution.

Example D158

400-500 ppm of Mogroside V is dissolved in a citric acid/potassium citrate composition equivalent to that in a diet lemon-lime beverage. Erythritol, fructose, potassium chloride and potassium dihydrogen phosphate are then mixed with the base solution.

Example D159

400-500 ppm of Mogroside V is dissolved in a citric acid/potassium citrate composition equivalent to that in a diet lemon-lime beverage. Fructose, potassium chloride and potassium dihydrogen phosphate are then mixed with the base solution.

Example D160

400-500 ppm of Mogroside V is dissolved in a citric acid/potassium citrate composition equivalent to that in a diet lemon-lime beverage. Erythritol and fibergum (e.g., gum *acacia* seyal) are then mixed with the base solution.

Example D161

400-500 ppm of Mogroside V is dissolved in a citric acid/potassium citrate composition equivalent to that in a diet lemon-lime beverage. Fibergum (e.g., gum *acacia* seyal) is then mixed with the base solution.

Example D162

400-500 ppm of Mogroside V is dissolved in a citric acid/potassium citrate composition equivalent to that in a diet lemon-lime beverage. Erythritol, glycine, alanine, potassium chloride and potassium dihydrogen phosphate are then mixed with the base solution.

Example D163

400-500 ppm of Mogroside V is dissolved in a citric acid/potassium citrate composition equivalent to that in a diet lemon-lime beverage. Glycine, alanine, potassium chloride and potassium dihydrogen phosphate are then mixed with the base solution.

Example D164

400-500 mg of Mogroside V is dissolved in one liter carbon-treated water and phosphoric acid (75%) is added until a pH between pH 2.4 and 2.5 is reached. D-Gluconic acid is then mixed with the base solution.

Example D165

400-500 mg of Mogroside V is dissolved in one liter carbon-treated water and phosphoric acid (75%) is added until a pH between pH 2.4 and 2.5 is reached. D-Gluconic acid, potassium salt is then mixed with the base solution.

Example D166

400-500 mg of Mogroside V is dissolved in one liter carbon-treated water and phosphoric acid (75%) is added until a pH between pH 2.4 and 2.5 is reached. L-Threonine is then mixed with the base solution.

Example D167

400-500 mg of Mogroside V is dissolved in one liter carbon-treated water and phosphoric acid (75%) is added until a pH between pH 2.4 and 2.5 is reached. L-Serine is then mixed with the base solution.

Example D168

400-500 mg of Mogroside V is dissolved in one liter carbon-treated water and phosphoric acid (75%) is added until a pH between pH 2.4 and 2.5 is reached. L-alanine is then mixed with the base solution.

Example D169

400-500 mg of Mogroside V is dissolved in one liter carbon-treated water and phosphoric acid (75%) is added until a pH between pH 2.4 and 2.5 is reached. Glycine is then mixed with the base solution.

Example D170

400-500 mg of Mogroside V is dissolved in one liter carbon-treated water and phosphoric acid (75%) is added until a pH between pH 2.4 and 2.5 is reached. β-alanine is then mixed with the base solution.

Example D171

400-500 mg of Mogroside V is dissolved in one liter carbon-treated water and phosphoric acid (75%) is added until a pH between pH 2.4 and 2.5 is reached. Glycine and poly-L-α-lysine are then mixed with the base solution.

Example D172

400-500 mg of Mogroside V is dissolved in one liter carbon-treated water and phosphoric acid (75%) is added until a pH between pH 2.4 and 2.5 is reached. Glycine and poly-L-ε-lysine are then mixed with the base solution.

Example D173

400-500 mg of Mogroside V is dissolved in one liter carbon-treated water and phosphoric acid (75%) is added until a pH between pH 2.4 and 2.5 is reached. Adipic acid is then mixed with the base solution.

Example D174

400-500 mg of Mogroside V is dissolved in one liter carbon-treated water and phosphoric acid (75%) is added until a pH between pH 2.4 and 2.5 is reached. Poly-L-α-lysine (molecular weight ~63,000) is then mixed with the base solution.

Example D175

400-500 mg of Mogroside V is dissolved in one liter carbon-treated water and phosphoric acid (75%) is added until a pH between pH 2.4 and 2.5 is reached. Poly-L-α-lysine (molecular weight ~6,000) is then mixed with the base solution.

Example D176

400-500 mg of Mogroside V is dissolved in one liter carbon-treated water and phosphoric acid (75%) is added until a pH between pH 2.4 and 2.5 is reached. Poly-L-α-lysine (molecular weight ~93,000) is then mixed with the base solution.

Example D177

400-500 mg of Mogroside V is dissolved in one liter carbon-treated water and phosphoric acid (75%) is added until a pH between pH 2.4 and 2.5 is reached. Poly-L-α-lysine (molecular weight ~1,300,000) is then mixed with the base solution.

Example D178

400-500 mg of Mogroside V is dissolved in one liter carbon-treated water and phosphoric acid (75%) is added until a pH between pH 2.4 and 2.5 is reached. Fruitaric acid is then mixed with the base solution.

Example D179

400-500 mg of Mogroside V is dissolved in one liter carbon-treated water and phosphoric acid (75%) is added until a pH between pH 2.4 and 2.5 is reached. Tartaric acid is then mixed with the base solution.

Example D180

400-500 mg of Mogroside V is dissolved in one liter carbon-treated water and phosphoric acid (75%) is added until a pH between pH 2.4 and 2.5 is reached. Sodium bisulfate is then mixed with the base solution.

Example D181

400-500 mg of Mogroside V is dissolved in one liter carbon-treated water and phosphoric acid (75%) is added until a pH between pH 2.4 and 2.5 is reached. Lauric arginate is then mixed with the base solution.

Example D182

400-500 mg of Mogroside V is dissolved in one liter carbon-treated water and phosphoric acid (75%) is added until a pH between pH 2.4 and 2.5 is reached. L-lysine is then mixed with the base solution.

Example D183

400-500 mg of Mogroside V is dissolved in one liter carbon-treated water and phosphoric acid (75%) is added until a pH between pH 2.4 and 2.5 is reached. Guanidine hydrochloride is then mixed with the base solution.

Example D184

400-500 mg of Mogroside V is dissolved in one liter carbon-treated water and phosphoric acid (75%) is added until a pH between pH 2.4 and 2.5 is reached. Urea and sodium chloride are then mixed with the base solution.

Example D185

400-500 mg of Mogroside V is dissolved in one liter carbon-treated water and phosphoric acid (75%) is added until a pH between pH 2.4 and 2.5 is reached. Urea is then mixed with the base solution.

Example D186

400-500 mg of Mogroside V is dissolved in one liter carbon-treated water and phosphoric acid (75%) is added until a pH between pH 2.4 and 2.5 is reached. Choline chloride is then mixed with the base solution.

Example D187

400-500 mg of Mogroside V is dissolved in one liter carbon-treated water and phosphoric acid (75%) is added until a pH between pH 2.4 and 2.5 is reached. D-glucosamine hydrochloride is then mixed with the base solution.

Example D188

400-500 mg of Mogroside V is dissolved in one liter carbon-treated water and phosphoric acid (75%) is added until a pH between pH 2.4 and 2.5 is reached. Poly-L-$\epsilon$-lysine is then mixed with the base solution.

Example D189

400-500 mg of Mogroside V is dissolved in one liter carbon-treated water and phosphoric acid (75%) is added until a pH between pH 2.4 and 2.5 is reached. Glycine, sodium chloride and potassium chloride are then mixed with the base solution.

Example D190

400-500 mg of Mogroside V is dissolved in one liter carbon-treated water and phosphoric acid (75%) is added until a pH between pH 2.4 and 2.5 is reached. Glycine and aluminum sulfate (alum) are then mixed with the base solution.

Example D191

400-500 mg of Mogroside V is dissolved in one liter carbon-treated water and phosphoric acid (75%) is added until a pH between pH 2.4 and 2.5 is reached. Glycine and potassium chloride are then mixed with the base solution.

Example D192

400-500 mg of Mogroside V is dissolved in one liter carbon-treated water and phosphoric acid (75%) is added until a pH between pH 2.4 and 2.5 is reached. Glycine and sodium gluconate are then mixed with the base solution.

Example D193

400-500 mg of Mogroside V is dissolved in one liter carbon-treated water and phosphoric acid (75%) is added until a pH between pH 2.4 and 2.5 is reached. Polyethylenimine is then mixed with the base solution.

Example D194

400-500 mg of Mogroside V is dissolved in one liter carbon-treated water and phosphoric acid (75%) is added until a pH between pH 2.4 and 2.5 is reached. Chitosan is then mixed with the base solution.

Example D195

400-500 mg of Mogroside V is dissolved in one liter carbon-treated water and phosphoric acid (75%) is added until a pH between pH 2.4 and 2.5 is reached. Poly L-ornithine is then mixed with the base solution.

Example D196

400-500 mg of Mogroside V is dissolved in one liter carbon-treated water and phosphoric acid (75%) is added until a pH between pH 2.4 and 2.5 is reached. Magnesium chloride is then mixed with the base solution.

Example D197

400-500 mg of Mogroside V is dissolved in one liter carbon-treated water and phosphoric acid (75%) is added until a pH between pH 2.4 and 2.5 is reached. Whey protein (concentrate 34%) is then mixed with the base solution.

Example D198

400-500 mg of Mogroside V is dissolved in one liter carbon-treated water and phosphoric acid (75%) is added until a pH between pH 2.4 and 2.5 is reached. Fumaric acid, malic acid and tartaric acid are then mixed with the base solution.

Example D199

400-500 ppm of Luo Han Guo sweetener is dissolved in a citric acid/potassium citrate composition equivalent to that in a diet lemon-lime beverage. Fibergum (e.g., gum *acacia seyal*) is then mixed with the base solution.

Example D200

5% sucrose and 400-500 ppm of Luo Han Guo sweetener are dissolved in a citric acid/potassium citrate composition equivalent to that in a lemon-lime beverage. Erythritol is then mixed with the base solution.

Example D201

5% sucrose and 400-500 ppm of Luo Han Guo sweetener are dissolved in a citric acid/potassium citrate composition equivalent to that in a lemon-lime beverage.

Example D202

5% sucrose and 400-500 ppm of Luo Han Guo sweetener are dissolved in a citric acid/potassium citrate composition equivalent to that in a lemon-lime beverage. D-Tagatose is then mixed with the base solution.

Example D203

5% sucrose and 400-500 ppm of Luo Han Guo sweetener are dissolved in a citric acid/potassium citrate composition equivalent to that in a lemon-lime beverage. Erythritol and D-tagatose are then mixed with the base solution.

Example D204

3.3% sucrose and 400-500 ppm of Luo Han Guo sweetener are dissolved in a citric acid/potassium citrate composition equivalent to that in a lemon-lime beverage. Erythritol is then mixed with the base solution.

Example D205

3.3% sucrose and 400-500 ppm of Luo Han Guo sweetener are dissolved in a citric acid/potassium citrate composition equivalent to that in a lemon-lime beverage. Erythritol and D-tagatose are then mixed with the base solution.

Example D206

400-500 ppm of Luo Han Guo sweetener is dissolved in a citric acid/potassium citrate composition equivalent to that in a diet lemon-lime beverage. Erythritol, glycine, potassium chloride and potassium dihydrogen phosphate are then mixed with the base solution.

Example D207

400-500 ppm of Luo Han Guo sweetener is dissolved in a citric acid/potassium citrate composition equivalent to that in a diet lemon-lime beverage. Glycine, potassium chloride and potassium dihydrogen phosphate are then mixed with the base solution.

Example D208

400-500 ppm of Luo Han Guo sweetener is dissolved in a citric acid/potassium citrate composition equivalent to that in a diet lemon-lime beverage. Erythritol, fructose, potassium chloride and potassium dihydrogen phosphate are then mixed with the base solution.

Example D209

400-500 ppm of Luo Han Guo sweetener is dissolved in a citric acid/potassium citrate composition equivalent to that in a diet lemon-lime beverage. Fructose, potassium chloride and potassium dihydrogen phosphate are then mixed with the base solution.

Example D210

400-500 ppm of Luo Han Guo sweetener is dissolved in a citric acid/potassium citrate composition equivalent to that in a diet lemon-lime beverage. Erythritol and fibergum (e.g., gum *acacia seyal*) are then mixed with the base solution.

Example D211

400-500 ppm of Luo Han Guo sweetener is dissolved in a citric acid/potassium citrate composition equivalent to that in a diet lemon-lime beverage. Fibergum (e.g., gum *acacia seyal*) is then mixed with the base solution.

Example D212

400-500 ppm of Luo Han Guo sweetener is dissolved in a citric acid/potassium citrate composition equivalent to that in a diet lemon-lime beverage. Erythritol, glycine, alanine, potassium chloride and potassium dihydrogen phosphate are then mixed with the base solution.

Example D213

400-500 ppm of Luo Han Guo sweetener is dissolved in a citric acid/potassium citrate composition equivalent to that in a diet lemon-lime beverage. Glycine, alanine, potassium chloride and potassium dihydrogen phosphate are then mixed with the base solution.

Example D214

400-500 mg of Luo Han Guo sweetener is dissolved in one liter carbon-treated water and phosphoric acid (75%) is added until a pH between pH 2.4 and 2.5 is reached. D-Gluconic acid is then mixed with the base solution.

Example D215

400-500 mg of Luo Han Guo sweetener is dissolved in one liter carbon-treated water and phosphoric acid (75%) is added until a pH between pH 2.4 and 2.5 is reached. D-Gluconic acid, potassium salt is then mixed with the base solution.

Example D216

400-500 mg of Luo Han Guo sweetener is dissolved in one liter carbon-treated water and phosphoric acid (75%) is added until a pH between pH 2.4 and 2.5 is reached. L-threonine is then mixed with the base solution.

Example D217

400-500 mg of Luo Han Guo sweetener is dissolved in one liter carbon-treated water and phosphoric acid (75%) is added until a pH between pH 2.4 and 2.5 is reached. L-Serine is then mixed with the base solution.

Example D218

400-500 mg of Luo Han Guo sweetener is dissolved in one liter carbon-treated water and phosphoric acid (75%) is added until a pH between pH 2.4 and 2.5 is reached. L-alanine is then mixed with the base solution.

Example D219

400-500 mg of Luo Han Guo sweetener is dissolved in one liter carbon-treated water and phosphoric acid (75%) is added until a pH between pH 2.4 and 2.5 is reached. Glycine is then mixed with the base solution.

Example D220

400-500 mg of Luo Han Guo sweetener is dissolved in one liter carbon-treated water and phosphoric acid (75%) is added until a pH between pH 2.4 and 2.5 is reached. β-alanine is then mixed with the base solution.

Example D221

400-500 mg of Luo Han Guo sweetener is dissolved in one liter carbon-treated water and phosphoric acid (75%) is added until a pH between pH 2.4 and 2.5 is reached. Glycine and poly-L-α-lysine are then mixed with the base solution.

Example D222

400-500 mg of Luo Han Guo sweetener is dissolved in one liter carbon-treated water and phosphoric acid (75%) is added until a pH between pH 2.4 and 2.5 is reached. Glycine and poly-L-ε-lysine are then mixed with the base solution.

Example D223

400-500 mg of Luo Han Guo sweetener is dissolved in one liter carbon-treated water and phosphoric acid (75%) is added until a pH between pH 2.4 and 2.5 is reached. Adipic acid is then mixed with the base solution.

Example D224

400-500 mg of Luo Han Guo sweetener is dissolved in one liter carbon-treated water and phosphoric acid (75%) is added until a pH between pH 2.4 and 2.5 is reached. Poly-L-α-lysine (molecular weight ~63,000) is then mixed with the base solution.

Example D225

400-500 mg of Luo Han Guo sweetener is dissolved in one liter carbon-treated water and phosphoric acid (75%) is added until a pH between pH 2.4 and 2.5 is reached. Poly-L-α-lysine (molecular weight ~6,000) is then mixed with the base solution.

Example D226

400-500 mg of Luo Han Guo sweetener is dissolved in one liter carbon-treated water and phosphoric acid (75%) is added until a pH between pH 2.4 and 2.5 is reached. Poly-L-α-lysine (molecular weight ~93,000) is then mixed with the base solution.

Example D227

400-500 mg of Luo Han Guo sweetener is dissolved in one liter carbon-treated water and phosphoric acid (75%) is added until a pH between pH 2.4 and 2.5 is reached. Poly-L-α-lysine (molecular weight ~1,300,000) is then mixed with the base solution.

Example D228

400-500 mg of Luo Han Guo sweetener is dissolved in one liter carbon-treated water and phosphoric acid (75%) is added until a pH between pH 2.4 and 2.5 is reached. Fruitaric acid is then mixed with the base solution.

Example D229

400-500 mg of Luo Han Guo sweetener is dissolved in one liter carbon-treated water and phosphoric acid (75%) is added until a pH between pH 2.4 and 2.5 is reached. Tartaric acid is then mixed with the base solution.

Example D230

400-500 mg of Luo Han Guo sweetener is dissolved in one liter carbon-treated water and phosphoric acid (75%) is added until a pH between pH 2.4 and 2.5 is reached. Sodium bisulfate is then mixed with the base solution.

Example D231

400-500 mg of Luo Han Guo sweetener is dissolved in one liter carbon-treated water and phosphoric acid (75%) is added until a pH between pH 2.4 and 2.5 is reached. Lauric arginate is then mixed with the base solution.

Example D232

400-500 mg of Luo Han Guo sweetener is dissolved in one liter carbon-treated water and phosphoric acid (75%) is added until a pH between pH 2.4 and 2.5 is reached. L-lysine is then mixed with the base solution.

Example D233

400-500 mg of Luo Han Guo sweetener is dissolved in one liter carbon-treated water and phosphoric acid (75%) is added until a pH between pH 2.4 and 2.5 is reached. Guanidine hydrochloride is then mixed with the base solution.

Example D234

400-500 mg of Luo Han Guo sweetener is dissolved in one liter carbon-treated water and phosphoric acid (75%) is added until a pH between pH 2.4 and 2.5 is reached. Urea and sodium chloride are then mixed with the base solution.

Example D235

400-500 mg of Luo Han Guo sweetener is dissolved in one liter carbon-treated water and phosphoric acid (75%) is added until a pH between pH 2.4 and 2.5 is reached. Urea is then mixed with the base solution.

Example D236

400-500 mg of Luo Han Guo sweetener is dissolved in one liter carbon-treated water and phosphoric acid (75%) is added until a pH between pH 2.4 and 2.5 is reached. Choline chloride is then mixed with the base solution.

Example D237

400-500 mg of Luo Han Guo sweetener is dissolved in one liter carbon-treated water and phosphoric acid (75%) is added until a pH between pH 2.4 and 2.5 is reached. D-glucosamine hydrochloride is then mixed with the base solution.

Example D238

400-500 mg of Luo Han Guo sweetener is dissolved in one liter carbon-treated water and phosphoric acid (75%) is added until a pH between pH 2.4 and 2.5 is reached. Poly-L-ε-lysine is then mixed with the base solution.

Example D239

400-500 mg of Luo Han Guo sweetener is dissolved in one liter carbon-treated water and phosphoric acid (75%) is added until a pH between pH 2.4 and 2.5 is reached. Glycine, sodium chloride and potassium chloride are then mixed with the base solution.

Example D240

400-500 mg of Luo Han Guo sweetener is dissolved in one liter carbon-treated water and phosphoric acid (75%) is added until a pH between pH 2.4 and 2.5 is reached. Glycine and aluminum sulfate (alum) are then mixed with the base solution.

Example D241

400-500 mg of Luo Han Guo sweetener is dissolved in one liter carbon-treated water and phosphoric acid (75%) is added until a pH between pH 2.4 and 2.5 is reached. Glycine and potassium chloride are then mixed with the base solution.

Example D242

400-500 mg of Luo Han Guo sweetener is dissolved in one liter carbon-treated water and phosphoric acid (75%) is added until a pH between pH 2.4 and 2.5 is reached. Glycine and sodium gluconate are then mixed with the base solution.

Example D243

400-500 mg of Luo Han Guo sweetener is dissolved in one liter carbon-treated water and phosphoric acid (75%) is added until a pH between pH 2.4 and 2.5 is reached. Polyethylenimine is then mixed with the base solution.

Example D244

400-500 mg of Luo Han Guo sweetener is dissolved in one liter carbon-treated water and phosphoric acid (75%) is added until a pH between pH 2.4 and 2.5 is reached. Chitosan is then mixed with the base solution.

Example D245

400-500 mg of Luo Han Guo sweetener is dissolved in one liter carbon-treated water and phosphoric acid (75%) is added until a pH between pH 2.4 and 2.5 is reached. Poly L-ornithine is then mixed with the base solution.

Example D246

400-500 mg of Luo Han Guo sweetener is dissolved in one liter carbon-treated water and phosphoric acid (75%) is added until a pH between pH 2.4 and 2.5 is reached. Magnesium chloride is then mixed with the base solution.

Example D247

400-500 mg of Luo Han Guo sweetener is dissolved in one liter carbon-treated water and phosphoric acid (75%) is added until a pH between pH 2.4 and 2.5 is reached. Whey protein (concentrate 34%) is then mixed with the base solution.

Example D248

400-500 mg of Luo Han Guo sweetener is dissolved in one liter carbon-treated water and phosphoric acid (75%) is added until a pH between pH 2.4 and 2.5 is reached. Fumaric acid, malic acid and tartaric acid are then mixed with the base solution.

Example D249

25-50 ppm of monatin is dissolved in a citric acid/potassium citrate composition equivalent to that in a diet lemon-lime beverage. Fibergum (e.g., gum *acacia* seyal) is then mixed with the base solution.

Example D250

5% sucrose and 25-50 ppm monatin are dissolved in a citric acid/potassium citrate composition equivalent to that in a lemon-lime beverage. Erythritol is then mixed with the base solution.

Example D251

5% sucrose and 25-50 ppm of monatin are dissolved in a citric acid/potassium citrate composition equivalent to that in a lemon-lime beverage. D-Tagatose is then mixed with the base solution.

Example D252

5% sucrose and 25-50 ppm of monatin are dissolved in a citric acid/potassium citrate composition equivalent to that in a lemon-lime beverage. Erythritol and D-tagatose are then mixed with the base solution.

Example D253

3.3% sucrose and 25-50 ppm of monatin are dissolved in a citric acid/potassium citrate composition equivalent to that in a lemon-lime beverage. Erythritol is then mixed with the base solution.

Example D254

3.3% sucrose and 25-50 ppm of monatin are dissolved in a citric acid/potassium citrate composition equivalent to that in a lemon-lime beverage. Erythritol and D-tagatose are then mixed with the base solution.

Example D255

25-50 ppm of monatin is dissolved in a citric acid/potassium citrate composition equivalent to that in a diet lemon-lime beverage. Erythritol, glycine, potassium chloride and potassium dihydrogen phosphate are then mixed with the base solution.

Example D256

25-50 ppm of monatin is dissolved in a citric acid/potassium citrate composition equivalent to that in a diet lemon-lime beverage. Glycine, potassium chloride and potassium dihydrogen phosphate are then mixed with the base solution.

Example D257

25-50 ppm of monatin is dissolved in a citric acid/potassium citrate composition equivalent to that in a diet lemon-lime beverage. Erythritol, fructose, potassium chloride and potassium dihydrogen phosphate are then mixed with the base solution.

Example D258

25-50 ppm of monatin is dissolved in a citric acid/potassium citrate composition equivalent to that in a diet lemon-lime beverage. Fructose, potassium chloride and potassium dihydrogen phosphate are then mixed with the base solution.

Example D259

25-50 ppm of monatin is dissolved in a citric acid/potassium citrate composition equivalent to that in a diet lemon-lime beverage. Erythritol and fibergum (e.g., gum *acacia seyal*) are then mixed with the base solution.

Example D260

25-50 ppm of monatin is dissolved in a citric acid/potassium citrate composition equivalent to that in a diet lemon-lime beverage. Fibergum (e.g., gum *acacia seyal*) is then mixed with the base solution.

Example D261

25-50 ppm of monatin is dissolved in a citric acid/potassium citrate composition equivalent to that in a diet lemon-lime beverage. Erythritol, glycine, alanine, potassium chloride and potassium dihydrogen phosphate are then mixed with the base solution.

Example D262

25-50 ppm of monatin is dissolved in a citric acid/potassium citrate composition equivalent to that in a diet lemon-lime beverage. Glycine, alanine, potassium chloride and potassium dihydrogen phosphate are then mixed with the base solution.

Example D263

25-50 mg of monatin is dissolved in one liter carbon-treated water and phosphoric acid (75%) is added until a pH between pH 2.4 and 2.5 is reached. D-Gluconic acid is then mixed with the base solution.

Example D264

25-50 mg of monatin is dissolved in one liter carbon-treated water and phosphoric acid (75%) is added until a pH between pH 2.4 and 2.5 is reached. D-Gluconic acid, potassium salt is then mixed with the base solution.

Example D265

25-50 mg of monatin is dissolved in one liter carbon-treated water and phosphoric acid (75%) is added until a pH between pH 2.4 and 2.5 is reached. L-Threonine is then mixed with the base solution.

Example D266

25-50 mg of monatin is dissolved in one liter carbon-treated water and phosphoric acid (75%) is added until a pH between pH 2.4 and 2.5 is reached. L-Serine is then mixed with the base solution.

Example D267

25-50 mg of monatin is dissolved in one liter carbon-treated water and phosphoric acid (75%) is added until a pH between pH 2.4 and 2.5 is reached. L-alanine is then mixed with the base solution.

Example D268

25-50 mg of monatin is dissolved in one liter carbon-treated water and phosphoric acid (75%) is added until a pH between pH 2.4 and 2.5 is reached. Glycine is then mixed with the base solution.

Example D269

25-50 mg of monatin is dissolved in one liter carbon-treated water and phosphoric acid (75%) is added until a pH between pH 2.4 and 2.5 is reached. β-alanine is then mixed with the base solution.

Example D270

25-50 mg of monatin is dissolved in one liter carbon-treated water and phosphoric acid (75%) is added until a pH between pH 2.4 and 2.5 is reached. Glycine and poly-L-α-lysine are then mixed with the base solution.

Example D271

25-50 mg of monatin is dissolved in one liter carbon-treated water and phosphoric acid (75%) is added until a pH between pH 2.4 and 2.5 is reached. Glycine and poly-L-ε-lysine are then mixed with the base solution.

Example D272

25-50 mg of monatin is dissolved in one liter carbon-treated water and phosphoric acid (75%) is added until a pH between pH 2.4 and 2.5 is reached. Adipic acid is then mixed with the base solution.

Example D273

25-50 mg of monatin is dissolved in one liter carbon-treated water and phosphoric acid (75%) is added until a pH between pH 2.4 and 2.5 is reached. Poly-L-α-lysine (molecular weight ~63,000) is then mixed with the base solution.

Example D274

25-50 mg of monatin is dissolved in one liter carbon-treated water and phosphoric acid (75%) is added until a pH between pH 2.4 and 2.5 is reached. Poly-L-α-lysine (molecular weight ~6,000) is then mixed with the base solution.

Example D275

25-50 mg of monatin is dissolved in one liter carbon-treated water and phosphoric acid (75%) is added until a pH between pH 2.4 and 2.5 is reached. Poly-L-α-lysine (molecular weight ~83,000) is then mixed with the base solution.

Example D276

25-50 mg of monatin is dissolved in one liter carbon-treated water and phosphoric acid (75%) is added until a pH between pH 2.4 and 2.5 is reached. Poly-L-α-lysine (molecular weight ~1,300,000) is then mixed with the base solution.

Example D277

25-50 mg of monatin is dissolved in one liter carbon-treated water and phosphoric acid (75%) is added until a pH between pH 2.4 and 2.5 is reached. Fruitaric acid is then mixed with the base solution.

Example D278

25-50 mg of monatin is dissolved in one liter carbon-treated water and phosphoric acid (75%) is added until a pH between pH 2.4 and 2.5 is reached. Tartaric acid is then mixed with the base solution.

Example D279

25-50 mg of monatin is dissolved in one liter carbon-treated water and phosphoric acid (75%) is added until a pH between pH 2.4 and 2.5 is reached. Sodium bisulfate is then mixed with the base solution.

Example D280

25-50 mg of monatin is dissolved in one liter carbon-treated water and phosphoric acid (75%) is added until a pH between pH 2.4 and 2.5 is reached. Lauric arginate is then mixed with the base solution.

Example D281

25-50 mg of monatin is dissolved in one liter carbon-treated water and phosphoric acid (75%) is added until a pH between pH 2.4 and 2.5 is reached. L-lysine is then mixed with the base solution.

Example D282

25-50 mg of monatin is dissolved in one liter carbon-treated water and phosphoric acid (75%) is added until a pH between pH 2.4 and 2.5 is reached. Guanidine hydrochloride is then mixed with the base solution.

Example D283

25-50 mg of monatin is dissolved in one liter carbon-treated water and phosphoric acid (75%) is added until a pH between pH 2.4 and 2.5 is reached. Urea and sodium chloride are then mixed with the base solution.

Example D284

25-50 mg of monatin is dissolved in one liter carbon-treated water and phosphoric acid (75%) is added until a pH between pH 2.4 and 2.5 is reached. Urea is then mixed with the base solution.

Example D285

25-50 mg of monatin is dissolved in one liter carbon-treated water and phosphoric acid (75%) is added until a pH between pH 2.4 and 2.5 is reached. Choline chloride is then mixed with the base solution.

Example D286

25-50 mg of monatin is dissolved in one liter carbon-treated water and phosphoric acid (75%) is added until a pH between pH 2.4 and 2.5 is reached. D-glucosamine hydrochloride is then mixed with the base solution.

Example D287

25-50 mg of monatin is dissolved in one liter carbon-treated water and phosphoric acid (75%) is added until a pH between pH 2.4 and 2.5 is reached. Poly-L-ϵ-lysine is then mixed with the base solution.

Example D288

25-50 mg of monatin is dissolved in one liter carbon-treated water and phosphoric acid (75%) is added until a pH between pH 2.4 and 2.5 is reached. Glycine, sodium chloride and potassium chloride are then mixed with the base solution.

Example D289

25-50 mg of monatin is dissolved in one liter carbon-treated water and phosphoric acid (75%) is added until a pH between pH 2.4 and 2.5 is reached. Glycine and aluminum sulfate (alum) are then mixed with the base solution.

Example D290

25-50 mg of monatin is dissolved in one liter carbon-treated water and phosphoric acid (75%) is added until a pH between pH 2.4 and 2.5 is reached. Glycine and potassium chloride are then mixed with the base solution.

Example D291

25-50 mg of monatin is dissolved in one liter carbon-treated water and phosphoric acid (75%) is added until a pH between pH 2.4 and 2.5 is reached. Glycine and sodium gluconate are then mixed with the base solution.

Example D292

25-50 mg of monatin is dissolved in one liter carbon-treated water and phosphoric acid (75%) is added until a pH between pH 2.4 and 2.5 is reached. Polyethylenimine is then mixed with the base solution.

Example D293

25-50 mg of monatin is dissolved in one liter carbon-treated water and phosphoric acid (75%) is added until a pH between pH 2.4 and 2.5 is reached. Chitosan is then mixed with the base solution.

Example D294

25-50 mg of monatin is dissolved in one liter carbon-treated water and phosphoric acid (75%) is added until a pH between pH 2.4 and 2.5 is reached. Poly L-omithine is then mixed with the base solution.

Example D295

25-50 mg of monatin is dissolved in one liter carbon-treated water and phosphoric acid (75%) is added until a pH between pH 2.4 and 2.5 is reached. Magnesium chloride is then mixed with the base solution.

Example D296

25-50 mg of monatin is dissolved in one liter carbon-treated water and phosphoric acid (75%) is added until a pH between pH 2.4 and 2.5 is reached. Whey protein (concentrate 34%) is then mixed with the base solution.

Example D297

25-50 mg of monatin is dissolved in one liter carbon-treated water and phosphoric acid (75%) is added until a pH between pH 2.4 and 2.5 is reached. Fumaric acid, malic acid and tartaric acid are then mixed with the base solution.

Example D298

50-200 ppm of curculin is dissolved in a citric acid/potassium citrate composition equivalent to that in a diet lemon-lime beverage. Fibergum (e.g., gum *acacia* seyal) is then mixed with the base solution.

Example D299

5% sucrose and 50-200 ppm curculin are dissolved in a citric acid/potassium citrate composition equivalent to that in a lemon-lime beverage. Erythritol is then mixed with the base solution.

Example D300

5% sucrose and 50-200 ppm of curculin are dissolved in a citric acid/potassium citrate composition equivalent to that in a lemon-lime beverage. D-Tagatose is then mixed with the base solution.

Example D301

5% sucrose and 50-200 ppm of curculin are dissolved in a citric acid/potassium citrate composition equivalent to that in a lemon-lime beverage. Erythritol and D-tagatose are then mixed with the base solution.

Example D302

3.3% sucrose and 50-200 ppm of curculin are dissolved in a citric acid/potassium citrate composition equivalent to that in a lemon-lime beverage. Erythritol is then mixed with the base solution.

Example D303

3.3% sucrose and 50-200 ppm of curculin are dissolved in a citric acid/potassium citrate composition equivalent to that in a lemon-lime beverage. Erythritol and D-tagatose are then mixed with the base solution.

Example D304

50-200 ppm of curculin is dissolved in a citric acid/potassium citrate composition equivalent to that in a diet lemon-lime beverage. Erythritol, glycine, potassium chloride and potassium dihydrogen phosphate are then mixed with the base solution.

Example D305

50-200 ppm of curculin is dissolved in a citric acid/potassium citrate composition equivalent to that in a diet lemon-lime beverage. Glycine, potassium chloride and potassium dihydrogen phosphate are then mixed with the base solution.

Example D306

50-200 ppm of curculin is dissolved in a citric acid/potassium citrate composition equivalent to that in a diet lemon-lime beverage. Erythritol, fructose, potassium chloride and potassium dihydrogen phosphate are then mixed with the base solution.

Example D307

50-200 ppm of curculin is dissolved in a citric acid/potassium citrate composition equivalent to that in a diet lemon-lime beverage. Fructose, potassium chloride and potassium dihydrogen phosphate are then mixed with the base solution.

Example D308

50-200 ppm of curculin is dissolved in a citric acid/potassium citrate composition equivalent to that in a diet lemon-lime beverage. Erythritol and fibergum (e.g., gum *acacia* seyal) are then mixed with the base solution.

Example D309

50-200 ppm of curculin is dissolved in a citric acid/potassium citrate composition equivalent to that in a diet lemon-lime beverage. Fibergum (e.g., gum *acacia* seyal) is then mixed with the base solution.

Example D310

50-200 ppm of curculin is dissolved in a citric acid/potassium citrate composition equivalent to that in a diet lemon-lime beverage. Erythritol, glycine, alanine, potassium chloride and potassium dihydrogen phosphate are then mixed with the base solution.

Example D311

50-200 ppm of curculin is dissolved in a citric acid/potassium citrate composition equivalent to that in a diet lemon-lime beverage. Glycine, alanine, potassium chloride and potassium dihydrogen phosphate are then mixed with the base solution.

Example D312

50-200 mg of curculin is dissolved in one liter carbon-treated water and phosphoric acid (75%) is added until a pH between pH 2.4 and 2.5 is reached. D-Gluconic acid is then mixed with the base solution.

Example D313

50-200 mg of curculin is dissolved in one liter carbon-treated water and phosphoric acid (75%) is added until a pH between pH 2.4 and 2.5 is reached. D-Gluconic acid, potassium salt is then mixed with the base solution.

Example D314

50-200 mg of curculin is dissolved in one liter carbon-treated water and phosphoric acid (75%) is added until a pH between pH 2.4 and 2.5 is reached. L-Threonine is then mixed with the base solution.

Example D315

50-200 mg of curculin is dissolved in one liter carbon-treated water and phosphoric acid (75%) is added until a pH between pH 2.4 and 2.5 is reached. L-Serine is then mixed with the base solution.

Example D316

50-200 mg of curculin is dissolved in one liter carbon-treated water and phosphoric acid (75%) is added until a pH between pH 2.4 and 2.5 is reached. L-alanine is then mixed with the base solution.

Example D317

50-200 mg of curculin is dissolved in one liter carbon-treated water and phosphoric acid (75%) is added until a pH between pH 2.4 and 2.5 is reached. Glycine is then mixed with the base solution.

Example D318

50-200 mg of curculin is dissolved in one liter carbon-treated water and phosphoric acid (75%) is added until a pH between pH 2.4 and 2.5 is reached. β-alanine is then mixed with the base solution.

Example D319

50-200 mg of curculin is dissolved in one liter carbon-treated water and phosphoric acid (75%) is added until a pH between pH 2.4 and 2.5 is reached. Glycine and poly-L-α-lysine are then mixed with the base solution.

Example D320

50-200 mg of curculin is dissolved in one liter carbon-treated water and phosphoric acid (75%) is added until a pH between pH 2.4 and 2.5 is reached. Glycine and poly-L-ε-lysine are then mixed with the base solution.

Example D321

50-200 mg of curculin is dissolved in one liter carbon-treated water and phosphoric acid (75%) is added until a pH between pH 2.4 and 2.5 is reached. Adipic acid is then mixed with the base solution.

Example D322

50-200 mg of curculin is dissolved in one liter carbon-treated water and phosphoric acid (75%) is added until a pH between pH 2.4 and 2.5 is reached. Poly-L-α-lysine (molecular weight ~63,000) is then mixed with the base solution.

Example D323

50-200 mg of curculin is dissolved in one liter carbon-treated water and phosphoric acid (75%) is added until a pH between pH 2.4 and 2.5 is reached. Poly-L-α-lysine (molecular weight ~6,000) is then mixed with the base solution.

Example D324

50-200 mg of curculin is dissolved in one liter carbon-treated water and phosphoric acid (75%) is added until a pH between pH 2.4 and 2.5 is reached. Poly-L-α-lysine (molecular weight ~93,000) is then mixed with the base solution.

Example D325

50-200 mg of curculin is dissolved in one liter carbon-treated water and phosphoric acid (75%) is added until a pH between pH 2.4 and 2.5 is reached. Poly-L-α-lysine (molecular weight ~1,300,000) is then mixed with the base solution.

Example D326

50-200 mg of curculin is dissolved in one liter carbon-treated water and phosphoric acid (75%) is added until a pH between pH 2.4 and 2.5 is reached. Fruitaric acid is then mixed with the base solution.

Example D327

50-200 mg of curculin is dissolved in one liter carbon-treated water and phosphoric acid (75%) is added until a pH between pH 2.4 and 2.5 is reached. Tartaric acid is then mixed with the base solution.

Example D328

50-200 mg of curculin is dissolved in one liter carbon-treated water and phosphoric acid (75%) is added until a pH between pH 2.4 and 2.5 is reached. Sodium bisulfate is then mixed with the base solution.

Example D329

50-200 mg of curculin is dissolved in one liter carbon-treated water and phosphoric acid (75%) is added until a pH between pH 2.4 and 2.5 is reached. Lauric arginate is then mixed with the base solution.

Example D330

50-200 mg of curculin is dissolved in one liter carbon-treated water and phosphoric acid (75%) is added until a pH between pH 2.4 and 2.5 is reached. L-lysine is then mixed with the base solution.

Example D331

50-200 mg of curculin is dissolved in one liter carbon-treated water and phosphoric acid (75%) is added until a pH between pH 2.4 and 2.5 is reached. Guanidine hydrochloride is then mixed with the base solution.

Example D332

50-200 mg of curculin is dissolved in one liter carbon-treated water and phosphoric acid (75%) is added until a pH between pH 2.4 and 2.5 is reached. Urea and sodium chloride are then mixed with the base solution.

Example D333

50-200 mg of curculin is dissolved in one liter carbon-treated water and phosphoric acid (75%) is added until a pH between pH 2.4 and 2.5 is reached. Urea is then mixed with the base solution.

Example D334

50-200 mg of curculin is dissolved in one liter carbon-treated water and phosphoric acid (75%) is added until a pH between pH 2.4 and 2.5 is reached. Choline chloride is then mixed with the base solution.

Example D335

50-200 mg of curculin is dissolved in one liter carbon-treated water and phosphoric acid (75%) is added until a pH between pH 2.4 and 2.5 is reached. D-glucosamine hydrochloride is then mixed with the base solution.

Example D336

50-200 mg of curculin is dissolved in one liter carbon-treated water and phosphoric acid (75%) is added until a pH between pH 2.4 and 2.5 is reached. Poly-L-ϵ-lysine is then mixed with the base solution.

Example D337

50-200 mg of curculin is dissolved in one liter carbon-treated water and phosphoric acid (75%) is added until a pH between pH 2.4 and 2.5 is reached. Glycine, sodium chloride and potassium chloride are then mixed with the base solution.

Example D338

50-200 mg of curculin is dissolved in one liter carbon-treated water and phosphoric acid (75%) is added until a pH between pH 2.4 and 2.5 is reached. Glycine and aluminum sulfate (alum) are then mixed with the base solution.

Example D339

50-200 mg of curculin is dissolved in one liter carbon-treated water and phosphoric acid (75%) is added until a pH between pH 2.4 and 2.5 is reached. Glycine and potassium chloride are then mixed with the base solution.

Example D340

50-200 mg of curculin is dissolved in one liter carbon-treated water and phosphoric acid (75%) is added until a pH between pH 2.4 and 2.5 is reached. Glycine and sodium gluconate are then mixed with the base solution.

Example D341

50-200 mg of curculin is dissolved in one liter carbon-treated water and phosphoric acid (75%) is added until a pH between pH 2.4 and 2.5 is reached. Polyethylenimine is then mixed with the base solution.

Example D342

50-200 mg of curculin is dissolved in one liter carbon-treated water and phosphoric acid (75%) is added until a pH between pH 2.4 and 2.5 is reached. Chitosan is then mixed with the base solution.

Example D343

50-200 mg of curculin is dissolved in one liter carbon-treated water and phosphoric acid (75%) is added until a pH between pH 2.4 and 2.5 is reached. Poly L-ornithine is then mixed with the base solution.

Example D344

50-200 mg of curculin is dissolved in one liter carbon-treated water and phosphoric acid (75%) is added until a pH between pH 2.4 and 2.5 is reached. Magnesium chloride is then mixed with the base solution.

Example D345

50-200 mg of curculin is dissolved in one liter carbon-treated water and phosphoric acid (75%) is added until a pH between pH 2.4 and 2.5 is reached. Whey protein (concentrate 34%) is then mixed with the base solution.

Example D346

50-200 mg of curculin is dissolved in one liter carbon-treated water and phosphoric acid (75%) is added until a pH between pH 2.4 and 2.5 is reached. Fumaric acid, malic acid and tartaric acid are then mixed with the base solution.

E. Example Set E

The formulations provided in Example Set E may be used in combination with other compounds found in orally ingestible compositions to form a total sum of 100% weight. The compounds which may be used in combination with the formulations provided may be in the form of a liquid, solid, gas, gel, or the like to act as a carrier for the formulation. For example, water (e.g., carbonated, carbon-treated, or non-carbonated), flavors, and/or acidulant may be used to in addition to the provided formulations to give 100% weight total.

Example E1

A composition comprising 3.5% erythritol, 400 ppm of REBA, 0.02% flavor, and 0.5% tagatose are combined.

Example E2

A composition comprising 3.5% erythritol, 400 ppm of REBA, 0.0015% flavor, and 0.5% tagatose are combined.

Example E3

A composition comprising 3.5% erythritol, 400 ppm of REBA, 0.0033% flavor, and 0.5% tagatose are combined.

Example E4

A composition comprising 3.4% sucrose, 3.5 erythritol, and 180 ppm of REBA are combined.

Example E5

A composition comprising 5% sucrose, 3.5% erythritol, and 100 ppm of REBA are combined.

Example E6

A composition comprising 360 ppm of REBA, 0.75% glycine, 250 ppm of KCl, and 650 ppm of $KH_2PO_4$ are combined.

Example E7

A composition comprising 3.5% erythritol, 320 ppm of REBA, 0.75% fructose, 250 ppm of KCl, and 650 ppm of $KH_2PO_4$ are combined.

Example E8

A composition comprising 3.5% erythritol, 360 ppm of REBA, and 400 ppm of Fibergum P (*acacia* seyal) are combined.

Example E9

A composition comprising 3.3% sucrose, 3.5% erythritol, and 160 ppm of REBA are combined.

Example E10

A composition comprising 5% sucrose, 3,5% erythritol, and 90 ppm of REBA are combined.

Example E11

A composition comprising 65 ppm of glutamic acid and 580 ppm of REBA are combined.

Example E12

A composition comprising 0.7 ppm of oleanolic acid, 3.5% erythritol, 580 ppm of REBA, and flavorants are combined.

Example E13

A composition comprising 0.2% tagatose and 580 ppm of REBA are combined. Example E14

A composition comprising 0.2% tagatose, 0.6 ppm of flavorants, and 580 ppm of REBA are combined.

Example E15

A composition comprising 3.5% erythritol, and 580 ppm of REBA are combined.

Example E16

A composition comprising 0.005% flavorant and 580 ppm of REBA are combined.

Example E17

A composition comprising 20 ppm of talin and 580 ppm of REBA are combined. Example E18

A composition comprising 30 ppm of citrus extract and 580 ppm of REBA are combined.

Example E19

A composition comprising 0.1 to 0.05% flavorant and 580 ppm of REBA are combined.

Example E20

A composition comprising 0.033 Luo Han Guo sweetener and 580 ppm of REBA are combined.

Example E21

A composition comprising 3 ppm of flavorant and 580 ppm of REBA are combined.

Example E22

A composition comprising 0.004 ppm of bitter orange and 580 ppm of REBA are combined.

Example E23

A composition comprising 0.004% of bitter orange and 580 ppm of REBA are combined.

Example E24

A composition comprising 2 ppm of heptadienal and 580 ppm of REBA are combined.

Example E25

A composition comprising 0.33% frutaric acid and 580 ppm of REBA are combined.

Example E26

A composition comprising 1,400 ppm of choline chloride and 580 ppm of REBA are combined.

Example E27

A composition comprising 0.1% colloid and 580 ppm of REBA are combined.

Example E28

A composition comprising 0.033% flavorant and 580 ppm of REBA are combined.

Example E29

A composition comprising 0.15% of flavorant and 580 ppm of REBA are combined.

Example E30

A composition comprising 0.1% polyhydroxy alcohol and 580 ppm of REBA are combined.

Example E31

A composition comprising 3.5% erythritol, 65 ppm of succinic acid, and 3 ppm of flavorant are combined with REBA.

F. Example Set F

Sweet taste improving compositions were combined with a REBA solution to determine their effect on sweetness linger. Screening of the initial sample, or further dilutions, allowed identification of concentrations which were just above-threshold, herein defined as "near-threshold concentrations." The near-threshold additive concentrations, a 6- to 100-fold higher additive concentration (depending on the off-taste intensity), and a mid-level additive concentration (halfway between the near-threshold and higher additive concentration) were evaluated to determine the effect on sweetness linger of a REBA solution.

Formulations of a 500 ppm REBA in a phosphoric acid solution (75%) at a pH of 2.5 with phosphoric acid or a pH of 3.1 with citric acid and potassium citrate were prepared prior to the addition of the additives at the three levels of concentration.

Sensory evaluation using the protocol described in Example Set G then was used to evaluate the sweetness linger of the REBA solutions.

Control Samples 500 ppm of REBA was dissolved in one liter of carbon-treated water and phosphoric acid (75%) was added until a pH between 2.4 and 2.5 was reached. The sweetness linger rating of this control sample was determined to be 5.

10 g of sugar was dissolved in 100 ml of carbon treated water and phosphoric acid (75%) was added until a pH between 2.4 and 2.5 was reached. The sweetness linger rating of this control sample was determined to be 0.

The following Examples F 1-148 illustrate combinations of rebaudioside A and sweet taste improving compositions in accordance with particular embodiments of this invention:

Example F1

500 ppm of REBA was dissolved in one liter carbon-treated water and phosphoric acid (75%) was added until a pH between pH 2.4 and 2.5 was reached. 5,000 ppm of D-fructose was then mixed with the base solution. The sweetness linger of this solution was determined to be 3. This formulation was found to have sugar-like taste characteristics.

Example F2

500 ppm of REBA was dissolved in one liter carbon-treated water and phosphoric acid (75%) was added until a pH between pH 2.4 and 2.5 was reached. 2,500 ppm to 20,000 ppm of propylene glycol was then mixed with the base solution. The sweetness linger of this solution was determined to be 4.

Example F3

360 ppm of REBA was dissolved in one liter carbon-treated water and phosphoric acid (75%) was added until a pH between pH 2.4 and 2.5 was reached. 35,000 ppm of erythritol was then mixed with the base solution. The sweetness linger of this solution was determined to be 4.

Example F4

500 ppm of REBA was dissolved in one liter carbon-treated water and phosphoric acid (75%) was added until a pH between pH 2.4 and 2.5 was reached. 93 ppm to 368 ppm of NaCl was then mixed with the base solution. The sweetness linger of this solution was determined to be 4.

Example F5

500 ppm of REBA was dissolved in one liter carbon-treated water and phosphoric acid (75%) was added until a pH between pH 2.4 and 2.5 was reached. 25,000 ppm to 50,000 ppm of NaCl was then mixed with the base solution. The sweetness linger of this solution was determined to be 1.

Example F6

500 ppm of REBA was dissolved in one liter carbon-treated water and phosphoric acid (75%) was added until a pH between pH 2.4 and 2.5 was reached. 1,192 ppm to 4,770 ppm of KCl was then mixed with the base solution. The sweetness linger of this solution was determined to be 3. This formulation was found to have sugar-like taste characteristics.

Example F7

500 ppm of REBA was dissolved in one liter carbon-treated water and phosphoric acid (75%) was added until a pH between pH 2.4 and 2.5 was reached. 10 ppm to 500 ppm of $NaHSO_4.H_2O$ was then mixed with the base solution. The sweetness linger of this solution was determined to be 4.

Example F8

500 ppm of REBA was dissolved in one liter carbon-treated water and phosphoric acid (75%) was added until a pH between pH 2.4 and 2.5 was reached. 10,000 ppm to 50,000 ppm of $NaH_2PO4.H_2O$ was then mixed with the base solution. The sweetness linger of this solution was determined to be 2.

Example F9

500 ppm of REBA was dissolved in one liter carbon-treated water and phosphoric acid (75%) was added until a pH between pH 2.4 and 2.5 was reached. 10,000 ppm to 20,000 ppm of $KH_2PO_4$ was then mixed with the base solution. The sweetness linger of this solution was determined to be 3.

Example F10

500 ppm of REBA was dissolved in one liter carbon-treated water and phosphoric acid (75%) was added until a pH between pH 2.4 and 2.5 was reached. 5,000 ppm of $MgSO_4$ was then mixed with the base solution. The sweetness linger of this solution was determined to be 3.

Example F11

500 ppm of REBA was dissolved in one liter carbon-treated water and phosphoric acid (75%) was added until a pH between pH 2.4 and 2.5 was reached. 404 ppm to 1,003 ppm of $KAl(SO_4)_2$ (alum) was then mixed with the base solution. The sweetness linger of this solution was determined to be 3.

Example F12

500 ppm of REBA was dissolved in one liter carbon-treated water and phosphoric acid (75%) was added until a pH between pH 2.4 and 2.5 was reached. 250 ppm of $KAl(SO_4)_2$ (alum) was then mixed with the base solution. The sweetness linger of this solution was determined to be 4.

Example F13

500 ppm of REBA was dissolved in one liter carbon-treated water and phosphoric acid (75%) was added until a pH between pH 2.4 and 2.5 was reached. 24 ppm to 700 ppm of zinc chloride was then mixed with the base solution. The sweetness linger of this solution was determined to be 3.

Example F14

500 ppm of REBA was dissolved in one liter carbon-treated water and phosphoric acid (75%) was added until a pH between pH 2.4 and 2.5 was reached. 450 ppm of KCl and 680 ppm of $KH_2PO_4$ were then mixed with the base solution. The sweetness linger of this solution was determined to be 3. This formulation was found to have sugar-like taste characteristics.

Example F15

500 ppm of REBA was dissolved in one liter carbon-treated water and phosphoric acid (75%) was added until a pH between pH 2.4 and 2.5 was reached. 470 ppm of choline chloride was then mixed with the base solution. The sweetness linger of this solution was determined to be 4.

Example F16

500 ppm of REBA was dissolved in one liter carbon-treated water and phosphoric acid (75%) was added until a pH between pH 2.4 and 2.5 was reached. 1,175 ppm to 1,400 ppm of choline chloride was then mixed with the base solution. The sweetness linger of this solution was determined to be 2.5.

Example F17

500 ppm of REBA was dissolved in one liter carbon-treated water and phosphoric acid (75%) was added until a pH between pH 2.4 and 2.5 was reached. 50 ppm to 1,000 ppm of D-gluconic acid, Na Salt was then mixed with the base solution. The sweetness linger of this solution was determined to be 3.

Example F18

500 ppm of REBA was dissolved in one liter carbon-treated water and phosphoric acid (75%) was added until a pH between pH 2.4 and 2.5 was reached. 50 ppm to 1,000 ppm of D-gluconic acid, K Salt was then mixed with the base solution. The sweetness linger of this solution was determined to be 4.

Example F19

500 ppm of REBA was dissolved in one liter carbon-treated water and phosphoric acid (75%) was added until a pH between pH 2.4 and 2.5 was reached. 10 ppm to 33 ppm of Guanidine HCl was then mixed with the base solution. The sweetness linger of this solution was determined to be 4.

Example F20

500 ppm of REBA was dissolved in one liter carbon-treated water and phosphoric acid (75%) was added until a pH between pH 2.4 and 2.5 was reached. 500 ppm to 2,000 ppm of potassium benzoate was then mixed with the base solution. The sweetness linger of this solution was determined to be 4.

Example F21

500 ppm of REBA was dissolved in one liter carbon-treated water and phosphoric acid (75%) was added until a pH between pH 2.4 and 2.5 was reached. 3,500 ppm to 7,000 ppm of D-Glucosamine HCl was then mixed with the base solution. The sweetness linger of this solution was determined to be 4.

Example F22

500 ppm of REBA was dissolved in one liter carbon-treated water and phosphoric acid (75%) was added until a pH between pH 2.4 and 2.5 was reached. 647 ppm of fumaric acid was then mixed with the base solution. The sweetness linger of this solution was determined to be 3.

Example F23

500 ppm of REBA was dissolved in one liter carbon-treated water and phosphoric acid (75%) was added until a pH between pH 2.4 and 2.5 was reached. 887 ppm of malic acid was then mixed with the base solution. The sweetness linger of this solution was determined to be 4.

Example F24

500 ppm of REBA was dissolved in one liter carbon-treated water and phosphoric acid (75%) was added until a pH between pH 2.4 and 2.5 was reached. 150 ppm to 200 ppm of malic acid was then mixed with the base solution. The sweetness linger of this solution was determined to be 3.

Example F25

500 ppm of REBA was dissolved in one liter carbon-treated water and phosphoric acid (75%) was added until a pH between pH 2.4 and 2.5 was reached. 2,500 ppm of malic acid was then mixed with the base solution. The sweetness linger of this solution was determined to be 2.

Example F26

500 ppm of REBA was dissolved in one liter carbon-treated water and phosphoric acid (75%) was added until a pH between pH 2.4 and 2.5 was reached. 813 ppm of tartaric acid was then mixed with the base solution. The sweetness linger of this solution was determined to be 4.

Example F27

500 ppm of REBA was dissolved in one liter carbon-treated water and phosphoric acid (75%) was added until a pH between pH 2.4 and 2.5 was reached. 50 ppm to 200 ppm of citric acid was then mixed with the base solution. The sweetness linger of this solution was determined to be 3.

Example F28

500 ppm of REBA was dissolved in one liter carbon-treated water and phosphoric acid (75%) was added until a pH between pH 2.4 and 2.5 was reached. 1,171 ppm of citric acid was then mixed with the base solution. The sweetness linger of this solution was determined to be 3.

Example F29

500 ppm of REBA was dissolved in one liter carbon-treated water and phosphoric acid (75%) was added until a pH between pH 2.4 and 2.5 was reached. 1,500 ppm of citric acid was then mixed with the base solution. The sweetness linger of this solution was determined to be 2.

Example F30

500 ppm of REBA was dissolved in one liter carbon-treated water and phosphoric acid (75%) was added until a pH between pH 2.4 and 2.5 was reached. 50 ppm to 1,400 ppm of adipic acid was then mixed with the base solution. The sweetness linger of this solution was determined to be 3. This formulation was found to have sugar-like taste characteristics.

Example F31

500 ppm of REBA was dissolved in one liter carbon-treated water and phosphoric acid (75%) was added until a pH between pH 2.4 and 2.5 was reached. 1,400 ppm of adipic acid was then mixed with the base solution. The sweetness linger of this solution was determined to be 2. This formulation was found to have sugar-like taste characteristics.

Example F32

500 ppm of REBA was dissolved in one liter carbon-treated water and phosphoric acid (75%) was added until a pH between pH 2.4 and 2.5 was reached. 2,553 ppm of ascorbic acid was then mixed with the base solution. The sweetness linger of this solution was determined to be 4.

Example F33

500 ppm of REBA was dissolved in one liter carbon-treated water and phosphoric acid (75%) was added until a pH between pH 2.4 and 2.5 was reached. 200 ppm to 400 ppm of tannic acid was then mixed with the base solution. The sweetness linger of this solution was determined to be 3.

Example F34

500 ppm of REBA was dissolved in one liter carbon-treated water and phosphoric acid (75%) was added until a pH between pH 2.4 and 2.5 was reached. 15,000 ppm of glycine was then mixed with the base solution. The sweetness linger of this solution was determined to be 1. This formulation was found to have sugar-like taste characteristics.

Example F35

500 ppm of REBA was dissolved in one liter carbon-treated water and phosphoric acid (75%) was added until a pH between pH 2.4 and 2.5 was reached. 3,750 ppm of glycine was then mixed with the base solution. The sweetness linger of this solution was determined to be 3.5. This formulation was found to have sugar-like taste characteristics.

Example F36

500 ppm of REBA was dissolved in one liter carbon-treated water and phosphoric acid (75%) was added until a pH between pH 2.4 and 2.5 was reached. 7,000 ppm of glycine was then mixed with the base solution. The sweetness linger of this solution was determined to be 2. This formulation was found to have sugar-like taste characteristics.

Example F37

500 ppm of REBA was dissolved in one liter carbon-treated water and phosphoric acid (75%) was added until a pH between pH 2.4 and 2.5 was reached. 5,000 ppm of L-alanine was then mixed with the base solution. The sweetness linger of this solution was determined to be 2. This formulation was found to have sugar-like taste characteristics.

Example F38

500 ppm of REBA was dissolved in one liter carbon-treated water and phosphoric acid (75%) was added until a pH between pH 2.4 and 2.5 was reached. 2,500 ppm, and 7,000 ppm to 10,000 ppm of L-alanine were then dissolved in their respective base solutions. The sweetness linger of both solutions was determined to be 3. This formulation was found to have sugar-like taste characteristics.

Example F39

500 ppm of REBA was dissolved in one liter carbon-treated water and phosphoric acid (75%) was added until a pH between pH 2.4 and 2.5 was reached. 5,000 ppm to 25,000 ppm of L-Serine was then mixed with the base solution. The sweetness linger of this solution was determined to be 3.

Example F40

500 ppm of REBA was dissolved in one liter carbon-treated water and phosphoric acid (75%) was added until a pH between pH 2.4 and 2.5 was reached. 150 ppm to 15,000 ppm of L-threonine was then mixed in their respective base solutions. The sweetness linger of these solutions were determined to be 4.

Example F41

500 ppm of REBA was dissolved in one liter carbon-treated water and phosphoric acid (75%) was added until a pH between pH 2.4 and 2.5 was reached. 2,500 ppm and 10,000 ppm of β-alanine were then mixed with the base solution. The sweetness linger of this solution was determined to be 2. The combination was found to have sugar-like characteristics.

Example F42

500 ppm of REBA was dissolved in one liter carbon-treated water and phosphoric acid (75%) was added until a pH between pH 2.4 and 2.5 was reached. 5,000 ppm of β-alanine was then mixed with the base solution. The sweetness linger of this solution was determined to be 3. This formulation was found to have sugar-like taste characteristics.

Example F43

500 ppm of REBA was dissolved in one liter carbon-treated water and phosphoric acid (75%) was added until a pH between pH 2.4 and 2.5 was reached. 100 ppm to 10,000 ppm of γ-amino butyric acid was then mixed with the base solution. The sweetness linger of this solution was determined to be 3.

Example F44

500 ppm of REBA was dissolved in one liter carbon-treated water and phosphoric acid (75%) was added until a pH between pH 2.4 and 2.5 was reached. 10 ppm to 100 ppm of γ-amino butyric acid was then mixed with the base solution. The sweetness linger of this solution was determined to be 4.

Example F45

500 ppm of REBA was dissolved in one liter carbon-treated water and phosphoric acid (75%) was added until a pH between pH 2.4 and 2.5 was reached. 100 ppm of L-aspartic acid was then mixed with the base solution. The sweetness linger of this solution was determined to be 4.

Example F46

500 ppm of REBA was dissolved in one liter carbon-treated water and phosphoric acid (75%) was added until a pH between pH 2.4 and 2.5 was reached. 1,000 ppm of L-aspartic acid was then mixed with the base solution. The sweetness linger of this solution was determined to be 3.

Example F47

500 ppm of REBA was dissolved in one liter carbon-treated water and phosphoric acid (75%) was added until a pH between pH 2.4 and 2.5 was reached. 4,000 ppm of L-glutamic acid, Na salt was then mixed with the base solution. The sweetness linger of this solution was determined to be 4.

Example F48

500 ppm of REBA was dissolved in one liter carbon-treated water and phosphoric acid (75%) was added until a pH between pH 2.4 and 2.5 was reached. 150 ppm to 750 ppm of L-lysine was then mixed with the base solution. The sweetness linger of this solution was determined to be 4.

Example F49

500 ppm of REBA was dissolved in one liter carbon-treated water and phosphoric acid (75%) was added until a pH between pH 2.4 and 2.5 was reached. 1,500 ppm of L-lysine was then mixed with the base solution. The sweetness linger of this solution was determined to be 3.

Example F50

500 ppm of REBA was dissolved in one liter carbon-treated water and phosphoric acid (75%) was added until a pH between pH 2.4 and 2.5 was reached. 5,000 ppm of glycine and 2,500 ppm of L-alanine were then mixed with the base solution. The sweetness linger of this solution was determined to be 2. This formulation was found to have sugar-like taste characteristics.

Example F51

500 ppm of REBA was dissolved in one liter carbon-treated water and phosphoric acid (75%) was added until a pH between pH 2.4 and 2.5 was reached. 3,750 ppm of glycine and 3,750 ppm of L-alanine were then mixed with the base solution. The sweetness linger of this solution was determined to be 2. This formulation was found to have sugar-like taste characteristics.

Example F52

500 ppm of REBA was dissolved in one liter carbon-treated water and phosphoric acid (75%) was added until a pH between pH 2.4 and 2.5 was reached. 150 ppm of dioctyl sulfosuccinate sodium was then mixed with the base solution. The sweetness linger of this solution was determined to be 3.

Example F53

500 ppm of REBA was dissolved in one liter carbon-treated water and phosphoric acid (75%) was added until a pH between pH 2.4 and 2.5 was reached. 10 ppm to 40 ppm of cetylpyridinium chloride was then mixed with the base solution. The sweetness linger of this solution was determined to be 4.

Example F54

500 ppm of REBA was dissolved in one liter carbon-treated water and phosphoric acid (75%) was added until a pH between pH 2.4 and 2.5 was reached. 0.4 ppm to 10 ppm of cetylpyridinium chloride was then mixed with the base solution. The sweetness linger of this solution was determined to be 4.5.

Example F55

500 ppm of REBA was dissolved in one liter carbon-treated water and phosphoric acid (75%) was added until a pH between pH 2.4 and 2.5 was reached. 20 ppm to 63 ppm of hexadecyltrimethylammonium bromide was then mixed with the base solution. The sweetness linger of this solution was determined to be 4.

Example F56

500 ppm of REBA was dissolved in one liter carbon-treated water and phosphoric acid (75%) was added until a pH between pH 2.4 and 2.5 was reached. 2,500 ppm of sucrose oleate was then mixed with the base solution. The sweetness linger of this solution was determined to be 2.

Example F57

500 ppm of REBA was dissolved in one liter carbon-treated water and phosphoric acid (75%) was added until a pH between pH 2.4 and 2.5 was reached. 400 ppm of sucrose oleate was then mixed with the base solution. The sweetness linger of this solution was determined to be 3.

Example F58

500 ppm of REBA was dissolved in one liter carbon-treated water and phosphoric acid (75%) was added until a pH between pH 2.4 and 2.5 was reached. 20 ppm to 5,000 ppm of sucrose stearate was then mixed with the base solution. The sweetness linger of this solution was determined to be 4.

Example F59

500 ppm of REBA was dissolved in one liter carbon-treated water and phosphoric acid (75%) was added until a pH between pH 2.4 and 2.5 was reached. 300 ppm of Polysorbate 20 was then mixed with the base solution. The sweetness linger of this solution was determined to be 4.

Example F60

500 ppm of REBA was dissolved in one liter carbon-treated water and phosphoric acid (75%) was added until a pH between pH 2.4 and 2.5 was reached. 600 ppm of Polysorbate 80 was then mixed with the base solution. The sweetness linger of this solution was determined to be 3.

Example F61

500 ppm of REBA was dissolved in one liter carbon-treated water and phosphoric acid (75%) was added until a pH between pH 2.4 and 2.5 was reached. 500 ppm of lecithin (HLB value: 9.0) was then mixed with the base solution. The sweetness linger of this solution was determined to be 3.

Example F62

500 ppm of REBA was dissolved in one liter carbon-treated water and phosphoric acid (75%) was added until a pH between pH 2.4 and 2.5 was reached. 5 ppm to 50 ppm of polyethyleneimine (50% in water) was then mixed with the base solution. The sweetness linger of this solution was determined to be 4.

Example F63

500 ppm of REBA was dissolved in one liter carbon-treated water and phosphoric acid (75%) was added until a pH between pH 2.4 and 2.5 was reached. 80 ppm to 200 ppm of poly-L-ornithine was then mixed with the base solution. The sweetness linger of this solution was determined to be 4.

Example F64

500 ppm of REBA was dissolved in one liter carbon-treated water and phosphoric acid (75%) was added until a pH between pH 2.4 and 2.5 was reached. 400 ppm of poly-L-ornithine was then mixed with the base solution. The sweetness linger of this solution was determined to be 3.

Example F65

500 ppm of REBA was dissolved in one liter carbon-treated water and phosphoric acid (75%) was added until a pH between pH 2.4 and 2.5 was reached. 200 ppm of poly-L-α-lysine, MW 1,300,000 was then mixed with the base solution. The sweetness linger of this solution was determined to be 3.

Example F66

500 ppm of REBA was dissolved in one liter carbon-treated water and phosphoric acid (75%) was added until a pH between pH 2.4 and 2.5 was reached. 400 ppm of poly-L-α-lysine, MW 1,300,000 was then mixed with the base solution. The sweetness linger of this solution was determined to be 2.

Example F67

500 ppm of REBA was dissolved in one liter carbon-treated water and phosphoric acid (75%) was added until a pH between pH 2.4 and 2.5 was reached. 200 ppm of poly-L-α-lysine, MW 1,500 was then mixed with the base solution. The sweetness linger of this solution was determined to be 3.

Example F68

500 ppm of REBA was dissolved in one liter carbon-treated water and phosphoric acid (75%) was added until a pH between pH 2.4 and 2.5 was reached. 400 ppm of poly-L-α-lysine, MW 1,500 was then mixed with the base solution. The sweetness linger of this solution was determined to be 2.

Example F69

500 ppm of REBA was dissolved in one liter carbon-treated water and phosphoric acid (75%) was added until a pH between pH 2.4 and 2.5 was reached. 40 ppm to 200 ppm of poly-L-α-lysine, MW 25,200 was then mixed with the base solution. The sweetness linger of this solution was determined to be 4.

Example F70

500 ppm of REBA was dissolved in one liter carbon-treated water and phosphoric acid (75%) was added until a pH between pH 2.4 and 2.5 was reached. 200 ppm of poly-L-α-lysine, MW 6,000 was then mixed with the base solution. The sweetness linger of this solution was determined to be 3.

Example F71

500 ppm of REBA was dissolved in one liter carbon-treated water and phosphoric acid (75%) was added until a pH between pH 2.4 and 2.5 was reached. 400 ppm of poly-L-α-lysine, MW 6,000 was then mixed with the base solution. The sweetness linger of this solution was determined to be 2.

Example F72

500 ppm of REBA was dissolved in one liter carbon-treated water and phosphoric acid (75%) was added until a pH between pH 2.4 and 2.5 was reached. 200 ppm of poly-L-α-lysine, MW 63,000 was then mixed with the base solution. The sweetness linger of this solution was determined to be 3.

Example F73

500 ppm of REBA was dissolved in one liter carbon-treated water and phosphoric acid (75%) was added until a pH between pH 2.4 and 2.5 was reached. 400 ppm of poly-L-α- lysine, MW 63,000 was then mixed with the base solution. The sweetness linger of this solution was determined to be 2.

Example F74

500 ppm of REBA was dissolved in one liter carbon-treated water and phosphoric acid (75%) was added until a pH between pH 2.4 and 2.5 was reached. 300 ppm of poly-L-α-lysine, MW 83000 was then mixed with the base solution. The sweetness linger of this solution was determined to be 3.

Example F75

500 ppm of REBA was dissolved in one liter carbon-treated water and phosphoric acid (75%) was added until a pH between pH 2.4 and 2.5 was reached. 40 ppm of poly-L-α-lysine, MW 83,000 was then mixed with the base solution. The sweetness linger of this solution was determined to be 4.

Example F76

500 ppm of REBA was dissolved in one liter carbon-treated water and phosphoric acid (75%) was added until a pH between pH 2.4 and 2.5 was reached. 10 ppm to 1,000 ppm of poly-L-ε-lysine was then mixed with the base solution. The sweetness linger of this solution was determined to be 2.

Example F77

500 ppm of REBA was dissolved in one liter carbon-treated water and phosphoric acid (75%) was added until a pH between pH 2.4 and 2.5 was reached. 502 ppm of poly-L-ε-lysine (25% solution) was then mixed with the base solution. The sweetness linger of this solution was determined to be 2.

Example F78

500 ppm of REBA was dissolved in one liter carbon-treated water and phosphoric acid (75%) was added until a pH between pH 2.4 and 2.5 was reached. 50 ppm of poly-L-ε-lysine (25% solution) was then mixed with the base solution. The sweetness linger of this solution was determined to be 4.

Example F79

500 ppm of REBA was dissolved in one liter carbon-treated water and phosphoric acid (75%) was added until a pH between pH 2.4 and 2.5 was reached. 10 ppm to 1,000 ppm of chitosan was then mixed with the base solution. The sweetness linger of this solution was determined to be 3.

Example F80

500 ppm of REBA was dissolved in one liter carbon-treated water and phosphoric acid (75%) was added until a pH between pH 2.4 and 2.5 was reached. 1,000 ppm of bovine serum albumin (BSA) was then mixed with the base solution. The sweetness linger of this solution was determined to be 3.

Example F81

500 ppm of REBA was dissolved in one liter carbon-treated water and phosphoric acid (75%) was added until a pH between pH 2.4 and 2.5 was reached. 200 ppm to 5,000 ppm of whey protein (concentrate 34%) was then mixed with the base solution. The sweetness linger of this solution was determined to be 4.

Example F82

500 ppm of REBA was dissolved in one liter carbon-treated water and phosphoric acid (75%) was added until a pH between pH 2.4 and 2.5 was reached. 200 ppm to 5,000 ppm of whey protein hydrolysate, 90% was then mixed with the base solution. The sweetness linger of this solution was determined to be 4.

Example F83

500 ppm of REBA was dissolved in one liter carbon-treated water and phosphoric acid (75%) was added until a pH between pH 2.4 and 2.5 was reached. 7,500 ppm of L-alanyl-L-glutamine was then mixed with the base solution. The sweetness linger of this solution was determined to be 3. This formulation was found to have sugar-like taste characteristics.

Example F84

500 ppm of REBA was dissolved in one liter carbon-treated water and phosphoric acid (75%) was added until a pH between pH 2.4 and 2.5 was reached. 15,000 ppm of glycine and 375 ppm of $KAl(SO_4)_2 \cdot 12H_2O$ (Alum) were then mixed with the base solution. The sweetness linger of this solution was determined to be 2. This formulation was found to have sugar-like taste characteristics.

Example F85

500 ppm of REBA was dissolved in one liter carbon-treated water and phosphoric acid (75%) was added until a pH between pH 2.4 and 2.5 was reached. 5,000 ppm of urea and 584 ppm of sodium chloride were then mixed with the base solution. The sweetness linger of this solution was determined to be 4.

Example F86

500 ppm of REBA was dissolved in one liter carbon-treated water and phosphoric acid (75%) was added until a pH between pH 2.4 and 2.5 was reached. 1,500 ppm of urea and 584 ppm of sodium chloride were then mixed with the base solution. The sweetness linger of this solution was determined to be 3. This formulation was found to have sugar-like taste characteristics.

Example F87

500 ppm of REBA was dissolved in one liter carbon-treated water and phosphoric acid (75%) was added until a pH between pH 2.4 and 2.5 was reached. 3,750 ppm of glycine and 60 ppm to 90 ppm of poly-L-α-lysine were then mixed with the base solution. The sweetness linger of this solution was determined to be 3. This formulation was found to have sugar-like taste characteristics.

Example F88

500 ppm of REBA was dissolved in one liter carbon-treated water and phosphoric acid (75%) was added until a pH between pH 2.4 and 2.5 was reached. 3,750 ppm of glycine and 10 ppm of poly-L-ε-lysine were then mixed with the base solution. The sweetness linger of this solution was determined to be 3. This formulation was found to have sugar-like taste characteristics.

Example F89

500 ppm of REBA was dissolved in one liter carbon-treated water and phosphoric acid (75%) was added until a pH between pH 2.4 and 2.5 was reached. 3,750 ppm of glycine and 119 ppm of potassium chloride were then mixed with the base solution. The sweetness linger of this solution was determined to be 4. This formulation was found to have sugar-like taste characteristics.

Example F90

500 ppm of REBA was dissolved in one liter carbon-treated water and phosphoric acid (75%) was added until a pH between pH 2.4 and 2.5 was reached. 15,000 ppm of glycine and 239 ppm of potassium chloride were then mixed with the base solution. The sweetness linger of this solution was determined to be 2. This formulation was found to have sugar-like taste characteristics.

Example F91

500 ppm of REBA was dissolved in one liter carbon-treated water and phosphoric acid (75%) was added until a pH between pH 2.4 and 2.5 was reached. 3,750 ppm of glycine and 238 ppm of sodium chloride were then mixed with the base solution. The sweetness linger of this solution was determined to be 4. This formulation was found to have sugar-like taste characteristics.

Example F92

500 ppm of REBA was dissolved in one liter carbon-treated water and phosphoric acid (75%) was added until a pH between pH 2.4 and 2.5 was reached. 3,750 ppm of glycine, 43 ppm of NaCl and 51 ppm of KCl were then mixed with the base solution. The sweetness linger of this solution was determined to be 4. This formulation was found to have sugar-like taste characteristics.

Example F93

500 ppm of REBA was dissolved in one liter carbon-treated water and phosphoric acid (75%) was added until a pH between pH 2.4 and 2.5 was reached. 15,000 ppm of glycine and 501 ppm of sodium gluconate were then mixed with the base solution. The sweetness linger of this solution was determined to be 2. This formulation was found to have sugar-like taste characteristics.

Example F94

500 ppm of REBA was dissolved in one liter carbon-treated water and phosphoric acid (75%) was added until a pH between pH 2.4 and 2.5 was reached. 1,000 ppm of lauric arginate was then mixed with the base solution. The sweetness linger of this solution was determined to be 4.

Example F95

500 ppm of REBA was dissolved in one liter carbon-treated water and phosphoric acid (75%) was added until a pH between pH 2.4 and 2.5 was reached. 2,500 ppm of L-alanine and 5,000 ppm of fructose were then mixed with the base solution. The sweetness linger of this solution was determined to be 4. This formulation was found to have sugar-like taste characteristics.

Example F96

500 ppm of REBA was dissolved in one liter carbon-treated water and phosphoric acid (75%) was added until a pH between pH 2.4 and 2.5 was reached. 164 ppm to 540 ppm of fruitaric acid was then mixed with the base solution. The sweetness linger of this solution was determined to be 4.

Example F97

360 ppm of REBA was dissolved in one liter carbon-treated water and phosphoric acid (75%) was added until a pH between pH 2.4 and 2.5 was reached. 3,750 ppm glycine and 35,000 ppm of erythritol were then mixed with the base solution. The sweetness linger of this solution was determined to be 2. This formulation was found to have sugar-like taste characteristics.

Example F98

360 ppm of REBA was dissolved in one liter carbon-treated water and phosphoric acid (75%) was added until a pH between pH 2.4 and 2.5 was reached. 35,000 ppm of erythritol, 3,750 ppm of glycine, 450 ppm of KCl, 680 ppm of $KH_2PO_4$, and 1,175 ppm of choline chloride were then mixed with the base solution. The sweetness linger of this solution was determined to be 1. This formulation was found to have sugar-like taste characteristics.

Example F99

360 ppm of REBA was dissolved in one liter carbon-treated water and phosphoric acid (75%) was added until a pH between pH 2.4 and 2.5 was reached. 2,500 ppm of L-alanine, 5,000 ppm of fructose, and 35,000 ppm of erythritol were then mixed with the base solution. The sweetness linger of this solution was determined to be 4. This formulation was found to have sugar-like taste characteristics.

Example F100

360 ppm of REBA was dissolved in one liter carbon-treated water and phosphoric acid (75%) was added until a pH between pH 2.4 and 2.5 was reached. 35,000 ppm of erythritol, 3,750 ppm of glycine, 450 ppm of KCl, and 680 ppm of $KH_2PO_4$ were then mixed with the base solution. The sweetness linger of this solution was determined to be 4. This formulation was found to have sugar-like taste characteristics.

Example F101

500 ppm of REBA was dissolved in one liter carbon-treated water and phosphoric acid (75%) was added until a pH between pH 2.4 and 2.5 was reached. 625 ppm to 10,000 ppm of D-tagatose was then mixed with the base solution. The sweetness linger of this solution was determined to be 2.

Example F102

500 ppm of REBA was dissolved in one liter carbon-treated water and phosphoric acid (75%) was added until a pH between pH 2.4 and 2.5 was reached. 625 ppm to 20,000 ppm of trehalose was then mixed with the base solution. The sweetness linger of this solution was determined to be 2.

Example F103

500 ppm of REBA was dissolved in one liter carbon-treated water and phosphoric acid (75%) was added until a pH between pH 2.4 and 2.5 was reached. 1,250 ppm to 20,000 ppm of Fructooligosaccharide was then mixed with the base solution. The sweetness linger of this solution was determined to be 2.

Example F104

500 ppm of REBA was dissolved in one liter carbon-treated water and phosphoric acid (75%) was added until a pH between pH 2.4 and 2.5 was reached. 25 ppm to 800 ppm of gum *acacia* senegal was then mixed with the base solution. The sweetness linger of this solution was determined to be 2.

Example F105

500 ppm of REBA was dissolved in one liter carbon-treated water and phosphoric acid (75%) was added until a pH between pH 2.4 and 2.5 was reached. 1,000 ppm of Fructooligosaccharide (55%) was then mixed with the base solution. The sweetness linger of this solution was determined to be 3. This formulation was found to have sugar-like taste characteristics.

Example F106

500 ppm of REBA was dissolved in one liter carbon-treated water and phosphoric acid (75%) was added until a pH between pH 2.4 and 2.5 was reached. 625 ppm to 10,000 ppm of ethanol was then mixed with the base solution. The sweetness linger of this solution was determined to be 2.

Example F107

500 ppm of REBA was dissolved in one liter carbon-treated water and phosphoric acid (75%) was added until a pH between pH 2.4 and 2.5 was reached. 312 ppm to 10,000 ppm of propylene glycol was then mixed with the base solution. The sweetness linger of this solution was determined to be 4.

Example F108

500 ppm of REBA was dissolved in one liter carbon-treated water and phosphoric acid (75%) was added until a pH between pH 2.4 and 2.5 was reached. 312 ppm to 10,000 ppm of β-cyclodextrin was then mixed with the base solution. The sweetness linger of this solution was determined to be 3.

Example F109

500 ppm of REBA was dissolved in one liter carbon-treated water and phosphoric acid (75%) was added until a pH between pH 2.4 and 2.5 was reached. 37 ppm to 600 ppm of NaCl was then mixed with the base solution. The sweetness linger of this solution was determined to be 4.

Example F110

500 ppm of REBA was dissolved in one liter carbon-treated water and phosphoric acid (75%) was added until a pH between pH 2.4 and 2.5 was reached. 37 ppm to 600 ppm of KCl was then mixed with the base solution. The sweetness linger of this solution was deter mined to be 2.

Example F111

500 ppm of REBA was dissolved in one liter carbon-treated water and phosphoric acid (75%) was added until a pH between pH 2.4 and 2.5 was reached. 37 ppm to 600 ppm of $KH_2PO_4$ was then mixed with the base solution. The sweetness linger of this solution was determined to be 3.

Example F112

500 ppm of REBA was dissolved in one liter carbon-treated water and phosphoric acid (75%) was added until a pH between pH 2.4 and 2.5 was reached. 16 ppm to 206 ppm of MSG was then mixed with the base solution. The sweetness linger of this solution was determined to be 4.

Example F113

500 ppm of REBA was dissolved in one liter carbon-treated water and phosphoric acid (75%) was added until a pH between pH 2.4 and 2.5 was reached. 12 ppm to 400 ppm of AMP was then mixed with the base solution. The sweetness linger of this solution was determined to be 3.

Example F114

500 ppm of REBA was dissolved in one liter carbon-treated water and phosphoric acid (75%) was added until a pH between pH 2.4 and 2.5 was reached. 125 ppm to 4,000 ppm of sodium gluconate was then mixed with the base solution. The sweetness linger of this solution was determined to be 4.

Example F115

500 ppm of REBA was dissolved in one liter carbon-treated water and phosphoric acid (75%) was added until a pH between pH 2.4 and 2.5 was reached. 31 ppm to 1,000 ppm of potassium tartrate was then mixed with the base solution. The sweetness linger of this solution was determined to be 3.

Example F116

500 ppm of REBA was dissolved in one liter carbon-treated water and phosphoric acid (75%) was added until a pH between pH 2.4 and 2.5 was reached. 31 ppm to 1,000 ppm of sodium tartrate was then mixed with the base solution. The sweetness linger of this solution was determined to be 3.

Example F117

500 ppm of REBA was dissolved in one liter carbon-treated water and phosphoric acid (75%) was added until a pH between pH 2.4 and 2.5 was reached. 200 ppm to 1,000 ppm of malic acid was then mixed with the base solution. The sweetness linger of this solution was determined to be 4.

Example F118

500 ppm of REBA was dissolved in one liter carbon-treated water and phosphoric acid (75%) was added until a pH between pH 2.4 and 2.5 was reached. 31 ppm to 500 ppm of 2,4-dihydroxybenzoic acid was then mixed with the base solution. The sweetness linger of this solution was determined to be 2.

Example F119

500 ppm of REBA was dissolved in one liter carbon-treated water and phosphoric acid (75%) was added until a pH between pH 2.4 and 2.5 was reached. 28 ppm to 900 ppm of caffeic acid was then mixed with the base solution. The sweetness linger of this solution was determined to be 3.

Example F120

500 ppm of REBA was dissolved in one liter carbon-treated water and phosphoric acid (75%) was added until a pH between pH 2.4 and 2.5 was reached. 25 ppm to 400 ppm of chlorogenic acid was then mixed with the base solution. The sweetness linger of this solution was determined to be 4.

Example F121

500 ppm of REBA was dissolved in one liter carbon-treated water and phosphoric acid (75%) was added until a pH between pH 2.4 and 2.5 was reached. 25 ppm to 400 ppm of D/L-alanine was then mixed with the base solution. The sweetness linger of this solution was determined to be 3.

Example F122

500 ppm of REBA was dissolved in one liter carbon-treated water and phosphoric acid (75%) was added until a pH between pH 2.4 and 2.5 was reached. 25 ppm to 800 ppm of threonine was then mixed with the base solution. The sweetness linger of this solution was determined to be 2.

Example F123

500 ppm of REBA was dissolved in one liter carbon-treated water and phosphoric acid (75%) was added until a pH between pH 2.4 and 2.5 was reached. 312 ppm to 10,000 ppm of taurine was then mixed with the base solution. The sweetness linger of this solution was determined to be 3.

Example F124

500 ppm of REBA was dissolved in one liter carbon-treated water and phosphoric acid (75%) was added until a pH between pH 2.4 and 2.5 was reached. 312 ppm to 10,000 ppm of glycine was then mixed with the base solution. The sweetness linger of this solution was determined to be 2.

Example F125

500 ppm of REBA was dissolved in one liter carbon-treated water and phosphoric acid (75%) was added until a pH between pH 2.4 and 2.5 was reached. 3 ppm to 100 ppm of naringin was then mixed with the base solution. The sweetness linger of this solution was determined to be 3.

Example F126

500 ppm of REBA was dissolved in one liter carbon-treated water and phosphoric acid (75%) was added until a pH between pH 2.4 and 2.5 was reached. 0.3 ppm to 10 ppm of quinine was then mixed with the base solution. The sweetness linger of this solution was determined to be 3.

Example F127

500 ppm of REBA was dissolved in one liter carbon-treated water and phosphoric acid (75%) was added until a pH between pH 2.4 and 2.5 was reached. 0.3 ppm to 10 ppm of viridiflorol was then mixed with the base solution. The sweetness linger of this solution was determined to be 3.

Example F128

500 ppm of REBA was dissolved in one liter carbon-treated water and phosphoric acid (75%) was added until a pH between pH 2.4 and 2.5 was reached. 31 ppm to 1,000 ppm of Polyphenon 60 was then mixed with the base solution. The sweetness linger of this solution was determined to be 4.

Example F129

500 ppm of REBA was dissolved in one liter carbon-treated water and phosphoric acid (75%) was added until a pH between pH 2.4 and 2.5 was reached. 31 ppm to 1,000 ppm of hydroxycitric acid was then mixed with the base solution. The sweetness linger of this solution was determined to be 4.

Example F130

500 ppm of REBA was dissolved in one liter carbon-treated water and phosphoric acid (75%) was added until a pH between pH 2.4 and 2.5 was reached. 300 ppm to 10,000 ppm of glucosamine HCl was then mixed with the base solution. The sweetness linger of this solution was determined to be 4.

Example F131

500 ppm of REBA was dissolved in one liter carbon-treated water and phosphoric acid (75%) was added until a pH between pH 2.4 and 2.5 was reached. 31 ppm to 1,000 ppm of Salicylic acid was then mixed with the base solution. The sweetness linger of this solution was determined to be 3.

Example F132

500 ppm of REBA was dissolved in one liter carbon-treated water and phosphoric acid (75%) was added until a pH between pH 2.4 and 2.5 was reached. 5% sucrose, 3.5% erythritol, and 0.75% D-tagatose were then mixed with the base solution. The sweetness linger of this solution was determined to be 0.

Example F133

500 ppm of REBA was dissolved in one liter carbon-treated water and phosphoric acid (75%) was added until a pH between pH 2.4 and 2.5 was reached. 5% sucrose and 0.75% D-tagatose were then mixed with the base solution. The sweetness linger of this solution was determined to be 2.

Example F134

500 ppm of REBA was dissolved in one liter carbon-treated water and phosphoric acid (75%) was added until a pH between pH 2.4 and 2.5 was reached. 3.3% sucrose, 3.5% erythritol, and 0.75% D-tagatose were then mixed with the base solution. The sweetness linger of this solution was determined to be 1.

Example F135

500 ppm of REBA was dissolved in one liter carbon-treated water and phosphoric acid (75%) was added until a pH between pH 2.4 and 2.5 was reached. 3.3% sucrose and 3.5% D-tagatose were then mixed with the base solution. The sweetness linger of this solution was determined to be 2.

Example F136

500 ppm of REBA was dissolved in one liter carbon-treated water and phosphoric acid (75%) was added until a pH between pH 2.4 and 2.5 was reached. 5% sucrose and 3.5% erythritol were then mixed with the base solution. The sweetness linger of this solution was determined to be 0.

Example F137

500 ppm of REBA was dissolved in one liter carbon-treated water and phosphoric acid (75%) was added until a pH between pH 2.4 and 2.5 was reached. 5% of sucrose was then mixed with the base solution. The sweetness linger of this solution was determined to be 2.

Example F138

500 ppm of REBA was dissolved in one liter carbon-treated water and phosphoric acid (75%) was added until a pH between pH 2.4 and 2.5 was reached. 3.3% sucrose and 3.5% erythritol were then mixed with the base solution. The sweetness linger of this solution was determined to be 1.

Example F139

500 ppm of REBA was dissolved in one liter carbon-treated water and phosphoric acid (75%) was added until a pH between pH 2.4 and 2.5 was reached. 3.30% of sucrose was then mixed with the base solution. The sweetness linger of this solution was determined to be 2.

Example F140

500 ppm of REBA was dissolved in one liter carbon-treated water and phosphoric acid (75%) was added until a pH between pH 2.4 and 2.5 was reached. 3.5% erythritol, 0.75% glycine, 250 ppm of KCl, 650 ppm of $KH_2PO_4$ were then mixed with the base solution. The sweetness linger of this solution was determined to be 2.

Example F141

500 ppm of REBA was dissolved in one liter carbon-treated water and phosphoric acid (75%) was added until a pH between pH 2.4 and 2.5 was reached. 0.75% glycine, 250 ppm of KCl, 650 ppm of $KH_2PO_4$ were then mixed with the base solution. The sweetness linger of this solution was determined to be 2.

Example F142

500 ppm of REBA was dissolved in one liter carbon-treated water and phosphoric acid (75%) was added until a pH between pH 2.4 and 2.5 was reached. 3.5% erythritol, 0.75% fructose, 250 ppm of KCl, 650 ppm of $KH_2PO_4$ were then mixed with the base solution. The sweetness linger of this solution was determined to be 2.

Example F143

500 ppm of REBA was dissolved in one liter carbon-treated water and phosphoric acid (75%) was added until a pH between pH 2.4 and 2.5 was reached. 0.75% fructose, 250 ppm of KCl, and 650 ppm of $KH_2PO_4$ were then mixed with the base solution. The sweetness linger of this solution was determined to be 3.

Example F144

500 ppm of REBA was dissolved in one liter carbon-treated water and phosphoric acid (75%) was added until a pH between pH 2.4 and 2.5 was reached. 3.5% erythritol and 400 ppm of gum *acacia* senegal were then mixed with the base solution. The sweetness linger of this solution was determined to be 2.

Example F145

500 ppm of REBA was dissolved in one liter carbon-treated water and phosphoric acid (75%) was added until a pH between pH 2.4 and 2.5 was reached. 400 ppm of gum *acacia* senegal was then mixed with the base solution. The sweetness linger of this solution was determined to be 3.

Example F146

500 ppm of REBA was dissolved in one liter carbon-treated water and phosphoric acid (75%) was added until a pH between pH 2.4 and 2.5 was reached. 3.5% erythritol, 0.5% glycine, 250 ppm of KCl, 650 ppm of $KH_2PO_4$, and 0.25% of D-alanine were then mixed with the base solution. The sweetness linger of this solution was determined to be 1.

Example F147

500 ppm of REBA was dissolved in one liter carbon-treated water and phosphoric acid (75%) was added until a pH between pH 2.4 and 2.5 was reached. 0.5% glycine, 250 ppm of KCl 650, ppm of $KH_2PO_4$, and 0.25% of D-alanine were then mixed with the base solution. The sweetness linger of this solution was determined to be 3.

The following Examples G1-G3, H1-H3, I, J1-J3, and K illustrate methods of making purified rebaudioside A in accordance with particular embodiments of this invention:

G. Example Set G

TABLE 3

Summary of Examples G1–3

| | Crude Rebaudioside A (g) | Ethanol (95%) (mL) | Solvent Methanol (99%) (mL) | Water (mL) | Heating T (° C.) | Drying T (° C.) | Yield (g) | HPLC Purity (wt/wt %) |
|---|---|---|---|---|---|---|---|---|
| G1 | 400 | 1200 | 400 | 320 | 50 | 50 | 130 | 98.9 |
| G2 | 100 | 320 | 120 | 50 | 30–40 | 60 | 72 | 98.3 |
| G3 | 50 | 160 | 60 | 25 | ~30 | 60 | 27.3 | 98.2 |

Example G1

Crude rebaudioside A (77.4% purity) mixture was obtained from a commercial source. The impurities (6.2% stevioside, 5.6% rebaudioside C, 0.6% rebaudioside F, 1.0% other steviolglycosides 2, 3.0% rebaudioside D, 4.9% rebaudioside B, 0.3% steviolbioside) were identified and quantified using HPLC on dry basis, moisture content 4.7%.

Crude rebaudioside A (400 g), ethanol (95%, 1200 mL), methanol (99%, 400 mL) and water (320 mL) were combined and heated to 50° C. for 10 minutes. The clear solution was cooled to 22° C. for 16 hours. The white crystals were filtered and washed twice with ethanol (2×200 mL, 95%) and dried in a vacuum oven at 50° C. for 16-24 hours under reduced pressure (20 mm).

The final composition of substantially pure rebaudioside A (130 g) comprised 98.91% rebaudioside A, 0.06% stevioside, 0.03% rebaudioside C, 0.12% rebaudioside F, 0.13% other steviolglycosides, 0.1% rebaudioside D, 0.49% rebaudioside B and 0.03% steviolbioside, all by weight.

Example G2

Crude rebaudioside A (80.37%) was obtained from a commercial source. The impurities (6.22% stevioside, 2.28% rebaudioside C, 0.35% Dulcoside, 0.78% rebaudioside F, 0.72% other steviolglycosides, 3.33% rebaudioside B, 0.07% steviolbioside) were identified by HPLC on dry basis, moisture content 3.4%.

Crude rebaudioside A (100 g), ethanol (95%, 320 mL), methanol (99%, 120 mL) and water (50 mL) were combined and heated to 30-40° C. for 10 minutes. The clear solution was cooled to 22° C. for 16 hours. The white crystals were filtered and washed twice with ethanol (2×50 mL, 95%). The wet filter cake (88 g) was slurried in ethanol (95%, 1320 mL) for 16 hours, filtered, washed with ethanol (95%, 2×100 mL) and dried in a vacuum oven at 60° C. for 16-24 hours under reduced pressure (20 mm).

The final composition of substantially pure rebaudioside A (72 g) comprised 98.29% rebaudioside A, 0.03% stevioside, 0.02% rebaudioside C. 0.17% rebaudioside F, 0.06% rebaudioside D and 1.09% rebaudioside B. Steviolbioside was not detected by HPLC.

Example G3

Crude rebaudioside A (80.37%) was obtained from a commercial source. The impurities (6.22% stevioside, 2.28% rebaudioside C, 0.35% Dulcoside, 0.78% rebaudioside F, 0.72% other steviolglycosides, 3.33% rebaudioside B, 0.07% steviolbioside) were identified by HPLC on dry basis, moisture content 3.4%.

Crude rebaudioside A (50 g), ethanol (95%, 160 mL), methanol (99%, 60 mL) and water (25 mL) were combined and heated to approximately 30° C. for 10 minutes. The clear solution was cooled to 22° C. for 16 hours. The white crystals were filtered and washed twice with ethanol (2×25 mL, 95%). The wet filter cake (40 g) was slurried in methanol (99%, 600 mL) for 16 hours, filtered, washed with methanol (99%, 2×25 mL) and dried in a vacuum oven at 60° C. for 16-24 hours under reduced pressure (20 mm).

The final composition of substantially pure rebaudioside A (27.3 g) comprised 98.22% rebaudioside A, 0.04% stevioside, 0.04% rebaudioside C, 0.18% rebaudioside F, 0.08% rebaudioside D and 1.03% rebaudioside B. Steviolbioside was not detected by HPLC.

H. Example Set H

TABLE 4

Summary of Examples H1–H3

| | Crude Rebaudioside A (g) | Ethanol (95%) (mL) | Organic Co-solvent (mL) | Water (mL) | Wash Solvent | Yield (g) | HPLC Purity (%) |
|---|---|---|---|---|---|---|---|
| H1 | 5 | 15 | Methanol (6) | 3.5 | EtOH/MeOH (3:1 v/v) | 2.6 | >99 |
| H2 | 5 | 15 | Methanol (5) | 4 | EtOH/MeOH (3:1 v/v) | 2.3 | >99 |
| H3 | 5 | 16 | Methanol (6) | 2.5 | *EtOH/MeOH (8:3 v/v) | 3.2 | >98 |

Example H1

A mixture of crude rebaudioside A (80.37% purity, 5 g), ethanol (95%, 15 mL), methanol (5 mL) and water (3.5 mL) were combined and heated to reflux for 10 minutes. The clear solution was cooled to 22° C. for 16 hours while stirring. The white crystalline product was filtered, washed twice with ethanol:methanol (5.0 mL, 3:1, v/v) mixture and dried in a vacuum oven at 50° C. for 16-24 hours under reduced pressure (20 mm) to yield 2.6 g of purified product (>99% by HPLC).

Example H2

A mixture of crude rebaudioside A (80.37% purity, 5 g), ethanol (95%, 15 mL), methanol (5 mL) and water (4.0 mL) were combined and heated to reflux for 10 minutes. The clear solution was cooled to 22° C. for 16 hours while stirring. The white crystalline product was filtered, washed twice with ethanol:methanol (5.0 mL, 3:1, v/v) mixture and dried in a vacuum oven at 50° C. for 16-24 hours under reduced pressure (20 mm) to yield 2.3 g of purified product (>99% by HPLC).

Example H3

A mixture of crude rebaudioside A (80.37% purity, 5 g), ethanol (95%, 16 mL), methanol (6 mL) and water (2.5 mL) were combined and heated to reflux for 10 minutes. The clear solution was cooled to 22° C. for 2 hours. During this time, crystals started to appear. The mixture is stirred at room temperature for 16 hours. The white crystalline product was filtered, washed twice with ethanol:methanol (5.0 mL, 8:3, v/v) mixture and dried in a vacuum oven at 50° C. for 16-24 hours under reduced pressure (20 mm) to yield 3.2 g of purified product (>98% by HPLC).

I. Example Set I

TABLE 5

Summary of Example I

| Crude Rebaudioside A (g) | Solvent | | Wash Solvent | Yield (g) | HPLC Purity (%) |
|---|---|---|---|---|---|
| | Organic Solvent (mL) | Water (mL) | | | |
| I  50 | EtOH (160) | 40 | EtOH | 19.8 | 99.5 |

A mixture of crude rebaudioside A (80.37% purity, 50 g), ethanol (95%, 160 mL) and water (40 mL) were combined and heated to reflux for 30 minutes. The mixture was then allowed to cool to ambient temperature for 16-24 hours. The white crystalline product was filtered, washed twice with ethanol (95%, 25 mL), and dried in a vacuum oven at 60° C. for 16-24 hours under reduced pressure (20 mm) to yield 19.8 g of purified product (99.5% by HPLC).

J. Example Set J

TABLE 6

Summary of Examples J1–J3

| | Crude Rebaudioside A (g) | Ethanol (95%) (mL) | Organic Co-solvent (mL) | Water (mL) | Methanol Slurry (mL) | Yield (g) | HPLC Purity (%) |
|---|---|---|---|---|---|---|---|
| J1 | 50 | 160 | Methanol (60) | 25 | 200 | 12.7 | >97 |
| J2 | 50 | 160 | Methanol (60) | 25 | 300 | 18.6 | >97 |
| J3 | 50 | 160 | Methanol (60) | 25 | 350 | 22.2 | >97 |

Example J1

A mixture of crude rebaudioside A (41% purity, 50 g), ethanol (95%, 160 mL), methanol (99.8%, 60 mL) and water (25 mL) were combined by stirring at 22° C. A white product crystallized out in 5-20 hours. The mixture was stirred for additional 48 hours. The white crystalline product was filtered and washed twice with ethanol (95%, 25 mL). The wet cake of white crystalline product then was slurried in methanol (99.8%, 200 mL) for 16 hours, filtered, washed twice with methanol (99.8%, 25 mL), and dried in a vacuum oven at 60° C. for 16-24 hours under reduced pressure (20 mm) to yield 12.7 g of purified product (>97% by HPLC).

Example J2

A mixture of crude rebaudioside A (48% purity, 50 g), ethanol (95%, 160 mL), methanol (99.8%, 60 mL) and water (25 mL) was combined by stirring at 22° C. The white product crystallized out in 3-6 hours. The mixture was stirred for additional 48 hours. The white crystalline product was filtered and washed twice with ethanol (95%, 25 mL). The wet cake of white crystalline product then was slurried in methanol (99.8%, 300 mL) for 16 hours, filtered, washed twice with methanol (99.8%, 25 mL) and dried in a vacuum oven at 60° C. for 16-24 hours under reduced pressure (20 mm) to yield 18.6 g of purified product (>97% by HPLC).

Example J3

A mixture of crude rebaudioside A (55% purity, 50 g), ethanol (95%, 160 mL), methanol (99.8%, 60 mL) and water (25 mL) was combined by stirring at 22° C. The white product crystallized out in 15-30 minutes. The mixture was stirred for an additional 48 hours. The white crystalline product was filtered and washed twice with ethanol (95%, 25 mL). The wet cake of white crystalline product was slurried in methanol (99.8%, 350 mL) for 16 hours, filtered, washed twice with methanol (99.8%, 25 mL) and dried in a vacuum oven at 60° C. for 16-24 hours under reduced pressure (20 mm) to yield 22.2 g of purified product (>97% by HPLC).

K. Example K

A solution of rebaudioside A (>97% pure by HPLC) was prepared in double distilled water (12.5 gm in 50 mL, 25% concentration) by stirring the mixture at 40° C. for 5 minutes. An amorphous form of rebaudioside A was formed by immediately using the clear solution for spray drying with the Lab-Plant spray drier SD-04 instrument (Lab-Plant Ltd., West Yorkshire, U.K.). The solution was fed through the feed pump into the nozzle atomizer which atomized it into a spray of droplets with the help of a constant flow of nitrogen/air. Moisture was evaporated from the droplets under controlled temperature conditions (about 90 to about 97° C.) and airflow conditions in the drying chamber and resulted in the formation of dry particles. This dry powder (11-12 g, $H_2O$ 6.74%) was discharged continuously from the drying chamber and was collected in a bottle. The solubility in water at room temperature was determined to be >35.0%.

While the invention has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereof.

The invention claimed is:

1. A sweetener composition comprising rebaudioside A and erythritol, wherein:
    the rebaudioside A has a purity greater than about 97% by weight on a dry basis; and
    the weight ratio of rebaudioside A to erythritol is about 1:75 to about 1:150.

2. The sweetener composition of claim 1, wherein the rebaudioside A has a purity greater than about 99% by weight on a dry basis.

3. The sweetener composition of claim 1, further comprising at least one steviolglycoside selected from the group consisting of rebaudioside B, rebaudioside C, rebaudioside E, rebaudioside F, dulcoside A, dulcoside B, stevioside, steviolbioside or combinations thereof.

4. The sweetener composition of claim 1, wherein the rebaudioside A is substantially free of steviolbioside as measured by HPLC.

5. The sweetener composition of claim 1, wherein the rebaudioside A has a rate of dissolution greater than about 30%/5 minutes in water at 25° C.

6. The sweetener composition of claim 1, further comprising at least one sweet taste improving composition selected from the group consisting of carbohydrates, amino acids and their corresponding salts, polyamino acids and their corresponding salts, sugar acids and their corresponding salts, organic acids, inorganic acids, organic salts, inorganic salts, bitter compounds, flavorants, astringent compounds, polymers, proteins, protein hydrolysates, surfactants, emulsifiers, flavonoids, alcohols, synthetic sweeteners or combinations thereof.

7. A sweetened composition comprising a sweetenable composition and a sweetener composition comprising rebaudioside A and erythritol, wherein:
the rebaudioside A has a purity greater than about 97% by weight on a dry basis; and
the weight ratio of rebaudioside A to erythritol is about 1:75 to about 1:150.

8. The sweetened composition of claim 7, wherein the rebaudioside A has a purity greater than about 99% by weight on a dry basis.

9. The sweetened composition of claim 7, wherein the rebaudioside A is present in an amount from about 100 ppm to about 3,000 ppm.

10. The sweetened composition of claim 7, wherein the erythritol is present in an amount from about 5,000 ppm to about 40,000 ppm.

11. The sweetened composition of claim 7, further comprising at least one steviolglycoside selected from the group consisting of rebaudioside B, rebaudioside C, rebaudioside E, rebaudioside F, dulcoside A, dulcoside B, stevioside, steviolbioside or combinations thereof.

12. The sweetened composition of claim 7, wherein the rebaudioside A is substantially free of steviolbioside as measured by HPLC.

13. The sweetened composition of claim 7, wherein the rebaudioside A has a rate of dissolution greater than about 30%/5 minutes in water at 25° C.

14. The sweetened composition of claim 7, further comprising at least one sweet taste improving composition selected from the group consisting of carbohydrates, amino acids and their corresponding salts, polyamino acids and their corresponding salts, sugar acids and their corresponding salts, organic acids, inorganic acids, organic salts, inorganic salts, bitter compounds, flavorants, astringent compounds, polymers, proteins, protein hydrolysates, surfactants, emulsifiers, flavonoids, alcohols, synthetic sweeteners or combinations thereof.

15. The sweetened composition of claim 7, wherein the sweetenable composition is a beverage selected from the group consisting of a non-carbonated beverage, carbonated beverage, cola, root beer, fruit-flavored beverage, citrus-flavored beverage, fruit juice, fruit-containing beverage, vegetable juice, vegetable containing beverage, tea, coffee, dairy beverage, sports drink, energy drink, and flavored water.

16. The sweetened composition of claim 14, wherein the one or more sweet taste improving compositions are present in an amount effective for the sweetener composition to impart a pH from about 2.3 to about 3.5 to an aqueous solution of the sweetener composition.

\* \* \* \* \*